(12) United States Patent
Brough et al.

(10) Patent No.: US 12,234,261 B2
(45) Date of Patent: *Feb. 25, 2025

(54) HEPATITIS B VACCINES AND USES OF THE SAME

(71) Applicant: Precigen, Inc., Germantown, MD (US)

(72) Inventors: Douglas E. Brough, Germantown, MD (US); Cheryl G. Bolinger, Germantown, MD (US); Ramya Yarlagadda, Germantown, MD (US); Vinodhbabu Kurella, Germantown, MD (US); Prabakaran Ponraj, Germantown, MD (US); Simon Metenou, Germantown, MD (US); Kuan-Fu Ding, Germantown, MD (US)

(73) Assignee: Precigen, Inc., Germantown, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/074,302

(22) Filed: Dec. 2, 2022

(65) Prior Publication Data

US 2023/0279057 A1    Sep. 7, 2023

Related U.S. Application Data

(63) Continuation of application No. 16/978,570, filed as application No. PCT/US2019/020930 on Mar. 6, 2019, now Pat. No. 11,608,362.

(60) Provisional application No. 62/639,354, filed on Mar. 6, 2018.

(51) Int. Cl.
| | | |
|---|---|---|
| A61K 39/29 | (2006.01) | |
| A61K 39/12 | (2006.01) | |
| A61K 48/00 | (2006.01) | |
| C07K 14/005 | (2006.01) | |
| C07K 14/02 | (2006.01) | |
| C12N 7/00 | (2006.01) | |
| C12N 15/86 | (2006.01) | |
| C12N 15/861 | (2006.01) | |

(52) U.S. Cl.
CPC ............ *C07K 14/005* (2013.01); *A61K 39/12* (2013.01); *A61K 39/292* (2013.01); *A61K 48/0066* (2013.01); *C07K 14/02* (2013.01); *C12N 7/00* (2013.01); *C12N 15/861* (2013.01); *C07K 2319/33* (2013.01); *C12N 2710/20022* (2013.01); *C12N 2710/20034* (2013.01)

(58) Field of Classification Search
None
See application file for complete search history.

(56) References Cited

U.S. PATENT DOCUMENTS

| | | |
|---|---|---|
| 4,985,461 A | 1/1991 | Hsu et al. |
| 5,117,057 A | 5/1992 | Hsu et al. |
| 5,122,464 A | 6/1992 | Wilson et al. |
| 5,225,443 A | 7/1993 | Murphy et al. |
| 5,283,173 A | 2/1994 | Fields et al. |
| 5,350,674 A | 9/1994 | Boenisch et al. |
| 5,378,726 A | 1/1995 | Yanagi et al. |
| 5,530,028 A | 6/1996 | Lidert et al. |
| 5,585,362 A | 12/1996 | Wilson et al. |
| 5,770,359 A | 6/1998 | Wilson et al. |
| 5,837,511 A | 11/1998 | Falck-Pedersen et al. |
| 5,851,806 A | 12/1998 | Kovesdi et al. |
| 5,880,333 A | 3/1999 | Goff et al. |
| 5,885,827 A | 3/1999 | Wabl et al. |
| 5,994,106 A | 11/1999 | Kovesdi et al. |
| 5,994,128 A | 11/1999 | Fallaux et al. |
| 5,998,205 A | 12/1999 | Hallenbeck et al. |
| 6,013,836 A | 1/2000 | Hsu et al. |
| 6,033,908 A | 3/2000 | Bout et al. |
| 6,127,175 A | 10/2000 | Vigne et al. |
| 6,225,289 B1 | 5/2001 | Kovesdi et al. |
| 6,265,173 B1 | 7/2001 | Evans et al. |
| 6,482,616 B1 | 11/2002 | Kovesdi et al. |
| 6,489,458 B2 | 12/2002 | Hackett et al. |
| 6,514,943 B2 | 2/2003 | Kovesdi et al. |
| 6,613,752 B2 | 9/2003 | Kay et al. |
| 6,677,156 B2 | 1/2004 | Brough et al. |
| 6,682,929 B2 | 1/2004 | Brough et al. |
| 7,091,038 B2 | 8/2006 | Palli et al. |
| 7,148,203 B2 | 12/2006 | Hackett et al. |
| 7,195,896 B2 | 3/2007 | Kovesdi et al. |
| 7,531,326 B2 | 5/2009 | Kapitskaya et al. |
| 7,563,879 B2 | 7/2009 | Palli |
| 7,601,508 B2 | 10/2009 | Palli et al. |

(Continued)

FOREIGN PATENT DOCUMENTS

| | | |
|---|---|---|
| EP | 0234994 B1 | 9/1991 |
| EP | 0461809 B1 | 12/1994 |

(Continued)

OTHER PUBLICATIONS

Karzenowski et al. Inducible control of transgene expression with ecdysone receptor: gene switches with high sensitivity, robust expression, and reduced size. BioTechniques (2005) 39(2): 191-200.*

(Continued)

*Primary Examiner* — Nianxiang Zou
(74) *Attorney, Agent, or Firm* — Barnes & Thornburg LLP; Gene J. Yao

(57) ABSTRACT

Provided herein are engineered hepatitis B virus (HBV) molecular vaccine constructs. Vaccine constructs can also include ligand-inducible engineered gene switch systems for modulating expression of heterologous genes, such as a cytokines, in host cells.

16 Claims, 26 Drawing Sheets

Specification includes a Sequence Listing.

(56) References Cited

U.S. PATENT DOCUMENTS

| | | | |
|---|---|---|---|
| 7,776,587 B2 | 8/2010 | Palli et al. |
| 7,807,417 B2 | 10/2010 | Palli et al. |
| 7,829,676 B2 | 11/2010 | Zhang et al. |
| 7,919,269 B2 | 4/2011 | Zhang et al. |
| 7,935,510 B2 | 5/2011 | Palli et al. |
| 7,985,739 B2 | 7/2011 | Kay et al. |
| 8,021,878 B2 | 9/2011 | Palli |
| 8,030,067 B2 | 10/2011 | Zhang et al. |
| 8,076,454 B2 | 12/2011 | Palli et al. |
| 8,076,517 B2 | 12/2011 | Hormann et al. |
| 8,105,825 B2 | 1/2012 | Dhadialla et al. |
| 8,168,426 B2 | 5/2012 | Dhadialla et al. |
| 8,202,718 B2 | 6/2012 | Palli et al. |
| 8,227,432 B2 | 7/2012 | Hackett et al. |
| 8,236,556 B2 | 8/2012 | Kapitskaya et al. |
| 8,293,233 B2 | 10/2012 | Tanha |
| 8,497,093 B2 | 7/2013 | Palli |
| 8,598,409 B2 | 12/2013 | Kapitskaya et al. |
| 8,603,950 B2 | 12/2013 | Bowers et al. |
| 8,715,959 B2 | 5/2014 | Palli et al. |
| 9,228,180 B2 | 1/2016 | Izsvak et al. |
| 9,249,207 B2 | 2/2016 | Palli et al. |
| 9,402,919 B2 | 8/2016 | Roeth et al. |
| 9,492,482 B2 | 11/2016 | Beech et al. |
| 9,493,540 B2 | 11/2016 | Palli et al. |
| 2004/0049037 A1 | 3/2004 | Tice et al. |
| 2004/0171651 A1 | 9/2004 | Hormann et al. |
| 2005/0209283 A1 | 9/2005 | Hormann et al. |
| 2005/0287161 A1 | 12/2005 | Dubin et al. |
| 2006/0020146 A1 | 1/2006 | Hormann et al. |
| 2006/0100416 A1 | 5/2006 | Palli et al. |
| 2007/0203326 A1 | 8/2007 | Dedhar et al. |
| 2008/0233650 A1 | 9/2008 | Gall et al. |
| 2009/0123441 A1 | 5/2009 | Braughler et al. |
| 2009/0136465 A1 | 5/2009 | Merenick et al. |
| 2010/0175141 A1 | 7/2010 | Collins et al. |
| 2011/0117072 A1 | 5/2011 | Izsvak et al. |
| 2011/0212528 A1 | 9/2011 | Palli et al. |
| 2011/0268766 A1 | 11/2011 | Beech et al. |
| 2012/0167239 A1 | 6/2012 | Palli et al. |
| 2013/0195800 A1 | 8/2013 | Roeth et al. |
| 2013/0243805 A1* | 9/2013 | Apelian ............... C07K 14/005 435/254.2 |
| 2016/0208285 A1 | 7/2016 | Roeth et al. |
| 2018/0002719 A1 | 1/2018 | Roeth et al. |
| 2021/0024586 A1 | 1/2021 | Brough et al. |

FOREIGN PATENT DOCUMENTS

| | | |
|---|---|---|
| JP | 2008536490 A | 9/2008 |
| JP | 2013501038 A | 1/2013 |
| JP | 2013527753 A | 7/2013 |
| JP | 2014507144 A | 3/2014 |
| JP | 2014527404 A | 10/2014 |
| JP | 2017518051 A | 7/2017 |
| WO | 9208796 A1 | 5/1992 |
| WO | 9428143 A1 | 12/1994 |
| WO | 9428152 A1 | 12/1994 |
| WO | 9502697 A1 | 1/1995 |
| WO | 9516772 A1 | 6/1995 |
| WO | 9534671 A1 | 12/1995 |
| WO | 9622378 A1 | 7/1996 |
| WO | 9700326 A1 | 1/1997 |
| WO | 9712986 A2 | 4/1997 |
| WO | 9721826 A2 | 6/1997 |
| WO | 9738117 A1 | 10/1997 |
| WO | 9902683 A1 | 1/1999 |
| WO | 9958155 A1 | 11/1999 |
| WO | 0000628 B1 | 3/2000 |
| WO | 0034444 A2 | 6/2000 |
| WO | 0170816 A2 | 9/2001 |
| WO | 0198333 A2 | 12/2001 |
| WO | 0229075 A2 | 4/2002 |
| WO | 02066612 A2 | 8/2002 |
| WO | 02066613 A2 | 8/2002 |
| WO | 02066614 A2 | 8/2002 |
| WO | 02066615 A2 | 8/2002 |
| WO | 03020879 A2 | 3/2003 |
| WO | 03022311 A1 | 3/2003 |
| WO | 03027266 A2 | 4/2003 |
| WO | 03027289 A1 | 4/2003 |
| WO | 2005108617 A2 | 11/2005 |
| WO | 2008145745 A1 | 12/2008 |
| WO | 2008153801 A1 | 12/2008 |
| WO | 2009045370 A2 | 4/2009 |
| WO | 2009048560 A1 | 4/2009 |
| WO | 2010042189 A2 | 4/2010 |
| WO | 2011015656 A3 | 2/2011 |
| WO | 2011119773 A1 | 9/2011 |
| WO | 2012109404 A1 | 8/2012 |
| WO | 2012122025 A2 | 9/2012 |
| WO | 2013007772 A1 | 1/2013 |
| WO | 013052799 A2 | 4/2013 |
| WO | 2013052811 A2 | 4/2013 |
| WO | 2013052832 A2 | 4/2013 |
| WO | 2015095249 A1 | 6/2015 |
| WO | 2015187009 A1 | 12/2015 |
| WO | 2016020538 A1 | 2/2016 |
| WO | 2016048903 A1 | 3/2016 |
| WO | 2016145146 A1 | 9/2016 |
| WO | 2017037280 A1 | 3/2017 |
| WO | 2017062953 A1 | 4/2017 |
| WO | 2017070284 A1 | 4/2017 |
| WO | 2017083750 A1 | 5/2017 |
| WO | 2017096432 A1 | 6/2017 |
| WO | 2019173463 A1 | 9/2019 |
| WO | 2019173465 A1 | 9/2019 |

OTHER PUBLICATIONS

Chen et al. Fusion protein linkers: Property, design and functionality. Advanced Drug Delivery Reviews 65 (2013) 1357-1369.*

GenBank: BAB39142.1. HBAustKWp [Hepatitis B virus]. Dated Mar. 23, 2001.*

Limbach et al. New gorilla adenovirus vaccine vectors induce potent immune responses and protection in a mouse malaria model. Malar J (2017) 16:263.*

Altschul, S.F., et al., "Basic Local Alignment Search Tool," Journal of Molecular Biology 215(3):403-410, Elsevier, United Kingdom (Oct. 1990).

Altschul, S.F., et al., "Gapped BLAST and PSI-BLAST: A New Generation of Protein Database Search Programs," Nucleic Acids Research 25(17):3389-3402, Oxford University Press, United Kingdom (Sep. 1997).

Bai, M., et al., "Mutations That Alter an Arg-gly-asp (Rgd) Sequence in the Adenovims Type 2 Penton Base Protein Abolish Its Cell-rounding Activity and Delay Vims Reproduction in Flat Cells," Journal of Virology 67(9):5198-5205, American Society for Microbiology, United States (Sep. 1993).

Biegert, A., and Soding, J., "Sequence Context-specific Profiles for Homology Searching," Proc Natl Acad Sci USA 106(10):3770-3775, National Academy of Sciences, United States (Mar. 2009).

Bird, RE., et al., "Single-chain Antigen-binding Proteins," Science 242(4877):423-426, Association for the Advancement of Science, United States (Oct. 1988).

Boulanger, P., et al., "Characterization of Adenovims Protein Ix," The Journal of General Virology 44(3):783-800, Press for the Society for General Microbiology, United Kingdom (Sep. 1979).

Brash, D .E., et al., "Strontium Phosphate Transfection of Human Cells in Primary Culture: Stable Expression of the Simian Vims 40 Large-T-Antigen Gene in Primary Human Bronchial Epithelial Cells," Molecular and Cellular Biology, 7(5):2031-2034, American Society for Microbiology, United States (May 1987).

Brough, D.E., et al., "Activation of Transgene Expression by Early Region 4 Is Responsible for a High Level of Persistent Transgene Expression From Adenovims Vectors in Vivo," Journal of Virology 71(12):9206-9213, American Society for Microbiology, United States (Dec. 1997).

(56) References Cited

OTHER PUBLICATIONS

Chen, H.H., et al., "Persistence in Muscle of an Adenoviral Vector that Lacks all Viral Genes," Proc Natl Acad Sci USA 94(5): 1645-1650, National Academy of Sciences, United States (Mar. 1997).
Christopherson, K.S., et al., "Ecdysteroid-dependent Regulation of Genes in Mammalian Cells by a *Drosophila ecdysone* Receptor and Chimeric Transactivators," Proc Natl Acad Sci USA 89(14):6314-6318, National Academy of Sciences, United States (1992).
Chroboczek, J., et al., "The Sequence of the Genome of Adenovims Type 5 and Its Comparison With the Genome of Adenovims Type 2," Virology 186(1):280-285, Academic Press, United States (Jan. 1992).
Colbere-Garapin, F., et al., "A New Dominant Hybrid Selective Marker for Higher Eukaryotic Cells," Journal of Molecular Biology 150(1 ): 1-14, Academic Press, United Kingdom (Jul. 1981).
Conese, M., et al., "Gene therapy progress and prospects: episomally maintained self-replicating systems," Gene Therapy 11(24): 1735-41, Nature Publishing Group, United Kingdom (2004).
Corpet. F, "Multiple Sequence Alignment With Hierarchical Clustering," Nucleic Acids Research 16(22): 10881-10890, Oxford University Press, United Kingdom (Nov. 1988).
Crawford-Miksza, L.C., and Schnurr, D.P., "Analysis of 15 Adenovirus Hexon Proteins Reveals the Location and Structure of Seven Hypervariable Regions Containing Serotype-specific Residues," Journal of Virology 70(3): 1836-1844, American Society for Microbiology, United States (Mar. 1996).
Curiel, D.T., et al., "High-efficiency gene transfer mediated by adenovirus coupled to DNA-polylysine complexes," Hum Gene Ther 3(2): 147-54, Mary Ann Liebert Inc., United States (1992).
Devaux, C., et al., "Structure of Adenovirus Fibre. I. Analysis of Crystals of Fibre From Adenovirus Serotypes 2 and 5 by Electron Microscopy and X-ray Crystallography," Journal of Molecular Biology 215(4):567-588, Academic Press, United Kingdom (Oct. 1990).
Field, J., et al., "Properties of the Adenovirus DNA Polymerase," The Journal of Biological Chemistry 259(15):9487-9495, American Society for Biochemistry and Molecular Biology, United States (Aug. 1984).
Funston, G.M., et al., "Expression of Heterologous Genes in Oncolytic Adenoviruses Using Picornaviral 2a Sequences That Trigger Ribosome Skipping," The Journal of General Virology 89(Pt 2):389-396, Cambridge Univ. Press for the Society for General Microbiology, United Kingdom (Feb. 2008).
Gall, J.G.D., et al., "Construction and Characterization of Hexon-chimeric Adenoviruses: Specification of Adenovirus Serotype," Journal of Virology 72(12): 10260-10264, American Society for Microbiology, United States (Sep. 1998).
GenBank, "E3 14.7K [Human adenovirus 5]," Accession No. AP 000224.1, accessed at https://www.ncbi.nlm.nih.gov/protein/AP_000224, accessed on Dec. 10, 2020, 1 page.
GenBank, "E3 12.5K [Human adenovirus 5]," Accession No. AP 000218.1, accessed at https://www.ncbi.nlm.nih.gov/protein/5616055 I/, accessed on Dec. 10, 2020, 1 page.
Ghosh-Choudhury, G., et al., "Protein Ix, A Minor Component of the Human Adenovirus Capsid, Is Essential for the Packaging of Full Length Genomes," The EMBO Journal 6( 6): 173 3-1739, Wiley Blackwell, United Kingdom (Jun. 1987).
Ginsberg, H.S., et al., "A Proposed Terminology for the Adenovirus Antigens and Virion Morphological Subunits," Virology 28(4):782-783, Academic Press, United States (Apr. 1966).
Graham, F.L., et al., "Characteristics of a Human Cell Line Transformed by Dna From Human Adenovirus Type," The Journal of General Virology 36(1):59-74, Microbiology Society, United Kingdom (Jul. 1977).
Green, N.M., et al., "Evidence for a Repeating Cross Sheet Structure in the Adenovirus Fibre," The EMBO Journal 2(8):1357-1365, IRL Press Limited, United Kingdom (Jun. 1983).

Henikoff, S. and Henikoff, J.G., "Amino Acid Substitution Matrices from Protein Blocks," Proc Natl Acad Sci USA 89(22):10915-10919, National Academy of Sciences, United States (Nov. 1992).
Henry, L.J., et al., "Characterization of the Knob Domain of the Adenovirus Type 5 Fiber Protein Expressed in *Escherichia coli*," Journal of Virology 68(8): 5239-5246, American Society for Microbiology, United States (Aug. 1994).
Higgins, D.G and Sharp, P.M, "CLUSTAL: A Package for Performing Multiple Sequence Alignment on a Microcomputer," Gene 73(1):237-244, Elsevier, Netherlands (Dec. 1988).
Higgins, D.G., and Sharp, P.M., "Fast and Sensitive Multiple Sequence Alignments on a Microcomputer," Computer Applications in the Biosciences 5(2):151-153, Oxford University Press, United Kingdom (Apr. 1989).
Holliger, P, and Hudson, P.J., "Engineered Antibody Fragments and the Rise of Single Domains," Nature Biotechnology 23(9): 1126-1136, Nature Publishing Group, United Kingdom (2005).
Horwitz, M.S., "Adenoviridae and their replication" in Fields Virology, 2nd Edition, pp. 1679-1721, Fields B.N., Knipe D.M., et al., eds., Raven Press, Ltd., United States (1990).
Huang, X., et al., "Parallelization of a Local Similarity Algorithm," Computer Applications in the Biosciences 8(2):155-165, Oxford University Press, United Kingdom (Apr. 1992).
Hurton, L.V., et al., "Tethered 11-15 Augments Antitumor Activity and Promotes a Stem-cell Memory Subset in Tumor-specific T Cells," Proc Natl Acad Sci USA 113(48): E7788-E7791, National Academy of Sciences, United States (Nov. 2016).
Huston, J.S., et al., "Protein Engineering of Antibody Binding Sites: Recovery of Specific Activity in an Anti-digoxin Single-chain Fv Analogue Produced in *Escherichia coli*," Proc Natl Acad Sci USA 85(16):5879-5883, National Academy of Sciences, United States (Aug. 1988).
International Search Report and Written Opinion for International Application No. PCT/US2019/020930, ISA/US, Alexandria, VA, mailed on Jul. 22, 2019, 13 pages.
International Search Report and Written Opinion for International Application No. PCT/US2019/020933, ISA/US, Alexandria, VA, mailed on Jul. 23, 2019, 13 pages.
Ivics, Z., et al., "Molecular Reconstruction of Sleeping Beauty, a Tcl-like Transposon From Fish, and Its Transposition in Human Cells," Cell 91(4):501-510, MIT Press, United States (Nov. 1997).
Jin, Z., et al., "The Hyperactive Sleeping Beauty Transposase Sbl00x Improves the Genetic Modification of T Cells to Express a Chimeric Antigen Receptor," Gene Therapy 18(9):849-856, Macmillan Press Ltd, United Kingdom (Sep. 2011).
Johnston, S.A., "Biolistic Transformation: Microbes to Mice," Nature 346(6286):776-777, Nature Publishing Group, United Kingdom (Aug. 1990).
Jornvall, H., et al., "The Adenovims Hexon Protein. The Primary Structure of the Polypeptide and Its Correlation With the Hexon Gene," The Journal of Biological Chemistry 256(12):6181-6186, American Society for Biochemistry and Molecular Biology, United States (Jun. 1981).
Kent, RB., et al., "Ouabain resistance conferred by expression of the cDNA for a murine Na+, K+-ATPase alpha subunit," Science 23 7 ( 4817): 901-903, American Association for the Advancement of Science, United States (Aug. 1987).
Kochanek, S., "High-capacity Adenoviral Vectors for Gene Transfer and Somatic Gene Therapy," Human Gene Therapy 10(15):2451-2459, Mary Ann Liebert Inc., United States (Oct. 1999).
Lowy, I., et al., "Isolation of Transforming DNA: Cloning the Hamster aprt Gene," Cell 22(3):817-823, Cell Press, United States (Dec. 1980).
Lutz, P., et al., "The Product of the Adenovims Intermediate Gene Ix Is a Transcriptional Activator," Journal of Virology 71(7): 5102-5109, American Society For Microbiology, United States (Jul. 1997).
Mates, L., et al., "Molecular Evolution of a Novel Hyperactive Sleeping Beauty Transposase Enables Robust Stable Gene Transfer in Vertebrates," Nature Genetics 41(6):753-761, Nature Publishing Group, United Kingdom (Jun. 2009).

(56) References Cited

OTHER PUBLICATIONS

Mattila, P.S., et al., "The Actions of Cyclosporin A and FK506 Suggest a Novel Step in the Activation of T Lymphocytes," EMBO J 9(13):4425-4433, Wiley Blackwell, United Kingdom (Dec. 1990).
Mitra, R., et al., "Functional Characterization of Piggybat from the Bat Myotis Lucifugus Unveils an Active Mammalian DNA Transposon," Proc Natl Acad Sci USA 110(1):234-239, National Academy of Sciences, United States (Jan. 2013).
Morsy, M.A., et al., "An adenoviral vector deleted for all viral coding sequences results in enhanced safety and extended expression of a leptin transgene," Proc Natl Acad Sci USA 95(14):7866-71, National Academy of Sciences, United States (1998).
Mountford, P.S and Smith, A.G., "Internal Ribosome Entry Sites and Dicistronic Rnas In Mammalian Trans genesis," Trends in Genetics 11 ( 5): 179-184, Elsevier Trends Journals, United Kingdom (May 1995).
Mulligan, RC. and Berg, P., "Selection for Animal Cells that Express the *Escherichia coli* Gene Coding for Xanthine-guanine Phosphoribosyltransferase," Proc Natl Acad Sci USA 78(4):2072-2076, National Academy of Sciences, United States (Apr. 1981).
Mumtaz, S., et al., "Design of Liposomes for Circumventing the Reticuloendothelial Cells," Glycobiology 1(5):505-510, IRL Press at Oxford University Press, United Kingdom (Nov. 1991).
Needleman S.B., et al., "A General Method Applicable to the Search for Similarities in the Amino Acid Sequence of Two Proteins," Journal of Molecular Biology 48(3):443-453, Academic Press Inc., United States (Mar. 1970).
Neumann, R., et al., "Determination of the Nucleotide Sequence for The Penton-Base Gene of Human Adenovirus Type 5," Gene 69(1): 153-157, Elsevier B.V., Netherlands (Sep. 1988).
No, D., et al., "Ecdysone-inducible Gene Expression in Mammalian Cells and Transgenic Mice," Proc Natl Acad Sci USA 93(8):3346-3351, National Academy of Sciences, United States (Apr. 1996).
Novelli, A., and Boulanger, P.A., "Deletion analysis of functional domains in baculovirus-expressed adenovirus type 2 fiber," Virology 185(1):365-76, Elsevier, Netherlands (1991).
Nuclear Receptors Nomenclature Committee, "A Unified Nomenclature System for the Nuclear Receptor Superfamily," Cell 97(2):161-163, Cell Press, United States (Apr. 1999).
O'Hare, K., et al., "Transformation of Mouse Fibroblasts to Methotrexate Resistance by a Recombinant Plasmid Expressing a Prokaryotic Dihydrofolate Reductase," Proc Natl Acad Sci USA 78(3):1527-1531, National Academy of Sciences, United States (Mar. 1981).
Osbourn, J.K., et al., "Directed Selection of Mip-1 Alpha Neutralizing Ccr5 Antibodies from a Phage Display Human Antibody Library," Nature Biotechnology 16(8):778-781, Nature Publishing Group, United Kingdom (Aug. 1998).
Paul, W. E., ed., "Fundamental Immunology," 3rd Edition, pp. 353-363, Raven Press, United States (1993).
Pearson, W.R. and Lipman, D.J., "Improved Tools for Biological Sequence Comparison," Proc Natl Acad Sci USA 85(8):2444-2448, National Academy of Sciences, United States (Apr. 1988).
Pearson, W.R., "Using the FASTA Program to Search Protein and DNA Sequence Databases," Methods in Molecular Biology 24:307-331, Humana Press, United States (Feb. 1994).
Roberts, M.M., et al., "Three-Dimensional Structure of the Adenovirus Major Coat Protein Hexon," Science 23 2( 4 754): 1148-1151, American Association for the Advancement of Science, United States (May 1986).
Rux, J.J., et al., "Structural and Phylogenetic Analysis of Adenovirus Hexons by Use of High-Resolution X-Ray Crystallographic, Molecular Modeling, and Sequence-Based Methods," Journal of Virology 77(17): 9553-9566, American Society for Microbiology, United States (Sep. 2003).
Santerre, R.F., et al., "Expression of Prokaryotic Genes for Hygromycin Band G418 Resistance as Dominant-selection Markers in Mouse L Cells," Gene 30( 1-3): 14 7-156, Elsevier, Netherlands (Oct. 1984).
Schirmbeck, R., et al., "Targeting Murine Immune Responses To Selected T Cell- or Antibody-Defined Determinants of the Hepatitis B Surface Antigen By Plasmid DNA Vaccines Encoding Chimeric Antigen," Journal of Immunology 166(2): 140 5-1413, American Association of Immunologists, United States (Jan. 2001).
Signas, C., et al., "Adenovirus 3 Fiber Polypeptide Gene: Implications for the Structure of the Fiber Protein," Journal of Virology 53(2):672-678, American Society For Microbiology, United States (Feb. 1985).
Smith, T.F., and Waterman, M.S., "Comparison of biosequences," Advances in Applied Mathematics 2(4):482-498, Academic Press Inc., United States (1981).
Soding, J., "Protein Homology Detection by Hmm-hmm Comparison," Bioinformatics 21(7):951-960, Oxford University Press, United Kingdom (Apr. 2005).
Soleimanjahi, H., et al., "Antitumor Response to a Codon-Optimized HPV-16 E7 /HSP70 Fusion Antigen DNA Vaccine," Iranian Journal of Immunology 14(3):180-191, Shiraz University of Medical Sciences, Iran (Sep. 2017).
Stewart, P.L., et al., "Image Reconstruction Reveals the Complex Molecular Organization of Adenovirus," Cell 67(1):145-154, Cell Press, United States (Oct. 1991).
Stewart, P.L., et al., "Difference Imaging of Adenovirus: Bridging the Resolution Gap between X-Ray Crystallography and Electron Microscopy," EMBO Journal 12(7):2589-2599, Wiley Blackwell, United Kingdom (Jul. 1993).
Suhr, S.T., et al., "High Level Transactivation by a Modified Bombyx Ecdysone Receptor in Mammalian Cells Without Exogenous Retinoid X Receptor," Proc Natl Acad Sci USA 95(14):7999-8004, National Academy of Sciences, United States (1998).
Szybalska, E.H. and Szybalski, W., "Genetics of Human Cess Line IV DNA-mediated Heritable Transformation of A Biochemical Trait," Proc Natl Acad Sci USA 48:2026-2034, National Academy of Sciences, United States (Dec. 1962).
Ui-Tei, K., et al., "Sensitive Assay of RNA Interference in *Drosophila* and Chinese Hamster Cultured Cells Using Firefly Luciferase Gene as Target," FEBS Letters 479(3): 79-82, John Wiley & Sons, Inc., United States (Aug. 2000).
Van Oostrum, J., et al., "Molecular Composition of the Adenovirus Type 2 Virion," Journal of Virology 56(2):439-448, American Society for Microbiology, United States (Nov. 1985).
Wieking, B.G., et al., "A non-oncogenic HPV 16 E6/E7 vaccine enhances treatment of HPV expressing tumors," Cancer Gene Therapy 19(10):667-674, Nature Publishing Group, United Kingdom (Oct. 2012).
Wigler, M., et al., "Transfer of Purified Herpes Virus Thymidine Kinase Gene to Cultured Mouse Cells," Cell 11(1):223-232, Cell Press, United States (May 1977).
Wigler, M., et al., "Transformation of Mammalian Cells with an Amplifiable Dominant-Acting Gene," Proc Natl Acad Sci USA 77(6):3567-3570, National Academy of Sciences, United States (Jun. 1980).
Wilson, M.H., et al., "Piggybac Transposon-Mediated Gene Transfer in Human Cells," Molecular Therapy 15(1):139-145, Cell Press, United States (Jan. 2007).
Yan, J., et al., "Induction of antitumor immunity in vivo following delivery of a novel HPV-16 DNA vaccine encoding an E6/E7 fusion antigen," Vaccine 2 7 (3) :4 31-440, Elsevier Science, Netherlands (2009).
Yeh, H.Y., et al., "Human adenovims type 41 contains two fibers," Virus Res 33(2):179-98, Elsevier, Netherlands (Aug. 1994).
Martin, P., et al., "TG1050, an immunotherapeutic to treat chronic hepatitis B, induces robust T cells and exerts an antiviral effect in HBV-persistent mice," Gut 64(12): 1961-1971, Elsevier, Netherlands (published online Nov. 2014, published in print Dec. 2015).
Li, J., et al., "Research progress of therapeutic vaccines for treating chronic hepatitis B," Hum Vaccin Immunother 13(5): 986-997, Taylor & Francis, United States (published online Jan. 2017, published in print May 2017).
Supplementary European Search Report for EP Application No. EP 19 76 4606, Munich, Germany, received Feb. 28, 2022, 12 pages.
Rostami, A., et al., "Design and expression of a chimeric vaccine candidate for avian necrotic enteritis," Protein Engingeering, Design & Selection 30(1):39-45, Oxford University Press, United Kingdom (Jan. 2017).

(56) References Cited

OTHER PUBLICATIONS

Stahl et al. Immunogenicity of peptide fusions to hepatitis B virus core antigen. Proc. Natl Acad Sci. USA 86 (1989), 86: 6283-6287.

* cited by examiner

```
TG1050 (MOD-1755595) HBV D Core   MDIDPYKEFGASVELLSFLPSDFFPSVRDLLDTATALYRDALESPEHCTPHHTALRhvcL
TG1050 GB  Y07587.1               MDIDPYKEFGATVELLSFLPSDFFPSVRDLLDTASALYREALESPEHCSPHHTALRqaiL TG1050 (MOD-1755595) HBV D Core   CWGDLMnLATWVGtNLEDqaSRDLVVSYVNTNMGLKFRQLLWFHISCLTFGRDlVLEYLV
TG1050 GB  Y07587.1               CWGELMTLATWVGgNLEDpiSRDLVVSYVNTNMGLKFRQLLWFHISCLTFGREtVIEYLV TG1050 (MOD-1755595) HBV D Core   SFGVWIRTPPAYRPsNAPILSTLPETTVmplsyqhfrrllllddeagpleeelprladeg
TG1050 GB  Y07587.1               SFGVWIRTPPAYRPpNAPILSTLPETTV--------------------------------

TG1050 (MOD-1755595) HBV D Core   lnrrvaedlnlgnlnvsipwthkvgnftglysstvpvfnphwktpsfpnihlhqdiikkc
TG1050 GB  Y07587.1               ------------------------------------------------------------

TG1050 (MOD-1755595) HBV D Core   eqfvgpltvnekrrlqlimparfypnvtkylpldkgikpyypehlvnhyfqtrhylhtlw
TG1050 GB  Y07587.1               ------------------------------------------------------------

TG1050 (MOD-1755595) HBV D Core   kagilykretthsasfcgspysweqklqhgaesfhqqssgilsrppvgsslqskhrksrl
TG1050 GB  Y07587.1               ------------------------------------------------------------
```

```
(MOD-1755596) HBV_D_SHB(Env)  ▼
HBV DB elements AB048701 HBe    MENITSGFLGPLLVLQAGFFLLTRILTITIPQSLDSWTSLSFLGGTTVCLGQNSQSPTSNH
                                MENITSGFLGPLLVLQAGFFLLTRILTITIPQSLDSWTSLSFLGGTTVCLGQNSQSPTSNH (MOD-1755596) HBV_D_SHB(Env)    SPTSCPPTCVGYRWMCLRRFITFLFILLICLIFLLVLLDYQGM

HEPATITIS B VACCINES AND USES OF THE SAME

REFERENCE TO SEQUENCE LISTING

The instant application contains a Sequence Listing that has been submitted electronically in XML format and is hereby incorporated by reference in its entirety. The XML copy was created on Jun. 14, 2024, is named 18074302SeqList.xml and is 403,442 bytes in size.

FIELD OF THE DISCLOSURE

The present disclosure relates to improved, broad-spectrum HBV molecular vaccines designed via use of advanced principles in bioinformatics and protein engineering.

BACKGROUND OF THE DISCLOSURE

Chronic hepatitis B is a disease involving multiple viral (HepB or HBV) genotypes. HBV genotypes/subgenotypes have been increasingly associated with differences in clinical and virological characteristics, such as severity of liver disease and response to antiviral therapies. Infection with HBV causes hepatitis that can result in cirrhosis, liver failure and hepatocellular carcinoma (HCC). The diagnosis of HBV is based on the serological findings. There is no cure for chronic HBV infection. Currently available treatment options are aimed at slowing the progression of cirrhosis and viral replication, reducing the incidence of HCC and liver failures.

The present disclosure relates to improved, broad-spectrum HBV molecular vaccines designed via use of advanced principles in bioinformatics and protein engineering. These novel HBV vaccines can be used as a therapeutic vaccine against HBV related diseases.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY OF THE DISCLOSURE

Provided herein is a non-naturally occurring polynucleotide encoding a polypeptide comprising at least one or more immune response-inducing hepatitis B virus (HBV) polypeptides.

In some embodiments, said non-naturally occurring polynucleotide encodes a polypeptide comprising said one or more HBV polypeptides. In some embodiments, said one or more HBV polypeptides comprises an HBV Core peptide. In some embodiments, said HBV Core peptide has any one of Core peptide sequences as shown in Table 3. In some embodiments, said one or more HBV peptides comprises an HBV Surface peptide. In some embodiments, said HBV Surface peptide has any one of Surface peptide sequences as shown in Table 3. In some embodiments, said one or more HBV peptides comprises an HBV Pol peptide. In some embodiments, said HBV Pol peptide has any one of Pol peptide sequences as shown in Table 3. In some embodiments, said one or more HBV peptides comprises an HBV HBSP/HBx peptide. In some embodiments, said HBV HBSP/HBx peptide has any one of HBSP/HBx peptide sequences as shown in Table 3. In some embodiments, said one or more HBV peptides comprises a KK linker. In some embodiments, said KK linker connects any one of peptide sequences as shown in Table 3 to any other peptide sequences as shown in Table 3.

Provided herein is a polynucleotide comprising any of the polynucleotides provided herein, further comprising one or more polynucleotides encoding a gene switch system for inducible control of heterologous gene expression, wherein heterologous gene expression is regulated by said gene switch system; and, wherein said heterologous gene comprises any of the polynucleotide described herein. In some embodiments, said gene switch system is an ecdysone receptor-based (EcR-based) gene switch system. In some embodiments, said one or more HBV polypeptides is for use in a vaccine.

Provided herein is a vector comprising any of the polynucleotides provided herein. In some embodiments, said vector is an adenoviral vector. In some embodiments, said adenoviral vector is a *gorilla* adenoviral vector.

Provided herein is a method of regulating the expression of a heterologous gene in a cell, the method comprising: introducing into said cell one or more polynucleotides that comprise (i) an repressible or inducible gene switch, and (ii) a heterologous immune response-inducing gene, wherein expression of said heterologous immune response-inducing gene is regulated by said gene switch, wherein said heterologous immune response-inducing gene encodes at least one of one or more HBV polypeptides; and exposing said cell to a compound in an amount sufficient to repress or induce expression of said heterologous immune response-inducing gene.

In some embodiments, said target cell is a mammalian cell in a method of regulating the expression of a heterologous gene in a cell described herein. In some embodiments, said gene switch comprises a ligand binding domain derived from at least one of an ecdysone receptor (EcR), a ubiquitous receptor, an orphan receptor 1, an NER-1, a steroid hormone nuclear receptor 1, a retinoid X receptor interacting protein-15, a liver X receptor β, a steroid hormone receptor like protein, a liver X receptor, a liver X receptor α, a farnesoid X receptor, a receptor interacting protein 14, and a farnesol receptor.

Provided herein is a polynucleotide encoding any of the presently described polypeptide constructs. Also provided herein is a vector comprising said polynucleotide. In some embodiments, said vector is an adenoviral vector. In some embodiments, said adenoviral vector is a *gorilla* adenoviral vector.

Provided herein is a vector, wherein said vector comprises a polynucleotide that encodes at least one HBV peptide, wherein said vector is an adenoviral vector.

Provided herein is a vector, wherein said vector comprises a polynucleotide that encodes at least one HBV peptide, wherein said vector is an adenoviral vector, wherein said adenoviral vector is a *gorilla* adenoviral vector.

Provided herein is a polypeptide construct, wherein said polypeptide construct comprises an HBV HBx domain and at least one of an HBV Pol domain, an HBV Core domain, an HBV pre-Core domain or an HBV Surface domain. Also provided herein is a polypeptide construct, wherein said polypeptide construct comprises a pre-Core domain and at least one of an HBV Pol domain, an HBV HBx domain or an HBV Surface domain. In some embodiments, said HBV HBx domain has a sequence as shown in SEQ ID NO: 98. In some embodiments, said HBV Pol domain comprises a deletion of at least one amino acid as compared to a wildtype HBV Pol domain. In some embodiments, said deletion comprises a deleted portion of said wildtype HBV Pol domain, wherein said deleted portion comprises at least one of amino acids 538-544 or amino acids 710-742. In some embodiments, said deleted portion comprises both of amino acids 538-544 and amino acids 710-742. In some embodiments, said HBV Pol domain has a sequence as shown in SEQ ID NO: 99. In some embodiments, said HBV Surface domain comprises at least one of a PreS1 domain, a PreS2 domain and an S domain. In some embodiments, said HBV Surface domain comprises an HBV S domain. In some embodiments, said Surface domain has a sequence as shown in SEQ ID NO: 100. In some embodiments, said polypeptide construct further comprises an HBV Core domain. In some embodiments, said polypeptide construct comprises a Core portion, wherein said Core portion comprises said HBV Core domain and said HBV pre-Core domain. In some embodiments, said Core portion has a sequence as shown in SEQ ID NO: 101. In some embodiments, said polypeptide construct comprises each of SHB(Env), HBeAg, HBx, and Pol domains. In some embodiments, said polypeptide construct comprises a structure, from N-terminus to C-terminus, of said SHB(Env), HBeAg, HBx, and Pol domains. In some embodiments, said SHB(Env) domain has a sequence as shown in SEQ ID NO: 102. In some embodiments, said HBeAg domain has a sequence as shown in SEQ ID NO: 103. In some embodiments, said HBx domain has a sequence as shown in SEQ ID NO: 104. In some embodiments, said Pol domain has a sequence as shown in SEQ ID NO: 105. In some embodiments, said polypeptide construct has a sequence as shown in SEQ ID NO: 106.

Provided herein is a polypeptide construct, wherein said polypeptide construct comprises one or more HBV HBx linkers and at least one of a Core domain, a Surface domain and a Pol domain, wherein one of said Core domain, said Surface domain and said Pol domain is connected to another of said Core domain, said Surface domain and said Pol domain by said one or more HBx linkers. In some embodiments, said Surface domain comprises at least one of an HBV PreS1 domain, an HBV PreS2 domain and an HBV S domain. In some embodiments, said one or more HBV HBx linkers comprises multiple HBV HBx linkers. In some embodiments, at least two of said multiple HBV HBx linkers differ in an amino acid sequence. In some embodiments, said HBV HBx linker has a sequence as shown in any one of HBx-1, HBx-2, HBx-3, HBx-4, HBx-5 or HBx-6 of Table 3. In some embodiments, said Core domain is adjacent to said Surface domain. In some embodiments, said Surface domain comprises a PreS1 domain. In some embodiments, said Surface domain is connected to said Core domain by one of said one or more HBx linkers. In some embodiments, said Pol domain is adjacent to a Surface domain. In some embodiments, said Surface domain comprises at least one of a PreS1 domain, a PreS2 domain and an S domain. In some embodiments, said Surface domain comprises said PreS1 domain, and an N-terminal portion of said Pol domain is adjacent to said PreS1 domain. In some embodiments, said N-terminal portion of said Pol domain is connected to said PreS1 domain by one of said one or more HBx linkers. In some embodiments, said Surface domain comprises said PreS2 domain, and an N-terminal portion of said Pol domain is adjacent to said PreS2 domain. In some embodiments, said N-terminal portion of said Pol domain is connected to said PreS2 domain by one of said one or more HBx linkers. In some embodiments, said Surface domain comprises said PreS2 domain, and a C-terminal portion of said Pol domain is adjacent to said PreS2 domain. In some embodiments, said C-terminal portion of said Pol domain is connected to said PreS2 domain by one of said one or more HBx linkers. In some embodiments, said Surface domain comprises said S domain, and a C-terminal portion of said Pol domain is adjacent to said S domain. In some embodiments, said C-terminal portion of said Pol domain is connected to said S domain by one of said one or more HBx linkers. In some embodiments, said polypeptide construct has a sequence as shown in SEQ ID NO: 107.

Provided herein is a polypeptide construct comprising an ankyrin-like repeat domain and one or more HBV peptides. In some embodiments, said ankyrin-like repeat protein is a human ankyrin-like repeat protein. In some embodiments, said one or more HBV peptides has a sequence as shown in any one of the amino acid sequences of Table 3. In some embodiments, said one or more HBV peptides comprises one or more of a Core peptide, a Surface peptide, a Pol peptide and an HBSP/HBx peptide. In some embodiments, said one or more HBV peptides comprises a Core peptide, and said Core peptide has a sequence as shown in any one of the Core amino acid sequences of Table 3. In some embodiments, said one or more HBV peptides comprises a Surface peptide, and said Surface peptide has a sequence as shown in any one of the Surface amino acid sequences of Table 3. In some embodiments, said one or more HBV peptides comprises a Pol peptide, and said Pol peptide has a sequence as shown in any one of the Pol amino acid sequences of Table 3. In some embodiments, said one or more HBV peptides comprises an HBSP/HBx peptide, and said HBSP/HBx peptide has a sequence as shown in any one of the HBSP/HBx amino acid sequences of Table 3. In some embodiments, said polypeptide construct has a sequence as shown in SEQ ID NO: 108.

Provided herein is a polypeptide construct, wherein said polypeptide construct comprises at least two HBV amino acid sequences as shown in Table 3, wherein said at least two HBV amino acid sequences are connected by a peptide linker, wherein said peptide linker is a KK linker. In some embodiments, said comprises at least two HBV amino acid sequences comprise at least one of a Core peptide, a Surface peptide, a Pol peptide and an HBSP/HBx peptide as shown in Table 3. In some embodiments, said at least two HBV amino acid sequences comprise each of the amino acid sequences as shown in Table 3. In some embodiments, said each of the amino acid sequences is connected to another of said each of the amino acid sequences by said KK linker. In some embodiments, said polypeptide construct has a sequence as shown in SEQ ID NO: 109. In some embodiments, any of the polypeptide constructs described herein is for use in a vaccine. Also provided herein is a polynucleotide encoding any of the polypeptide constructs presently described. Also provided herein is a vector comprising said polynucleotide. In some embodiments, said vector is an adenoviral vector. In some embodiments, said adenoviral vector is a *gorilla* adenoviral vector.

BRIEF DESCRIPTION OF THE DRAWINGS

The features of the present disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 15A shows core sequence comparisons of HBV design 1 and TG1050 control (SEQ ID NOS: 143 and 144). FIG. 15C shows sequence comparisons of HBV design 1 and TG1050 control (SEQ ID NOs: 147 and 148).

DETAILED DESCRIPTION OF THE DISCLOSURE

Figure 1:
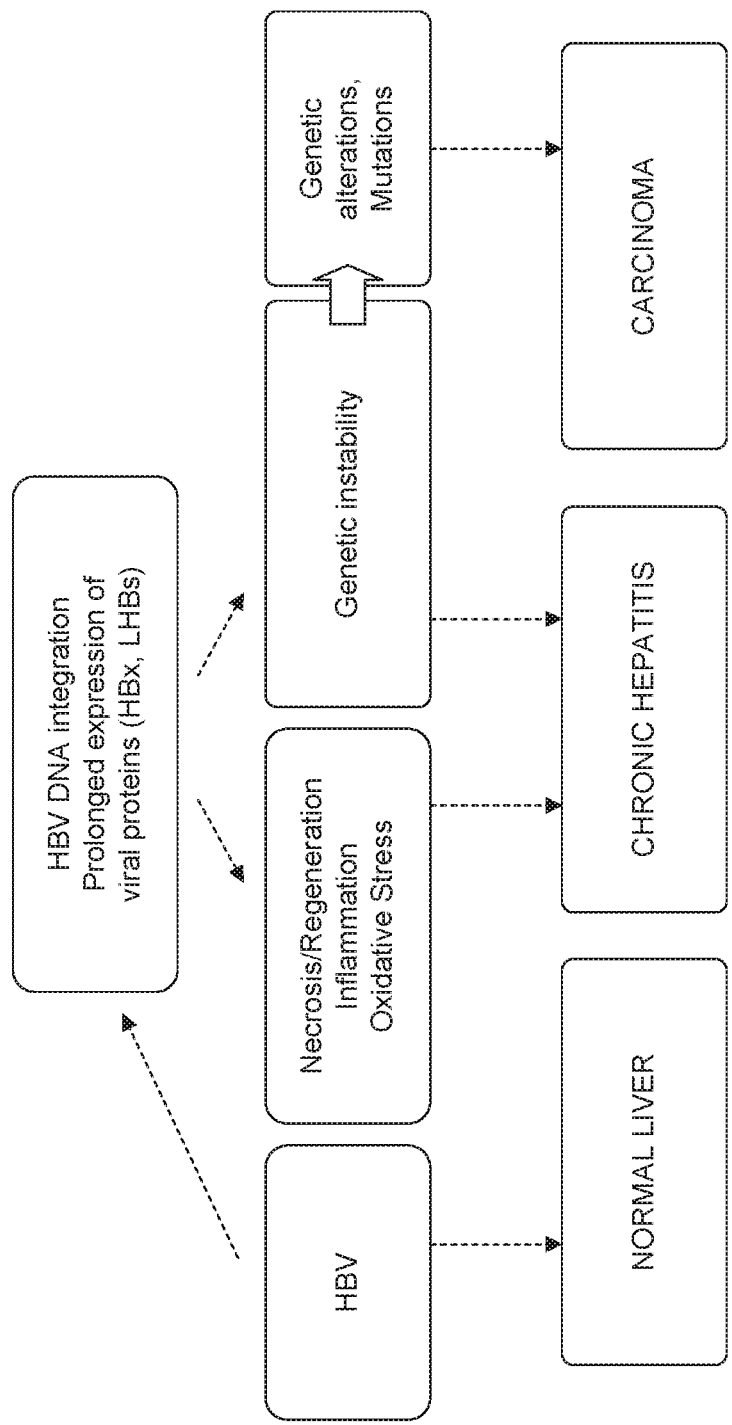
FIG. 1 is a schematic of chronic HBV infection.

The following description and examples illustrate embodiments of the present disclosure in detail.

It is to be understood that the present disclosure is not limited to the particular embodiments described herein and as such can vary. Those of skill in the art will recognize that there are variations and modifications of the present disclosure, which are encompassed within its scope.

All terms are intended to be understood as they would be understood by a person skilled in the art. Unless defined otherwise, all technical and scientific terms used herein have the same meaning as commonly understood by one of ordinary skill in the art to which the disclosure pertains.

The section headings used herein are for organizational purposes only and are not to be construed as limiting the subject matter described.

Although various features of the disclosure can be described in the context of a single embodiment, the features can also be provided separately or in any suitable combination. Conversely, although the present disclosure can be described herein in the context of separate embodiments for clarity, the present disclosure can also be implemented in a single embodiment.

The following definitions supplement those in the art and are directed to the current application and are not to be imputed to any related or unrelated case, e.g., to any commonly owned patent or application. Although any methods and materials similar or equivalent to those described herein can be used in the practice for testing of the present disclosure, the preferred materials and methods are described herein. Accordingly, the terminology used herein is for the purpose of describing particular embodiments only, and is not intended to be limiting.

Definitions

In this application, the use of the singular includes the plural unless specifically stated otherwise. It must be noted that, as used in the specification, the singular forms "a," "an" and "the" include plural referents unless the context clearly dictates otherwise.

In this application, the use of "or" means "and/or" unless stated otherwise. The terms "and/or" and "any combination thereof" and their grammatical equivalents as used herein, can be used interchangeably. These terms can convey that any combination is specifically contemplated. Solely for illustrative purposes, the following phrases "A, B, and/or C"

or "A, B, C, or any combination thereof" can mean "A individually; B individually; C individually; A and B; B and C; A and C; and A, B, and C." The term "or" can be used conjunctively or disjunctively, unless the context specifically refers to a disjunctive use.

Furthermore, use of the term "including" as well as other forms, such as "include," "includes," and "included," is not limiting.

Reference in the specification to "some embodiments," "an embodiment," "one embodiment" or "other embodiments" means that a particular feature, structure, or characteristic described in connection with the embodiments is included in at least some embodiments, but not necessarily all embodiments, of the present disclosures.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the disclosure, and vice versa. Furthermore, compositions of the present disclosure can be used to achieve methods of the present disclosure.

The term "about" in relation to a reference numerical value and its grammatical equivalents as used herein can include the numerical value itself and a range of values plus or minus 10% from that numerical value.

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, up to 10%, up to 5%, or up to 1% of a given value. In another example, the amount "about 10" includes 10 and any amounts from 9 to 11. In yet another example, the term "about" in relation to a reference numerical value can also include a range of values plus or minus 10%, 9%, 8%, 7%, 6%, 5%, 4%, 3%, 2%, or 1% from that value. Alternatively, particularly with respect to biological systems or processes, the term "about" can mean within an order of magnitude, preferably within 5-fold, and more preferably within 2-fold, of a value. Where particular values are described in the application and claims, unless otherwise stated the term "about" meaning within an acceptable error range for the particular value should be assumed.

The term "isolated" and its grammatical equivalents as used herein refer to the removal of a nucleic acid from its natural environment. The term "purified" and its grammatical equivalents as used herein refer to a molecule or composition, whether removed from nature (including genomic DNA and mRNA) or synthesized (including cDNA) and/or amplified under laboratory conditions, that has been increased in purity, wherein "purity" is a relative term, not "absolute purity." It is to be understood, however, that nucleic acids and proteins can be formulated with diluents or adjuvants and still for practical purposes be isolated. For example, nucleic acids typically are mixed with an acceptable carrier or diluent when used for introduction into cells. The term "substantially purified" and its grammatical equivalents as used herein refer to a nucleic acid sequence, polypeptide, protein or other compound which is essentially free, i.e., is more than about 50% free of, more than about 70% free of, more than about 90% free of, the polynucleotides, proteins, polypeptides and other molecules that the nucleic acid, polypeptide, protein or other compound is naturally associated with.

"Polynucleotide", "oligonucleotide", "polynucleotide construct", "gene", "gene construct", "heterologous gene" and their grammatical equivalents as used herein refer to a polymeric form of nucleotides or nucleic acids of any length, either ribonucleotides or deoxyribonucleotides. This term refers only to the primary structure of the molecule. Thus, this term includes double and single stranded DNA, triplex DNA, as well as double and single stranded RNA. It also includes modified, for example, by methylation and/or by capping, and unmodified forms of the polynucleotide. The term is also meant to include molecules that include non-naturally occurring or synthetic nucleotides as well as nucleotide analogs. The nucleic acid sequences and vectors disclosed or contemplated herein can be introduced into a cell by, for example, transfection, transformation, or transduction.

"Transfection," "transformation," or "transduction" as used herein refer to the introduction of one or more exogenous polynucleotides into a host cell by using physical or chemical methods. Many transfection techniques are known in the art and include, for example, calcium phosphate DNA co-precipitation (see, e.g., Murray E. J. (ed.), Methods in Molecular Biology, Vol. 7, Gene Transfer and Expression Protocols, Humana Press (1991)); DEAE-dextran; electroporation; cationic liposome-mediated transfection; tungsten particle-facilitated microparticle bombardment (Johnston, *Nature*, 346:776-777 (1990)); and strontium phosphate DNA co-precipitation (Brash et al., *Mol. Cell Biol.*, 7:2031-2034 (1987)). Phage or viral vectors can be introduced into host cells, after growth of infectious particles in suitable packaging cells, many of which are commercially available.

"Polypeptide", "peptide" "polypeptide construct" and "peptide construct" and their grammatical equivalents as used herein refer to a polymer of amino acid residues. A "mature protein" is a protein which is full-length and which, optionally, includes glycosylation or other modifications typical for the protein in a given cellular environment. Polypeptides and proteins disclosed herein (including functional portions and functional variants thereof) can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine. The present disclosure further contemplates that expression of polypeptides described herein in an engineered cell can be associated with post-translational modifications of one or more amino acids of the polypeptide constructs. Non-limiting examples of post-translational modifications include phosphorylation, acylation including acetylation and formylation, glycosylation (including N-linked and O-linked), amidation, hydroxylation, alkylation including methylation and ethylation, ubiquitylation, addition of pyrrolidone carboxylic acid, formation of disulfide bridges, sulfation, myristoylation, palmitoylation, isoprenylation, farnesylation, geranylation, glypiation, lipoylation and iodination.

Nucleic acids and/or nucleic acid sequences are "homologous" when they are derived, naturally or artificially, from a common ancestral nucleic acid or nucleic acid sequence. Proteins and/or protein sequences are "homologous" when their encoding DNAs are derived, naturally or artificially, from a common ancestral nucleic acid or nucleic acid sequence. The homologous molecules can be termed homologs. For example, any naturally occurring proteins, as described herein, can be modified by any available mutagenesis method. When expressed, this mutagenized nucleic acid encodes a polypeptide that is homologous to the protein encoded by the original nucleic acid. Homology is generally inferred from sequence identity between two or more nucleic acids or proteins (or sequences thereof). The precise percentage of identity between sequences that is useful in establishing homology varies with the nucleic acid and protein at issue, but as little as 25% sequence identity is routinely used to establish homology. Higher levels of sequence identity, e.g., 30%, 40%, 50%, 60%, 70%, 80%, 90%, 95% or 99% or more can also be used to establish homology. Methods for determining sequence identity percentages (e.g., BLASTP and BLASTN using default parameters) are described herein and are generally available.

The term "identical" and its grammatical equivalents as used herein or "sequence identity" in the context of two nucleic acid sequences or amino acid sequences of polypeptides refers to the residues in the two sequences which are the same when aligned for maximum correspondence over a specified comparison window. A "comparison window", as used herein, refers to a segment of at least about 20 contiguous positions, usually about 50 to about 200, more usually about 100 to about 150 in which a sequence can be compared to a reference sequence of the same number of contiguous positions after the two sequences are aligned optimally. Methods of alignment of sequences for comparison are well-known in the art. Optimal alignment of sequences for comparison can be conducted by the local homology algorithm of Smith and Waterman, *Adv. Appl. Math.*, 2:482 (1981); by the alignment algorithm of Needleman and Wunsch, *J. Mol. Biol.*, 48:443 (1970); by the search for similarity method of Pearson and Lipman, *Proc. Nat. Acad. Sci U.S.A.*, 85:2444 (1988); by computerized implementations of these algorithms (including, but not limited to CLUSTAL in the PC/Gene program by Intelligentics, Mountain View Calif., GAP, BESTFIT, BLAST, FASTA, and TFASTA in the Wisconsin Genetics Software Package, Genetics Computer Group (GCG), 575 Science Dr., Madison, Wis., U.S.A.); the CLUSTAL program is well described by Higgins and Sharp, *Gene*, 73:237-244 (1988) and Higgins and Sharp, *CABIOS*, 5:151-153 (1989); Corpet et al., *Nucleic Acids Res.*, 16:10881-10890 (1988); Huang et al., *Computer Applications in the Biosciences*, 8:155-165 (1992); and Pearson et al., *Methods in Molecular Biology*, 24:307-331 (1994). Alignment is also often performed by inspection and manual alignment. In one class of embodiments, the polypeptides herein are at least 80%, 85%, 90%, 98% 99% or 100% identical to a reference polypeptide, or a fragment thereof, e.g., as measured by BLASTP (or CLUSTAL, or any other available alignment software) using default parameters. Similarly, nucleic acids can also be described with reference to a starting nucleic acid, e.g., they can be 50%, 60%, 70%, 75%, 80%, 85%, 90%, 98%, 99% or 100% identical to a reference nucleic acid or a fragment thereof, e.g., as measured by BLASTN (or CLUSTAL, or any other available alignment software) using default parameters. When one molecule is said to have certain percentage of sequence identity with a larger molecule, it means that when the two molecules are optimally aligned, said percentage of residues in the smaller molecule finds a match residue in the larger molecule in accordance with the order by which the two molecules are optimally aligned.

The term "substantially identical" and its grammatical equivalents as applied to nucleic acid or amino acid sequences mean that a nucleic acid or amino acid sequence comprises a sequence that has at least 90% sequence identity or more, at least 95%, at least 98% and at least 99%, compared to a reference sequence using the programs described above, e.g., BLAST, using standard parameters. For example, the BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff, Proc. Natl. Acad. Sci. USA 89:10915 (1992)). Percentage of sequence identity is determined by comparing two optimally aligned sequences over a comparison window, wherein the portion of the polynucleotide sequence in the comparison window can comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. In embodiments, the substantial identity exists over a region of the sequences that is at least about 50 residues in length, over a region of at least about 100 residues, and in embodiments, the sequences are substantially identical over at least about 150 residues. In embodiments, the sequences are substantially identical over the entire length of the coding regions.

An "expression vector" or "vector" is any genetic element, e.g., a plasmid, chromosome, virus, transposon, behaving either as an autonomous unit of polynucleotide replication within a cell. (i.e. capable of replication under its own control) or being rendered capable of replication by insertion into a host cell chromosome, having attached to it another polynucleotide segment, so as to bring about the replication and/or expression of the attached segment. Suitable vectors include, but are not limited to, plasmids, transposons, bacteriophages and cosmids. Vectors can contain polynucleotide sequences which are necessary to effect ligation or insertion of the vector into a desired host cell and to effect the expression of the attached segment. Such sequences differ depending on the host organism; they include promoter sequences to effect transcription, enhancer sequences to increase transcription, ribosomal binding site sequences and transcription and translation termination sequences. Alternatively, expression vectors can be capable of directly expressing nucleic acid sequence products encoded therein without ligation or integration of the vector into host cell DNA sequences. In some embodiments, the vector is an "episomal expression vector" or "episome," which is able to replicate in a host cell, and persists as an extrachromosomal segment of DNA within the host cell in the presence of appropriate selective pressure (see, e.g., Conese et al., *Gene Therapy*, 11:1735-1742 (2004)). Representative commercially available episomal expression vectors include, but are not limited to, episomal plasmids that utilize Epstein Barr Nuclear Antigen 1 (EBNA1) and the Epstein Barr Virus (EBV) origin of replication (oriP). The vectors pREP4, pCEP4, pREP7, and pcDNA3.1 from Invitrogen (Carlsbad, Calif.) and pBK-CMV from Stratagene (La Jolla, Calif.) represent non-limiting examples of an episomal vector that uses T-antigen and the SV40 origin of replication in lieu of EBNA1 and oriP. Vector also can comprise a selectable marker gene.

The term "adenovirus," as used herein, refers to an adenovirus that retains the ability to participate in the adenovirus life cycle and has not been physically inactivated by, for example, disruption (e.g., sonication), denaturing (e.g., using heat or solvents), or cross-linkage (e.g., via formalin cross-linking). The "adenovirus life cycle" includes (1) virus binding and entry into cells, (2) transcription of the adenoviral genome and translation of adenovirus proteins, (3) replication of the adenoviral genome, and (4) viral particle assembly (see, e.g., Fields Virology, 5$^{th}$ ed., Knipe et al. (eds.), Lippincott Williams & Wilkins, Philadelphia, PA (2006)). The term "adenoviral vector," as used herein, refers to an adenovirus in which the adenoviral genome has been manipulated to accommodate a nucleic acid sequence that is non-native with respect to the adenoviral genome. Typically, an adenoviral vector is generated by introducing one or more mutations (e.g., a deletion, insertion, or substitution) into the adenoviral genome of the adenovirus so as to accommodate the insertion of a non-native nucleic acid sequence, for example, for gene transfer, into the adenovirus.

The term "selectable marker gene" as used herein refers to a nucleic acid sequence that allows cells expressing the nucleic acid sequence to be specifically selected for or against, in the presence of a corresponding selective agent. Suitable selectable marker genes are known in the art and described in, e.g., International Patent Application Publications WO 1992/08796 and WO 1994/28143; Wigler et al., *Proc. Natl. Acad. Sci. USA*, 77: 3567 (1980); O'Hare et al., *Proc. Natl. Acad. Sci. USA*, 78: 1527 (1981); Mulligan & Berg, *Proc. Natl. Acad. Sci. USA*, 78: 2072 (1981); Colberre-Garapin et al., *J. Mol. Biol.*, 150:1 (1981); Santerre et al., *Gene*, 30: 147 (1984); Kent et al., *Science*, 237: 901-903 (1987); Wigler et al., *Cell*, 11: 223 (1977); Szybalska & Szybalski, *Proc. Natl. Acad. Sci. USA*, 48: 2026 (1962); Lowy et al., *Cell*, 22: 817 (1980); and U.S. Pat. Nos. 5,122,464 and 5,770,359.

The term "coding sequence" as used herein refers to a segment of a polynucleotide that codes for protein. The region or sequence is bounded nearer the 5' end by a start codon and nearer the 3' end with a stop codon. Coding sequences can also be referred to as open reading frames.

The term "operably linked" as used herein refers to refers to the physical and/or functional linkage of a DNA segment to another DNA segment in such a way as to allow the segments to function in their intended manners. A DNA sequence encoding a gene product is operably linked to a regulatory sequence when it is linked to the regulatory sequence, such as, for example, promoters, enhancers and/or silencers, in a manner which allows modulation of transcription of the DNA sequence, directly or indirectly. For example, a DNA sequence is operably linked to a promoter when it is ligated to the promoter downstream with respect to the transcription initiation site of the promoter, in the correct reading frame with respect to the transcription initiation site and allows transcription elongation to proceed through the DNA sequence. An enhancer or silencer is operably linked to a DNA sequence coding for a gene product when it is ligated to the DNA sequence in such a manner as to increase or decrease, respectively, the transcription of the DNA sequence Enhancers and silencers can be located upstream, downstream or embedded within the coding regions of the DNA sequence. A DNA for a signal sequence is operably linked to DNA coding for a polypeptide if the signal sequence is expressed as a pre-protein that participates in the secretion of the polypeptide. Linkage of DNA sequences to regulatory sequences is typically accomplished by ligation at suitable restriction sites or via adapters or linkers inserted in the sequence using restriction endonucleases known to one of skill in the art.

The terms "induce", "induction" and its grammatical equivalents as used herein refer to an increase in nucleic acid sequence transcription, promoter activity and/or expression brought about by a transcriptional regulator, relative to some basal level of transcription.

The term "transcriptional regulator" refers to a biochemical element that acts to prevent or inhibit the transcription of a promoter-driven DNA sequence under certain environmental conditions (e.g., a repressor or nuclear inhibitory protein), or to permit or stimulate the transcription of the promoter-driven DNA sequence under certain environmental conditions (e.g., an inducer or an enhancer).

The term "enhancer" as used herein, refers to a DNA sequence that increases transcription of, for example, a nucleic acid sequence to which it is operably linked. Enhancers can be located many kilobases away from the coding region of the nucleic acid sequence and can mediate the binding of regulatory factors, patterns of DNA methylation, or changes in DNA structure. A large number of enhancers from a variety of different sources are well known in the art and are available as or within cloned polynucleotides (from, e.g., depositories such as the ATCC as well as other commercial or individual sources). A number of polynucleotides comprising promoters (such as the commonly-used CMV promoter) also comprise enhancer sequences. Enhancers can be located upstream, within, or downstream of coding sequences. The term "Ig enhancers" refers to enhancer elements derived from enhancer regions mapped within the immunoglobulin (Ig) locus (such enhancers include for example, the heavy chain (mu) 5' enhancers, light chain (kappa) 5' enhancers, kappa and mu intronic enhancers, and 3' enhancers (see generally Paul W. E. (ed), Fundamental Immunology, 3rd Edition, Raven Press, New York (1993), pages 353-363; and U.S. Pat. No. 5,885,827).

The term "promoter" refers to a region of a polynucleotide that initiates transcription of a coding sequence. Promoters are located near the transcription start sites of genes, on the same strand and upstream on the DNA (towards the 5' region of the sense strand). Some promoters are constitutive as they are active in all circumstances in the cell, while others are regulated becoming active in response to specific stimuli, e.g., an inducible promoter. The term "promoter activity" and its grammatical equivalents as used herein refer to the extent of expression of nucleotide sequence that is operably linked to the promoter whose activity is being measured. Promoter activity can be measured directly by determining the amount of RNA transcript produced, for example by Northern blot analysis or indirectly by determining the amount of product coded for by the linked nucleic acid sequence, such as a reporter nucleic acid sequence linked to the promoter.

"Inducible promoter" as used herein refers to a promoter which is induced into activity by the presence or absence of transcriptional regulators, e.g., biotic or abiotic factors. Inducible promoters are useful because the expression of genes operably linked to them can be turned on or off at certain stages of development of an organism or in a particular tissue. Non-limiting examples of inducible promoters include alcohol-regulated promoters, tetracycline-regulated promoters, steroid-regulated promoters, metal-regulated promoters, pathogenesis-regulated promoters, temperature-regulated promoters and light-regulated promoters. The inducible promoter can be part of a gene switch or genetic switch. The inducible promoter can be a gene switch ligand inducible promoter. In some cases, an inducible promoter can be a small molecule ligand-inducible two polypeptide ecdysone receptor-based gene switch. In some cases, a gene switch can be selected from ecdysone-based receptor components as described in, but without limitation to, any of the systems described in: International Patent Applications WO 2001/070816; WO 2002/029075; WO 2002/066613; WO 2002/066614; WO 2002/066612; WO 2002/066615; WO 2003/027266; WO 2003/027289; WO 2005/108617; WO 2009/045370; WO 2009/048560; WO 2010/042189; WO 2010/042189; WO 2011/119773; and WO 2012/122025; and U.S. Pat. Nos. 7,091,038; 7,776,587; 7,807,417; 8,202,718; 8,105,825; 8,168,426; 7,531,326; 8,236,556; 8,598,409; 8,715,959; 7,601,508; 7,829,676; 7,919,269; 8,030,067; 7,563,879; 8,021,878; 8,497,093; 7,935,510; 8,076,454; 9,402,919; 9,493,540; 9,249,207; and 9,492,482, each of which is incorporated by reference in its entirety).

The term "gene switch" or "genetic switch" refers to the combination of a response element associated with a promoter, and for instance, an EcR based system, which, in the presence of one or more ligands, modulates the expression of a gene into which the response element and promoter are incorporated. Tightly regulated inducible gene expression systems or gene switches are useful for various applications such as gene therapy, large scale production of proteins in cells, cell based high throughput screening assays, functional genomics and regulation of traits in transgenic plants and animals. Such inducible gene expression systems can include ligand inducible heterologous gene expression systems.

"Sleeping Beauty (SB) Transposon System" refers a synthetic DNA transposon system for to introducing DNA sequences into the chromosomes of vertebrates. Some exemplary embodiments of the system are described, for example, in U.S. Pat. Nos. 6,489,458, 8,227,432, 9,228,180 and WO/2016/145146. The Sleeping Beauty transposon system is composed of a Sleeping Beauty (SB) transposase and a SB transposon. In embodiments, the Sleeping Beauty transposon system can include the SB11 transposon system, the SB100X transposon system, or the SB110 transposon system.

"Transposon" or "transposable element" (TE) is a vector DNA sequence that can change its position within the genome, sometimes creating or reversing mutations and altering the cell's genome size. Transposition often results in duplication of the TE. Class I TEs are copied in two stages: first they are transcribed from DNA to RNA, and the RNA produced is then reverse transcribed to DNA. This copied DNA is then inserted at a new position into the genome. The reverse transcription step is catalyzed by a reverse transcriptase, which can be encoded by the TE itself. The characteristics of retrotransposons are similar to retroviruses, such as HIV. The cut-and-paste transposition mechanism of class II TEs does not involve an RNA intermediate. The transpositions are catalyzed by several transposase enzymes. Some transposases non-specifically bind to any target site in DNA, whereas others bind to specific DNA sequence targets. The transposase makes a staggered cut at the target site resulting in single-strand 5' or 3' DNA overhangs (sticky ends). This step cuts out the DNA transposon, which is then ligated into a new target site; this process involves activity of a DNA polymerase that fills in gaps and of a DNA ligase that closes the sugar-phosphate backbone. This results in duplication of the target site. The insertion sites of DNA transposons can be identified by short direct repeats which can be created by the staggered cut in the target DNA and filling in by DNA polymerase, followed by a series of inverted repeats important for the TE excision by transposase. Cut-and-paste TEs can be duplicated if their transposition takes place during S phase of the cell cycle when a donor site has already been replicated, but a target site has not yet been replicated. Transposition can be classified as either autonomous or non-autonomous in both Class I and Class II TEs. Autonomous TEs can move by themselves while non-autonomous TEs require the presence of another TE to move. This is often because non-autonomous TEs lack transposase (for class II) or reverse transcriptase (for class I).

"Transposase" refers an enzyme that binds to the end of a transposon and catalyzes the movement of the transposon to another part of the genome by a cut and paste mechanism or a replicative transposition mechanism.

"T cell" or "T lymphocyte" as used herein is a type of lymphocyte that plays a central role in cell-mediated immunity. They can be distinguished from other lymphocytes, such as B cells and natural killer cells (NK cells), by the presence of a T-cell receptor (TCR) on the cell surface.

"T helper cells" ($T_H$ cells) assist other white blood cells in immunologic processes, including maturation of B cells into plasma cells and memory B cells, and activation of cytotoxic T cells and macrophages. These cells are also known as CD4+ T cells because they express the CD4 glycoprotein on their surfaces. Helper T cells become activated when they are presented with peptide antigens by MHC class II molecules, which are expressed on the surface of antigen-presenting cells (APCs). Once activated, they divide rapidly and secrete small proteins called cytokines that regulate or assist in the active immune response. These cells can differentiate into one of several subtypes, including $T_H1$, $T_H2$, $T_H3$, $T_H9$, $T_H17$, $T_H22$ or $T_{FH}$ (T follicular helper cells), which secrete different cytokines to facilitate different types of immune responses. Signaling from the APCs directs T cells into particular subtypes.

"Cytotoxic T cells" (TC cells, or CTLs) or "cytotoxic T lymphocytes" destroy virus-infected cells and tumor cells, and are also implicated in transplant rejection. These cells are also known as CD8+ T cells since they express the CD8 glycoprotein at their surfaces. These cells recognize their targets by binding to antigen associated with MHC class I molecules, which are present on the surface of all nucleated cells. Through IL-10, adenosine, and other molecules secreted by regulatory T cells, the CD8+ cells can be inactivated to an anergic state, which prevents autoimmune diseases.

"Memory T cells" are a subset of antigen-specific T cells that persist long-term after an infection has resolved. They quickly expand to large numbers of effector T cells upon re-exposure to their cognate antigen, thus providing the immune system with memory against past infections. Memory T cells comprise three subtypes: central memory T cells (Tcm cells) and two types of effector memory T cells (TEM cells and TEN4RA cells). Memory cells can be either CD4+ or CD8+. Memory T cells typically express the cell surface proteins CD45RO, CD45RA and/or CCR7.

"Regulatory T cells" (Treg cells), formerly known as suppressor T cells, play a role in the maintenance of immunological tolerance. Their major role is to shut down T cell-mediated immunity toward the end of an immune reaction and to suppress autoreactive T cells that escaped the process of negative selection in the thymus.

"Natural killer T cells" (NKT cells—not to be confused with natural killer cells of the innate immune system) bridge the adaptive immune system with the innate immune system. Unlike conventional T cells that recognize peptide antigens presented by major histocompatibility complex (MHC) molecules, NKT cells recognize glycolipid antigen presented by a molecule called CD1d. Once activated, these cells can perform functions ascribed to both T helper ($T_H$) and cytotoxic T (TC) cells (i.e., cytokine production and release of cytolytic/cell killing molecules). They are also able to recognize and eliminate some tumor cells and cells infected with herpes viruses.

"Adoptive T cell transfer" refers to the isolation and ex vivo expansion of tumor specific T cells to achieve greater number of T cells than what could be obtained by vaccination alone or the patient's natural tumor response. The tumor specific T cells are then infused into patients with cancer in an attempt to give their immune system the ability to overwhelm remaining tumor via T cells which can attack and kill cancer. There are many forms of adoptive T cell therapy being used for cancer treatment; culturing tumor infiltrating lymphocytes or TIL, isolating and expanding one particular T cell or clone, and even using T cells that have been engineered to potently recognize and attack tumors.

"Antibody" as used herein refers to monoclonal or polyclonal antibodies. The term "monoclonal antibodies," as used herein, refers to antibodies that are produced by a single clone of B-cells and bind to the same epitope. In contrast, "polyclonal antibodies" refer to a population of antibodies that are produced by different B-cells and bind to different epitopes of the same antigen. A whole antibody typically consists of four polypeptides: two identical copies of a heavy (H) chain polypeptide and two identical copies of a light (L) chain polypeptide. Each of the heavy chains contains one N-terminal variable (VH) region and three C-terminal constant (CH1, CH2 and CH3) regions, and each light chain contains one N-terminal variable (VL) region and one C-terminal constant (CL) region. The variable regions of each pair of light and heavy chains form the antigen binding site of an antibody. The VH and VL regions have a similar general structure, with each region comprising four framework regions, whose sequences are relatively conserved. The framework regions are connected by three complementarity determining regions (CDRs). The three CDRs, known as CDR1, CDR2, and CDR3, form the "hypervariable region" of an antibody, which is responsible for antigen binding.

"Antibody like molecules" can be for example proteins that are members of the Ig-superfamily which are able to selectively bind a partner. MHC molecules and T cell receptors are such molecules. In one embodiment, the antibody-like molecule is an TCR. In one embodiment, the TCR has been modified to increase its MHC binding affinity.

The terms "fragment of an antibody," "antibody fragment," "functional fragment of an antibody," "antigen-binding portion" or its grammatical equivalents are used interchangeably herein to mean one or more fragments or portions of an antibody that retain the ability to specifically bind to an antigen (see, generally, Holliger et al., *Nat. Biotech.*, 23(9):1126-1129 (2005)). The antibody fragment desirably comprises, for example, one or more CDRs, the variable region (or portions thereof), the constant region (or portions thereof), or combinations thereof. Non-limiting examples of antibody fragments include (i) a Fab fragment, which is a monovalent fragment consisting of the VL, VH, CL, and CH1 domains; (ii) a F(ab')2 fragment, which is a bivalent fragment comprising two Fab fragments linked by a disulfide bridge at the stalk region; (iii) a Fv fragment consisting of the VL and VH domains of a single arm of an antibody; (iv) a single chain Fv (scFv), which is a monovalent molecule consisting of the two domains of the Fv fragment (i.e., VL and VH) joined by a synthetic linker which enables the two domains to be synthesized as a single polypeptide chain (see, e.g., Bird et al., *Science*, 242: 423-426 (1988); Huston et al., *Proc. Natl. Acad. Sci. USA*, 85: 5879-5883 (1988); and Osbourn et al., *Nat. Biotechnol.*, 16: 778 (1998)) and (v) a diabody, which is a dimer of polypeptide chains, wherein each polypeptide chain comprises a VH connected to a VL by a peptide linker that is too short to allow pairing between the VH and VL on the same polypeptide chain, thereby driving the pairing between the complementary domains on different VH-VL polypeptide chains to generate a dimeric molecule having two functional antigen binding sites. Antibody fragments are known in the art and are described in more detail in, e.g., U.S. Pat. No. 8,603,950.

"Antigen recognition moiety" or "antigen recognition domain" refers to a molecule or portion of a molecule that specifically binds to an antigen. In one embodiment, the antigen recognition moiety is an antibody, antibody like molecule or fragment thereof and the antigen is a tumor antigen.

The term "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz, G. E. and Schirmer, R. H., Principles of Protein Structure, Springer-Verlag, New York (1979)). According to such analyses, groups of amino acids can be defined where amino acids within a group exchange preferentially with each other, and therefore resemble each other most in their impact on the overall protein structure (Schulz, G. E. and Schirmer, R. H., supra). Examples of conservative mutations include amino acid substitutions of amino acids within the sub-groups above, for example, lysine for arginine and vice versa such that a positive charge can be maintained; glutamic acid for aspartic acid and vice versa such that a negative charge can be maintained; serine for threonine such that a free —OH can be maintained; and glutamine for asparagine such that a free —$NH_2$ can be maintained. Alternatively or additionally, the functional variants can comprise the amino acid sequence of the reference protein with at least one non-conservative amino acid substitution.

The term "non-conservative mutations" involve amino acid substitutions between different groups, for example, lysine for tryptophan, or phenylalanine for serine, etc. In this case, it is preferable for the non-conservative amino acid substitution to not interfere with, or inhibit the biological activity of, the functional variant. The non-conservative amino acid substitution can enhance the biological activity of the functional variant, such that the biological activity of the functional variant is increased as compared to the homologous parent protein.

The term "ankyrin" refers to a family of adaptor proteins that mediate the attachment of integral membrane proteins to the spectrin-actin based membrane cytoskeleton. Ankyrins have binding sites for the beta subunit of spectrin and at least 12 families of integral membrane proteins. This linkage is required to maintain the integrity of the plasma membranes and to anchor specific ion channels, ion exchangers and ion transporters in the plasma membrane. Ankyrins contain four functional domains: an N-terminal domain that contains 24 tandem ankyrin repeats, a central domain that binds to spectrin, a death domain that binds to proteins involved in apoptosis, and a C-terminal regulatory domain that is highly variable between different ankyrin proteins. The 24 tandem ankyrin repeats are responsible for the recognition of a wide range of membrane proteins. These 24 repeats contain 3 structurally distinct binding sites ranging from repeat 1-14. These binding sites are quasi-independent of each other and can be used in combination. The interactions the sites use to bind to membrane proteins are non-specific and consist of: hydrogen bonding, hydrophobic interactions and electrostatic interactions. These non-specific interactions gives ankyrin the property to recognize a large range of proteins as the sequence doesn't have to be conserved just the properties of the amino acids. The quasi-independence means that if a binding site is not used, it won't have a large effect on the overall binding. These two properties in combination give rise to large repertoire of proteins ankyrin can recognize. Ankyrins are encoded by three genes (ANK1, ANK2 and ANK3) in mammals. Each gene in turn produces multiple proteins through alternative splicing.

The term "proliferative disease" as referred to herein refers to a unifying concept in which excessive proliferation of cells and/or turnover of cellular matrix contributes significantly to the pathogenesis of the disease, including cancer.

"Patient" or "subject" as used herein refers to a mammalian subject diagnosed with or suspected of having or developing a proliferative disorder such as cancer. In some embodiments, the term "patient" refers to a mammalian subject with a higher than average likelihood of developing a proliferative disorder such as cancer. Exemplary patients can be humans, apes, dogs, pigs, cattle, cats, horses, goats, sheep, rodents and other mammalians that can benefit from the therapies disclosed herein. Exemplary human patients can be male and/or female. "Patient in need thereof" or "subject in need thereof" is referred to herein as a patient diagnosed with or suspected of having a disease or disorder, for instance, but not restricted to chronic hepatitis B infection.

"Administering" is referred to herein as providing one or more compositions described herein to a patient or a subject. By way of example and not limitation, composition administration, e.g., injection, can be performed by intravenous (i.v.) injection, sub-cutaneous (s.c.) injection, intradermal (i.d.) injection, intraperitoneal (i.p.) injection, or intramuscular (i.m.) injection. One or more such routes can be employed. Parenteral administration can be, for example, by bolus injection or by gradual perfusion over time. Alternatively, or concurrently, administration can be by the oral route. Additionally, administration can also be by surgical deposition of a bolus or pellet of cells, or positioning of a medical device. In an embodiment, a composition of the present disclosure can comprise engineered cells or host cells expressing nucleic acid sequences described herein, or a vector comprising at least one nucleic acid sequence described herein, in an amount that is effective to treat or prevent proliferative disorders. A pharmaceutical composition can comprise a target cell population as described herein, in combination with one or more pharmaceutically or physiologically acceptable carriers, diluents or excipients. Such compositions can comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

As used herein, the term "treatment", "treating", or its grammatical equivalents refers to obtaining a desired pharmacologic and/or physiologic effect. In embodiments, the effect is therapeutic, i.e., the effect partially or completely cures a disease and/or adverse symptom attributable to the disease. To this end, the inventive method comprises administering a therapeutically effective amount of the composition comprising the host cells expressing the inventive nucleic acid sequence, or a vector comprising the inventive nucleic acid sequences.

The term "therapeutically effective amount", therapeutic amount", "immunologically effective amount", "anti-tumor effective amount", "tumor-inhibiting effective amount" or its grammatical equivalents refers to an amount effective, at dosages and for periods of time necessary, to achieve a desired therapeutic result. The therapeutically effective amount can vary according to factors such as the disease state, age, sex, and weight of the individual, and the ability of a composition described herein to elicit a desired response in one or more subjects. The precise amount of the compositions of the present disclosure to be administered can be determined by a physician with consideration of individual differences in age, weight, tumor size, extent of infection or metastasis, and condition of the patient (subject).

Alternatively, the pharmacologic and/or physiologic effect of administration of one or more compositions described herein to a patient or a subject of can be "prophylactic," i.e., the effect completely or partially prevents a disease or symptom thereof. A "prophylactically effective amount" refers to an amount effective, at dosages and for periods of time necessary, to achieve a desired prophylactic result (e.g., prevention of disease onset).

HBV Molecular Vaccine

Hepatitis B (HepB) is a potentially life-threatening liver infection caused by the hepatitis B virus (HBV). HBV can cause chronic infection and puts people at high risk of death from cirrhosis and liver cancer. The evolution of HBV is strikingly highlighted by the geographical distribution of the genotypes. HBV genotypes/subgenotypes have been increasingly associated with differences in clinical and virological characteristics, such as severity of liver disease and response to antiviral therapies. When comparing sequences, HBV is classified into eight genotypes (A to H), each with a distinct geographic distribution. Researchers have correlated an association between the different HBV genotypes and the severity and outcome of HBV disease.

HBV is a double stranded DNA virus with high liver tropism. HBV DNA is 3.2 kb circular, enveloped, partially double strand DNA genome (FIGS. 3A-3D). HBV has four genes (S, C, P, and X). The S gene codes for envelope (lipid bilayer) surface protein (HBsAg) consisting of small surface protein (S), medium surface protein (S+PreS2), and large surface protein (S+PreS2+PreS1). The C gene codes for the capsid or core proteins. The C gene has a precore and a core region. If translation is initiated at the precore region, the protein is HBeAg. If translation is initiated at the core region, the protein is HBcAg. The P gene codes for the DNA polymerase (Pol). The X gene codes for the x protein (HBxAg) (FIGS. 3A-3D). The HBV genome comprises Pol (832 amino acids) comprising TP, SP, RT and RH; PreS1 (108 amino acids); PreS2 (55 amino acids); S (226 amino acids); PreC (29 amino acids); C (183 amino acids); and HBx (154 amino acids) (FIGS. 3A-3D).

Acute HBV infection is characterized by the presence of hepatitis B surface antigen (HBsAg) and immunoglobulin M (IgM) antibody to the core antigen, HBcAg. During the initial phase of infection, patients are also seropositive for hepatitis B e antigen (HBeAg). HBeAg is usually a marker of high levels of replication of the virus. The presence of HBeAg indicates that the blood and body fluids of the infected individual are highly infectious. Chronic infection is characterized by the persistence of HBsAg for at least 6 months (with or without concurrent HBeAg). Persistence of HBsAg is the principal marker of risk for developing chronic liver disease and liver cancer (hepatocellular carcinoma) later in life.

The hepatitis B virus can survive outside the body for at least 7 days. During this time, the virus can still cause infection if it enters the body of a person who is not protected by the vaccine. The incubation period of the hepatitis B virus is 75 days on average, but can vary from 30 to 180 days. The virus can be detected within 30 to 60 days after infection and can persist and develop into chronic hepatitis B. In highly endemic areas, hepatitis B is most commonly spread from mother to child at birth (perinatal transmission), or through horizontal transmission (exposure to infected blood), especially from an infected child to an uninfected child during the first 5 years of life. The development of chronic infection is very common in infants infected from their mothers or before the age of 5 years. Hepatitis B is also spread by percutaneous or mucosal exposure to infected blood and various body fluids, as well as through saliva, menstrual, vaginal, and seminal fluids. Sexual transmission of hepatitis B can also commonly occur. Infection in adulthood leads to chronic hepatitis in less than 5% of cases. Transmission of the virus can also occur through the reuse of needles and syringes either in healthcare settings or among persons who inject drugs. In addition, infection can occur during medical, surgical and dental procedures, through tattooing, or through the use of razors and similar objects that are contaminated with infected blood.

Figure 2:
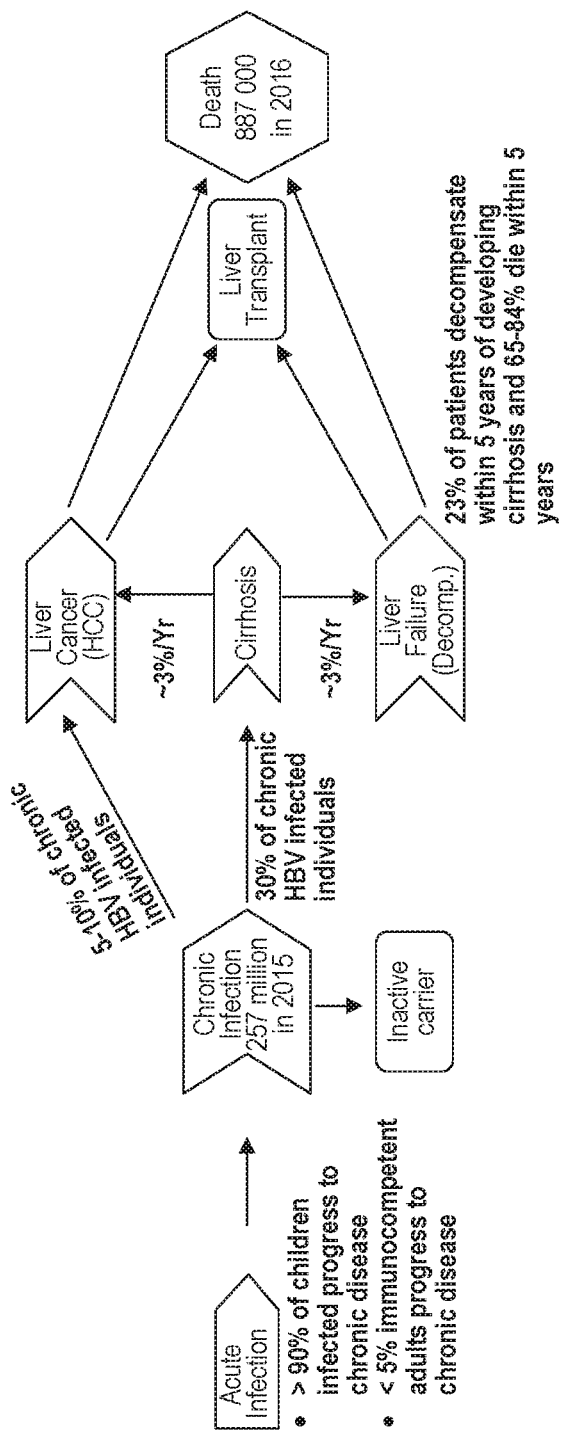
FIG. 2 is a schematic showing history of chronic HBV infection.
Figure 3A:
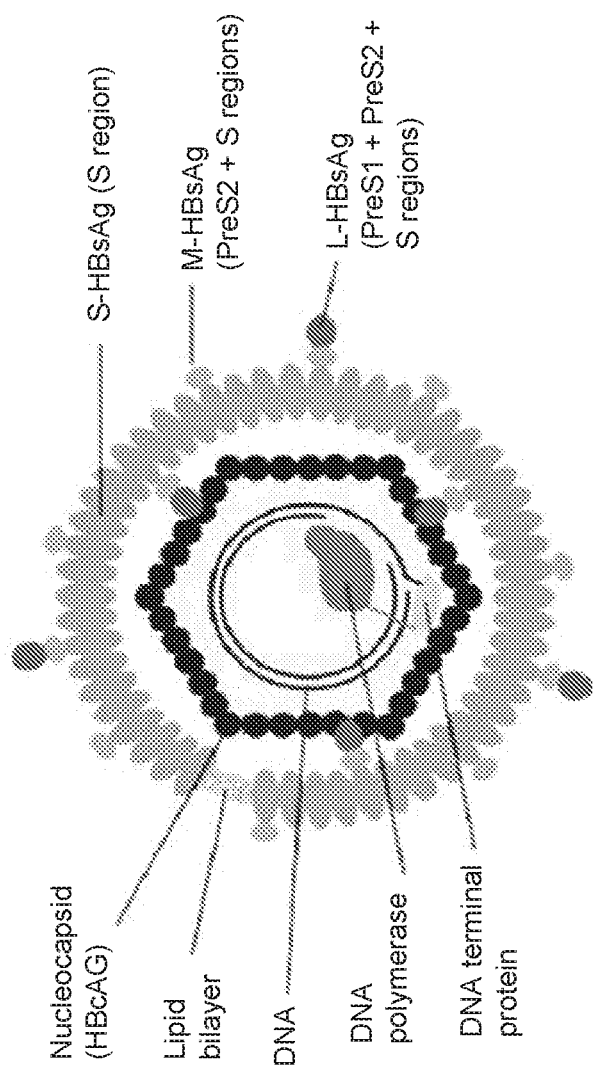
FIG. 3A is a schematic overview of hepatitis B virus. HBV DNA is 3.2 kb circular, enveloped, partially double strand DNA genome. HBV has four genes (S, C, P, and X). The S gene codes for envelope (lipid bilayer) surface protein (HBsAg) consisting of small surface protein (S), medium surface protein (S+PreS2), and large surface protein (S+PreS2+PreS1). The C gene codes for the capsid or core proteins. The C gene has a precore and a core region. If translation is initiated at the precore region, the protein is HBeAg. If translation is initiated at the core region, the protein is HBcAg. The P gene codes for the DNA polymerase (Pol). The X gene codes for the x protein (HBxAg).
Figure 3B:
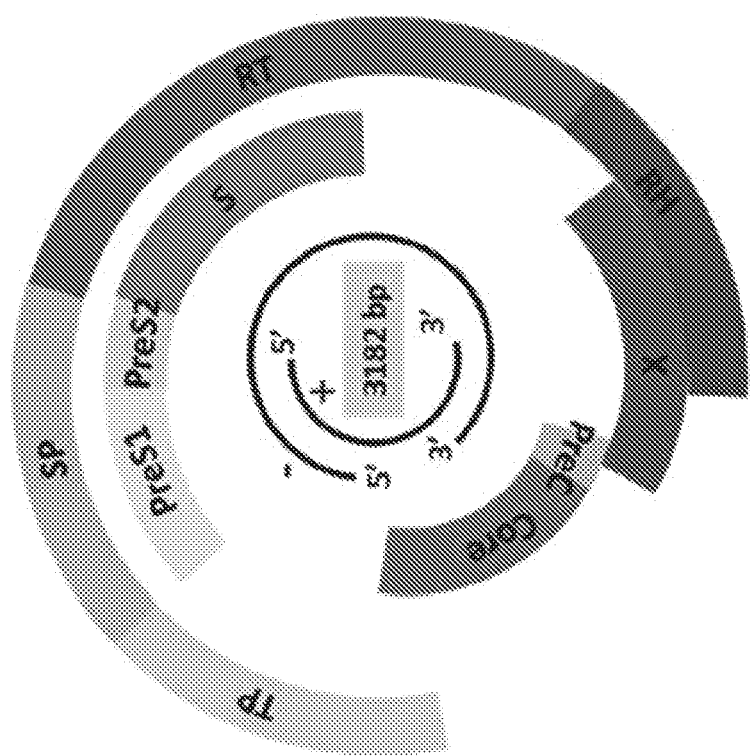
FIG. 3B is an overview of hepatitis B virus genome. The HBV genome comprises Pol (832 amino acids) comprising TP, SP, RT and RH; PreS1 (108 amino acids); PreS2 (55 amino acids); S (226 amino acids); PreC (29 amino acids); C (183 amino acids); and HBx (154 amino acids).
Figure 3C:
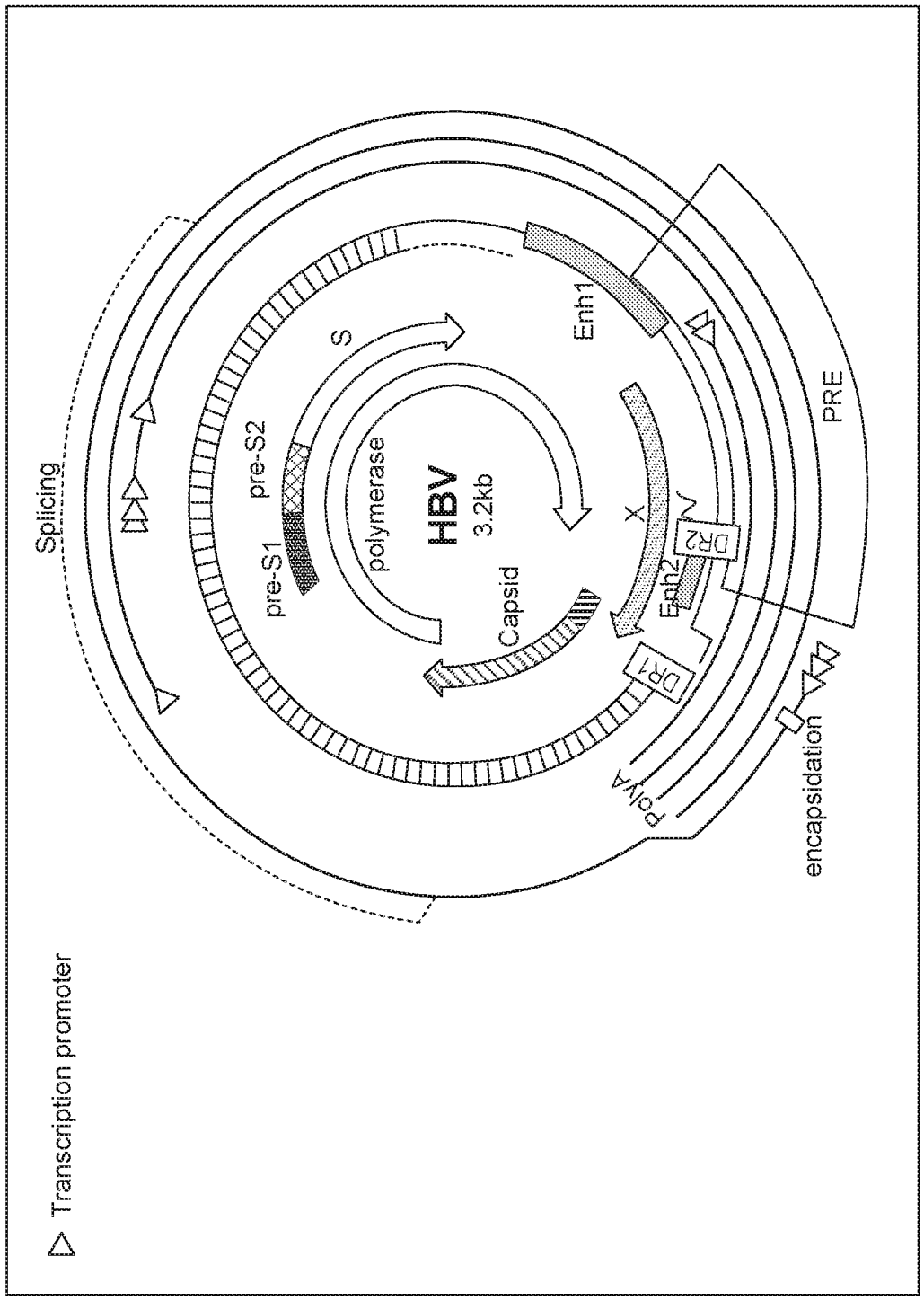
FIG. 3C shows a schematic of the HBV genome encoding several overlapping viral proteins, including the polymerase core, core envelop (Pre-S1, S2, S), HBe, and HBx proteins.
Figure 3D:
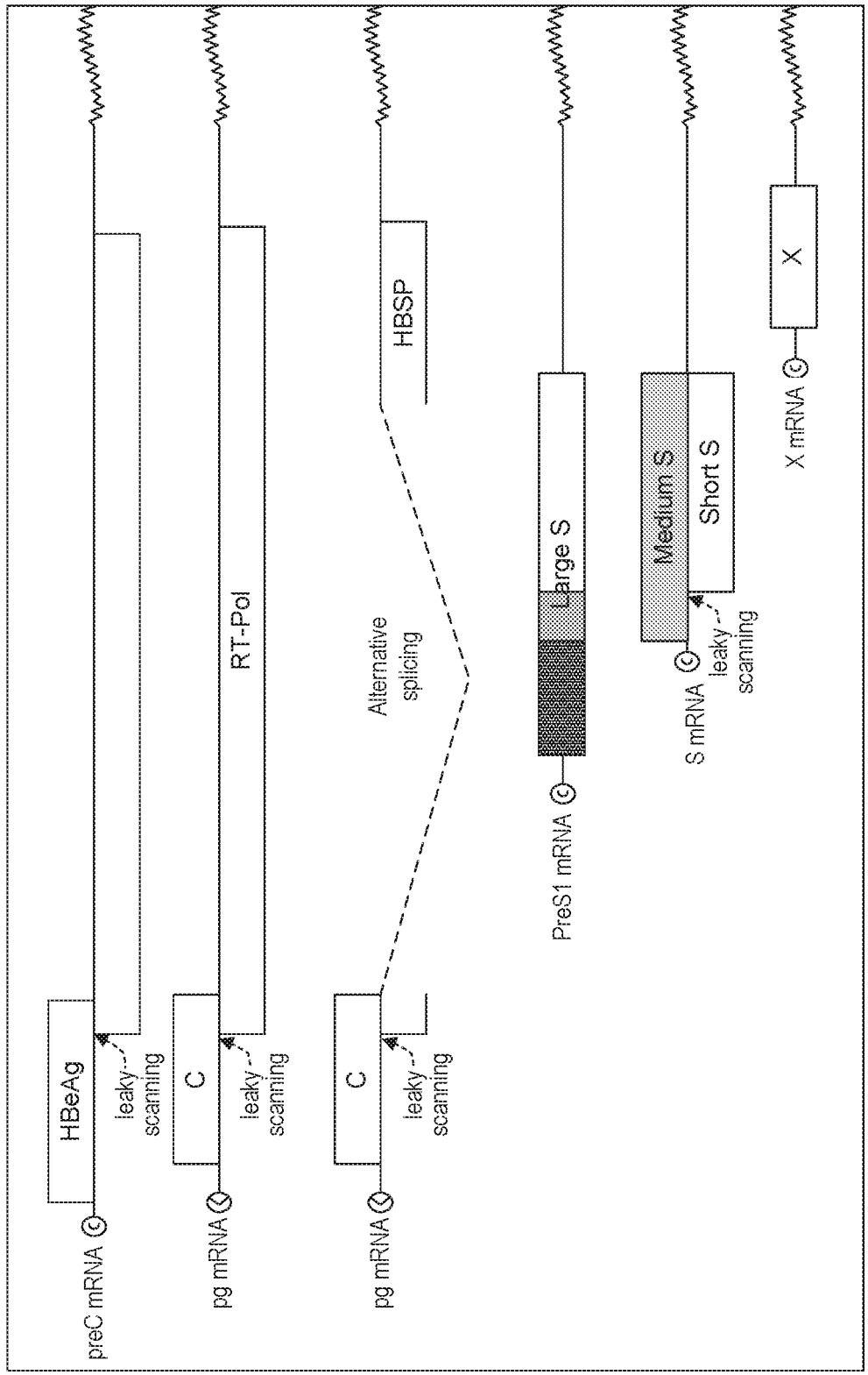
FIG. 3D shows a schematic of the HBV genome encoding several overlapping viral proteins, including the polymerase core, core envelop (Pre-S1, S2, S), HBe, and HBx proteins.

Most people do not experience any symptoms during the acute infection phase. However, some people have acute illness with symptoms that last several weeks, including yellowing of the skin and eyes (jaundice), dark urine, extreme fatigue, nausea, vomiting and abdominal pain. A small subset of persons with acute hepatitis can develop acute liver failure, which can lead to death. In some people, the hepatitis B virus can also cause a chronic liver infection that can later develop into cirrhosis (a scarring of the liver) or liver cancer. The likelihood that infection becomes chronic depends upon the age at which a person becomes infected. Children less than 6 years of age who become infected with the hepatitis B virus are the most likely to develop chronic infections. 80-90% of infants infected during the first year of life develop chronic infections; and 30-50% of children infected before the age of 6 years develop chronic infections. In adults, less than 5% of otherwise healthy persons who are infected as adults will develop chronic infection; and 20-30% of adults who are chronically infected will develop cirrhosis and/or liver cancer (FIG. 1 and FIG. 2).

There is no specific treatment for acute hepatitis B. Therefore, care is aimed at maintaining comfort and adequate nutritional balance, including replacement of fluids lost from vomiting and diarrhea. Chronic hepatitis B infection can be treated with medicines, including oral antiviral agents. Treatment (e.g., liver transplant or IFN-α nucleotide analogs) can slow the progression of cirrhosis, reduce incidence of liver cancer and improve long term survival. Recent more advanced therapeutic vaccines (i.e., GS-4777, Gilead; ABX203, Abivax) have failed in clinical trial phase 2/3. In most people, however, the treatment does not cure hepatitis B infection, but only suppresses the replication of the virus. Therefore, most people who start hepatitis B treatment must continue it for life. There is still limited access to diagnosis and treatment of hepatitis B in many resource-constrained settings.

An estimated 257 million people are living with chronic hepatitis B virus (HBV) infection (positive confirmation through surface antigen detection). In 2015, hepatitis B infection resulted in 887,000 deaths, with liver failure or liver cancer as the leading cause of death. Currently, HBV vaccines prevent infection in 95% of the cases, thereby preventing infection, liver cancer, and chronic diseases due to hepatitis B. However, there is still a large need for developing a HBV vaccine with broad coverage against multiple HBV subtypes and functionality against liver cancer. The present disclosure relates to novel HBV vaccine antigens based on bioinformatics methods and protein engineering approaches. These novel HBV vaccine candidates can be used as therapeutic vaccines against HBV and HBV-related diseases.

Treatment Options

Figure 4:
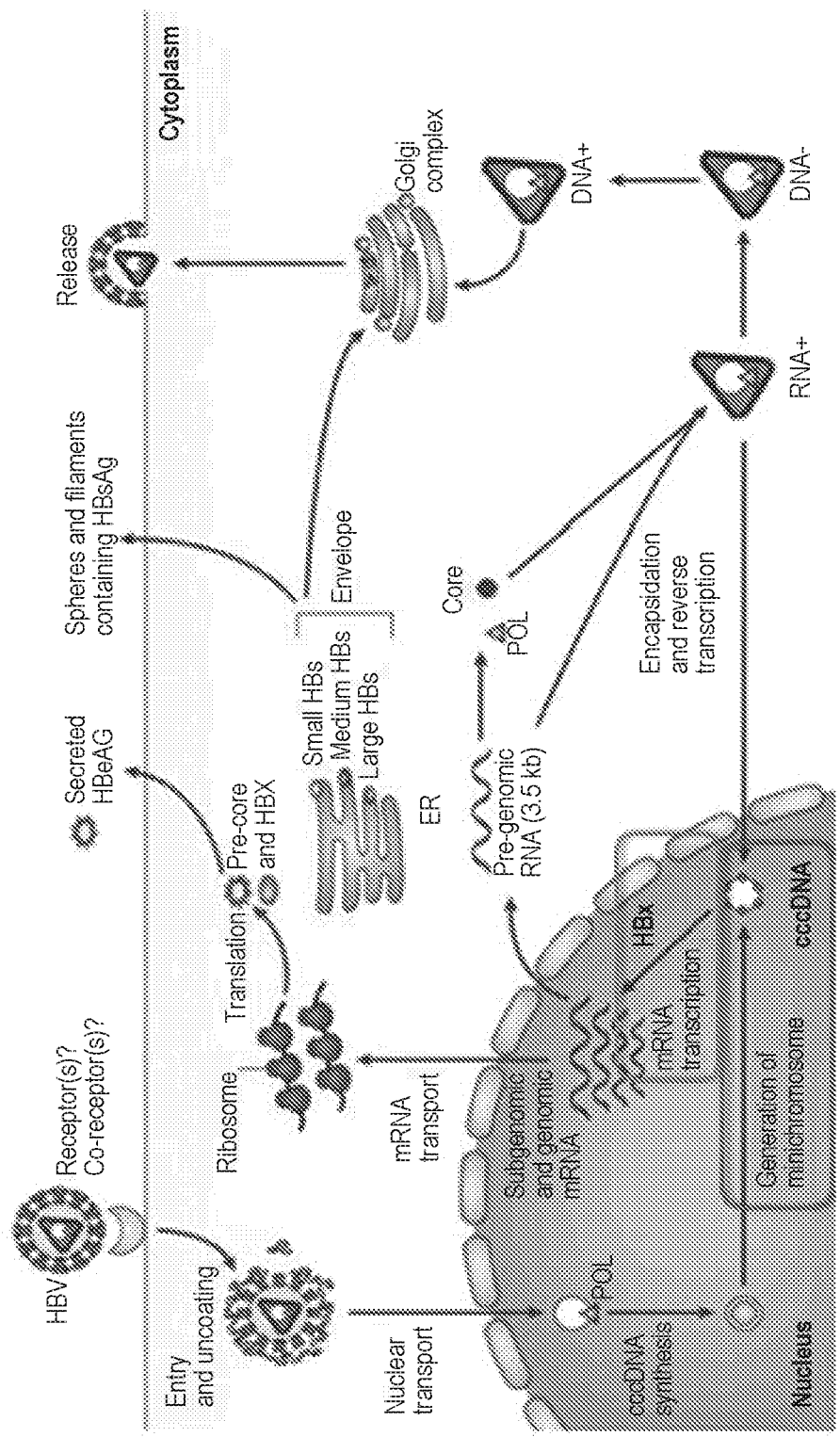
FIG. 4 shows a schematic overview of HBV infection mechanism.

Standard of care (SOC) for chronic hepatitis B infection include PEG-IFN, and/or nucleotide analogues. However, cccDNA and immune tolerance and exhaustion can persist (FIG. 4). Infection with HBV causes hepatitis that can result in cirrhosis, liver failure and hepatocellular carcinoma (HCC). The diagnosis of HBV is based on the serological findings. In fact, viral DNA, antigens and their respective antibodies can be found in the serum. HBV is subdivided into four major serotypes (adr, adw, ayr, ayw) based on a based on a common antigenic determinant (a) and two mutually exclusive determinant pairs (d/y and w/r) found on the HBsAg. There exist ten known genotypes (A-J) and forty known subgenotypes according to overall nucleotide sequence variation of the genome. The genotypes have a distinct geographical distribution and different genotypes are associated with different disease severity, course and likelihood of complications, and response to treatment and possibly vaccination. The serotypes and genotypes do not necessarily correspond (e.g., genotype D has 10 subgenotypes).

Currently, there is no cure for chronic HBV infection. Treatment options are aimed at slowing the progression of cirrhosis and viral replication, reducing the incidence of HCC and liver failures. Current treatments are divided into two major categories: (1) immune modulator drugs, i.e., mainly type I interferon (interferon alpha and pegylated interferon alpha) designed to boost the immune system to fight viral infected cells; and (2) antiviral drugs, which include nucleoside analogues (lamivudine, entecavir and telbivudine) and nucleotide analogues (adefovir, dipivoxil and tenofovir), and aimed at interfering with viral replication. The death toll to HBV infection currently is almost 0.7 million/year on par with HIV and tuberculosis. Although the rate of new HBV infection is decreasing, the increase in overall death from hepatitis requires urgent need of the development of new treatment options.

Therapeutic Approaches

HBV epitopes from surface (S), core (C), and polymerase (Pol) proteins are targeted by T cells during infection which mediate cellular immune responses to HBV. The HBV X protein (HBx), which includes MHC-I and MHC-II epitopes, is a multifunctional regulatory protein involved in viral pathogenesis and carcinogenesis. The HBV vaccine designs described herein include all major components that have potential T cell epitopes. Specifically, provided herein are the HBV vaccines comprising two different unique designs with genetic modifications (in the form of point mutations) and truncations in Pol, Core, Env and HBx. Also provided herein are uniquely designed multi-epitope constructs (i.e., cytotoxic T lymphocytes) with specific peptides grafted onto a human protein scaffold and linked by charged dipeptide that can stimulate the cellular immune responses required for controlling and clearing HBV infection.

Provided herein are various gene therapeutic approaches to treat HBV infection. For example, described in Table 1 are some of the strategies used to improve the immune system-mediated control of HBV. Also provided herein is an HBV therapeutic vaccine, intelligent design of a prime/boost DNA-based vaccine encompassing the combination of immunogenic regions of the main component of the HBV (HBsAg, HBcAg, HBxAg, HBeAg and HB PolAg) for priming and a combination of agonist CD8 T cell epitope for boosting.

Provided herein are compositions, kits, and systems comprising and methods of making HBV recombinant vaccines. The HBV recombinant vaccines (e.g., HBV designs 1-5) in could lead to MHC-I binding and cytokine production following T cell activation). The overall workflow of the presently disclosed HBV vaccine designs is shown in FIG. 5, and further detailed in Example 1. The present disclosure provides five HBV antigen designs (HBV designs 1-5) constructed in a multi-deleted *gorilla* adenovector (GC46).

Four antigen designs (HBV designs 1-4) and a control antigen were synthesized and cloned into expression plasmids—pAdShuttles for adenovector construction (FIG. 6). HBV design was analyzed to assess whether different linkers cause prediction of different epitopes. Initial antigen screening evaluated in vitro antigen expression in transient transfection, in vitro antigen processing and presentation in transient transfection studies of monocyte-derived dendritic cells. As shown in FIG. 6, HBV designs 1 and 2 were designed based on Glade D consensus. 32 HBV peptides from Core (8), Surface (8), Polymerase (8), HBx (6) and HBPS (2) were curated from literature that have experimental and functional data, such as immunogenicity data, Mass-spec. etc. (Table 4). For HBV design 3, human ankyrin-like repeat (ALR) protein scaffold (PDB code 1QYM) peptides were grafted at the helical and loop regions in a tandem manner Two ALR scaffolds were used, connected by a cleavable linker VSQTSKLTR (SEQ ID NO: 111). ALR proteins have generally high expression and high stability. Thus, ALR proteins were used as a scaffold for the HBV peptides to create novel CTLs. HBV design 4 epitopes were separated by KK linkers (FIG. 6). For RNA qPCR relative expression assay, 5'-TGCCAAGAGTGACGTGTCCA-3' (SEQ ID NO: 110) was used as a splice primer, and 5'-CCCAGGTCCAACTGCAGCCGG-3' (SEQ ID NO: 128) was used as a splice probe. Specific primers designed for each antigen were used as reverse primers (FIG. 14).

TABLE 1

Strategies to Improve the Immune Mediated Control of HBV

| Characteristics of chronic HBV infection | Therapeutic goals | Tools | Expected effects |
|---|---|---|---|
| High viral load | To decrease viral and antigen loads | Nucleoside analogs | Transient restoration of T-cell functions |
| High levels of PD-1 expression on HBV-specific T cells | To decrease the inhibitory signal | Anti-PD-L1 antibody | Restoration of T-cell functions |
| HBV-specific T-cell exhaustion | To reactivate/activate functional HBV-specific T cells in vivo<br>To activate T cells ex vivo | Vaccines<br>Novel adjuvants<br>DNA vaccines<br>Viral vaccines<br>Ag/Ab IC<br>Cytokines<br>Modified DCs<br>Stimulation of PBMCs | Reactivation of Th1 responses<br>De novo activation of CD4 and CD8 T cells<br>Improvement of antigen presentation<br>T-cell expansion<br>Improvement of antigen presentation<br>Activation of killer cells |
| HBV-specific T-cell deletion | To engineer new HBV-specific T cells | TCR-redirected T cells | Non exhausted, functional HBV-specific T cells<br>Recognition of HBV-infected cells |
| Suppressive environment | To target functional non HBV-specific T cells to the liver | Liver gene therapy | Elimination of HBV-infected hepatocytes | the present disclosure are engineered through protein engineering of HBe, HBx, LHBs, Pol, and HBSP. Each HBV vaccine antigen design was inspired via inventor-selected combinatorial guidance using bioinformatics analyses and in silico protein engineering methods (e.g., selection of antigenic sequences that match closer to consensus sequences, antigenicity predictions, and T cell epitope mapping, which Delivery System

*Gorilla* Adenovirus Shuttle Vector

Certain aspects of the present disclosure are directed to a vector comprising a polynucleotide encoding a polypeptide comprising one or more immune response-inducing HBV polypeptides. In certain embodiments, the vector is a viral vector. In particular embodiments, the vector is an adenoviral vector. Adenoviruses are generally associated with benign pathologies in humans, and the genomes of adenoviruses isolated from a variety of species, including humans, have been extensively studied. Adenovirus is a medium-sized (90-100 nm), non-enveloped icosahedral virus containing approximately 36 kb of double-stranded DNA. The adenovirus capsid mediates the key interactions of the early stages of the infection of a cell by the virus, and is required for packaging adenovirus genomes at the end of the adenovirus life cycle. The capsid comprises 252 capsomeres, which includes 240 hexons, 12 penton base proteins, and 12 fibers (Ginsberg et al., *Virology,* 28: 782-83 (1966)). The hexon comprises three identical proteins, namely polypeptide II (Roberts et al., *Science,* 232: 1148-51 (1986)). The penton base comprises five identical proteins and the fiber comprises three identical proteins. Proteins IIIa, VI, and IX are present in the adenoviral coat and are believed to stabilize the viral capsid (Stewart et al., *Cell,* 67: 145-54 (1991), and Stewart et al., *EMBO J.,* 12(7): 2589-99 (1993)). The expression of the capsid proteins, with the exception of pIX, is dependent on the adenovirus polymerase protein. Therefore, major components of an adenovirus particle are expressed from the genome only when the polymerase protein gene is present and expressed.

Several features of adenoviruses make them ideal vehicles for transferring genetic material to cells for therapeutic applications (i.e., "gene therapy"), or for use as antigen delivery systems for vaccine applications. For example, adenoviruses can be produced in high titers (e.g., about 1013 particle units (pu)), and can transfer genetic material to non-replicating and replicating cells. The adenoviral genome can be manipulated to carry a large amount of exogenous DNA (up to about 8 kb), and the adenoviral capsid can potentiate the transfer of even longer sequences (Curiel et al., *Hum. Gene Ther.,* 3: 147-154 (1992)). Additionally, adenoviruses generally do not integrate into the host cell chromosome, but rather are maintained as a linear episome, thereby minimizing the likelihood that a recombinant adenovirus will interfere with normal cell function.

In some embodiments, the adenovirus described herein is isolated from a *gorilla*. There are four widely recognized *gorilla* subspecies within the two species of Eastern *Gorilla* (*Gorilla beringei*) and Western *Gorilla* (*Gorilla gorilla*). The Western *Gorilla* species includes the subspecies Western Lowland *Gorilla* (*Gorilla gorilla gorilla*) and Cross River *Gorilla* (*Gorilla gorilla diehli*). The Eastern *Gorilla* species includes the subspecies Mountain *Gorilla* (*Gorilla beringei beringei*) and Eastern Lowland *Gorilla* (*Gorilla beringei graueri*) (see, e.g., Wilson and Reeder, eds., *Mammalian Species of the World,* 3$^{rd}$ ed., Johns Hopkins University Press, Baltimore, Maryland (2005)). In some embodiments, the adenovirus of the present disclosure is isolated from Mountain *Gorilla* (*Gorilla beringei beringei*).

Various *Gorilla* adenoviruses or adenoviral vectors are described in International Patent Application Publications WO 2013/052832; WO 2013/052811; and WO 2013 052799, each of which is herein incorporated by reference in its entirety.

The genomes of several such adenoviruses have been analyzed, and it has been determined that the adenovirus can have the nucleic acid sequence of, for example, SEQ ID NO: 21, SEQ ID NO: 22, SEQ ID NO: 23, SEQ ID NO: 24, or SEQ ID NO: 25, each of which includes a number of sub-sequences that serve to uniquely define the adenovirus, namely the nucleic acid sequences SEQ ID NOs: 1-10, and amino acid sequences SEQ ID NOs: 11-20. SEQ ID NOs: 6-10 encode the amino acid sequences of SEQ ID NOs: 16-20, respectively. SEQ ID NOs: 1-5 are a subset of the nucleic acid sequences of SEQ ID NOs: 6-10, respectively. SEQ ID NOs: 11-15 are a subset of the amino acid sequences of SEQ ID NOs: 16-20, respectively.

The adenovirus can be modified in the same manner as previously known adenoviruses to be used as an adenoviral vector, e.g., a gene delivery vehicle. The adenovirus and adenoviral vector can be replication-competent, conditionally replication-competent, or replication-deficient.

A replication-competent adenovirus or adenoviral vector can replicate in typical host cells, i.e., cells typically capable of being infected by an adenovirus. A replication-competent adenovirus or adenoviral vector can have one or more mutations as compared to the wild-type adenovirus (e.g., one or more deletions, insertions, and/or substitutions) in the adenoviral genome that do not inhibit viral replication in host cells. For example, the adenovirus or adenoviral vector can have a partial or entire deletion of the adenoviral early region known as the E3 region, which is not essential for propagation of the adenovirus or adenoviral genome.

A conditionally-replicating adenovirus or adenoviral vector is an adenovirus or adenoviral vector that has been engineered to replicate under pre-determined conditions. For example, replication-essential gene functions, e.g., gene functions encoded by the adenoviral early regions, can be operably linked to an inducible, repressible, or tissue-specific transcription control sequence, e.g., promoter. In such an embodiment, replication requires the presence or absence of specific factors that interact with the transcription control sequence. Conditionally-replicating adenoviral vectors are further described in U.S. Pat. No. 5,998,205.

A replication-deficient adenovirus or adenoviral vector is an adenovirus or adenoviral vector that requires complementation of one or more gene functions or regions of the adenoviral genome that are required for replication, as a result of, for example, a deficiency in one or more replication-essential gene function or regions, such that the adenovirus or adenoviral vector does not replicate in typical host cells, especially those in a human to be infected by the adenovirus or adenoviral vector.

A deficiency in a gene function or genomic region, as used herein, is defined as a disruption (e.g., deletion) of sufficient genetic material of the adenoviral genome to obliterate or impair the function of the gene (e.g., such that the function of the gene product is reduced by at least about 2-fold, 5-fold, 10-fold, 20-fold, 30-fold, or 50-fold) whose nucleic acid sequence was disrupted (e.g., deleted) in whole or in part. Deletion of an entire gene region often is not required for disruption of a replication-essential gene function. However, for the purpose of providing sufficient space in the adenoviral genome for one or more transgenes, removal of a majority of one or more gene regions can be desirable. While deletion of genetic material is preferred, mutation of genetic material by addition or substitution also is appropriate for disrupting gene function. Replication-essential gene functions are those gene functions that are required for adenovirus replication (e.g., propagation) and are encoded by, for example, the adenoviral early regions (e.g., the E1, E2, and E4 regions), late regions (e.g., the L1, L2, L3, L4, and L5 regions), genes involved in viral packaging (e.g., the IVa2 gene), and virus-associated RNAs (e.g., VA-RNA-1 and/or VA-RNA-2).

Whether the adenovirus or adenoviral vector is replication-competent or replication-deficient, the adenovirus or adenoviral vector retains at least a portion of the adenoviral genome. The adenovirus or adenoviral vector can comprise any portion of the adenoviral genome, including protein coding and non-protein coding regions. Desirably, the adenovirus or adenoviral vector comprises at least one nucleic acid sequence that encodes an adenovirus protein. The adenovirus or adenoviral vector can comprise a nucleic acid sequence that encodes any suitable adenovirus protein, such as, for example, a protein encoded by any one of the early region genes (i.e., E1A, E1B, E2A, E2B, E3, and/or E4 regions), or a protein encoded by any one of the late region genes, which encode the virus structural proteins (i.e., L1, L2, L3, L4, and L5 regions).

The adenovirus or adenoviral vector desirably comprises one or more nucleic acid sequences that encode the pIX protein, the DNA polymerase protein, the penton protein, the hexon protein, and/or the fiber protein. The adenovirus or adenoviral vector can comprise a full-length nucleic acid sequence that encodes a full-length amino acid sequence of an adenovirus protein. Alternatively, the adenovirus or adenoviral vector can comprise a portion of a full-length nucleic acid sequence that encodes a portion of a full-length amino acid sequence of an adenovirus protein.

A "portion" of a nucleic acid sequence comprises at least ten nucleotides (e.g., about 10 to about 5000 nucleotides). Preferably, a "portion" of a nucleic acid sequence comprises 10 or more (e.g., 15 or more, 20 or more, 25 or more, 30 or more, 35 or more, 40 or more, 45 or more, 50 or more, or 100 or more) nucleotides, but less than 5,000 (e.g., 4900 or less, 4000 or less, 3000 or less, 2000 or less, 1000 or less, 800 or less, 500 or less, 300 or less, or 100 or less) nucleotides. Preferably, a portion of a nucleic acid sequence is about 10 to about 3500 nucleotides (e.g., about 10, 20, 30, 50, 100, 300, 500, 700, 1000, 1500, 2000, 2500, or 3000 nucleotides), about 10 to about 1000 nucleotides (e.g., about 25, 55, 125, 325, 525, 725, or 925 nucleotides), or about 10 to about 500 nucleotides (e.g., about 15, 30, 40, 50, 60, 70, 80, 90, 150, 175, 250, 275, 350, 375, 450, 475, 480, 490, 495, or 499 nucleotides), or a range defined by any two of the foregoing values. More preferably, a "portion" of a nucleic acid sequence comprises no more than about 3200 nucleotides (e.g., about 10 to about 3200 nucleotides, about 10 to about 3000 nucleotides, or about 30 to about 500 nucleotides, or a range defined by any two of the foregoing values).

A "portion" of an amino acid sequence comprises at least three amino acids (e.g., about 3 to about 1,200 amino acids). Preferably, a "portion" of an amino acid sequence comprises 3 or more (e.g., 5 or more, 10 or more, 15 or more, 20 or more, 25 or more, 30 or more, 40 or more, or 50 or more) amino acids, but less than 1,200 (e.g., 1,000 or less, 800 or less, 700 or less, 600 or less, 500 or less, 400 or less, 300 or less, 200 or less, or 100 or less) amino acids. Preferably, a portion of an amino acid sequence is about 3 to about 500 amino acids (e.g., about 10, 100, 200, 300, 400, or 500 amino acids), about 3 to about 300 amino acids (e.g., about 20, 50, 75, 95, 150, 175, or 200 amino acids), or about 3 to about 100 amino acids (e.g., about 15, 25, 35, 40, 45, 60, 65, 70, 80, 85, 90, 95, or 99 amino acids), or a range defined by any two of the foregoing values. More preferably, a "portion" of an amino acid sequence comprises no more than about 500 amino acids (e.g., about 3 to about 400 amino acids, about 10 to about 250 amino acids, or about 50 to about 100 amino acids, or a range defined by any two of the foregoing values).

The adenovirus pIX protein is present in the adenovirus capsid, has been shown to strengthen hexon nonamer interactions, and is essential for the packaging of full-length genomes (see, e.g., Boulanger et al., *J. Gen. Virol.*, 44: 783-800 (1979); Horwitz M. S., "Adenoviridae and their replication" in *Virology*, $2^{nd}$ ed., B. N. Fields et al. (eds.), Raven Press, Ltd., New York, pp. 1679-1721 (1990), Ghosh-Choudhury et al., *EMBO J.*, 6: 1733-1739 (1987), and van Oostrum et al, *J. Virol.*, 56: 439-448 (1985)). In addition to its contribution to adenovirus structure, pIX also has been shown to exhibit transcriptional properties, such as stimulation of adenovirus major late promoter (MLP) activity (see, e.g., Lutz et al., *J. Virol.*, 71(7): 5102-5109 (1997)). Nucleic acid sequences that encode all or a portion of an adenovirus pIX protein include, for example, SEQ ID NO: 6 and SEQ ID NO: 1. Amino acid sequences that comprise a full-length pIX protein, or a portion thereof, include, for example, SEQ ID NO: 16 and SEQ ID NO: 11.

The adenovirus DNA polymerase protein is essential for viral DNA replication both in vitro and in vivo. The polymerase co-purifies in a complex with the precursor (pTP) of the terminal protein (TP), which is covalently attached to the 5' ends of adenovirus DNA (Field et al., *J. Biol. Chem.*, 259: 9487-9495 (1984)). Both the adenovirus DNA polymerase and pTP are encoded by the E2 region. The polymerase protein is required for the expression of all the structural proteins except for pIX. Without the gene sequence for polymerase protein, polymerase protein is not produced. As a result, the viral genome is not replicated, the Major Late Promoter is not activated, and the capsid proteins are not expressed. Nucleic acid sequences that encode all or a portion of an adenovirus DNA polymerase protein include, for example, SEQ ID NO: 7 and SEQ ID NO. 2 Amino acid sequences that comprise a full-length adenovirus DNA polymerase, or a portion thereof, include, for example, SEQ ID NO: 17 and SEQ ID NO: 12.

The adenovirus hexon protein is the largest and most abundant protein in the adenovirus capsid. The hexon protein is essential for virus capsid assembly, determination of the icosahedral symmetry of the capsid (which in turn defines the limits on capsid volume and DNA packaging size), and integrity of the capsid. In addition, hexon is a primary target for modification in order to reduce neutralization of adenoviral vectors (see, e.g., Gall et al., *J. Virol.*, 72: 10260-264 (1998), and Rux et al., *J. Virol.*, 77(17): 9553-9566 (2003)). The major structural features of the hexon protein are shared by adenoviruses across serotypes, but the hexon protein differs in size and immunological properties between serotypes (Jornvall et al., *J. Biol. Chem.*, 256(12): 6181-6186 (1981)). A comparison of 15 adenovirus hexon proteins revealed that the predominant antigenic and serotype-specific regions of the hexon appear to be in loops 1 and 2 (i.e., LI or l1, and LII or l2, respectively), within which are seven discrete hypervariable regions (HVR1 to HVR7) varying in length and sequence between adenoviral serotypes (Crawford-Miksza et al., *J. Virol.*, 70(3): 1836-1844 (1996)). Nucleic acid sequences that encode all or a portion of an adenovirus hexon protein include, for example, SEQ ID NO: 9 and SEQ ID NO: 4. Amino acid sequences that comprise a full-length adenovirus hexon protein, or a portion thereof, include, for example, SEQ ID NO: 19 and SEQ ID NO: 14.

The adenovirus fiber protein is a homotrimer of the adenoviral polypeptide IV that has three domains: the tail, shaft, and knob. (Devaux et al., *J. Molec. Biol.*, 215: 567-88 (1990), Yeh et al., *Virus Res.*, 33: 179-98 (1991)). The fiber protein mediates primary viral binding to receptors on the cell surface via the knob and the shaft domains (Henry et al., *J. Virol.*, 68(8): 5239-46 (1994)). The amino acid sequences for trimerization are located in the knob, which appears necessary for the amino terminus of the fiber (the tail) to properly associate with the penton base (Novelli et al., Virology, 185: 365-76 (1991)). In addition to recognizing cell receptors and binding the penton base, the fiber contributes to serotype identity. Fiber proteins from different adenoviral serotypes differ considerably (see, e.g., Green et al., *EMBO J.*, 2: 1357-65 (1983), Chroboczek et al., *Virology*, 186: 280-85 (1992), and Signas et al., *J. Virol.*, 53: 672-78 (1985)). Thus, the fiber protein has multiple functions key to the life cycle of adenovirus. Nucleic acid sequences that encode all or a portion of an adenovirus fiber protein include, for example, SEQ ID NO: 10 and SEQ ID NO: 5. Amino acid sequences that comprise a full-length adenovirus fiber protein, or a portion thereof, include, for example, SEQ ID NO: 20 and SEQ ID NO: 15.

The adenovirus penton base protein is located at the vertices of the icosahedral capsid and comprises five identical monomers. The penton base protein provides a structure for bridging the hexon proteins on multiple facets of the icosahedral capsid, and provides the essential interface for the fiber protein to be incorporated in the capsid. Each monomer of the penton base contains an RGD tripeptide motif (Neumann et al., *Gene*, 69: 153-157 (1988)). The RGD tripeptide mediates binding to αv integrins and adenoviruses that have point mutations in the RGD sequence of the penton base are restricted in their ability to infect cells (Bai et al., *J. Virol.*, 67: 5198-5205 (1993)). Thus, the penton base protein is essential for the architecture of the capsid and for maximum efficiency of virus-cell interaction. Nucleic acid sequences that encode all or a portion of an adenovirus penton base protein include, for example, SEQ ID NO: 8 and SEQ ID NO. 3 Amino acid sequences that comprise a full-length adenovirus penton base protein, or a portion thereof, include, for example, SEQ ID NO: 18 and SEQ ID NO: 13.

Nucleic acid or amino acid sequence "identity," as described herein, can be determined by comparing a nucleic acid or amino acid sequence of interest to a reference nucleic acid or amino acid sequence. The numbers of nucleotides or amino acid residues that have been changed and/or modified (such as, e.g., by point mutations, insertions, or deletions) in the reference sequence so as to result in the sequence of interest are counted. The total number of such changes is subtracted from the total length of the sequence of interest, and the difference is divided by the length of the sequence of interest and expressed as a percentage. A number of mathematical algorithms for obtaining the optimal alignment and calculating identity between two or more sequences are known and incorporated into a number of available software programs. Examples of such programs include CLUSTAL-W, T-Coffee, and ALIGN (for alignment of nucleic acid and amino acid sequences), BLAST programs (e.g., BLAST 2.1, BL2SEQ, and later versions thereof) and FASTA programs (e.g., FASTA3x, FAS™, and SSEARCH) (for sequence alignment and sequence similarity searches). Sequence alignment algorithms also are disclosed in, for example, Altschul et al., *J. Molecular Biol.*, 215(3): 403-410 (1990), Beigert et al., *Proc. Natl. Acad. Sci. USA*, 106(10): 3770-3775 (2009), Durbin et al., eds., *Biological Sequence Analysis: Probabilistic Models of Proteins and Nucleic Acids*, Cambridge University Press, Cambridge, UK (2009), Soding, *Bioinformatics*, 21(7): 951-960 (2005), Altschul et al., *Nucleic Acids Res.*, 25(17): 3389-3402 (1997), and Gusfield, *Algorithms on Strings, Trees and Sequences*, Cambridge University Press, Cambridge UK (1997)).

The adenovirus or adenoviral vector can comprise one, two, three, four, or all five of the aforementioned sequences alone or in any combination. In this respect, the adenovirus or adenoviral vector can comprise any combination of any two of the aforementioned sequences, any combination of any three of the aforementioned sequences, any combination of any four of the aforementioned sequences, or all five of the aforementioned sequences.

As discussed herein, the adenovirus or adenoviral vector can be replication-competent, conditionally-replicating, or replication-deficient. Preferably, the adenovirus or adenoviral vector is replication-deficient, such that the replication-deficient adenovirus or adenoviral vector requires complementation of at least one replication-essential gene function of one or more regions of the adenoviral genome for propagation (e.g., to form adenoviral vector particles).

The replication-deficient adenovirus or adenoviral vector can be modified in any suitable manner to cause the deficiencies in the one or more replication-essential gene functions in one or more regions of the adenoviral genome for propagation. The complementation of the deficiencies in the one or more replication-essential gene functions of one or more regions of the adenoviral genome refers to the use of exogenous means to provide the deficient replication-essential gene functions. Such complementation can be effected in any suitable manner, for example, by using complementing cells and/or exogenous DNA (e.g., helper adenovirus) encoding the disrupted replication-essential gene functions.

The adenovirus or adenoviral vector can be deficient in one or more replication-essential gene functions of only the early regions (i.e., E1-E4 regions) of the adenoviral genome, only the late regions (i.e., L1-L5 regions) of the adenoviral genome, both the early and late regions of the adenoviral genome, or all adenoviral genes (i.e., a high capacity adenovector (HC-Ad). See Morsy et al., *Proc. Natl. Acad. Sci. USA*, 95: 965-976 (1998); Chen et al., *Proc. Natl. Acad. Sci. USA*, 94: 1645-1650 (1997); and Kochanek et al., *Hum. Gene Ther.*, 10: 2451-2459 (1999). Examples of replication-deficient adenoviral vectors are disclosed in U.S. Pat. Nos. 5,837,511; 5,851,806; 5,994,106; 6,127,175; 6,482,616; and 7,195,896, and International Patent Application Publications WO 1994/028152, WO 1995/002697, WO 1995/016772, WO 1995/034671, WO 1996/022378, WO 1997/012986, WO 1997/021826, and WO 2003/022311.

The early regions of the adenoviral genome include the E1, E2, E3, and E4 regions. The E1 region comprises the E1A and E1B subregions, and one or more deficiencies in replication-essential gene functions in the E1 region can include one or more deficiencies in replication-essential gene functions in either or both of the E1A and E1B subregions, thereby requiring complementation of the E1A subregion and/or the E1B subregion of the adenoviral genome for the adenovirus or adenoviral vector to propagate (e.g., to form adenoviral vector particles). The E2 region comprises the E2A and E2B subregions, and one or more deficiencies in replication-essential gene functions in the E2 region can include one or more deficiencies in replication-essential gene functions in either or both of the E2A and E2B subregions, thereby requiring complementation of the E2A subregion and/or the E2B subregion of the adenoviral genome for the adenovirus or adenoviral vector to propagate (e.g., to form adenoviral vector particles).

The E3 region does not include any replication-essential gene functions, such that a deletion of the E3 region in part or in whole does not require complementation of any gene functions in the E3 region for the adenovirus or adenoviral vector to propagate (e.g., to form adenoviral vector particles). In the context of the present disclosure, the E3 region is defined as the region that initiates with the open reading frame that encodes a protein with high homology to the 12.5K protein from the E3 region of human adenovirus 5 (NCBI reference sequence AP_000218) and ends with the open reading frame that encodes a protein with high homology to the 14.7K protein from the E3 region of human adenovirus 5 (NCBI reference sequence AP_000224.1). The E3 region can be deleted in whole or in part, or retained in whole or in part. The size of the deletion can be tailored so as to retain an adenovirus or adenoviral vector whose genome closely matches the optimum genome packaging size. A larger deletion will accommodate the insertion of larger heterologous nucleic acid sequences in the adenovirus or adenoviral genome. In one embodiment of the present disclosure, the L4 polyadenylation signal sequences, which reside in the E3 region, are retained.

The E4 region comprises multiple open reading frames (ORFs). An adenovirus or adenoviral vector with a deletion of all of the open reading frames of the E4 region except ORF6, and in some cases ORF3, does not require complementation of any gene functions in the E4 region for the adenovirus or adenoviral vector to propagate (e.g., to form adenoviral vector particles). Conversely, an adenovirus or adenoviral vector with a disruption or deletion of ORF6, and in some cases ORF3, of the E4 region (e.g., with a deficiency in a replication-essential gene function based in ORF6 and/or ORF3 of the E4 region), with or without a disruption or deletion of any of the other open reading frames of the E4 region or the native E4 promoter, polyadenylation sequence, and/or the right-side inverted terminal repeat (ITR), requires complementation of the E4 region (specifically, of ORF6 and/or ORF3 of the E4 region) for the adenovirus or adenoviral vector to propagate (e.g., to form adenoviral vector particles). The late regions of the adenoviral genome include the L1, L2, L3, L4, and L5 regions. The adenovirus or adenoviral vector also can have a mutation in the major late promoter (MLP), as discussed in International Patent Application Publication WO 2000/000628, which can render the adenovirus or adenoviral vector replication-deficient if desired.

The one or more regions of the adenoviral genome that contain one or more deficiencies in replication-essential gene functions desirably are one or more early regions of the adenoviral genome, i.e., the E1, E2, and/or E4 regions, optionally with the deletion in part or in whole of the E3 region.

The replication-deficient adenovirus or adenoviral vector also can have one or more mutations as compared to the wild-type adenovirus (e.g., one or more deletions, insertions, and/or substitutions) in the adenoviral genome that do not inhibit viral replication in host cells. Thus, in addition to one or more deficiencies in replication-essential gene functions, the adenovirus or adenoviral vector can be deficient in other respects that are not replication-essential. For example, the adenovirus or adenoviral vector can have a partial or entire deletion of the adenoviral early region known as the E3 region, which is not essential for propagation of the adenovirus or adenoviral genome.

In one embodiment, the adenovirus or adenoviral vector is replication-deficient and requires, at most, complementation of the E1 region or the E4 region of the adenoviral genome, for propagation (e.g., to form adenoviral vector particles). Thus, the replication-deficient adenovirus or adenoviral vector requires complementation of at least one replication-essential gene function of the E1A subregion and/or the E1B region of the adenoviral genome (denoted an E1-deficient adenoviral vector) or the E4 region of the adenoviral genome (denoted an E4-deficient adenoviral vector) for propagation (e.g., to form adenoviral vector particles). The adenovirus or adenoviral vector can be deficient in at least one replication-essential gene function (desirably all replication-essential gene functions) of the E1 region of the adenoviral genome and at least one gene function of the nonessential E3 region of the adenoviral genome (denoted an E1/E3-deficient adenoviral vector). The adenovirus or adenoviral vector can be deficient in at least one replication-essential gene function (desirably all replication-essential gene functions) of the E4 region of the adenoviral genome and at least one gene function of the nonessential E3 region of the adenoviral genome (denoted an E3/E4-deficient adenoviral vector).

In one embodiment, the adenovirus or adenoviral vector is replication-deficient and requires, at most, complementation of the E2 region, preferably the E2A subregion, of the adenoviral genome, for propagation (e.g., to form adenoviral vector particles). Thus, the replication-deficient adenovirus or adenoviral vector requires complementation of at least one replication-essential gene function of the E2A subregion of the adenoviral genome (denoted an E2A-deficient adenoviral vector) for propagation (e.g., to form adenoviral vector particles). The adenovirus or adenoviral vector can be deficient in at least one replication-essential gene function (desirably all replication-essential gene functions) of the E2A region of the adenoviral genome and at least one gene function of the nonessential E3 region of the adenoviral genome (denoted an E2A/E3-deficient adenoviral vector).

In one embodiment, the adenovirus or adenoviral vector is replication-deficient and requires, at most, complementation of the E1 and E4 regions of the adenoviral genome for propagation (e.g., to form adenoviral vector particles). Thus, the replication-deficient adenovirus or adenoviral vector requires complementation of at least one replication-essential gene function of both the E1 and E4 regions of the adenoviral genome (denoted an E1/E4-deficient adenoviral vector) for propagation (e.g., to form adenoviral vector particles). The adenovirus or adenoviral vector can be deficient in at least one replication-essential gene function (desirably all replication-essential gene functions) of the E1 region of the adenoviral genome, at least one replication-essential gene function of the E4 region of the adenoviral genome, and at least one gene function of the nonessential E3 region of the adenoviral genome (denoted an E1/E3/E4-deficient adenoviral vector). The adenovirus or adenoviral vector preferably requires, at most, complementation of the E1 region of the adenoviral genome for propagation, and does not require complementation of any other deficiency of the adenoviral genome for propagation. More preferably, the adenovirus or adenoviral vector requires, at most, complementation of the E1 and E4 regions of the adenoviral genome for propagation, and does not require complementation of any other deficiency of the adenoviral genome for propagation.

The adenovirus or adenoviral vector, when deficient in multiple replication-essential gene functions of the adenoviral genome (e.g., an E1/E4-deficient adenoviral vector), can include a spacer sequence to provide viral growth in a complementing cell line similar to that achieved by adenoviruses or adenoviral vectors deficient in a single replication-essential gene function (e.g., an E1-deficient adenoviral vector). The spacer sequence can contain any nucleotide sequence or sequences which are of a desired length, such as sequences at least about 15 base pairs (e.g., between about 15 nucleotides and about 12,000 nucleotides), preferably about 100 nucleotides to about 10,000 nucleotides, more preferably about 500 nucleotides to about 8,000 nucleotides, even more preferably about 1,500 nucleotides to about 6,000 nucleotides, and most preferably about 2,000 to about 3,000 nucleotides in length, or a range defined by any two of the foregoing values. The spacer sequence can be coding or non-coding and native or non-native with respect to the adenoviral genome, but does not restore the replication-essential function to the deficient region. The spacer also can contain an expression cassette. More preferably, the spacer comprises a polyadenylation sequence and/or a gene that is non-native with respect to the adenovirus or adenoviral vector. The use of a spacer in an adenoviral vector is further described in, for example, U.S. Pat. No. 5,851,806 and International Patent Application Publication WO 1997/021826.

By removing all or part of the adenoviral genome, for example, the E1, E3, and E4 regions of the adenoviral genome, the resulting adenovirus or adenoviral vector is able to accept inserts of exogenous nucleic acid sequences while retaining the ability to be packaged into adenoviral capsids. An exogenous nucleic acid sequence can be inserted at any position in the adenoviral genome so long as insertion in the position allows for the formation of adenovirus or the adenoviral vector particle. The exogenous nucleic acid sequence preferably is positioned in the E1 region, the E3 region, or the E4 region of the adenoviral genome.

The replication-deficient adenovirus or adenoviral vector of the present disclosure can be produced in complementing cell lines that provide gene functions not present in the replication-deficient adenovirus or adenoviral vector, but required for viral propagation, at appropriate levels in order to generate high titers of viral vector stock. Such complementing cell lines are known and include, but are not limited to, 293 cells (described in, e.g., Graham et al., J. Gen. Virol., 36: 59-72 (1977)), PER.C6 cells (described in, e.g., International Patent Application Publication WO 1997/000326, and U.S. Pat. Nos. 5,994,128 and 6,033,908), and 293-ORF6 cells (described in, e.g., International Patent Application Publication WO 95/34671 and Brough et al., J. Virol., 71: 9206-9213 (1997)). Other suitable complementing cell lines to produce the replication-deficient adenovirus or adenoviral vector of the present disclosure include complementing cells that have been generated to propagate adenoviral vectors encoding transgenes whose expression inhibits viral growth in host cells (see, e.g., U.S. Patent Application Publication No. 2008/0233650). Additional suitable complementing cells are described in, for example, U.S. Pat. Nos. 6,677,156 and 6,682,929, and International Patent Application Publication WO 2003/020879. In some instances, the cellular genome need not comprise nucleic acid sequences, the gene products of which complement for all of the deficiencies of a replication-deficient adenoviral vector. One or more replication-essential gene functions lacking in a replication-deficient adenoviral vector can be supplied by a helper virus, e.g., an adenoviral vector that supplies in trans one or more essential gene functions required for replication of the replication-deficient adenovirus or adenoviral vector. Alternatively, the inventive adenovirus or adenoviral vector can comprise a non-native replication-essential gene that complements for the one or more replication-essential gene functions lacking in the inventive replication-deficient adenovirus or adenoviral vector. For example, an E1/E4-deficient adenoviral vector can be engineered to contain a nucleic acid sequence encoding E4 ORF 6 that is obtained or derived from a different adenovirus (e.g., an adenovirus of a different serotype than the inventive adenovirus or adenoviral vector, or an adenovirus of a different species than the inventive adenovirus or adenoviral vector).

The adenovirus or adenoviral vector can further comprise a transgene. The term "transgene" is defined herein as a non-native nucleic acid sequence that is operably linked to appropriate regulatory elements (e.g., a promoter), such that the non-native nucleic acid sequence can be expressed to produce a protein (e.g., peptide or polypeptide). The regulatory elements (e.g., promoter) can be native or non-native to the adenovirus or adenoviral vector.

A "non-native" nucleic acid sequence is any nucleic acid sequence (e.g., DNA, RNA, or cDNA sequence) that is not a naturally occurring nucleic acid sequence of an adenovirus in a naturally occurring position. Thus, the non-native nucleic acid sequence can be naturally found in an adenovirus, but located at a non-native position within the adenoviral genome and/or operably linked to a non-native promoter. The terms "non-native nucleic acid sequence," "heterologous nucleic acid sequence," and "exogenous nucleic acid sequence" are synonymous and can be used interchangeably in the context of the present disclosure. The non-native nucleic acid sequence preferably is DNA and preferably encodes a protein (i.e., one or more nucleic acid sequences encoding one or more proteins).

The non-native nucleic acid sequence can encode a therapeutic protein that can be used to prophylactically or therapeutically treat a mammal for a disease. Examples of suitable therapeutic proteins include cytokines, toxins, tumor suppressor proteins, growth factors, hormones, receptors, mitogens, immunoglobulins, neuropeptides, neurotransmitters, and enzymes. Alternatively, the non-native nucleic acid sequence can encode an antigen of a pathogen (e.g., a bacterium or a virus), and the adenovirus or adenoviral vector can be used as a vaccine.

Viral Based Delivery System

The present disclosure also provides delivery systems, such as viral-based systems, in which a nucleic acid described herein is inserted. Representative viral expression vectors include, but are not limited to, adeno-associated viral vectors, adenovirus-based vectors, lentivirus-based vectors, retroviral vectors, and herpes virus-based vectors. In an embodiment, the viral vector is a lentivirus vector. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. In an additional embodiment, the viral vector is an adeno-associated viral vector. In a further embodiment, the viral vector is a retroviral vector. In general, and in embodiments, a suitable vector contains an origin of replication functional in at least one organism, a promoter sequence, convenient restriction endonuclease sites, and one or more selectable markers.

Additional suitable vectors include integrating expression vectors, which can randomly integrate into the host cell's DNA, or can include a recombination site to enable the specific recombination between the expression vector and the host cell's chromosome. Such integrating expression vectors can utilize the endogenous expression control sequences of the host cell's chromosomes to effect expression of the desired protein. Examples of vectors that integrate in a site specific manner include, for example, components of the flp-in system from Invitrogen (Carlsbad, Calif.) (e.g., pcDNATM5/FRT), or the cre-lox system, such as can be found in the pExchange-6 Core Vectors from Stratagene (La Jolla, Calif.). Examples of vectors that randomly integrate into host cell chromosomes include, for example, pcDNA3.1 (when introduced in the absence of T-antigen) from Invitrogen (Carlsbad, Calif.), and pCI or pFN10A (ACT) FLEXI™ from Promega (Madison, Wis.). Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto.

However, other constitutive promoter sequences can also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the present disclosure should not be limited to the use of constitutive promoters. Inducible promoters are also contemplated as part of the present disclosure. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

Reporter genes can be used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes can include genes encoding luciferase, beta-galactosidase, chloramphenicol acetyl transferase, secreted alkaline phosphatase, or the green fluorescent protein gene (e.g., Ui-Tei et al., FEBS Letters 479: 79-82 (2000)). Suitable expression systems are well known and can be prepared using known techniques or obtained commercially. In general, the construct with the minimal 5' flanking region showing the highest level of expression of reporter gene is identified as the promoter. Such promoter regions can be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (Molecular Cloning: A Laboratory Manual, Cold Spring Harbor Laboratory, New York (2001)). In embodiments, a method for the introduction of a polynucleotide into a host cell is calcium phosphate transfection or polyethylenimine (PEI) Transfection.

Biological methods for introducing a polynucleotide of interest into a host cell include the use of DNA and RNA vectors. Viral vectors, and especially retroviral vectors, have become the most widely used method for inserting genes into mammalian, e g, human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Non-Viral Based Delivery System

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

The use of lipid formulations is contemplated for the introduction of the nucleic acids into a host cell (in vitro, ex vivo or in vivo). In another aspect, the nucleic acid can be associated with a lipid. The nucleic acid associated with a lipid can be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they can be present in a bilayer structure, as micelles, or with a "collapsed" structure. They can also simply be interspersed in a solution, possibly forming aggregates that are not uniform in size or shape. Lipids are fatty substances which can be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Chol") can be obtained from Calbiochem-Behring; dimyristyl phosphatidylglycerol ("DMPG") and other lipids can be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., *Glycobiology* 5: 505-10 (1991)). However, compositions that have different structures in solution than the normal vesicular structure are also encompassed. For example, the lipids can assume a micellar structure or merely exist as nonuniform aggregates of lipid molecules. Also contemplated are lipofectamine-nucleic acid complexes.

In some instances, polynucleotides encoding polypeptides can also be introduced into cells using non-viral based delivery systems, such as the "Sleeping Beauty (SB) Transposon System," which refers a synthetic DNA transposon system for introducing DNA sequences into the chromosomes of vertebrates. Some exemplary embodiments of the system are described, for example, in U.S. Pat. Nos. 6,489,458 and 8,227,432. The Sleeping Beauty transposon system is composed of a Sleeping Beauty (SB) transposase and a SB transposon. In embodiments, the Sleeping Beauty transposon system can include the SB11 transposon system, the SB100X transposon system, or the SB110 transposon system.

DNA transposons translocate from one DNA site to another in a simple, cut-and-paste manner Transposition is a precise process in which a defined DNA segment is excised from one DNA molecule and moved to another site in the same or different DNA molecule or genome. As do other Tc1/mariner-type transposases, SB transposase inserts a transposon into a TA dinucleotide base pair in a recipient DNA sequence. The insertion site can be elsewhere in the same DNA molecule, or in another DNA molecule (or chromosome). In mammalian genomes, including humans, there are approximately 200 million TA sites. The TA insertion site is duplicated in the process of transposon integration. This duplication of the TA sequence is a hallmark of transposition and used to ascertain the mechanism in some experiments. The transposase can be encoded either within the transposon or the transposase can be supplied by another source, for instance a DNA or mRNA source, in which case the transposon becomes a non-autonomous element. Non-autonomous transposons are most useful as genetic tools because after insertion they cannot independently continue to excise and re-insert. SB transposons envisaged to be used as non-viral vectors for introduction of genes into genomes of vertebrate animals and for gene therapy.

Regardless of the method used to introduce exogenous nucleic acids into a host cell or otherwise expose a cell to the inhibitor of the present disclosure, in order to confirm the presence of the recombinant DNA sequence in the host cell, a variety of assays can be performed. Such assays include, for example, molecular assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the present disclosure.

In embodiments, a modified effector cell described herein and other genetic elements are delivered to a cell using the SB11 transposon system, the SB100X transposon system, the SB110 transposon system, the piggyBac transposon system (see, e.g., Wilson et al, "PiggyBac Transposon-mediated Gene Transfer in Human Cells," *Molecular Therapy* 15:139-145 (2007), incorporated herein by reference in its entirety) and/or the piggyBac transposon system (see, e.g., Mitra et al., "Functional characterization of piggyBac from the bat *Myotis lucifugus* unveils an active mammalian DNA transposon," *Proc. Natl. Acad. Sci USA* 110:234-239 (2013). Additional transposases and transposon systems are provided in U.S. Pat. Nos. 6,489,458; 6,613,752, 7,148,203; 7,985,739; 8,227,432; 9,228,180; U.S. Patent Publn. No. 2011/0117072; Mates et al., *Nat Genet.*, 41(6):753-61 (2009). doi: 10.1038/ng.343. Epub 2009 May 3, *Gene Ther.*, 18(9):849-56 (2011). doi: 10.1038/gt.2011.40. Epub 2011 Mar. 31 and in Ivics et al., *Cell.* 91(4):501-10, (1997), each of which is incorporated herein by reference in their entirety.

Additional suitable non-viral systems can include integrating expression vectors, which can randomly integrate into the host cell's DNA, or can include a recombination site to enable the specific recombination between the expression vector and the host cell's chromosome. Targeted integration of transgenes into predefined genetic loci is a desirable goal for many applications. First, a first recombination site for a site-specific recombinase is inserted at a genomic site, either at a random or at a predetermined location. Subsequently, the cells are transfected with a plasmid carrying the gene or DNA of interest and the second recombination site and a source for recombinase (expression plasmid, RNA, protein, or virus-expressing recombinase). Recombination between the first and second recombination sites leads to integration of plasmid DNA.

Such integrating expression vectors can utilize the endogenous expression control sequences of the host cell's chromosomes to effect expression of the desired protein. In some embodiments, targeted integration is promoted by the presence of sequences on the donor polynucleotide that are homologous to sequences flanking the integration site. For example, targeted integration using the donor polynucleotides described herein can be achieved following conventional transfection techniques, e.g. techniques used to create gene knockouts or knockins by homologous recombination. In other embodiments, targeted integration is promoted both by the presence of sequences on the donor polynucleotide that are homologous to sequences flanking the integration site, and by contacting the cells with donor polynucleotide in the presence of a site-specific recombinase. By a site-specific recombinase, or simply a recombinase, it is meant is a polypeptide that catalyzes conservative site-specific recombination between its compatible recombination sites. As used herein, a site-specific recombinase includes native polypeptides as well as derivatives, variants and/or fragments that retain activity, and native polynucleotides, derivatives, variants, and/or fragments that encode a recombinase that retains activity.

Also provided herein is a system for integrating heterologous genes in a host cell, said system comprising one or more gene expression cassettes. In some instances, the system includes a first gene expression cassette comprising a first polynucleotide encoding a first polypeptide construct. In other instances, the system can include a second gene expression cassette comprising a second polynucleotide encoding a second polypeptide construct. In yet other instances, the system can include a third gene expression cassette. In one embodiment, one of the gene expression cassettes can comprise a gene switch polynucleotide encoding one or more of: (i) a transactivation domain; (ii) nuclear receptor ligand binding domain; (iii) a DNA-binding domain; and (iv) ecdysone receptor binding domain. In another embodiment, the system further includes recombinant attachment sites; and a serine recombinase; such that upon contacting said host cell with at least said first gene expression cassette, in the presence of said serine recombinase, said heterologous genes are integrated in said host cell.

In some instances, the system further comprises a ligand; such that upon contacting said host cell, in the presence of said ligand, said heterologous gene are expressed in said host cell. In one instance, the system also includes recombinant attachment sites. In some instances, one recombination attachment site is a phage genomic recombination attachment site (attP) or a bacterial genomic recombination attachment site (attB). In one instance, the host cell is an eukaryotic cell. In another instance, the host cell is a human cell. In further instances, the host cell is a T cell or NK cell.

Promoters

"Promoter" refers to a region of a polynucleotide that initiates transcription of a coding sequence. Promoters are located near the transcription start sites of genes, on the same strand and upstream on the DNA (towards the 5' region of the sense strand). Some promoters are constitutive as they are active in all circumstances in the cell, while others are regulated becoming active in response to specific stimuli, e.g., an inducible promoter. Yet other promoters are tissue specific or activated promoters, including but not limited to T-cell specific promoters.

The term "promoter activity" and its grammatical equivalents as used herein refer to the extent of expression of nucleotide sequence that is operably linked to the promoter whose activity is being measured. Promoter activity can be measured directly by determining the amount of RNA transcript produced, for example by Northern blot analysis or indirectly by determining the amount of product coded for by the linked nucleic acid sequence, such as a reporter nucleic acid sequence linked to the promoter.

"Inducible promoter" as used herein refers to a promoter which is induced into activity by the presence or absence of transcriptional regulators, e.g., biotic or abiotic factors. Inducible promoters are useful because the expression of genes operably linked to them can be turned on or off at certain stages of development of an organism or in a particular tissue. Examples of inducible promoters are alcohol-regulated promoters, tetracycline-regulated promoters, steroid-regulated promoters, metal-regulated promoters, pathogenesis-regulated promoters, temperature-regulated promoters and light-regulated promoters. In one embodiment, the inducible promoter is part of a genetic switch. The inducible promoter can be a gene switch ligand inducible promoter. In some cases, an inducible promoter can be a small molecule ligand-inducible two polypeptide ecdysone receptor-based gene switch, such as RHEOSWITCH® gene switch. In some cases, a gene switch can be selected from ecdysone-based receptor components as described in, but without limitation to, any of the systems described in: PCT/US2001/009050 (WO 2001/070816); U.S. Pat. Nos. 7,091,038; 7,776,587; 7,807,417; 8,202,718; PCT/US2001/030608 (WO 2002/029075); U.S. Pat. Nos. 8,105,825; 8,168,426; PCT/IJ52002/005235 (WO 2002/066613); U.S. application Ser. No. 10/468,200 (U.S. Pub. No. 20120167239); PCT/US2002/005706 (WO 2002/066614); U.S. Pat. Nos. 7,531,326; 8,236,556; 8,598,409; PCT/US2002/005090 (WO 2002/066612); U.S. Pat. No. 8,715,959 (U.S. Pub. No. 20060100416); PCT/US2002/005234 (WO 2003/027266); U.S. Pat. Nos. 7,601,508; 7,829,676; 7,919,269; 8,030,067; PCT/US2002/005708 (WO 2002/066615); U.S. application Ser. No. 10/468,192 (U.S. Pub. No. 20110212528); PCT/US2002/005026 (WO 2003/027289); U.S. Pat. Nos. 7,563,879; 8,021,878; 8,497,093; PCT/US2005/015089 (WO 2005/108617); U.S. Pat. Nos. 7,935,510; 8,076,454; PCT/US2008/011270 (WO 2009/045370); U.S. application Ser. No. 12/241,018 (U.S. Pub. No. 20090136465); PCT/US2008/011563 (WO 2009/048560); U.S. application Ser. No. 12/247,738 (U.S. Pub. No. 20090123441); PCT/US2009/005510 (WO 2010/042189); U.S. application Ser. No. 13/123,129 (U.S. Pub. No. 20110268766); PCT/US2011/029682 (WO 2011/119773); U.S. application Ser. No. 13/636,473 (U.S. Pub. No. 20130195800); PCT/US2012/027515 (WO 2012/122025); and, U.S. Pat. No. 9,402,919 each of which is incorporated by reference in its entirety).

Provided herein are methods comprising administering to a subject at least one non-viral vector comprising a polynucleotide encoding a polypeptide sequence described herein comprising at least two functional proteins or portions thereof; at least one promoter; and at least one engineered recombination site; wherein said at least one promoter drives expression of said at least two functional proteins. In some cases, at least one promoter can be constitutive. In some cases, at least one promoter can be tissue-specific. In some cases, at least one promoter can be inducible. In some cases, an inducible promoter is a small molecule ligand-inducible two polypeptide ecdysone receptor-based gene switch. In other cases, a combination of promoters wherein at least one promoter can be inducible and at least one promoter can be activation specific can be utilized.

An inducible promoter utilizes a ligand for dose-regulated control of expression of said at least two genes. In some cases, a ligand can be selected from a group consisting of ecdysteroid, 9-cis-retinoic acid, synthetic analogs of retinoic acid, N,N'-diacylhydrazines, oxadiazolines, dibenzoylalkyl cyanohydrazines, N-alkyl-N,N'-diaroylhydrazines, N-acyl-N-alkylcarbonylhydrazines, N-aroyl-N-alkyl-N'-aroylhydrazines, amidoketones, 3,5-di-tert-butyl-4-hydroxy-N-isobutyl-benzamide, 8-O-acetylharpagide, oxysterols, 22(R) hydroxycholesterol, 24(S) hydroxycholesterol, 25-epoxycholesterol, T0901317, 5-alpha-6-alpha-epoxycholesterol-3-sulfate (ECHS), 7-ketocholesterol-3-sulfate, framesol, bile acids, 1,1-biphosphonate esters, juvenile hormone III, RG-115819 (3,5-Dimethyl-benzoic acid N-(1-ethyl-2,2-dimethyl-propyl)-N'-(2-methyl-3-methoxy-benzoyl)-hydrazide-), RG-115932 ((R)-3,5-Dimethyl-benzoic acid N-(1-tert-butyl-butyl)-N'-(2-ethyl-3-methoxy-benzoyl)-hydrazide), and RG-115830 (3,5-Dimethyl-benzoic acid N-(1-tert-butyl-butyl)-N'-(2-ethyl-3-methoxy-benzoyl)-hydrazide), and any combination thereof.

In some embodiments, a promoter is an inducible promoter. In some embodiments, a promoter is a non-inducible promoter. In some cases, a promoter can be a tissue-specific promoter. Herein "tissue-specific" refers to regulated expression of a gene in a subset of tissues or cell types. In some cases, a tissue-specific promoter can be regulated spatially such that the promoter drives expression only in certain tissues or cell types of an organism. In other cases, a tissue-specific promoter can be regulated temporally such that the promoter drives expression in a cell type or tissue differently across time, including during development of an organism. In some cases, a tissue-specific promoter is regulated both spatially and temporally. In certain embodiments, a tissue-specific promoter is activated in certain cell types either constitutively or intermittently at particular times or stages of the cell type. For example, a tissue-specific promoter can be a promoter that is activated when a specific cell such as a T cell or a NK cell is activated. T cells can be activated in a variety of ways, for example, when presented with peptide antigens by MHC class II molecules.

In one case, at least one promoter is an engineered promoter or variants thereof. As described herein, the promoter can incorporate minimal promoter sequences from IL-2 and one or more of the following: nuclear factor of activated T-cells (NFAT) response element(s); NFIL2D response element, NFkB/TCF response element, NF_AT/NFIL2B response element or NFIL2A/OCT response element. Examples of response elements are described in Mattila et al., *EMBO J.* 9(13):4425-33 (1990); incorporated herein in its entirety.

In some embodiments, at least one promoter comprises IL-2 core promoter (SEQ ID NO: 26). In one embodiment, at least one promoter comprises IL-2 minimal promoter (SEQ ID NO: 27). In another embodiment, at least one promoter comprises IL-2 enhancer and promoter variant (SEQ ID NOS: 26-28). In yet another embodiment, at least one promoter comprises NF-κB binding site (SEQ ID NOS: 30-32). In some embodiments, at least one promoter comprises (NF-κB)$_1$-IL2 promoter variant (SEQ ID NO: 30). In some embodiments, at least one promoter comprises (NF-κB)$_3$-IL2 promoter variant (SEQ ID NO: 31). In some embodiments, at least one promoter comprises (NF-κB)$_6$-IL2 promoter variant (SEQ ID NO: 32). In one embodiment, at least one promoter comprises 1× nuclear factor of activated T-cells (NFAT) response elements-IL2 promoter variant (SEQ ID NO: 33). In another embodiment, at least one promoter comprises 3×NFAT response element (SEQ ID NOS: 34-35). In yet another embodiment, at least one promoter comprises 6×NFAT response elements-IL2 promoter variant (SEQ ID NOS: 36-39). In some embodiments, at least one promoter comprises human EF1A1 promoter variant (SEQ ID NOS: 40-41). In some embodiment, at least one promoter comprises human EF1A1 promoter and enhancer (SEQ ID NO: 42). In some embodiments, at least one promoter comprises human UBC promoter (SEQ ID NO: 43). In some embodiments, at least one promoter comprises 6 site GAL4-inducible proximal factor binding element (PFB). In some embodiment, at least one promoter comprises synthetic minimal promoter 1 (inducible promoter) (SEQ ID NO: 44).

Use of gene switch for ligand inducible control of IL-12 expression described herein can improve the safety profile of IL-12 by for example allowing for regulated expression and improving therapeutic index. However, a condition for ligand dose dependent expression of IL-12 using gene switch(es) is the presence or absence of activator ligand (e.g. veledimex). In certain embodiments, an additional conditional control for induction of IL-12 expression is contemplated. Gene switch components under the control of T cell activated specific promoters are provided. This results in conditional expression (e.g., T cell activation) of gene switch components necessary for veledimex controlled expression of transgene(s) under control of a gene switch. In some embodiments, this results in preferential expression of cytokines such as IL-12 or IL-15 by tumor specific T cells when veledimex is present and T cells are activated. This can lead to increased localized levels of gene switch controlled transgene expression.

For example, T cell activation specific expression of gene switch components can be controlled by promoter comprising Nuclear Factor of Activated T-cells (NFAT) response element(s). NFAT transcription factors are key modulators of effector T-cell states. NFATs are early transcriptional checkpoint progressively driving exhaustion. NFATs are quickly activated in T cells following TCR stimulation and form a protein complex with AP-1 induced by appropriate co-stimulation signaling and regulate effector genes and T-cell functions. NFAT response element(s) can be fused with other minimal promoter sequences (e.g. IL2 minimal promoter) to drive expression of transgenes in response to T cell activation.

Other examples of activation specific promoters include but are not limited to interleukin-2 (IL2) promoter and Programmed Death (PD)-1 (CD279) promoter. Gene switch components can also be conditionally expressed upon immune cell activation by fusing binding sites for other nuclear factors like NF-κB of proinflammatory signaling pathway to minimal promoter sequence (e.g. IL2).

In certain embodiments, the promoter can be any one or more of: IL-2 core promoter, IL-2 minimal promoter, IL-2 enhancer and promoter variant, (NF-κB)$_1$-IL2 promoter variant, (NF-κB)$_3$-IL2 promoter variant, (NF-κB)$_6$-IL2 promoter variant, 1×NFAT response elements-IL2 promoter variant, 3×NFAT response elements-IL2 promoter variant, 6×NFAT response elements-IL2 promoter variant, human EEF1A1 promoter variant, human EEF1A1 promoter and enhancer, human UBC promoter and synthetic minimal promoter 1. In certain embodiments, the promoter nucleotides can comprise SEQ ID NOs: 26-44.

Gene Switch

Provided herein are gene switch polypeptides, polynucleotides encoding ligand-inducible gene switch polypeptides, and methods and systems incorporating these polypeptides and/or polynucleotides. In certain aspects, the present disclosure is directed to a polynucleotide comprising one or more polynucleotides encoding a gene switch system for inducible control of heterologous gene expression, wherein the heterologous gene expression is regulated by said gene switch system; and, wherein said heterologous gene comprises a polynucleotide encoding a polypeptide comprising one or more immune response-inducing hepatitis B virus (HBV) polypeptides, disclosed herein.

The term "gene switch" refers to the combination of a response element associated with a promoter, and for instance, an EcR based system which, in the presence of one or more ligands, modulates the expression of a gene into which the response element and promoter are incorporated. Tightly regulated inducible gene expression systems or gene switches are useful for various applications such as gene therapy, large scale production of proteins in cells, cell based high throughput screening assays, functional genomics and regulation of traits in transgenic plants and animals. Such inducible gene expression systems can include ligand inducible heterologous gene expression systems.

An early version of EcR-based gene switch used *Drosophila melanogaster* EcR (DmEcR) and *Mus musculus* RXR (MmRXR) polypeptides and showed that these receptors in the presence of steroid, ponasteroneA, transactivate reporter genes in mammalian cell lines and transgenic mice (Christopherson et al., *Proc. Natl. Acad. Sci. USA* 89(14):6314-18 (1992); No et al., *Proc. Natl. Acad. Sci. USA* 93(8):3346-51 (1996)). Later, Suhr et al. (*Proc. Natl. Acad. Sci. USA* 95(14):7999-8004 (1998)) showed that non-steroidal ecdysone agonist, tebufenozide, induced high level of transactivation of reporter genes in mammalian cells through *Bombyx mori* EcR (BmEcR) in the absence of exogenous heterodimer partner.

International Patent Applications No. PCT/US97/05330 (WO 97/38117) and PCT/US99/08381 (WO99/58155) disclose methods for modulating the expression of an exogenous gene in which a DNA construct comprising the exogenous gene and an ecdysone response element is activated by a second DNA construct comprising an ecdysone receptor that, in the presence of a ligand therefor, and optionally in the presence of a receptor capable of acting as a silent partner, binds to the ecdysone response element to induce gene expression. In this example, the ecdysone receptor was isolated from *Drosophila melanogaster*. Typically, such systems require the presence of the silent partner, preferably retinoid X receptor (RXR), in order to provide optimum activation. In mammalian cells, insect ecdysone receptor (EcR) is capable of heterodimerizing with mammalian retinoid X receptor (RXR) and, thereby, be used to regulate expression of target genes or heterologous genes in a ligand dependent manner. International Patent Application No. PCT/US98/14215 (WO 99/02683) discloses that the ecdysone receptor isolated from the silk moth *Bombyx mori* is functional in mammalian systems without the need for an exogenous dimer partner.

U.S. Pat. No. 6,265,173 discloses that various members of the steroid/thyroid superfamily of receptors can combine with *Drosophila melanogaster* ultraspiracle receptor (USP) or fragments thereof comprising at least the dimerization domain of USP for use in a gene expression system. U.S. Pat. No. 5,880,333 discloses a *Drosophila melanogaster* EcR and ultraspiracle (USP) heterodimer system used in plants in which the transactivation domain and the DNA binding domain are positioned on two different hybrid proteins. In each of these cases, the transactivation domain and the DNA binding domain (either as native EcR as in International Patent Application No. PCT/US98/14215 or as modified EcR as in International Patent Application No. PCT/US97/05330) were incorporated into a single molecule and the other heterodimeric partners, either USP or RXR, were used in their native state.

International Patent Application No. PCT/US01/0905 discloses an ecdysone receptor-based inducible gene expression system in which the transactivation and DNA binding domains are separated from each other by placing them on two different proteins results in greatly reduced background activity in the absence of a ligand and significantly increased activity over background in the presence of a ligand. This two-hybrid system is a significantly improved inducible gene expression modulation system compared to the two systems disclosed in applications PCT/US97/05330 and PCT/US98/14215. The two-hybrid system is believed to exploit the ability of a pair of interacting proteins to bring the transcription activation domain into a more favorable position relative to the DNA binding domain such that when the DNA binding domain binds to the DNA binding site on the gene, the transactivation domain more effectively activates the promoter (see, for example, U.S. Pat. No. 5,283, 173). The two-hybrid gene expression system comprises two gene expression cassettes; the first encoding a DNA binding domain fused to a nuclear receptor polypeptide, and the second encoding a transactivation domain fused to a different nuclear receptor polypeptide. In the presence of ligand, it is believed that a conformational change is induced which promotes interaction of the first polypeptide with the second polypeptide thereby resulting in dimerization of the DNA binding domain and the transactivation domain. Since the DNA binding and transactivation domains reside on two different molecules, the background activity in the absence of ligand is greatly reduced.

Another surprising discovery was that certain modifications of the two-hybrid system could also provide improved sensitivity to non-steroidal ligands for example, diacylhydrazines, when compared to steroidal ligands for example, ponasterone A ("PonA") or muristerone A ("MurA"). That is, when compared to steroids, the non-steroidal ligands provided higher gene transcription activity at a lower ligand concentration. Furthermore, the two-hybrid system avoids some side effects due to overexpression of RXR that can occur when unmodified RXR is used as a switching partner. In a preferred two-hybrid system, native DNA binding and transactivation domains of EcR or RXR are eliminated and as a result, these hybrid molecules have less chance of interacting with other steroid hormone receptors present in the cell, thereby resulting in reduced side effects.

The ecdysone receptor (EcR) is a member of the nuclear receptor superfamily and is classified into subfamily 1, group H (referred to herein as "Group H nuclear receptors"). The members of each group share 40-60% amino acid identity in the E (ligand binding) domain (Laudet et al., A Unified Nomenclature System for the Nuclear Receptor Subfamily, 1999; *Cell* 97: 161-163). In addition to the ecdysone receptor, other members of this nuclear receptor subfamily 1, group H include: ubiquitous receptor (UR), Orphan receptor 1 (OR-1), steroid hormone nuclear receptor 1 (NER-1), RXR interacting protein-15 (RIP-15), liver x receptor β (LXRβ), steroid hormone receptor like protein (RLD-1), liver x receptor (LXR), liver x receptor α (LXRα), farnesoid x receptor (FXR), receptor interacting protein 14 (RIP-14), and farnesol receptor (HRR-1).

In some cases, an inducible promoter can be a small molecule ligand-inducible two polypeptide ecdysone receptor-based gene switch, such as Intrexon Corporation's RHEOSWITCH® gene switch. In some cases, a gene switch can be selected from ecdysone-based receptor components as described in, but without limitation to, any of the systems described in: PCT/US2001/009050 (WO 2001/070816); U.S. Pat. Nos. 7,091,038; 7,776,587; 7,807,417; 8,202,718; PCT/US2001/030608 (WO 2002/029075); U.S. Pat. Nos. 8,105,825; 8,168,426; PCT/IJ52002/005235 (WO 2002/ 066613); U.S. application Ser. No. 10/468,200 (U.S. Pub. No. 20120167239); PCT/US2002/005706 (WO 2002/ 066614); U.S. Pat. Nos. 7,531,326; 8,236,556; 8,598,409; PCT/US2002/005090 (WO 2002/066612); U.S. Pat. No. 8,715,959 (U.S. Pub. No. 20060100416); PCT/US2002/ 005234 (WO 2003/027266); U.S. Pat. Nos. 7,601,508; 7,829,676; 7,919,269; 8,030,067; PCT/US2002/005708 (WO 2002/066615); U.S. application Ser. No. 10/468,192 (U.S. Pub. No. 20110212528); PCT/US2002/005026 (WO 2003/027289); U.S. Pat. Nos. 7,563,879; 8,021,878; 8,497, 093; PCT/US2005/015089 (WO 2005/108617); U.S. Pat. Nos. 7,935,510; 8,076,454; PCT/US2008/011270 (WO 2009/045370); U.S. application Ser. No. 12/241,018 (U.S. Pub. No. 20090136465); PCT/US2008/011563 (WO 2009/ 048560); U.S. application Ser. No. 12/247,738 (U.S. Pub. No. 20090123441); PCT/US2009/005510 (WO 2010/ 042189); U.S. application Ser. No. 13/123,129 (U.S. Pub. No. 20110268766); PCT/US2011/029682 (WO 2011/ 119773); U.S. application Ser. No. 13/636,473 (U.S. Pub. No. 20130195800); PCT/US2012/027515 (WO 2012/ 122025); and, U.S. Pat. No. 9,402,919 each of which is incorporated by reference in its entirety.

Provided are systems for modulating the expression of a heterologous gene and an interleukin in a host cell, comprising polynucleotides expressing gene-switch polypeptides disclosed herein.

In some embodiments are systems for modulating the expression of a heterologous gene and a cytokine in a host cell, comprising a first gene expression cassette comprising a first polynucleotide encoding a first polypeptide; a second gene expression cassette comprising a second polynucleotide encoding a second polypeptide; and a ligand; wherein said first and second polypeptides comprise one or more of: (i) a transactivation domain; (ii) a DNA-binding domain; and (iii) a ligand binding domain; (iv) said heterologous gene; and (vi) said cytokine such that upon contacting said host cell with said first gene expression cassette and said second gene expression cassette in the presence of said ligand, said heterologous gene and said cytokine are expressed in said host cell. In some cases, the heterologous gene comprises an antigen binding polypeptide described herein. In some cases, the cytokine comprises at least one chemokine, interferon, interleukin, lymphokine, tumor necrosis factor, or variant or combination thereof. In some cases, the cytokine is an interleukin. In some cases the interleukin is at least one of IL12, IL2, IL15, IL21, and functional variants and fragments thereof. In some embodiments, the cytokines can be membrane bound or secreted. In other embodiments, the cytokines can be intracellular. The interleukin can comprise membrane bound IL-15 (mbIL-15) or a fusion of IL-15 and IL-15Rα. In some embodiments, a tribIL-15 is a membrane-bound chimeric IL-15 which can be co-expressed with a modified effector cell described herein. In some embodiments, the mbIL-15 comprises a full-length IL-15 (e.g., a native IL-15 polypeptide) or fragment or variant thereof, fused in frame with a full length IL-15Rα, functional fragment or variant thereof. In some cases, the IL-15 is indirectly linked to the IL-15Rα through a linker. In some instances, the mbIL-15 is as described in Hui-ton et al., "Tethered IL-15 augments antitumor activity and promotes a stem-cell memory subset in tumor-specific T cells," *Proc. Natl. Acad. Sci. USA* 113(48):E7788-E7797 (2016). In another aspect, the interleukin can comprise IL-12. In some embodiments, the IL-12 is a single chain IL-12 (scIL-12), protease sensitive IL-12, destabilized IL-12, membrane hound IL-12, intercalated IL-12. In some instances, the IL-12 variants are as described in WO2015/095249, WO2016/048903, WO2017/062953, all of which is incorporated by reference in their entireties.

Provided herein are polynucleotides encoding gene switch polypeptides, wherein said gene switch polypeptides comprise: a) a first gene switch polypeptide comprising a DNA-binding domain fused to a nuclear receptor ligand binding domain, and b) a second gene switch polypeptide comprising a transactivation domain fused to a nuclear receptor ligand binding domain, wherein the first gene switch polypeptide and the second gene switch polypeptide are connected by a linker. In some cases, the linker can be a linker described herein, for instance GSG linker, furinlink, a 2A linker such as F/T2A, T2A, p2A, GSG-p2A, variants and derivatives thereof. In other instances, the linker can be an IRES.

In some cases, the DNA binding domain (DBD) comprises a DBD described herein, for instance at least one of GAL4 (GAL4 DBD), a LexA DBD, a transcription factor DBD, a steroid/thyroid hormone nuclear receptor superfamily member DBD, a bacterial LacZ DBD, and a yeast DBD. The transactivation domain can comprise a transactivation domain described herein, for instance one of a VP16 transactivation domain, a p53 transactivation domain and a B42 acidic activator transactivation domain. The Nuclear receptor ligand binding domain can comprise at least one of a ecdysone receptor (EcR), a ubiquitous receptor, an orphan receptor 1, a NER-1, a steroid hormone nuclear receptor 1, a retinoid X receptor interacting protein-15, a liver X receptor β, a steroid hormone receptor like protein, a liver X receptor, a liver X receptor α, a farnesoid X receptor, a receptor interacting protein 14, and a farnesol receptor.

In some cases, the gene switch polypeptides connected by a polypeptide linker or ribosome-skipping sequence exhibit improved dose-dependent ligand-inducible control of gene expression compared to a ligand-inducible gene switch wherein the gene switch polypeptides are connected by non-coding sequences, such as an IRES. In some cases, the gene switch polypeptides connected by a 2A linker can exhibit improved dose-dependent ligand-inducible control of heterologous gene expression compared to a gene switch wherein said gene switch polypeptides are separated by an IRES.

In some embodiments, the gene switch comprises a VP16 transactivation domain. In one embodiment, the gene switch comprises at least one of an ecdysone receptor (EcR), a ubiquitous receptor, an orphan receptor 1, a NER-1, a steroid hormone nuclear receptor 1, a retinoid X receptor interacting protein-15, a liver X receptor β, a steroid hormone receptor like protein, a liver X receptor, a liver X receptor α, a farnesoid X receptor, a receptor interacting protein 14, and a farnesol receptor. In another embodiment, a DNA-binding domain (DBD) of the gene switch comprises at least one of GAL4 (GAL4 DBD), a LexA DBD, a transcription factor DBD, a steroid/thyroid hormone nuclear receptor superfamily member DBD, a bacterial LacZ DBD, and a yeast DBD. In yet another case, the gene switch further comprises at least one of ultraspiracle protein (USP), retinoid receptor X (RXR), functional fragments and variants thereof wherein said functional fragments and variants are capable of binding to an EcR.

The polypeptides and polynucleotides as described herein can be expressed in an engineered cell. Herein an engineered cell is a cell which has been modified from its natural or endogenous state. An example of an engineered cell is a cell described herein which has been modified (e.g., by transfection of a polynucleotide into the cell) to encode for example, gene switch polypeptides, gene of interest (GOI), cell tags, heterologous genes and any other polypeptides and polynucleotides described herein.

Ligands

In some embodiments, a ligand used for inducible gene switch regulation can be selected from any of, but without limitation to, following: N-[(1R)-1-(1,1-dimethylethyl) butyl]-N'-(2-ethyl-3-methoxybenzoyl)-3,5-dimethylbenzohydrazide (also referred to as veledimex), (2S,3R,5R,9R, 10R,13R,14S,17R)-17-[(2S,3R)-3,6-dihydroxy-6-methylheptan-2-yl]-2,3,14-trihydroxy-10,13-dimethyl-2,3, 4,5,9,11,12,15,16,17-decahydro-1H-cyclopenta[a] phenanthren-6-one; N'-(3,5-Dimethylbenzoyl)-N'-[(3R)-2, 2-dimethyl-3-hexanyl]-2-ethyl-3-methoxybenzohydrazide; 5-Methyl-2,3-dihydro-benzo[1,4]dioxine-6-carboxylic acid N'-(3,5-dimethyl-benzoyl)-N'-(1-ethyl-2,2-dimethyl-propyl)-hydrazide; 5-Methyl-2,3-dihydro-benzo[1,4]dioxine-6-carboxylic acid N'-(3,5-dimethoxy-4-methyl-benzoyl)-N'-(1-ethyl-2,2-dimethyl-propyl)-hydrazide; 5-Methyl-2,3-dihydro-benzo[1,4]dioxine-6-carboxylic acid N'-(1-tert-butyl-butyl)-N'-(3,5-dimethyl-benzoyl)-hydrazide; 5-Methyl-2,3-dihydro-benzo[1,4]dioxine-6-carboxylic acid N'-(1-tert-butyl-butyl)-N'-(3,5-dimethoxy-4-methyl-benzoyl)-hydrazide; 5-Ethyl-2,3-dihydro-benzo[1,4]dioxine-6-carboxylic acid N'-(3,5-dimethyl-benzoyl)-N'-(1-ethyl-2,2-dimethyl-propyl)-hydrazide; 5-Ethyl-2,3-dihydro-benzo[1, 4]dioxine-6-carboxylic acid N'-(3,5-dimethoxy-4-methyl-benzoyl)-N'-(1-ethyl-2,2-dimethyl-propyl)-hydrazide; 5-Ethyl-2,3-dihydro-benzo[1,4]dioxine-6-carboxylic acid N'-(1-tert-butyl-butyl)-N'-(3,5-dimethyl-benzoyl)-hydrazide; 5-Ethyl-2,3-dihydro-benzo[1,4]dioxine-6-carboxylic acid N'-(1-tert-butyl-butyl)-N'-(3,5-dimethoxy-4-methyl-benzoyl)-hydrazide; 3,5-Dimethyl-benzoic acid N-(1-ethyl-2,2-dimethyl-propyl)-N'-(3-methoxy-2-methyl-benzoyl)-hydrazide; 3,5-Dimethoxy-4-methyl-benzoic acid N-(1-ethyl-2,2-dimethyl-propyl)-N'-(3-methoxy-2-methyl-benzoyl)-hydrazide; 3,5-Dimethyl-benzoic acid N-(1-tert-butyl-butyl)-N'-(3-methoxy-2-methyl-benzoyl)-hydrazide; 3,5-Dimethoxy-4-methyl-benzoic acid N-(1-tert-butyl-butyl)-N'-(3-methoxy-2-methyl-benzoyl)-hydrazide; 3,5-Dimethyl-benzoic acid N-(1-ethyl-2,2-dimethyl-propyl)-N'-(2-ethyl-3-methoxy-benzoyl)-hydrazide; 3,5-Dimethoxy-4-methyl-benzoic acid N-(1-ethyl-2,2-dimethyl-propyl)-N'-(2-ethyl-3-methoxy-benzoyl)-hydrazide; 3,5-Dimethyl-benzoic acid N-(1-tert-butyl-butyl)-N'-(2-ethyl-3-methoxy-benzoyl)-hydrazide; 3,5-Dimethoxy-4-methyl-benzoic acid N-(1-tert-butyl-butyl)-N'-(2-ethyl-3-methoxy-benzoyl)-hydrazide; 2-Methoxy-nicotinic acid N-(1-tert-butyl-pentyl)-N'-(4-ethyl-benzoyl)-hydrazide; 3,5-Dimethyl-benzoic acid N-(2,2-dimethyl-1-phenyl-propyl)-N'-(4-ethyl-benzoyl)-hydrazide; 3,5-Dimethyl-benzoic acid N-(1-tert-butyl-pentyl)-N'-(3-methoxy-2-methyl-benzoyl)-hydrazide; and 3,5-Dimethoxy-4-methyl-benzoic acid N-(1-tert-butyl-pentyl)-N'-(3-methoxy-2-methyl-benzoyl)-hydrazide.

In some cases, a ligand used for dose-regulated control of ecdysone receptor-based inducible gene switch can be selected from any of, but without limitation to, an ecdysteroid, such as ecdysone, 20-hydroxyecdysone, ponasterone A, muristerone A, and the like, 9-cis-retinoic acid, synthetic analogs of retinoic acid, N,N'-diacylhydrazines such as those disclosed in U.S. Pat. Nos. 6,013,836; 5,117,057; 5,530,028; and 5,378,726 and U.S. Published Application Nos. 2005/0209283 and 2006/0020146; oxadiazolines as described in U.S. Published Application No. 2004/0171651; dibenzoylalkyl cyanohydrazines such as those disclosed in European Application No. 461,809; N-alkyl-N,N'-diaroyl-hydrazines such as those disclosed in U.S. Pat. No. 5,225,443; N-acyl-N-alkylcarbonylhydrazines such as those disclosed in European Application No. 234,994; N-aroyl-N-alkyl-N'-aroylhydrazines such as those described in U.S. Pat. No. 4,985,461; arnidoketones such as those described in U.S. Published Application No. 2004/0049037; each of which is incorporated herein by reference and other similar materials including 3,5-di-tert-butyl-4-hydroxy-N-isobutyl-benzamide, 8-O-acetylharpagide, oxysterols, 22(R) hydroxycholesterol, 24(S) hydroxycholesterol, 25-epoxycholesterol, T0901317, 5-alpha-6-alpha-epoxycholesterol-3-sulfate (ECHS), 7-ketocholesterol-3-sulfate, framesol, bile acids, 1,1-biphosphonate esters, juvenile hormone III, and the like. Examples of diacylhydrazine ligands useful in the present disclosure include RG-115819 (3,5-Dimethyl-benzoic acid N-(1-ethyl-2,2-dimethyl-propyl)-N'-(2-methyl-3-methoxy-benzoyl)-hydrazide-), RG-115932 ((R)-3,5-Dimethyl-benzoic acid N-(1-tert-butyl-butyl)-N'-(2-ethyl-3-methoxy-benzoyl)-hydrazide), and RG-115830 (3,5-Dimethyl-benzoic acid N-(1-tert-butyl-butyl)-N'-(2-ethyl-3-methoxy-benzoyl)-hydrazide). See, e.g., U.S. patent application Ser. No. 12/155,111, and PCT Appl. No. PCT/US2008/006757, both of which are incorporated herein by reference in their entireties.

Cytokines

In certain embodiments, HBV vaccine antigens provided herein may be co-delivered and/or co-expressed (e.g., as part of the same HBV antigen delivery vector or via a separate vector) along with other cytokines. Provided herein are polynucleotides encoding gene-switch polypeptides and a cytokine, or variant or derivative thereof, and methods and systems incorporating the same. Cytokine is a category of small proteins between about 5-20 kDa that are involved in cell signaling. In some instances, cytokines include chemokines, interferons, interleukins, colony-stimulating factors or tumor necrosis factors. In some embodiments, chemokines play a role as a chemoattractant to guide the migration of cells, and is classified into four subfamilies CXC, CC, CX3C, and XC. Exemplary chemokines include chemokines from the CC subfamily: CCL1, CCL2 (MCP-1), CCL3, CCL4, CCL5 (RANTES), CCL6, CCL7, CCL8, CCL9 (or CCL10), CCL11, CCL12, CCL13, CCL14, CCL15, CCL16, CCL17, CCL18, CCL19, CCL20, CCL21, CCL22, CCL23, CCL24, CCL25, CCL26, CCL27, and CCL28; the CXC subfamily CXCL1, CXCL2, CXCL3, CXCL4, CXCL5, CXCL6, CXCL7, CXCL8, CXCL9, CXCL10, CXCL11, CXCL12, CXCL13, CXCL14, CXCL15, CXCL16, and CXCL17; the XC subfamily XCL1 and XCL2; and the CX3C subfamily CX3CL1.

In certain embodiments, HBV vaccine antigens provided herein may be co-delivered and/or co-expressed (e.g., as part of the same HBV antigen delivery vector or via a separate vector) along with other interferons. Interferons (IFNs) comprise interferon type I (e.g. IFN-α, IFN-β, IFN-ε, IFN-κ, and IFN-ω), interferon type II (e.g. IFN-γ), and interferon type III. In some embodiments, IFN-α is further classified into about 13 subtypes including IFNA1, IFNA2, IFNA4, IFNA5, IFNA6, IFNA7, IFNA8, IFNA10, IFNA13, IFNA14, IFNA16, IFNA17, and IFNA21.

In certain embodiments, HBV vaccine antigens provided herein may be co-delivered and/or co-expressed (e.g., as part of the same HBV antigen delivery vector or via a separate vector) along with other interleukins. Interleukins are expressed by leukocytes or white blood cells and they promote the development and differentiation of T and B lymphocytes and hematopoietic cells. Exemplary interleukines include IL-1, IL-2, IL-3, IL-4, IL-5, IL-6, IL-7, IL-8 (CXCL8), IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IL-35, and IL-36. In some embodiments, interleukins are IL-2, IL-12, IL-15, IL-21 or a fusion of IL-15 and IL-15a.

In some aspects, the interleukin can comprise IL-12. In some embodiments, the IL-12 is a single chain IL-12 (scIL-12), protease sensitive IL-12, destabilized IL-12, membrane bound IL-12, intercalated IL-12. In some instances, the IL-12 variants are as described in WO2015/095249, WO2016/048903, WO2017/062953, all of which is incorporated by reference in their entireties.

In some embodiments, an interleukin comprises mbIL-15. In some embodiments, a mbIL-15 is a membrane-bound chimeric IL-15 which can be co-expressed with a modified effector cell described herein. In some embodiments, the mbIL-15 comprises a full-length IL-15 (e.g., a native IL-15 polypeptide) or fragment or variant thereof, fused in frame with a full length IL-15Rα, functional fragment or variant thereof. In some cases, the IL-15 is indirectly linked to the IL-15Ra through a linker. In some instances, the mbIL-15 is as described in Hurton et al., 2016.

In certain embodiments, HBV vaccine antigens provided herein may be co-delivered and/or co-expressed (e.g., as part of the same HBV antigen delivery vector or via a separate vector) along with other tumor necrosis factors. Tumor necrosis factors (TNFs) are a group of cytokines that modulate apoptosis. In some instances, there are about 19 members within the TNF family, including, not limited to, TNFα, lymphotoxin-alpha (LT-alpha), lymphotoxin-beta (LT-beta), T cell antigen gp39 (CD40L), CD27L, CD30L, FASL, 4-1BBL, OX40L, and TNF-related apoptosis inducing ligand (TRAIL).

In certain embodiments, HBV vaccine antigens provided herein may be co-delivered and/or co-expressed (e.g., as part of the same HBV antigen delivery vector or via a separate vector) along with other colony stimulating factors. Colony-stimulating factors (CSFs) are secreted glycoproteins that interact with receptor proteins on the surface of hemopoietic stem cells, which subsequently modulates cell proliferation and differentiation into specific kind of blood cells. In some instances, a CSF comprises macrophage colony-stimulating factor, granulocyte macrophage colony-stimulating factor (GM-CSF), granulocyte colony-stimulating factor (G-CSF) or promegapoietin.

In some embodiments, the cytokine is a membrane-bound cytokine, which is co-expressed with a chimeric antigen receptor described herein. In some embodiments, one or more methods described herein further comprise administration of a cytokine. In some instances, the cytokine comprises a chemokine, an interferon, an interleukin, a colony-stimulating factor or a tumor necrosis factor. In some instances, one or more methods described herein further comprise administration of a cytokine selected from a chemokine, an interferon, an interleukin, a colony-stimulating factor or a tumor necrosis factor. In some instances, one or more methods described herein further comprise administration of a cytokine selected from IL2, IL7, IL12, IL15, a fusion of IL-15 and IL-15Rα, IL21, IFNγ or TNF-α.

Interleukin-12

In particular embodiments, HBV vaccine antigens provided herein may be co-delivered and/or co-expressed (e.g., as part of the same HBV antigen delivery vector or via a separate vector) along with Interleukin-12. Interleukin 12 (IL-12) is an interleukin that is naturally produced by dendritic cells, macrophages, neutrophils, and human B-lymphoblastoid cells (NC-37) in response to antigenic stimulation. IL-12 is composed of a bundle of four alpha helices. It is a heterodimeric cytokine encoded by two separate genes, IL-12A (p35) and IL-12B (p40). The active heterodimer (referred to as p70), and a homodimer of p40 are formed following protein synthesis. IL-12 is the master regulator of the immune system. IL-12 promotes immune response by activating NK cells and T cells (FIG. 18).

Figure 8:
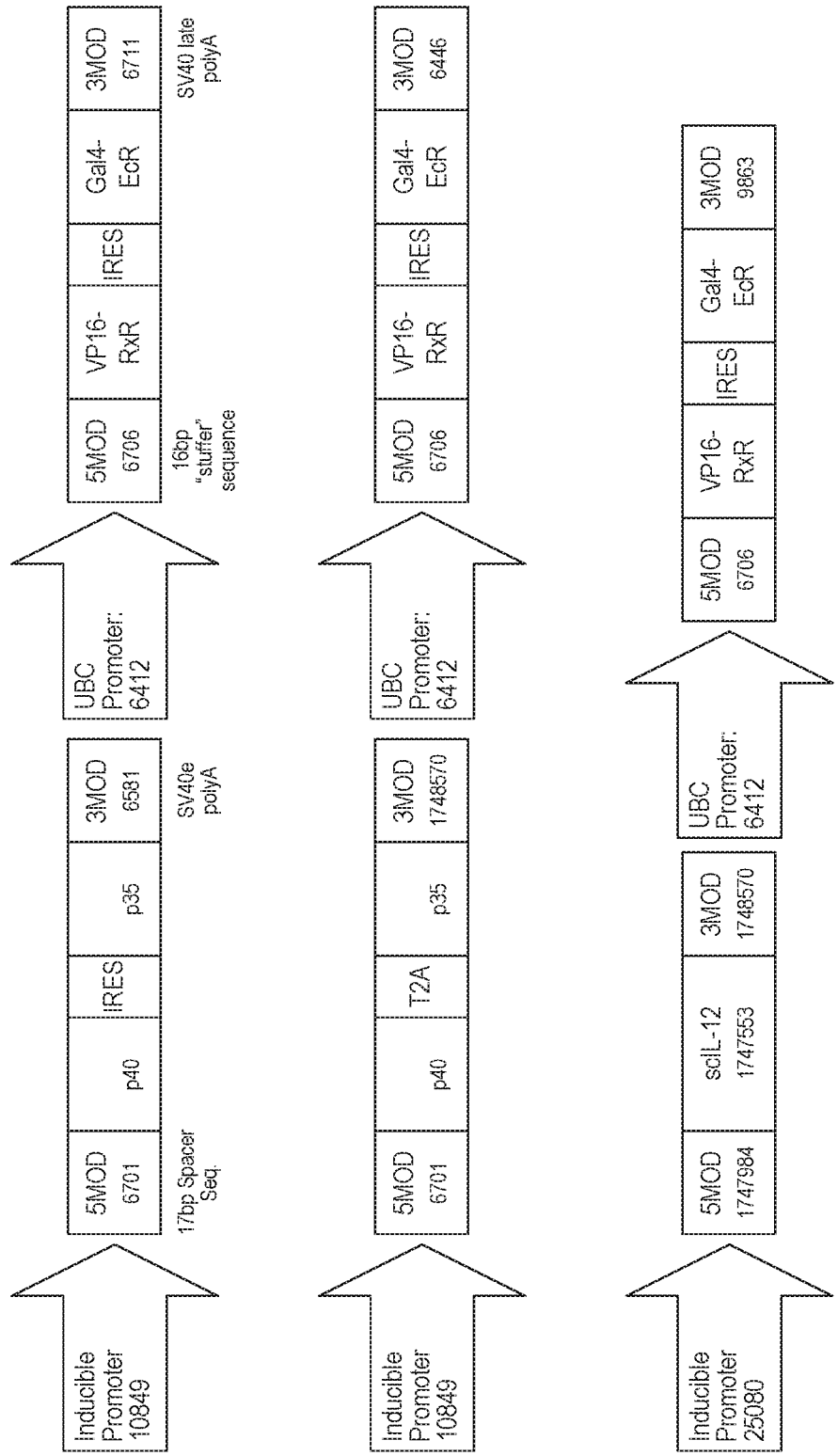
FIG. 8 shows various structural components of diverse IL-12 ligand-inducible gene switch vector systems.

Provided herein are compositions, kits, and system comprising and methods of making HBV recombinant vaccines. The present disclosure provides HBV antigen designs (HBV designs 1-5) constructed in a multi-deleted *gorilla* adenovector (GC46) (SEQ ID NOS: 61-63). Also provided herein are polynucleotides encoding gene-switch polypeptides and IL-12 or variant or derivative thereof, and methods and systems incorporating the same (FIG. 8).

Linkers

Also disclosed are constructs comprising a linker to facilitate the expression and functionality of the polynucleotides and polypeptides described herein. In some embodiments, a polynucleotide linker can be utilized in a polynucleotide described herein. A polynucleotide linker can be a double-stranded segment of DNA containing desired restriction sites that can be added to create end structures that are compatible with a vector comprising a polynucleotide described herein. In some cases, a polynucleotide linker can be useful for modifying vectors comprising polynucleotides described herein. For example, a vector modification comprising a polynucleotide linker can be a change in a multiple cloning site, or the addition of a poly-histidine tail. Polynucleotide linkers can also be used to adapt the ends of blunt insert DNA for cloning into a vector cleaved with a restriction enzyme with cohesive end termini. The use of polynucleotide linkers can be more efficient than a blunt ligation into a vector and can provide a method of releasing an insert from a vector in downstream applications. In some cases an insert can be a polynucleotide sequence encoding polypeptides useful for therapeutic applications. In some cases, a linker can be a cleavable linker.

A polynucleotide linker can be an oligomer. A polynucleotide linker can be a DNA double strand, single strand, or a combination thereof. In some cases, a linker can be RNA. A polynucleotide linker can be ligated into a vector comprising a polynucleotide described herein by a T4 ligase in some cases. To facilitate a ligation an excess of polynucleotide linkers can be added to a composition comprising an insert and a vector. In some cases, an insert and vector are pre-treated before a linker is introduced. For example, pre-treatment with a methylase can prevent unwanted cleavage of insert DNA.

In certain embodiments, two or more polypeptides encoded by a polynucleotide described herein can be separated by an intervening sequence encoding an intervening linker polypeptide. Herein the term "intervening linker polypeptide" referring to an amino acid sequence separating two or more polypeptides encoded by a polynucleotide is distinguished from the term "peptide linker" which refers to the sequence of amino acids which is optionally included in a polypeptide construct disclosed herein to connect the transmembrane domain to the cell surface polypeptide (e.g., comprising a truncated variant of a natural polypeptide). In certain cases, the intervening linker is a cleavage-susceptible intervening linker polypeptide. In some embodiments, the linker is a cleavable or ribosome skipping linker. In some embodiments, the cleavable linker or ribosome skipping linker sequence is selected from the group consisting of 2A, GSG-2A, GSG linker, SGSG linker, furinlink variants and derivatives thereof. In some embodiments, the 2A linker is a p2A linker, a T2A linker, F2A linker or E2A linker. In some embodiments, polypeptides of interest are expressed as fusion proteins linked by a cleavage-susceptible intervening linker polypeptide. In certain embodiments, cleavage-susceptible intervening linker polypeptide(s) can be any one or more of: F/T2A, T2A, p2A, 2A, GSG-p2A, GSG linker, and furinlink variants. Linkers (polynucleotide and polypeptide sequences) as disclosed in PCT/US2016/061668 (WO2017083750) published 18 May 2017 are incorporated by reference herein. In certain embodiments, the linker polypeptide comprises disclosed in the table below:

TABLE 2

Linker amino acid sequences and polynucleotide sequences

| Linker Name | SEQ ID NO: | Polynucleotide Sequence (5' to 3' where applicable) | SEQ ID NO: | Amino Acids Sequence (5' to 3' where applicable) |
|---|---|---|---|---|
| Whitlow Linker | 64 | GGCAGCACCTCCGGCAGCGGCAAGCCTGGCAGCGGCGAGGGCAGCACCAAGGGC | 81 | GSTSGSGKPGSGEGSTKG |

TABLE 2-continued

Linker amino acid sequences and polynucleotide sequences

| Linker Name | SEQ ID NO: | Polynucleotide Sequence (5' to 3' where applicable) | SEQ ID NO: | Amino Acids Sequence (5' to 3' where applicable) |
|---|---|---|---|---|
| Linker | 65 | TCTGGCGGAGGATCTGGAGGAGGCGGATCTGGAGGAGGAGGCAGTGGAGGCGGAGGATCTGGCGGAGGATCTCTGCAG | 82 | SGGGSGGGSGGGGSGGGGSGGGGSLQ |
| GSG linker | 66 | GGAAGCGGA | 83 | GSG |
| SGSG linker | 67 | AGTGGCAGCGGC | 84 | SGSG |
| (G4S)3 linker | 68 | GGTGGCGGTGGCTCGGGCGGTGGTGGGTCGGGTGGCGGCGGATCT | 85 | GGGGSGGGGSGGGGS |
| Furin cleavage site/Furinlink1 | 69 | CGTGCAAAGCGT | 86 | RAKR |
| Fmdv | 70 | AGAGCCAAGAGGGCACCGGTGAAACAGACTTTGAATTTTGACCTTCTGAAGTTGGCAGGAGACGTTGAGTCCAACCCTGGGCCC | 87 | RAKRAPVKQTLNFDLLKLAGDVESNPGP |
| *Thosea asigna* virus 2A region (T2A) | 71 | GAGGGCAGAGGAAGTCTGCTAACATGCGGTGACGTCGAGGAGAATCCTGGACCT | 88 | EGRGSLLTCGDVEENPGP |
| Furin-GSG-T2A | 72 | AGAGCTAAGAGGGGAAGCGGAGAGGGCAGAGGAAGTCTGCTAACATGCGGTGACGTCGAGGAGAATCCTGGACCT | 89 | RAKRGSGEGRGSLLTCGDVEENPGP |
| Furin-SGSG-T2A | 73 | AGGGCCAAGAGGAGTGGCAGCGGCGAGGGCAGAGGAAGTCTTCTAACATGCGGTGACGTGGAGGAGAATCCCGGCCCT | 90 | RAKRSGSGEGRGSLLTCGDVEENPGP |
| Porcine *teschovirus*-1 2A region (P2A) | 74 | GCAACGAACTTCTCTCTCCTAAAACAGGCTGGTGATGTGGAGGAGAATCCTGGTCCA | 91 | ATNFSLLKQAGDVEENPGP |
| GSG-P2A | 75 | GGAAGCGGAGCTACTAACTTCAGCCTGCTGAAGCAGGCTGGAGACGTGGAGGAGAACCCTGGACCT | 92 | GSGATNFSLLKQAGDVEENPGP |
| *Equine rhinitis* A virus 2A region (E2A) | 76 | CAGTGTACTAATTATGCTCTCTTGAAATTGGCTGGAGATGTTGAGAGCAACCCTGGACCT | 93 | QCTNYALLKLAGDVESNPGP |
| Foot-and-mouth disease virus 2A region (F2A) | 77 | GTCAAACAGACCCTAAACTTTGATCTGCTAAAACTGGCCGGGGATGTGGAAAGTAATCCCGGCCCC | 94 | VKQTLNFDLLKLAGDVESNPGP |
| FP2A | 78 | CGTGCAAAGCGTGCACCGGTGAAACAGGGAAGCGGAGCTACTAACTTCAGCCTGCTGAAGCAGGCTGGAGACGTGGAGGAGAACCCTGGACCT | 95 | RAKRAPVKQGSGATNFSLLKQAGDVEENPGP |
| Linker-GSG | 79 | GCACCGGTGAAACAGGGAAGCGGA | 96 | APVKQGSG |
| Linker | 80 | GCACCGGTGAAACAG | 97 | APVKQ |

In some embodiments, an intervening linker polypeptide comprises an amino acid sequence having at least 70%, 75%, 80%, 85%, 90%, 95%, 99%, 99.5% or 100% identity with the amino acid sequence of Whitlow linker (SEQ ID NO: 64), GSG linker (SEQ ID NO: 66), SGSG linker (SEQ ID NO: 67), (G4S)3 linker (SEQ ID NO: 68), Furin cleavage site/Furlink1 (SEQ ID NO: 69), Fmdv linker (SEQ ID NO: 70), Thosea asigna virus 2A region (T2A) (SEQ ID NO: 71), Furin-GSG-T2A (SEQ ID NO: 72), Furin-SGSG-T2A (SEQ ID NO: 73), porcine teschovirus-1 2A region (P2A) (SEQ ID NO: 74), GSG-P2A (SEQ ID NO: 75), equine rhinitis A virus 2A region (E2A) (SEQ ID NO: 76), or foot-and-mouth disease virus 2A region (F2A) (SEQ ID NO: 78) (Table 2). In some cases, an intervening linker polypeptide comprises an amino acid sequence having at least 70%, 75%, 80%, 85%, 90%, 95%, 99%, 99.5% or 100% identity with the amino acid sequence of linkers (SEQ ID NOS: 65, 79 80) In some cases, a viral 2A sequence can be used. 2A elements can be shorter than IRES, having from 5 to 100 base pairs. In some cases, a 2A sequence can have 5, 10, 15, 20, 25, 30, 35, 40, 45, 50, 55, 60, 65, 70, 75, 80, 85, 90, or 100 nucleotides in length. 2A linked genes can be expressed in one single open reading frame and "self-cleavage" can occur co-translationally between the last two amino acids, GP, at the C-terminus of the 2A polypeptide, giving rise to equal amounts of co-expressed proteins.

A viral 2A sequence can be about 20 amino acids. In some cases, a viral 2A sequence can contain a consensus motif Asp-Val/Ile-Glu-X-Asn-Pro-Gly-Pro. A consensus motif sequence can act co-translationally. For example, formation of a normal peptide bond between a glycine and proline residue can be prevented, which can result in ribosomal skipping and cleavage of a nascent polypeptide. This effect can produce multiple genes at equimolar levels.

A 2A peptide can allow translation of multiple proteins in a single open reading frame into a polypeptide that can be subsequently cleaved into individual polypeptide through a ribosome-skipping mechanism (Funston et al., *J. Gen. Virol.* 89(Pt 2):389-96 (2008)). In some embodiments, a 2A sequence can include: F/T2A, T2A, p2A, 2A, T2A, E2A, F2A, and BmCPV2A, BmIFV2A, and any combination thereof.

In some cases, a vector can comprise an IRES sequence and a 2A linker sequence. In other cases, expression of multiple genes linked with 2A peptides can be facilitated by a spacer sequence (GSG) ahead of the 2A peptides. In some cases, constructs can combine a spacers, linkers, adaptors, promoters, or combinations thereof. For example, a linker can have a spacer (SGSG or GSG or Whitlow linker) and furin linker (R-A-K-R) cleavage site with different 2A peptides. A spacer can be an I-Ceui. In some cases, a linker can be engineered. For example, a linker can be designed to comprise chemical characteristics such as hydrophobicity. In some cases, at least two linker sequences can produce the same protein. In other cases, multiple linkers can be used in a vector. For example, genes of interest can be separated by at least two linkers.

In certain embodiments, two or more polypeptides encoded by a polynucleotide described herein can be separated by an intervening sequence encoding a linker polypeptide. In certain cases, the linker is a cleavage-susceptible linker. In some embodiments, polypeptides of interest are expressed as fusion proteins linked by a cleavage-susceptible linker polypeptide. In certain embodiments, cleavage-susceptible linker polypeptide(s) can be any one or two of: Furinlink, fmdv, p2a, GSG-p2a, and/or fp2a described below. In some cases, a linker is APVKQGSG (SEQ ID NO: 96).

In certain cases, a linker polypeptide can comprise an amino acid sequence "RAKR" (SEQ ID NO: 86). In certain cases, a Furin linker polypeptide can be encoded by a polynucleotide sequence polynucleotide sequence comprising "CGTGCAAAGCGT" (SEQ ID NO: 69) or "AGAGCTAAGAGG." (SEQ ID NO: 130).

In some embodiments, a linker can be utilized in a polynucleotide described herein. A linker can be a flexible linker, a rigid linker, an in vivo cleavable linker, or any combination thereof. In some cases, a linker can link functional domains together (as in flexible and rigid linkers) or releasing free functional domain in vivo as in in vivo cleavable linkers.

Linkers can improve biological activity, increase expression yield, and achieving desirable pharmacokinetic profiles. A linker can also comprise hydrazone, peptide, disulfide, or thioesther.

In some cases, a linker sequence described herein can include a flexible linker. Flexible linkers can be applied when a joined domain requires a certain degree of movement or interaction. Flexible linkers can be composed of small, non-polar (e.g., Gly) or polar (e.g., Ser or Thr) amino acids. A flexible linker can have sequences consisting primarily of stretches of Gly and Ser residues ("GS" linker). An example of a flexible linker can have the sequence of (Gly-Gly-Gly-Gly-Ser)n (SEQ ID NO: 85). By adjusting the copy number "n", the length of this exemplary GS linker can be optimized to achieve appropriate separation of functional domains, or to maintain necessary inter-domain interactions. Besides GS linkers, other flexible linkers can be utilized for recombinant fusion proteins. In some cases, flexible linkers can also be rich in small or polar amino acids such as Gly and Ser, but can contain additional amino acids such as Thr and Ala to maintain flexibility. In other cases, polar amino acids such as Lys and Glu can be used to improve solubility.

Flexible linkers included in linker sequences described herein, can be rich in small or polar amino acids such as Gly and Ser to provide good flexibility and solubility. Flexible linkers can be suitable choices when certain movements or interactions are desired for fusion protein domains. In addition, although flexible linkers cannot have rigid structures, they can serve as a passive linker to keep a distance between functional domains. The length of flexible linkers can be adjusted to allow for proper folding or to achieve optimal biological activity of the fusion proteins.

A linker described herein can further include a rigid linker in some cases. A rigid linker can be utilized to maintain a fixed distance between domains of a polypeptide. Examples of rigid linkers can be: Alpha helix-forming linkers, Pro-rich sequence, (XP)n, X-Pro backbone, A(EAAAK)nA (n=2-5), to name a few. Rigid linkers can exhibit relatively stiff structures by adopting α-helical structures or by containing multiple Pro residues in some cases.

A linker described herein can be cleavable in some cases. In other cases a linker is not cleavable. Linkers that are not cleavable can covalently join functional domains together to act as one molecule throughout an in vivo processes or an ex vivo process. A linker can also be cleavable in vivo. A cleavable linker can be introduced to release free functional domains in vivo. A cleavable linker can be cleaved by the presence of reducing reagents, proteases, to name a few. For example, a reduction of a disulfide bond can be utilized to produce a cleavable linker. In the case of a disulfide linker, a cleavage event through disulfide exchange with a thiol, such as glutathione, could produce a cleavage. In other cases, an in vivo cleavage of a linker in a recombinant fusion protein can also be carried out by proteases that can be expressed in vivo under pathological conditions (e.g. cancer or inflammation), in specific cells or tissues, or constrained within certain cellular compartments. In some cases, a cleavable linker can allow for targeted cleavage. For example, the specificity of many proteases can offer slower cleavage of a linker in constrained compartments. A cleavable linker can also comprise hydrazone, peptides, disulfide, or thioester. For example, a hydrazone can confer serum stability. In other cases, a hydrazone can allow for cleavage in an acidic compartment. An acidic compartment can have a pH up to 7. A linker can also include a thioether. A thioether can be nonreducible A thioether can be designed for intracellular proteolytic degradation.

In certain embodiments, an fmdv linker polypeptide comprises a sequence that can be at least about 45%, 50%, 55%, 60%, 65%, 70%, 75%, 80%, 85%, 90%, 95%, 97%, 98%, 99% or 100% identical to SEQ ID NO: 87. In certain embodiments, an fmdv linker polypeptide is one or more of the linkers encoded in a single vector linking two or more fusion proteins. In certain cases, an fmdv linker polypeptide can be encoded by a polynucleotide open reading frame (ORF) nucleic acid sequence. In some cases, an ORF encoding fmdv comprises or consists of a sequence of SEQ ID NO: 70). In certain embodiments, a polynucleotide encoding fmdv is at least 45%, 50%, 55%, 60%, 65%, 70%, 75%, 80%, 85%, 90%, 95%, 97%, 98%, 99% or 100% identical to SEQ ID NO: 70).

In certain cases, a linker polypeptide can be a "p2a" linker. In certain embodiments, a p2a polypeptide can comprise a sequence that can be about at least 45%, 50%, 55%, 60%, 65%, 70%, 75%, 80%, 85%, 90%, 95%, 97%, 98%, 99% or 100% identical to SEQ ID NO: 91). In certain embodiments, the p2a linker polypeptide can be one or more of the linkers encoded in a single vector linking two or more fusion proteins. In some cases, a p2a linker polypeptide can be encoded by a polynucleotide open reading frame (ORF) nucleic acid sequence. In certain embodiments, an ORF encoding p2a comprises or consists of the sequence of SEQ ID NO: 74). In certain cases, a polynucleotide encoding p2a can be or can be about at least 45%, 50%, 55%, 60%, 65%, 70%, 75%, 80%, 85%, 90%, 95%, 97%, 98%, 99% or 100% identical to SEQ ID NO: 74).

In some cases, a linker polypeptide can be a "GSG-p2a" linker. In certain embodiments, a GSG-p2a linker polypeptide can comprise a sequence that can be about at least 45%, 50%, 55%, 60%, 65%, 70%, 75%, 80%, 85%, 90%, 95%, 97%, 98%, 99% or 100% identical to SEQ ID NO: 92). In certain embodiments, a GSG-p2a linker polypeptide can be one or more of the linkers encoded in a single vector linking two or more fusion proteins. In some cases, a GSG-p2a linker polypeptide can be encoded by a polynucleotide open-reading frame (ORF) nucleic acid sequence. An ORF encoding GSG p2a can comprise the sequence of SEQ ID NO: 75). In some cases, a polynucleotide encoding GSG-p2a can be or can be about at least 45%, 50%, 55%, 60%, 65%, 70%, 75%, 80%, 85%, 90%, 95%, 97%, 98%, 99% or 100% identical to SEQ ID NO: 75).

A linker polypeptide can be an "fp2a" linker as provided herein. In certain embodiments, a fp2a linker polypeptide can comprise a sequence that can be about at least 45%, 50%, 55%, 60%, 65%, 70%, 75%, 80%, 85%, 90%, 95%, 97%, 98%, 99% or 100% identical to SEQ ID NO: 95). In certain cases, an fp2a linker polypeptide can be one or more of the linkers encoded in a single vector linking two or more fusion proteins. In some cases, a fp2a linker polypeptide can be encoded by a polynucleotide open reading frame (ORF) nucleic acid sequence. In certain embodiments, a polynucleotide encoding an fp2a linker can be or can be about at least 45%, 50%, 55%, 60%, 65%, 70%, 75%, 80%, 85%, 90%, 95%, 97%, 98%, 99% or 100% identical to SEQ ID NO: 78).

In some cases, a linker can be engineered. For example, a linker can be designed to comprise chemical characteristics such as hydrophobicity. In some cases, at least two linker sequences can produce the same protein. A sequence can be or can be about 45%, 50%, 55%, 60%, 65%, 70%, 75%, 80%, 85%, 90%, 95%, 96%, 97%, 98%, 99%, or 100% identical to a polypeptide sequence of SEQ ID NOS: 82, 96 or 97. In other cases, multiple linkers can be used in a vector. For example, genes of interest, and one or more gene switch polypeptide sequences described herein can be separated by at least two linkers. In some cases, genes can be separated by 2, 3, 4, 5, 6, 7, 8, 9, or up to 10 linkers.

A linker can be an engineered linker. Methods of designing linkers can be computational. In some cases, computational methods can include graphic techniques. Computation methods can be used to search for suitable peptides from libraries of three-dimensional peptide structures derived from databases. For example, a Brookhaven Protein Data Bank (PDB) can be used to span the distance in space between selected amino acids of a linker.

In some embodiments are polynucleotides encoding a polypeptide construct comprising a furin polypeptide and a 2A polypeptide, wherein the furin polypeptide and the 2A polypeptide are connected by a polypeptide linker comprising at least three hydrophobic amino acids. In some cases, at least three hydrophobic amino acids are selected from the list consisting of glycine (Gly)(G), alanine (Ala)(A), valine (Val)(V), leucine (Leu)(L), isoleucine (Ile)(I), proline (Pro) (P), phenylalanine (Phe)(F), methionine (Met)(M), tryptophan (Trp)(W). In some cases, a polypeptide linker can also include one or more GS linker sequences, for instance (GS)n, (SG)n, (GSG)n, and (SGSG)n, wherein n can be any number from zero to fifteen.

Provided are methods of obtaining an improved expression of a polypeptide construct comprising: providing a polynucleotide encoding said polypeptide construct comprising a first functional polypeptide and a second functional polypeptide, wherein said first functional polypeptide and second functional polypeptide are connected by a linker polypeptide comprising a sequence with at least 60% identity to the sequence APVKQ; and expressing said polynucleotide in a host cell, wherein said expressing results in an improved expression of the polypeptide construct as compared to a corresponding polypeptide construct that does not have a linker polypeptide comprising a sequence with at least 60% identity to the sequence APVKQ.

IRES Elements

Also disclosed herein are constructs comprising an IRES element to facilitate the expression and functionality of the polynucleotides and polypeptides described herein. The term "internal ribosome entry site (IRES)" as used herein can be intended to mean internal ribosomal entry site. In a vector comprising an IRES sequence, a first gene can be translated by a cap-dependent, ribosome scanning, mechanism with its own 5'-UTR, whereas translation of a subsequent gene can be accomplished by direct recruitment of a ribosome to an IRES in a cap-independent manner. An IRES sequence can allow eukaryotic ribosomes to bind and begin translation without binding to a 5' capped end. An IRES sequence can allow expression of multiple genes from one transcript (Mountford and Smith 1995).

The term "CAP" or "cap" as used herein refers to a modified nucleotide, generally a 7-methyl guanosine, linked 3' to 5' (7meG-ppp-G), to the 5' end of a eukaryotic mRNA, that serves as a required element in the normal translation initiation pathway during expression of protein from that mRNA.

In certain cases, an IRES region can be derived from a virus, such as picornavirus, encephalomyocarditis virus, hepatitis C virus IRES sequence. In other cases, an IRES sequence can be derived from an encephalomyocarditis virus. The term "EMCV" or "encephalomyocarditis virus" as used herein refers to any member isolate or strain of the encephalomyocarditis virus species of the genus of the family Picornaviridae. Examples are: EMCV-R (Rueckert) strain virus, Columbia-SK virus. In some cases, a cellular IRES element, such as eukaryotic initiation factor 4G, immunoglobulin heavy chain binding protein, c-myc proto-oncogene, vascular endothelial growth factor, fibroblast growth factor-1 IRES, or any combination or modification thereof can be used. In some cases, a cellular IRES can have increased gene expression when compared to a viral IRES.

An IRES sequence of viral, cellular or a combination thereof can be utilized in a vector. An IRES can be from encephalomyocarditis (EMCV) or poliovirus (PV). In some cases, an IRES element is selected from a group consisting of Poliovirus (PV), Encephalomyelitis virus (EMCV), Foot-and-mouth disease virus (FMDV), Porcine teschovirus-1 (PTV-1), Aichivirus (AiV), Seneca Valley virus (SVV), Hepatitis C virus (HCV), Classical swine fever virus (CSFV), Human immunodeficiency virus-2 (HIV-2), Human immunodeficiency virus-1 (HIV-1), Moloney murine leukemia virus (MoMLV), Feline immunodeficiency virus (FIV), Mouse mammary tumor virus (MMTV), Human cytomegalovirus latency (pUL138), Epstein-Barr virus (EBNA-1), Herpes virus Marek's disease (MDV RLORF9), SV40 polycistronic 19S (SV40 19S), *Rhopalosiphum padi* virus (RhPV), Cricket paralysis virus (CrPV), Ectropis obliqua picorna-like virus (EoPV), *Plautia stali* intestine virus (PSIV), *Triatoma* virus (TrV), Bee paralysis dicistrovirus (IAPV, KBV), Black currant reversion virus (BRV), *Pelargonium* flower break virus (PFBV), Hibiscus chlorotic ringspot virus (HCRSV), Crucifer-infecting tobamovirus (CrTMV), Potato leaf roll polerovirus (PLRV), Tobacco etch virus (TEV), Giardiavirus (GLV), *Leishmania* RNA virus-1 (LRV-1), and combinations or modifications thereof. In some cases, an IRES is selected from a group consisting of Apaf-1, XIAP, HIAP2/c-IAP1, DAPS, Bcl-2, c-myc, CAT-1, INR, Differentiation LEF-1, PDGF2, HIF-1a, VEGF, FGF2, BiP, BAG-1, CIRP, p53, SHMT1, PITSL-REp58, CDK1, Rpr, hid, hsp70, grim, skl, Antennapedia, dFoxO, dInR, Adh-Adhr, HSP101, ADH, URE-2, GPR1, NCE102, YMR181a, MSN1, BOI1, FLOG, GIC1, and any combination or modification thereof. When an IRES element is included between two open reading frames (ORFs), initiation of translation can occur by a canonical 5'-m7GpppN cap-dependent mechanism in a first ORF and a cap-independent mechanism in a second ORF downstream of the IRES element.

In some cases, genes can be linked by an internal ribosomal entry site (IRES). An IRES can allow simultaneous expression of multiple genes. For example, an IRES sequence can permit production of multiple proteins from a single mRNA transcript. A ribosome can bind to an IRES in a 5'-cap independent manner and initiate translation.

In some cases, an IRES sequence can be or can be about 500 base pairs. An IRES sequence can be from 300 base pairs to 1000 base pairs. For example, an IRES can be 300, 350, 400, 450, 500, 550, 600, 650, 700, 750, 800, 850, 900, 950, or 1000 base pairs long.

In some cases, expression of a downstream gene within a vector comprising an IRES sequence can be reduced. For example, a gene following an IRES sequence can have reduced expression over a gene preceding an IRES sequence. Reduced expression can be from 1% to 99% reduction over a preceding gene.

Methods of Regulating Expression

In one embodiment, a method of regulating the expression of a heterologous gene in an engineered cell is provided. Polynucleotides encoding for gene switch polypeptides for ligand inducible control of a heterologous gene expression, an antigen binding polypeptide and a heterologous gene is provided. In some instances, the polynucleotides are in one or more gene expression cassettes as depicted in any one of FIGS. 1 through 16. In another instance, the polynucleotides are incorporated into an engineered cell via viral or non-viral vectors. Viral vectors can include lentiviral vectors, retroviral vectors or adenoviral vectors. Non-viral vectors can include Sleeping Beauty transposons. In other instances, the polynucleotides are incorporated into an engineered cell via recombinases or gene editing techniques. Examples of recombinases are serine recombinases as described herein. Examples of gene editing techniques can include CRISPR or Argonaute systems. Herein a "CRISPR gene editing system" of "CRISPR system" refers to any RNA-guided Cas protein-mediated process for targeting a change in DNA sequence to a specific region of a genome. Herein "Argonaute gene editing system" refers to any single-stranded DNA guided Argonaute endonuclease-mediated process for targeting a change in DNA sequence to a specific region of a genome.

Pharmaceutical Compostions and Dosage

The present disclosure provides a composition comprising the adenovirus or adenoviral vector described herein and a carrier therefor (e.g., a pharmaceutically acceptable carrier). The composition desirably is a physiologically acceptable (e.g., pharmaceutically acceptable) composition, which comprises a carrier, preferably a physiologically (e.g., pharmaceutically) acceptable carrier, and the adenovirus or adenoviral vector. Any suitable carrier can be used within the context of the present disclosure, and such carriers are well known in the art. The choice of carrier will be determined, in part, by the particular use of the composition (e.g., administration to an animal) and the particular method used to administer the composition. Ideally, in the context of replication-deficient adenoviral vectors, the pharmaceutical composition preferably is free of replication-competent adenovirus. The pharmaceutical composition optionally can be sterile.

Suitable compositions include aqueous and non-aqueous isotonic sterile solutions, which can contain anti-oxidants, buffers, and bacteriostats, and aqueous and non-aqueous sterile suspensions that can include suspending agents, solubilizers, thickening agents, stabilizers, and preservatives. The composition can be presented in unit-dose or multi-dose sealed containers, such as ampules and vials, and can be stored in a freeze-dried (lyophilized) condition requiring only the addition of the sterile liquid carrier, for example, water, immediately prior to use. Extemporaneous solutions and suspensions can be prepared from sterile powders, granules, and tablets. Preferably, the carrier is a buffered saline solution. More preferably, the adenovirus or adenoviral vector is part of a composition formulated to protect the adenovirus or adenoviral vector from damage prior to administration. For example, the composition can be formulated to reduce loss of the adenovirus or adenoviral vector on devices used to prepare, store, or administer the adenovirus or adenoviral vector, such as glassware, syringes, or needles. The composition can be formulated to decrease the light sensitivity and/or temperature sensitivity of the adenovirus or adenoviral vector. To this end, the composition preferably comprises a pharmaceutically acceptable liquid carrier, such as, for example, those described above, and a stabilizing agent selected from the group consisting of polysorbate 80, L-arginine, polyvinylpyrrolidone, trehalose, and combinations thereof. Use of such a composition will extend the shelf life of the adenovirus or adenoviral vector, and facilitate its administration. Formulations for adenovirus or adenoviral vector-containing compositions are further described in, for example, U.S. Pat. Nos. 6,225,289, 6,514,943, and International Patent Application Publication WO 2000/034444.

The composition also can be formulated to enhance transduction efficiency. In addition, one of ordinary skill in the art will appreciate that the adenovirus or adenoviral vector can be present in a composition with other therapeutic or biologically-active agents. For example, factors that control inflammation, such as ibuprofen or steroids, can be part of the composition to reduce swelling and inflammation associated with in vivo administration of the adenovirus or adenoviral vector. If the adenovirus or adenoviral vector is used to deliver an antigen-encoding nucleic acid sequence to a host, immune system stimulators or adjuvants, e.g., interleukins, lipopolysaccharide, or double-stranded RNA, can be administered to enhance or modify any immune response to the antigen. Antibiotics, i.e., microbicides and fungicides, can be present to treat existing infection and/or reduce the risk of future infection, such as infection associated with gene transfer procedures.

In some embodiments, disclosed herein are compositions comprising a polynucleotide or polypeptide disclosed herein for administration in a subject. In some instances, are modified effector cell compositions encoding a polynucleotide or polypeptide disclosed herein, and optionally containing a cytokine and/or an additional therapeutic agent. In some instances, also included herein are vectors encoding gene-switch polypeptides for regulating expression of a chimeric antigen receptor for modification of an effector cell.

In some instances, pharmaceutical compositions of a modified effector cell or a vector encoding gene-switch polypeptides and a chimeric antigen receptor are formulated in a conventional manner using one or more physiologically acceptable carriers including excipients and auxiliaries which facilitate processing of the active compounds into preparations which can be used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

Pharmaceutical compositions are optionally manufactured in a conventional manner, such as, by way of example only, by means of conventional mixing, dissolving, granulating, dragee-making, levigating, emulsifying, encapsulating, entrapping or compression processes.

In certain embodiments, compositions can also include one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In other embodiments, compositions can also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

The pharmaceutical compositions described herein are administered by any suitable administration route, including but not limited to, oral, parenteral (e.g., intravenous, subcutaneous, intramuscular, intracerebral, intracerebroventricular, intra-articular, intraperitoneal, or intracranial), intranasal, buccal, sublingual, or rectal administration routes. In some instances, the pharmaceutical composition is formulated for parenteral (e.g., intravenous, subcutaneous, intramuscular, intracerebral, intracerebroventricular, intra-articular, intraperitoneal, or intracranial) administration.

The pharmaceutical compositions described herein are formulated into any suitable dosage form, including but not limited to, aqueous oral dispersions, liquids, gels, syrups, elixirs, slurries, suspensions and the like, for oral ingestion by an individual to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations. In some embodiments, the pharmaceutical compositions are formulated into capsules. In some embodiments, the pharmaceutical compositions are formulated into solutions (for example, for IV administration). In some cases, the pharmaceutical composition is formulated as an infusion. In some cases, the pharmaceutical composition is formulated as an injection.

The pharmaceutical solid dosage forms described herein optionally include a compound described herein and one or more pharmaceutically acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof.

In still other aspects, using standard coating procedures, such as those described in Remington's Pharmaceutical Sciences, 20th Edition (2000), a film coating is provided around the compositions. In some embodiments, the compositions are formulated into particles (for example for administration by capsule) and some or all of the particles are coated. In some embodiments, the compositions are formulated into particles (for example for administration by capsule) and some or all of the particles are microencapsulated. In some embodiments, the compositions are formulated into particles (for example for administration by capsule) and some or all of the particles are not microencapsulated and are uncoated.

In certain embodiments, compositions provided herein can also include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide and cetylpyridinium chloride.

"Antifoaming agents" reduce foaming during processing which can result in coagulation of aqueous dispersions, bubbles in the finished film, or generally impair processing. Exemplary anti-foaming agents include silicon emulsions or sorbitan sesquoleate.

"Antioxidants" include, for example, butylated hydroxytoluene (BHT), sodium ascorbate, ascorbic acid, sodium metabisulfite and tocopherol. In certain embodiments, antioxidants enhance chemical stability where required.

Formulations described herein can benefit from antioxidants, metal chelating agents, thiol containing compounds and other general stabilizing agents. Examples of such stabilizing agents, include, but are not limited to: (a) about 0.5% to about 2% w/v glycerol, (b) about 0.1% to about 1% w/v methionine, (c) about 0.1% to about 2% w/v monothioglycerol, (d) about 1 mM to about 10 mM EDTA, (e) about 0.01% to about 2% w/v ascorbic acid, (f) 0.003% to about 0.02% w/v polysorbate 80, (g) 0.001% to about 0.05% w/v. polysorbate 20, (h) arginine, (i) heparin, (j) dextran sulfate, (k) cyclodextrins, (l) pentosan polysulfate and other heparinoids, (m) divalent cations such as magnesium and zinc; or (n) combinations thereof.

"Binders" impart cohesive qualities and include, e.g., alginic acid and salts thereof; cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinylpyrrolidone/vinyl acetate copolymer; crospovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum, mucilage of isapol husks, polyvinylpyrrolidone (e.g., Polyvidone® CL, Kollidon® CL, Polyplasdone® XL-10), larch arabogalactan, Veegum®, polyethylene glycol, waxes, sodium alginate, and the like.

A "carrier" or "carrier materials" include any commonly used excipients in pharmaceutics and should be selected on the basis of compatibility with compounds disclosed herein, such as, compounds of ibrutinib and An anticancer agent, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" can include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999).

"Dispersing agents," and/or "viscosity modulating agents" include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), non-crystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

Combinations of one or more erosion facilitator with one or more diffusion facilitator can also be used in the present compositions.

The term "diluent" refers to chemical compounds that are used to dilute the compound of interest prior to delivery. Diluents can also be used to stabilize compounds because they can provide a more stable environment. Salts dissolved in buffered solutions (which also can provide pH control or maintenance) are utilized as diluents in the art, including, but not limited to a phosphate buffered saline solution. In certain embodiments, diluents increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

"Filling agents" include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

"Lubricants" and "glidants" are compounds that prevent, reduce or inhibit adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil (Sterotex®), higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

"Plasticizers" are compounds used to soften the microencapsulation material or film coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl cellulose and triacetin. In some embodiments, plasticizers can also function as dispersing agents or wetting agents.

"Solubilizers" include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

"Stabilizers" include compounds such as any antioxidation agents, buffers, acids, preservatives and the like.

"Suspending agents" include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

"Surfactants" include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g., octoxynol 10, octoxynol 40. In some embodiments, surfactants can be included to enhance physical stability or for other purposes.

"Viscosity enhancing agents" include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

"Wetting agents" include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

Kits/Article of Manufacture

Disclosed herein, in certain embodiments, are kits and articles of manufacture for use with one or more methods described herein. Such kits include a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In one embodiment, the containers are formed from a variety of materials such as glass or plastic.

The articles of manufacture provided herein contain packaging materials. Examples of pharmaceutical packaging materials include, but are not limited to, blister packs, bottles, tubes, bags, containers, bottles, and any packaging material suitable for a selected formulation and intended mode of administration and treatment.

A kit typically includes labels listing contents and/or instructions for use, and package inserts with instructions for use. A set of instructions will also typically be included.

In some embodiments, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

EXAMPLES

These examples are provided for illustrative purposes only and not to limit the scope of the claims provided herein.

Example 1

Antigenicity Bioinformatics Workflow for HBV Vaccine Designs

Figure 5:
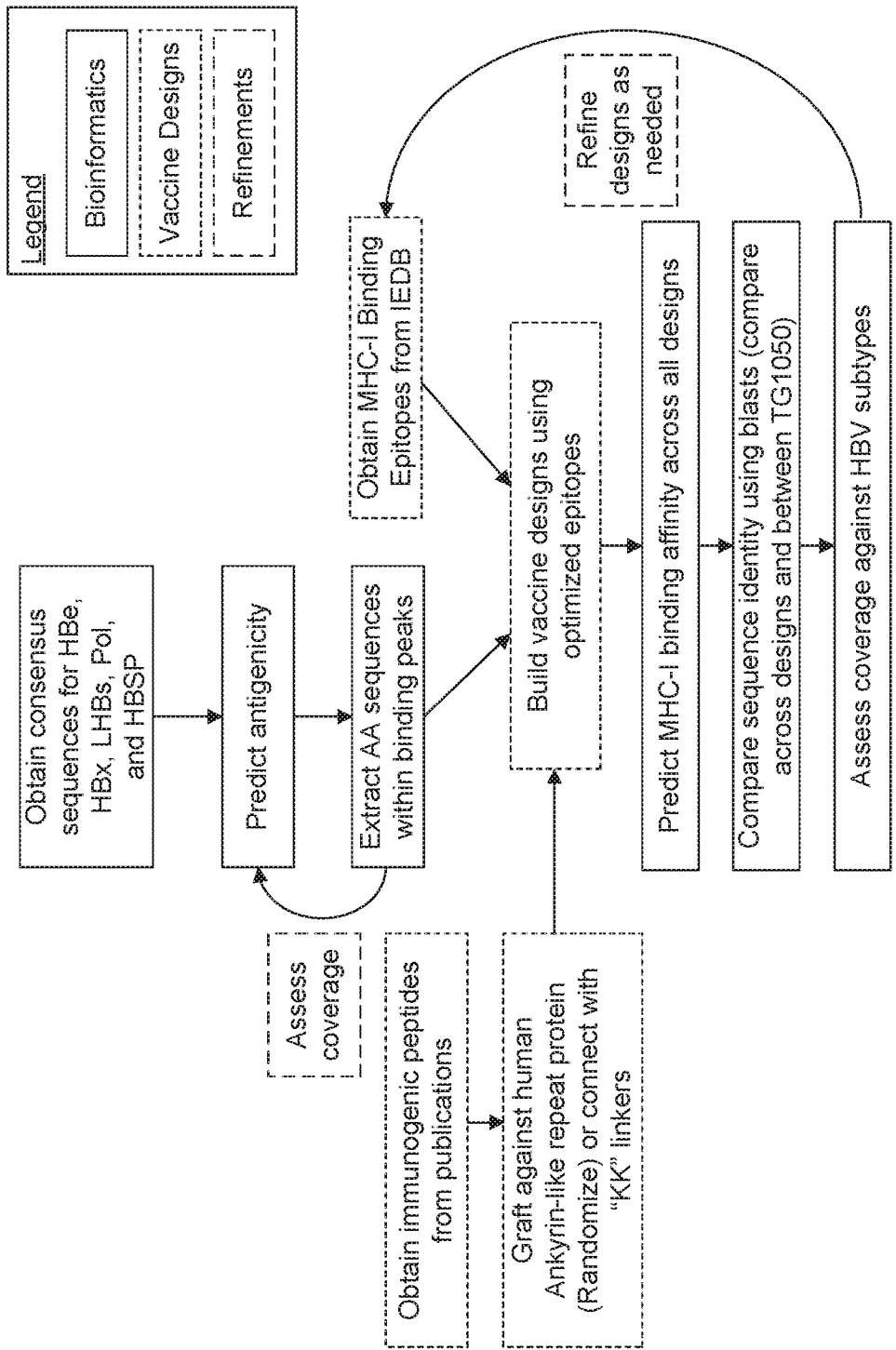
FIG. 5 is schematic overall workflow implemented for designing HBV vaccine antigens.

The HBV vaccine antigen designs provided herein were inspired via inventor-selected combinatorial guidance provided via use of bioinformatics analysis and in silico protein engineering methods. HBV antigen sequences were selected based on genotype D protein sequences, antigenicity predictions and T cell epitope mapping with broad coverages, which could lead to MHC-I binding and cytokine production following T cell activation. The overall workflow of the HBV vaccine designs provided herein is shown in FIG. 5 and is further detailed below.

Obtaining Consensus Sequences

The HBV genome encodes several overlapping viral proteins, including the polymerase, core, envelope (Pre-S1, S2, S), HBe, and HBx proteins (FIGS. 3A-3D). Consensus AA sequences were obtained from the Hepatitis B Virus database (HBVdb) for A, C, and D subtypes.

Predicting Binding Affinity

Figure 9A:
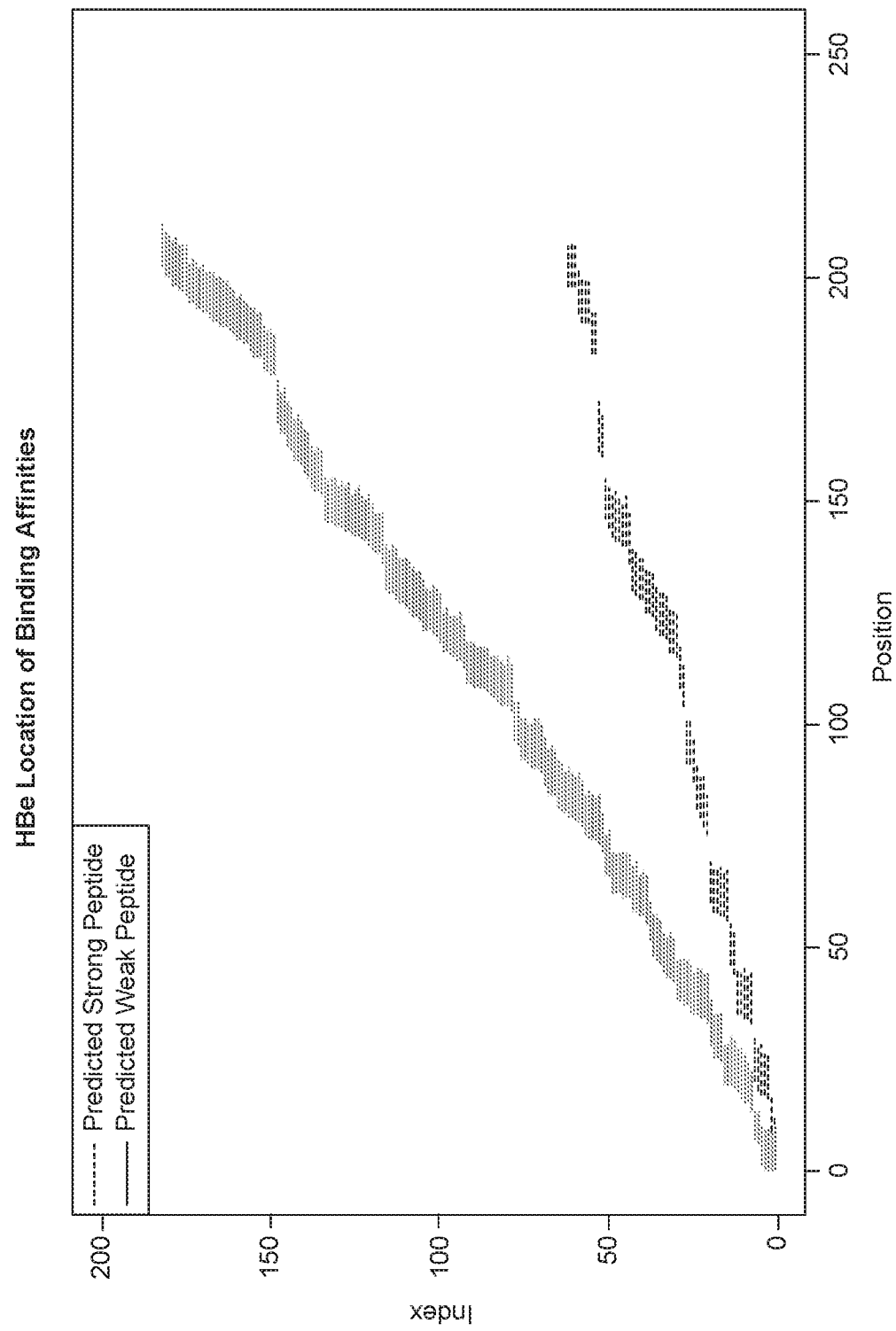
FIG. 9A shows NetMHC4.0 antigenicity predictions for HBe. Predicted strong and weak binding peptides indices were plated against peptide locations.
Figure 9B:
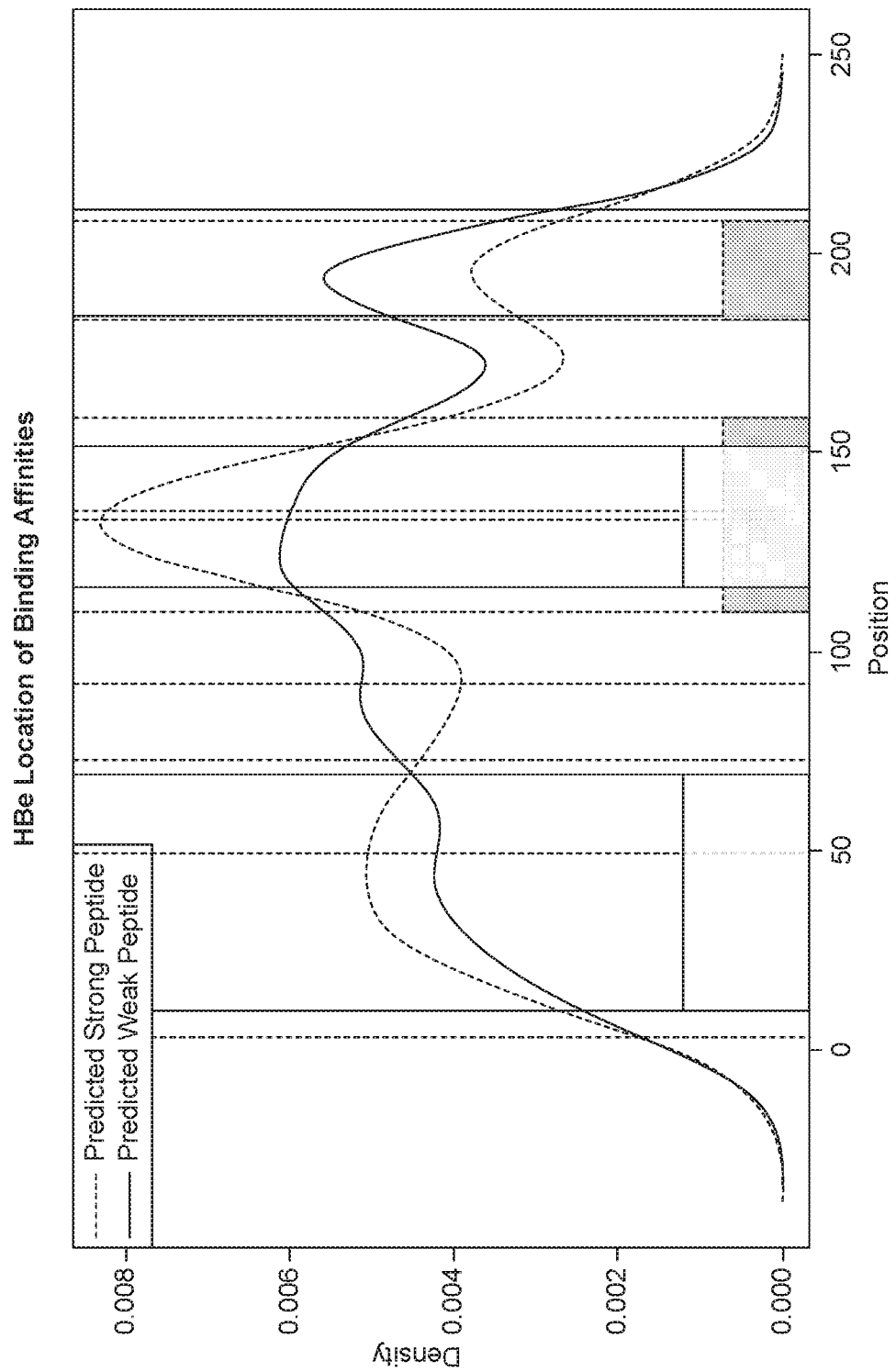
FIG. 9B shows NetMHC4.0 antigenicity predictions for HBe. First and second order differentials were employed on density plots in order to identify peaks.
Figure 9C:
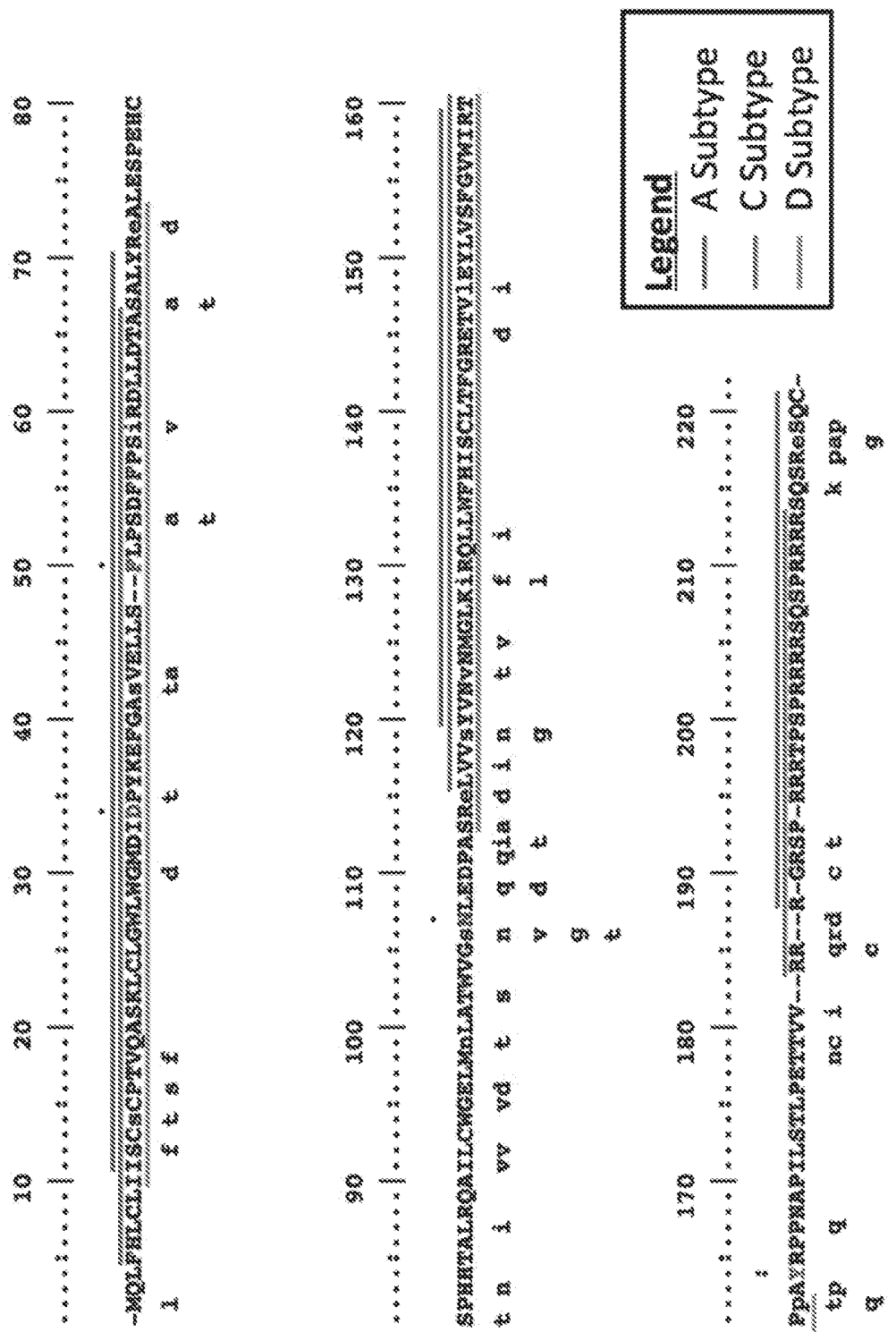
FIG. 9C shows amino acid sequences aligned against consensus sequences in order to determine coverage across HBV subtypes (SEQ ID NOs: 132-136).

NetMHC 4.0 was applied to each consensus sequence to predict binding affinity against all major MHC-I alleles (HLA-A0101, HLA-A0201, HLA-A0301, HLA-A2402, HLA-A2601, HLA-B0702, HLA-B0801, HLA-B2705, HLA-B3901, HLA-B4001, HLA-B5801, and HLA-B1501). NetMHC 4.0 uses artificial neural networks to predict the binding affinity of peptide sequences. This analysis was performed across HBV genotypes A, C, and D. Thresholds were arbitrarily established at 0.5% (strong binders) and 2% (weak binders) ranks. Peptides with predicted binding affinity greater than 99.5% were classified as strong binders and peptides with predicted binding affinity greater than 98% were classified as weak binders. The position of each AA within the peptide sequences were extracted and used to generate density curves (FIG. 9A). Using these density curves, first and second order differentials were calculated to determine peaks for strong and weak binders (FIG. 9B). Finally, the union of these positions was used to extract AA sequences likely to elicit a response (FIG. 9C).

Example 2

HBV Molecular Vaccine Designs

The HBV vaccines described herein include the following HBV designs 1-5 engineered proteins (peptides with genetic modifications). Once the designs were finalized the entire sequence for each design was subjected to NetMHC prediction to assess antigenicity and coverage against A, C, and D genotypes (Example 1). The vaccines described herein were compared against TG1050, an adenovirus-based immunotherapeutic HBV vaccine currently in clinical trials, that encodes a unique large fusion protein composed of: (a) a truncated core, (b) a modified polymerase, and (c) two envelope domains. The core region of TG1050 lacked the pre-core and its polymerase was split into three segments along with four point mutations to improve the vaccine construct stability (Pol1, Plo2 and Pol3; Δ AA 538-544 and Δ AA 710-742 and mutations D689H, V769Y, T776Y, D777H). The two selected envelope domains were inserted in between those polymerase segments as shown in FIG. 5. TG1050 polymerase, Env 1 and Env2 sequences were obtained from Genbank (Y07587.1), and the TG1050 core sequences were obtained from HBV DB (AB048701).

Figure 6:
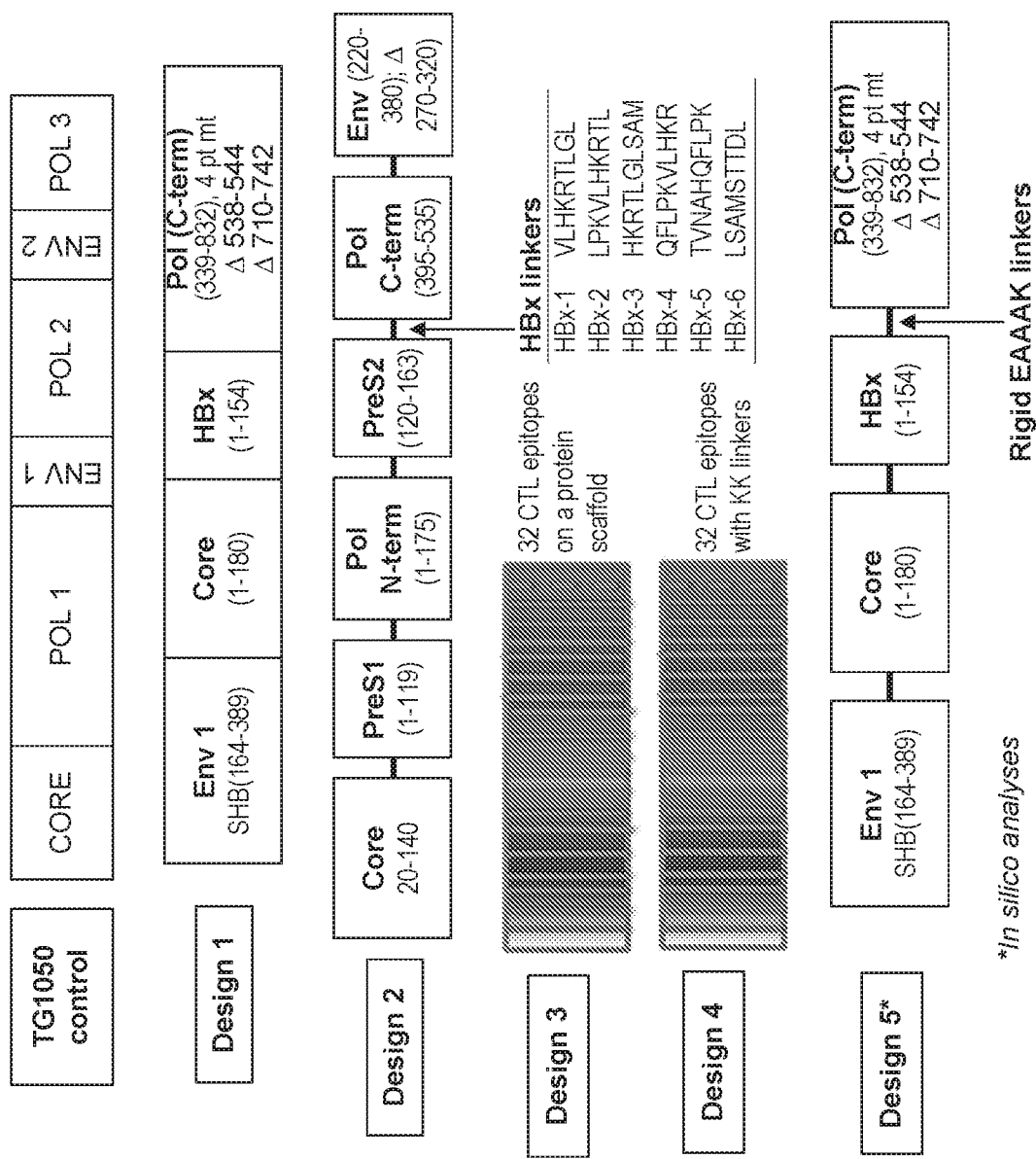
FIG. 6 shows schematic structural diagrams of HBV designs 1-5. HBV designs 1 and 2 were designed based on clade D consensus. For HBV design 3, human ankyrin-like repeat (ALR) protein scaffold (PDB code 1QYM) peptides were grafted at the helical and loop regions in a tandem manner. Two ALR scaffolds were used, connected by a cleavable linker (VSQTSKLTR) (SEQ ID NO: 111). HBV design 4 epitopes were separated by KK linkers. Different linkers, such as EAAAK linkers (SEQ ID NO: 131), were used in HBV design 5 to connect the peptides.
Figure 7:
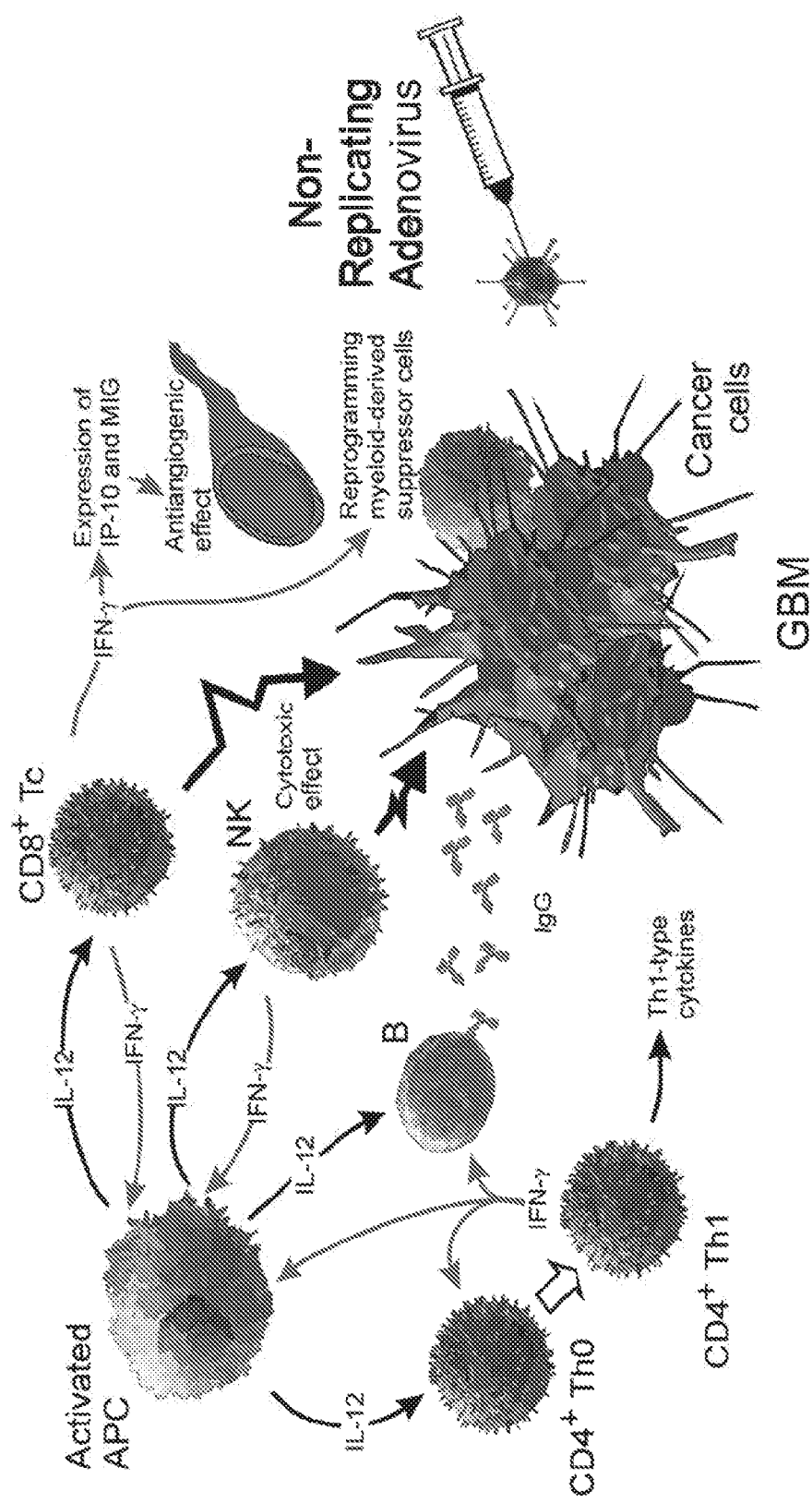
FIG. 7 shows an overview of IL-12 promoting immune response by activating NK cells and T cells.

Five antigen designs (HBV designs 1-5) and a control antigen were synthesized and cloned into expression plasmids—pAdShuttles for adenovector construction (FIG. 6). Initial antigen screening evaluated in vitro antigen expression in transient transfection, in vitro antigen processing and presentation in transient transfection studies of monocyte-derived dendritic cells. As shown in FIG. 17, HBV designs 1 and 2 were designed based on Glade D consensus. 32 HBV peptides from Core (8), Surface (8), Polymerase (8), HBx (6) and HBPS (2) were curated from literature that have experimental and functional data, such as immunogenicity data, Mass-spec. etc. (Table 3). For HBV design 3, human ankyrin-like repeat (ALR) protein scaffold (PDB code 1QYM) peptides were grafted at the helical and loop regions in a tandem manner. Two ALR scaffolds were used, connected by a cleavable linker (VSQTSKLTR; SEQ ID NO:111). ALR proteins have generally high expression and high stability. Thus, ALR proteins were used as a scaffold for the HBV peptides to create novel CTLs. HBV design 4 epitopes were separated by KK linkers (FIG. 6).

HBV Design 1

Figure 10:
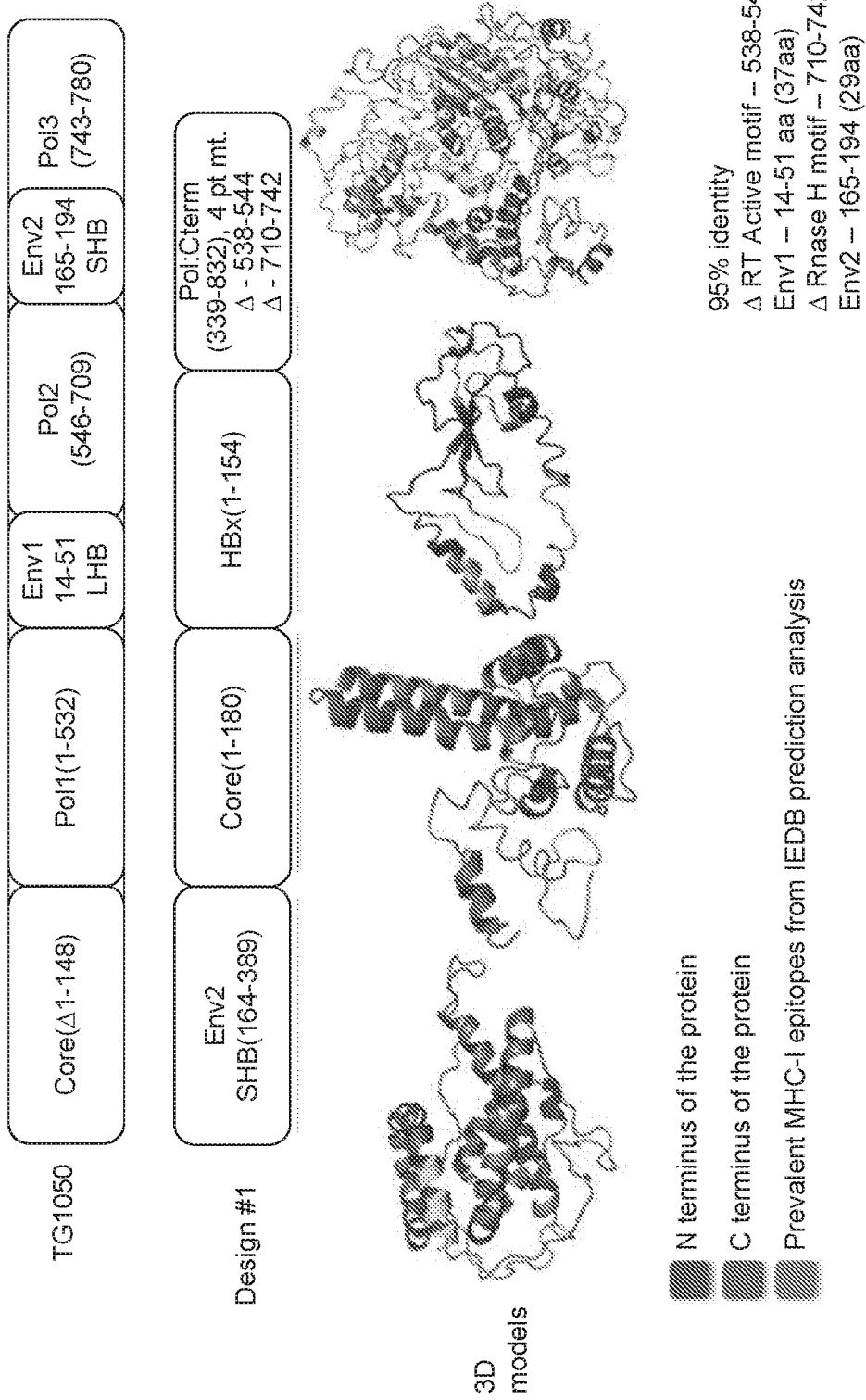
FIG. 10 is a schematic representation of TG1050 and HBV design 1 highlighting the fused domains of different HBV protein. Homology models were used to further assess the design.
Figure 15B:
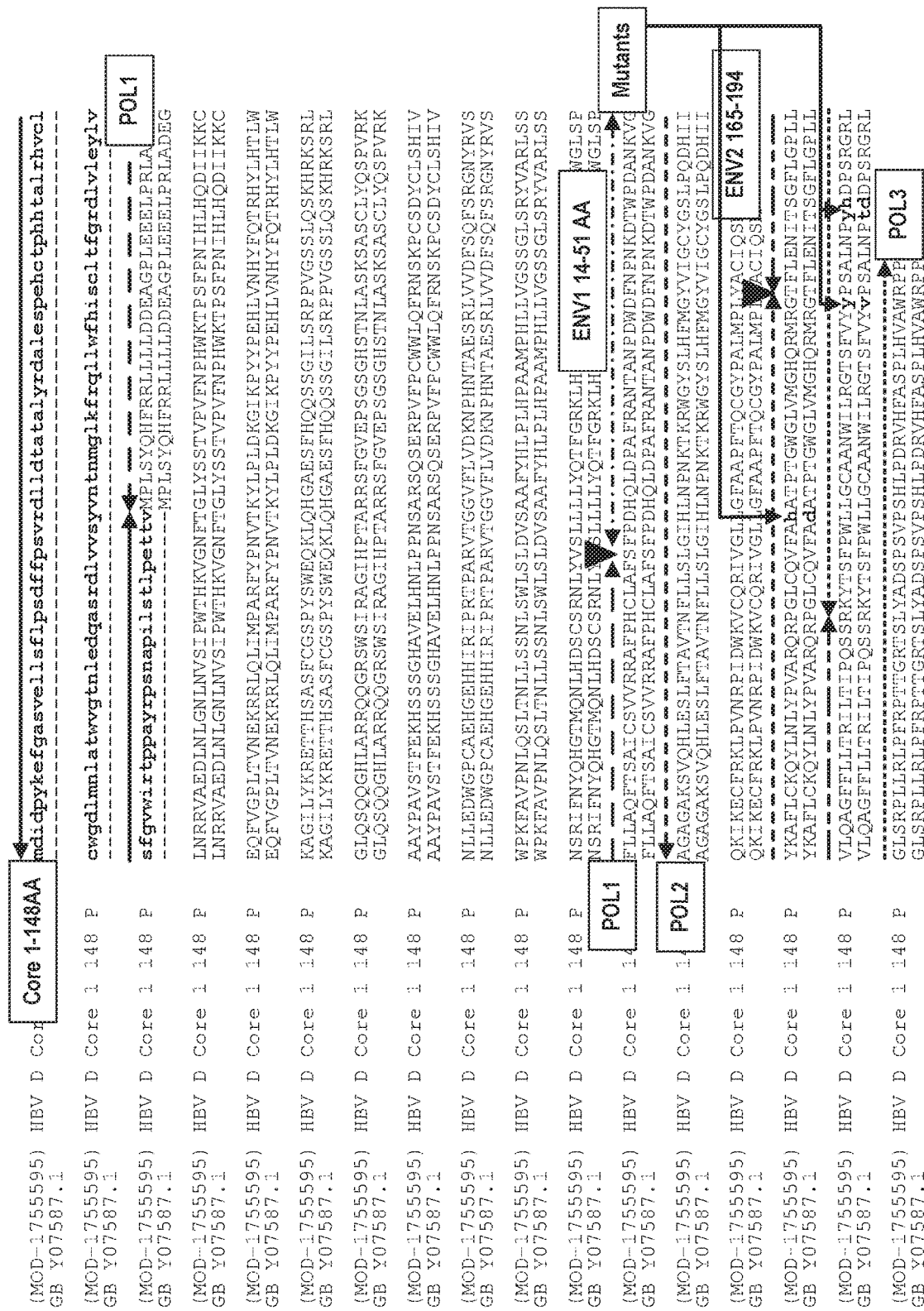
FIG. 15B shows sequence comparisons of HBV design 1 and TG1050 control (SEQ ID NOs: 145 and 146).
Figure 16:
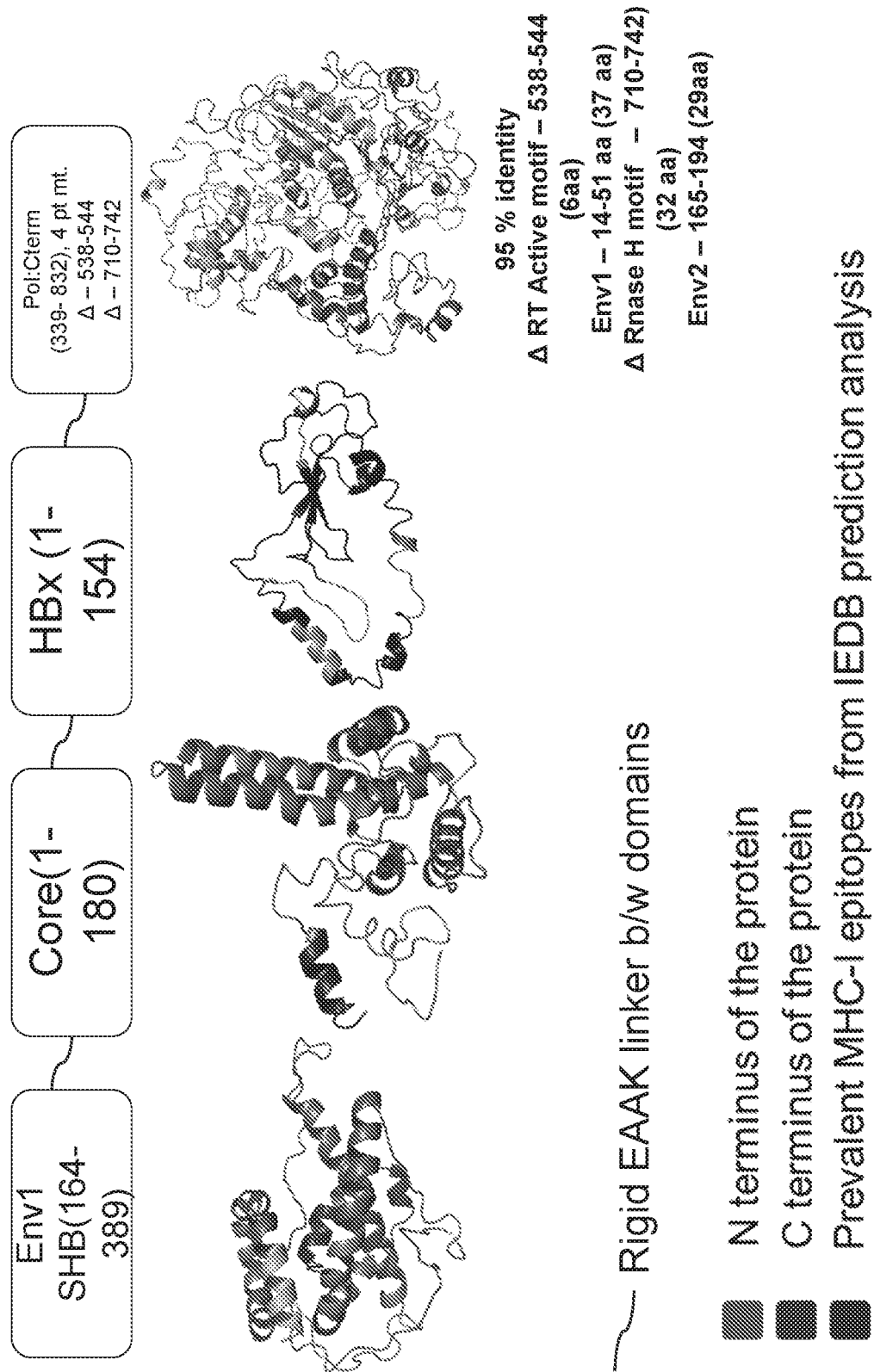
FIG. 16 is a schematic representation of HBV design 5.

HBV D genotype protein sequence (HBV DB: AB048701) was used in this design. Antigenicity prediction analysis (Example 1) and homology models of HBV proteins guided this Design. Comparison of HBV Design 1 and TG1050 along with homology models of protein antigens is shown in FIG. 10, and sequence comparisons are shown in FIGS. 15A-15C. This design contained four native HBV antigens: (1) extended Env2/S region 165-382 AA; (2) core region 1-151 AA and pre-core region; (3) HBx region 1-154 AA; and (4) Polymerase (339-832 AA), del 538-544, 710-742 AA. The TG1050 comparator had two HBV antigens with a third envelope peptide fused to polymerase.

This design encompassed entire protein domains from envelope, core, HBx and the reverse transcriptase domain of polymerase. The TG1050 comparator had truncated core and envelope peptides fused into the modified polymerase domain, but did not encode any HBx sequences.

Different HBV domains were seamlessly fused together as a one long open reading frame. The TG1050 comparator had only two domains (core and polymerase) with truncations as well as deletions. The TG1050 comparator had random insertion of envelope peptides within the polymerase domain.

Truncations were made in the envelope protein and polymerase domains. Only the C terminus region of the envelope protein was used in this design. Only the C terminus region of reverse transcriptase was included. The entire RNaseH domain was included. Truncations were made to inactivate the reverse transcriptase function in ΔRT active motif (538-544: 6aa) and in ΔRNase H motif (710-742: 32 aa).

HBV design 1 novelty: Overall, HBV design 1 had an extended Env2/S region along with both pre-core and core regions compared to TG1050. Unlike TG1050, it also contained the HBx domain. The N-term truncated polymerase along with deletions similar to TG1050 was also used.

HBV Design 2

Figure 11:
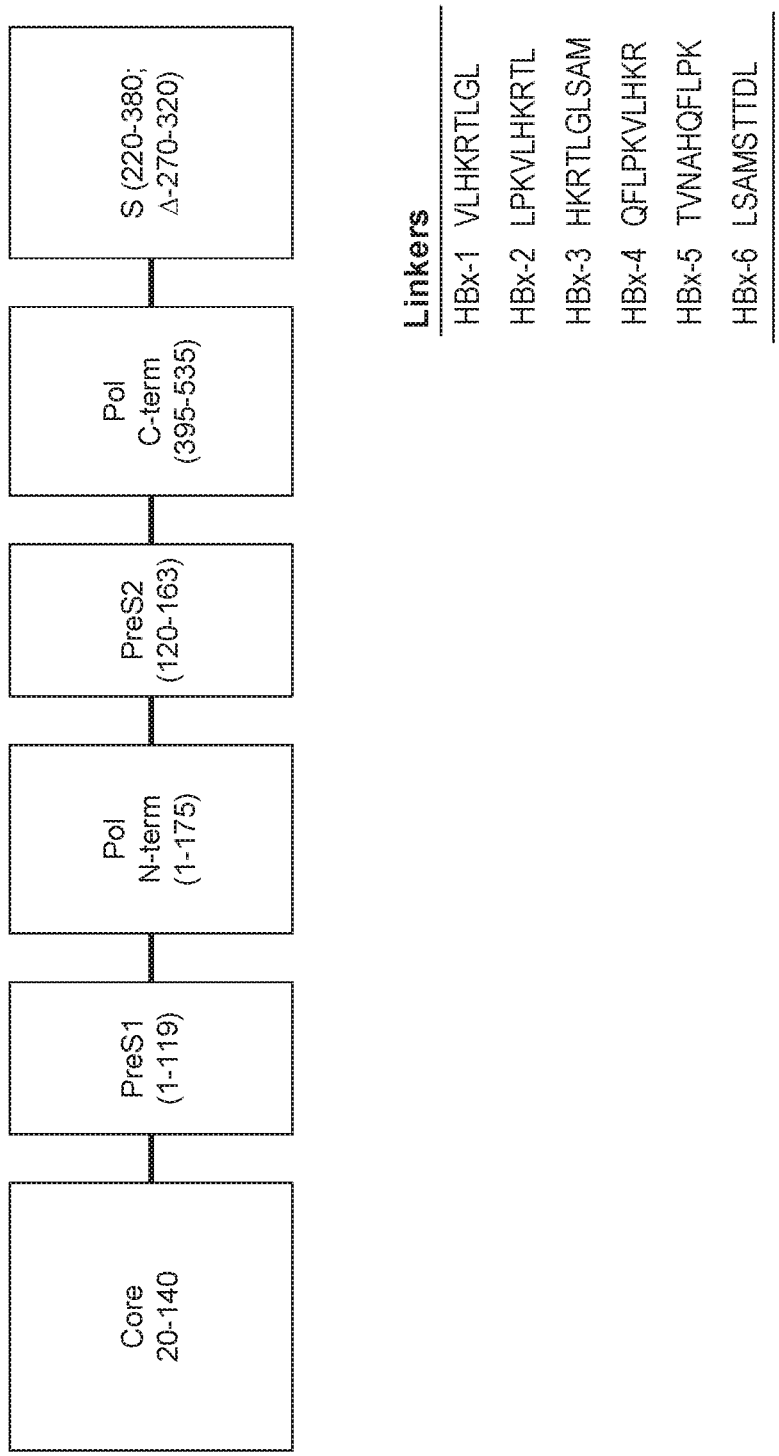
FIG. 11 is a schematic representation of the HBV design 2 consisting of all three major proteins (core, surface splice variants, and polymerase) linked with HBx peptides (HBx-1 (SEQ ID NO: 122), HBx-2 (SEQ ID NO: 123), HBx-3 (SEQ ID NO: 124), HBx-4 (SEQ ID NO: 125), HBx-5 (SEQ ID NO: 126), and HBx-6 (SEQ ID NO: 127)
Figure 12A:
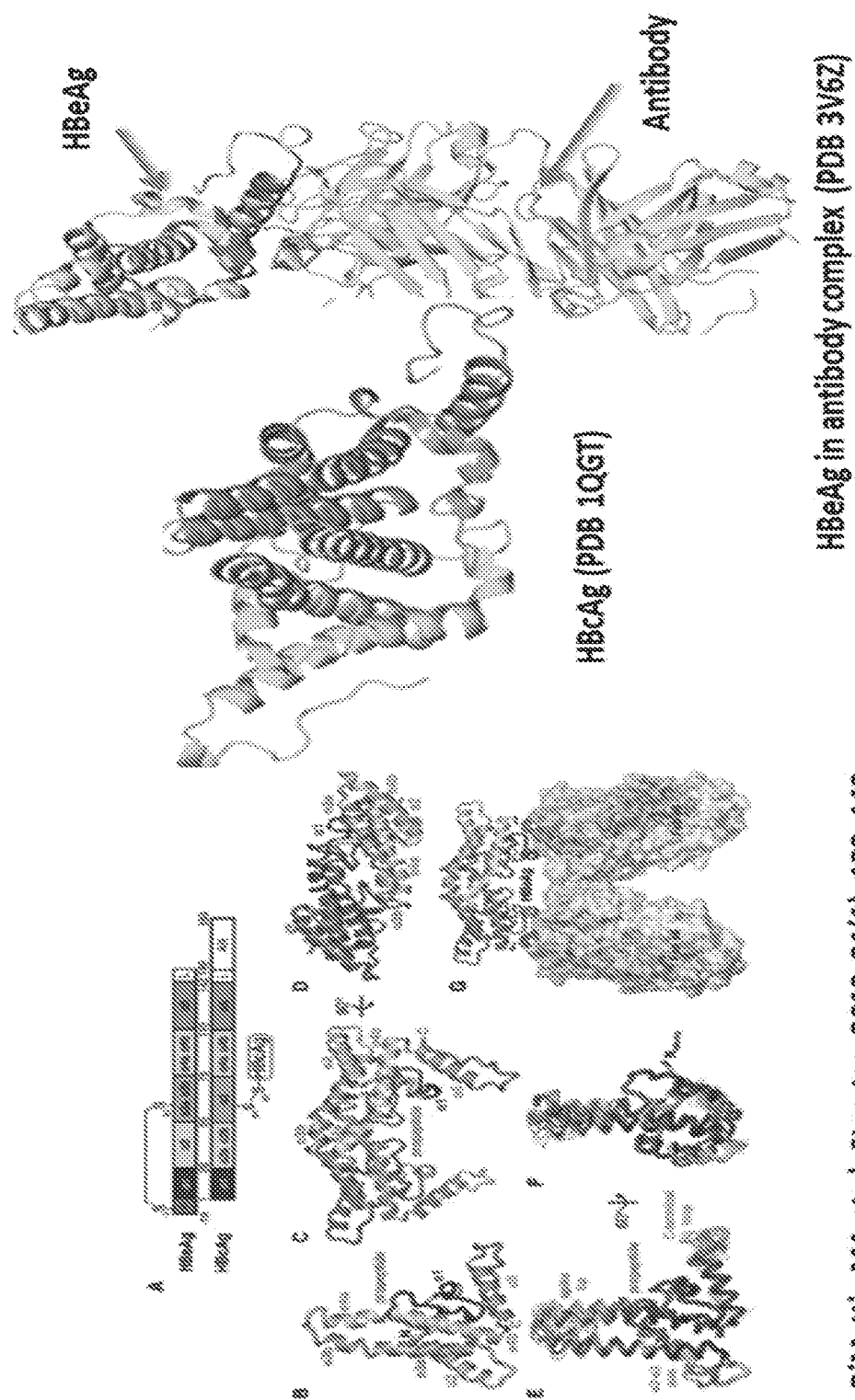
FIG. 12A shows a structure of core HBV protein domain.
Figure 12B:
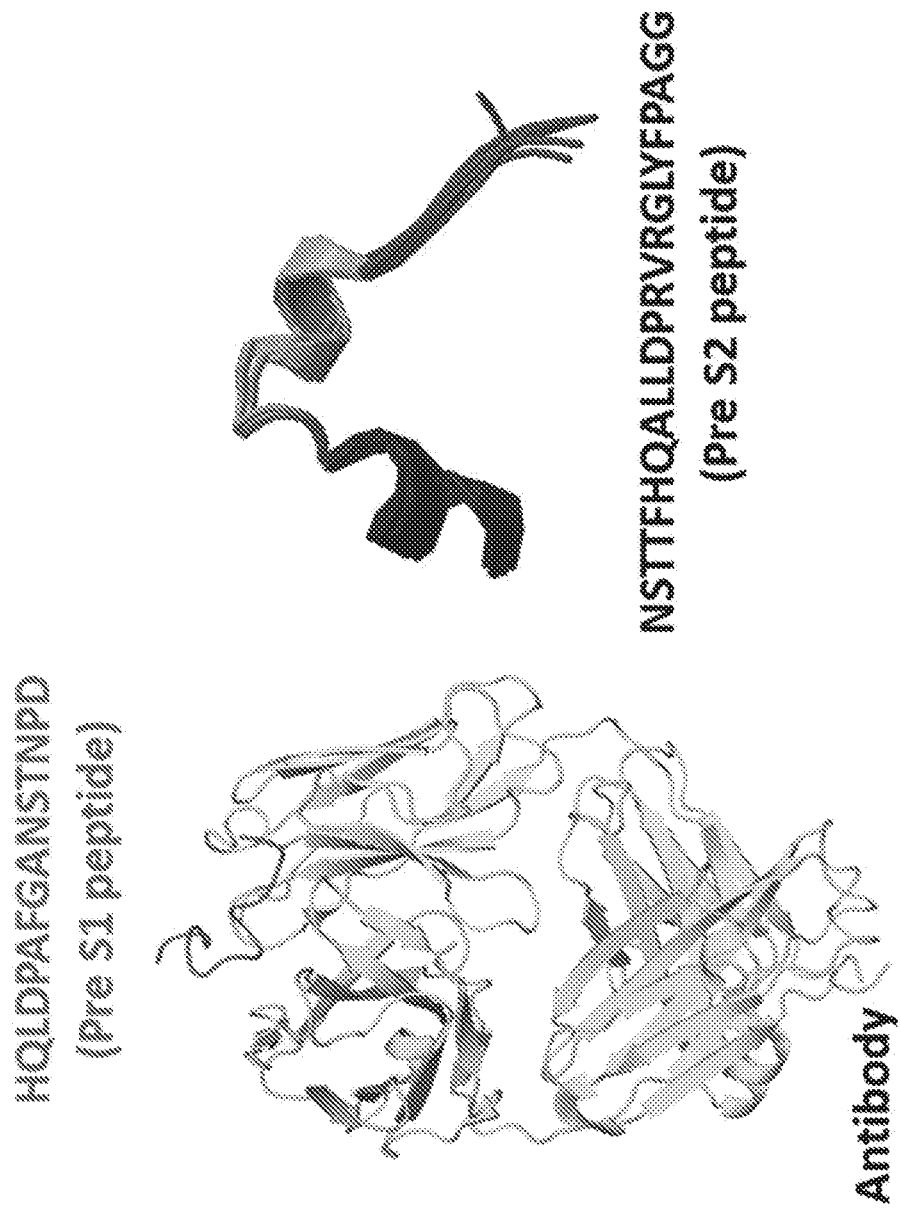
FIG. 12B shows a structure of HBV preS1 (SEQ ID NO: 137) and S2 peptides (SEQ ID NO: 138).
Figure 12C:
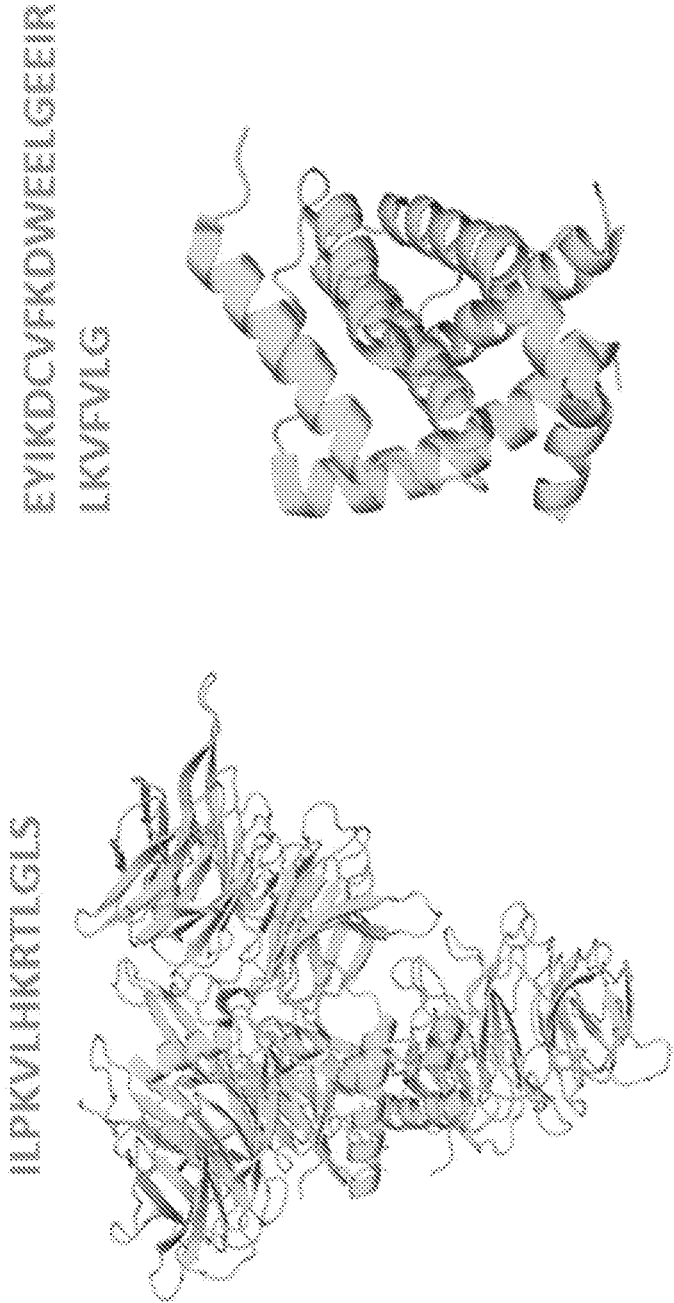
FIG. 12C shows structures of HBV HBx (SEQ ID NOs: 139 and 140).
Figure 12D:
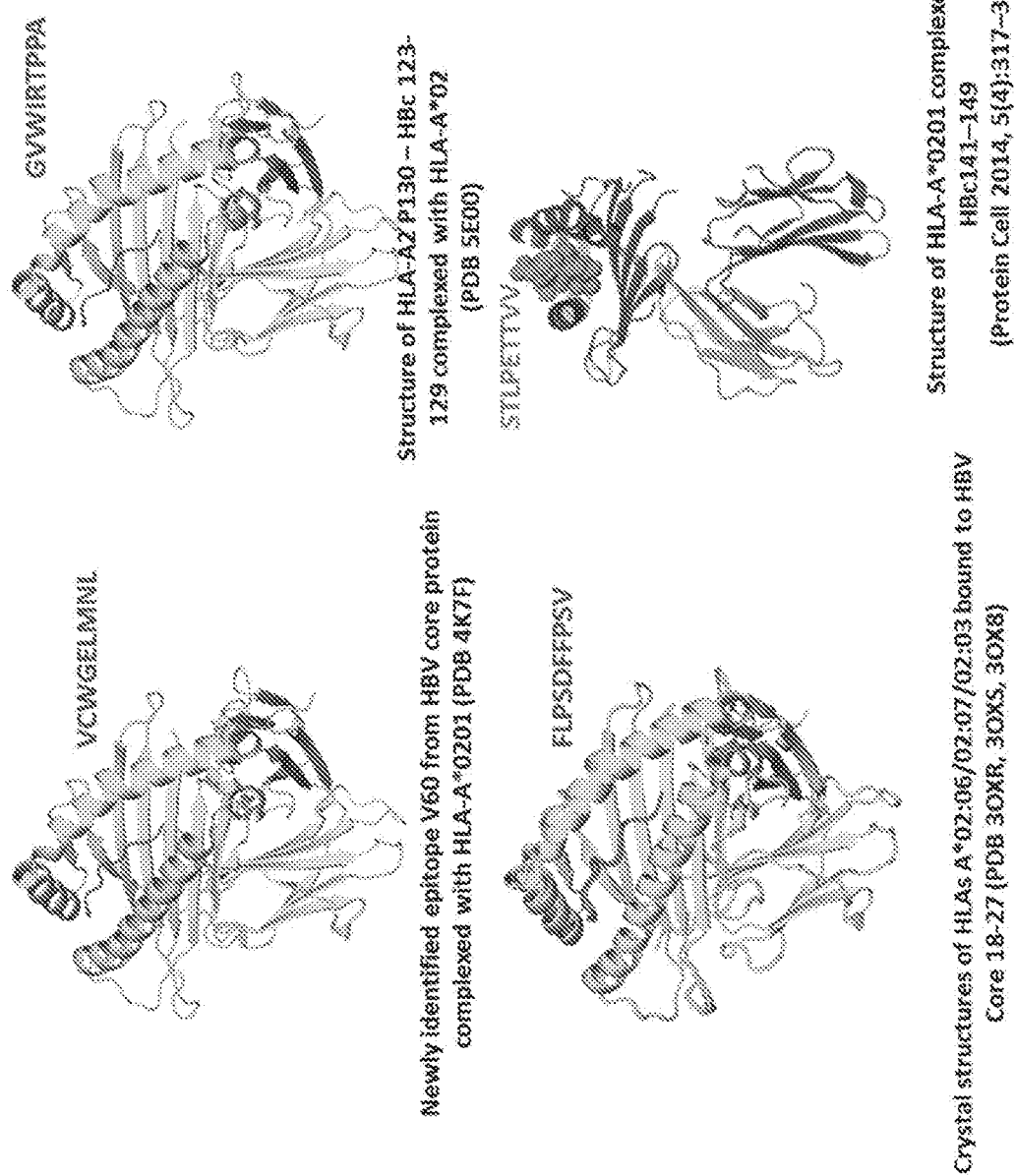
FIG. 12D shows structures of four core peptides-MHC complexes (SEQ ID NOs: 141 and 142).
Figure 13:
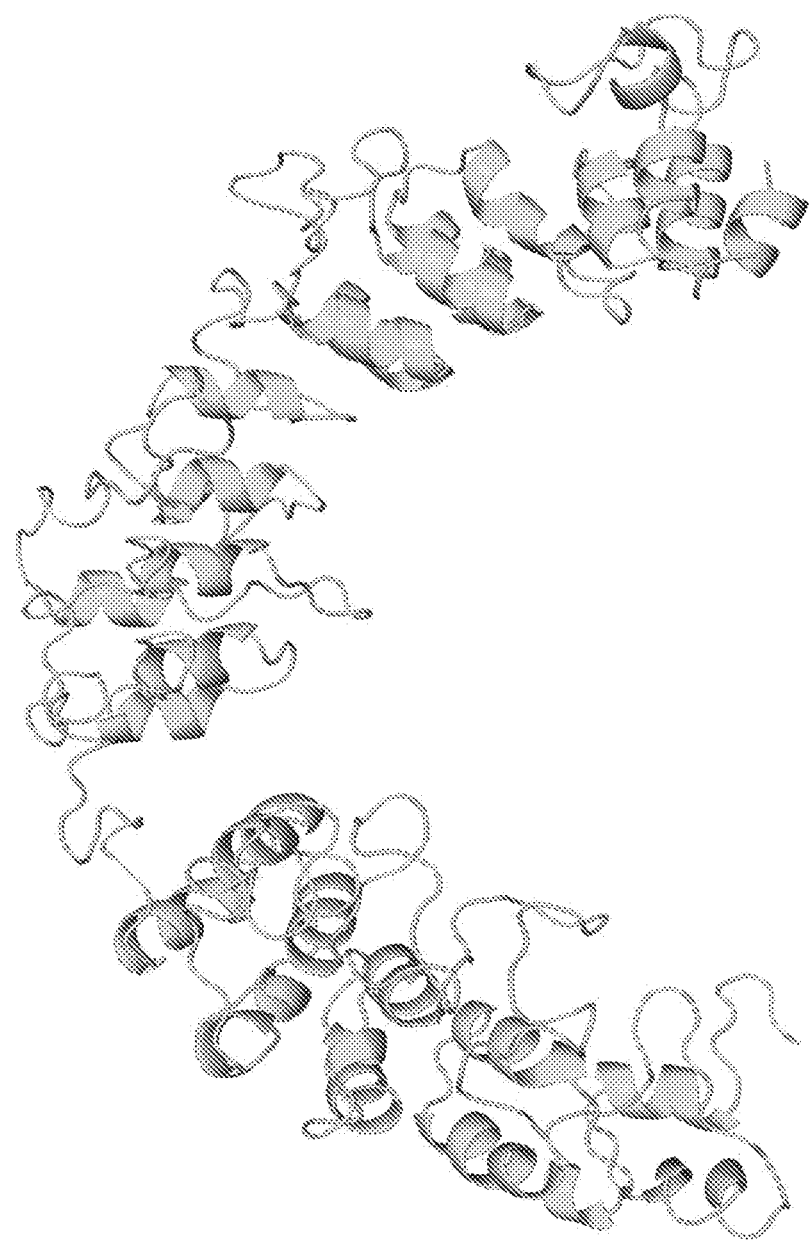
FIG. 13 shows a homology model of HBV design 4 based on multi-epitope antigens.
Figure 14:
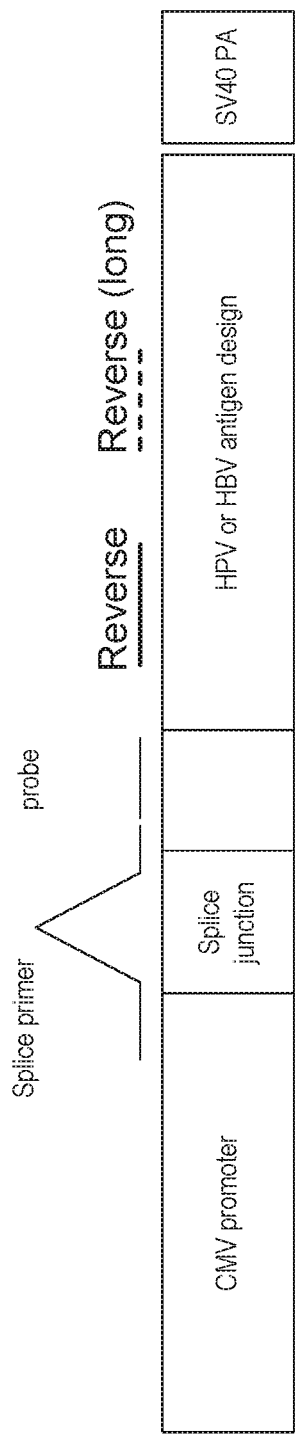
FIG. 14 is a schematic illustration showing short and long primer and probe sets generated for RNA qPCR relative expression assay. Specific primers were designed for each HBV antigen design.

This design consisted of all three major proteins including Core, Surface splice variants, and Polymerase that were linked with HBx peptides as depicted in FIG. 11. Selected protein components were fused together to make a one long open reading frame. This design was based on the following: (a) functional genomics data (HBVdb: AB048701); (b) T cell epitope predictions (Example 1); and (c) analysis of available HBV protein structures as illustrated in FIGS. 12A-12D. When compared to the TG1050 comparator and HBV design design 1, this design has additional and/or modified protein domains as follows: (a) truncated C terminus; (b) spliced variants of surface proteins (PreS1 and PreS2, S); (c) split Pol N- and C-terminus fragments; and (d) six HBx peptides. The protein domains were shuffled to avoid any HBV infectivity, and HBV design 2 used a different ordering scheme than the TG1050 comparator and HBV design 1.

HBV Design 3

This design was based on multi-epitopes containing a total of 32 CTL specific epitopes (Table 3) and was selected from the following: (1) literature review based on multiple immunological assays and immunoproteomics; and (2) the IEDB; (3) NetMHC 4.0 epitope predictions. Human Ankyrin-like repeat protein (PDB code 1QYM) was selected as a scaffold on to which the 32 peptides were grafted replacing the repeat regions. A homology model of the this design (FIG. 13) was generated, which suggested that ankyrin scaffold with grafted peptides can retain the overall tertiary structure. Scaffold backbone amino acids connecting the 32 grafted CTL epitopes can serve as adequate linkers.

HBV Design 4

This design was comprised of the same 32 CTL epitopes from Core, Surface, Pol, HBx and HBSP as Design 3 (Table 3). The peptides were assembled with charged dipeptide KK residue linkers instead of grafting onto a scaffold.

TABLE 3

32 HBV Peptides from Core, Surface, Polymerase, HBx, and HBPS

| Source | Sequence | SEQ | Length | Source | Sequence | SEQ | Length |
|---|---|---|---|---|---|---|---|
| Core-1 | FLPSDFFPSV | #45 | 10 | Surface-1 | GGPNLDNIL | #112 | 9 |
| Core-2 | CWGELMTL | #46 | 8 | Surface-2 | LTTVPAASLLA | #113 | 11 |
| Core-3 | GVWIRTPPA | #47 | 9 | Surface-3 | ILRSFIPLL | #114 | 9 |
| Core-4 | STLPETTVVRR | #48 | 11 | Surface-4 | FLGGPPVCL | #115 | 9 |
| Core-5 | LTFGRETVLEY | #49 | 11 | Surface-5 | FLLTRILTI | #116 | 9 |
| Core-6 | DLLDTASALY | #50 | 10 | Surface-6 | WLSLLVPFV | #117 | 9 |
| Core-7 | LWFHISCLTF | #51 | 10 | Surface-7 | GLSPTVWLSV | #118 | 10 |
| Core-8 | EYLVSFGVW | #52 | 9 | Surface-8 | LLVPFVQWFV | #119 | 10 |
| Pol-1 | FLKQQYMNL | #53 | 9 | HBSP-1 | LLLKATLCI | #120 | 9 |
| Pol-2 | FLSKQYMDL | #54 | 9 | HBSP-2 | TLCIPHVAV | #121 | 9 |
| Pol-3 | TVSTKLCKI | #55 | 9 | HBx-1 | VLHKRTLGL | #122 | 9 |
| Pol-4 | GLSRYVARL | #56 | 9 | HBx-2 | LPKVLHKRTL | #123 | 10 |
| Pol-5 | KLHLYSHPI | #57 | 9 | HBx-3 | HKRTLGLSAM | #124 | 10 |
| Pol-6 | FLLSLGIHL | #58 | 9 | HBx-4 | QFLPKVLHKR | #25 | 10 |
| Pol-7 | SLYADSPSV | #59 | 9 | HBx-5 | TVNAHQFLPK | #126 | 10 |
| Pol-8 | ALMPLYACI | #60 | 9 | HBx-6 | LSAMSTTDL | #127 | 9 |

HBV Design 5

This design is similar to design 1 and has rigid linker (EAAAK)2 (SEQ ID NO: 129) between the fusion components (SEQ ID NOs: 112 and 113; Table 6; FIG. 16).

For RNA qPCR relative expression assay, 5'-TGCCAAGAGTGACGTGTCCA-3' (SEQ ID NO: 110) was used as a splice primer, and 5'-CCCAGGTCCAACTGCAGCCGG-3' (SEQ ID NO: 128) was used as a splice probe. Specific primers designed for each antigen were used as reverse primers (FIG. 14). A549 cells were lipotransfected (Table 4), and HT1080 cells were nucleofected (Table 5).

TABLE 4 qPCR Expression Assay (A549 Cells)

| | One-step qPCR 0.1 ng total RNA | | | | Two-step qPCR 0.2 ng cDNA | | | |
|---|---|---|---|---|---|---|---|---|
| Sample | Short Amplicon bp | GOI Ave. Ct | HPRT1 Ave. Ct | Fold difference in GOI relative to untreated | long Amplicon bp | GOI Ave. Ct | HPRT1 Ave. Ct | Fold difference in GOI relative to untreated |
| Mock | | 40.0 | 31.1 | 1 | | 40.0 | 31.3 | 1 |
| 4825853 | 141 | 23.1 | 31.3 | 145618 | 993 | 32.0 | 31.6 | 300 |
| Mock | | 40.0 | 31.1 | 1 | | 40.0 | 31.3 | 1 |

TABLE 4-continued qPCR Expression Assay (A549 Cells)

| | One-step qPCR 0.1 ng total RNA | | | | Two-step qPCR 0.2 ng cDNA | | | |
|---|---|---|---|---|---|---|---|---|
| Sample | Short Amplicon bp | GOI Ave. Ct | HPRT1 Ave. Ct | Fold difference in GOI relative to untreated | long Amplicon bp | GOI Ave. Ct | HPRT1 Ave. Ct | Fold difference in GOI relative to untreated |
| 4825811 | 162 | 23.2 | 31.4 | 138449 | 948 | 31.2 | 31.6 | 531 |
| Mock | | 40.0 | 31.1 | 1 | | 40.0 | 31.3 | 1 |
| 4825790 | 125 | 22.5 | 31.5 | 241891 | 839 | 29.0 | 31.3 | 2016 |
| Mock | | 40.0 | 31.1 | 1 | | 40.0 | 31.3 | 1 |
| 4825791 | 127 | 22.3 | 31.6 | 304806 | 895 | 28.1 | 31.4 | 3882 |
| Mock | | 40.0 | 31.1 | 1 | | 40.0 | 31.3 | 1 |
| 4825852 | 143 | 20.8 | 31.6 | 827615 | 777 | 24.5 | 31.7 | 58169 |

TABLE 5 qPCR Expression Assay (HT1080 Cells)

| | One-step qPCR 5 ng total RNA | | | | Two-step qPCR 5 ng cDNA | | | |
|---|---|---|---|---|---|---|---|---|
| Sample | Short Amplicon bp | GOI Ave. Ct | HPRT1 Ave. Ct | Fold difference in GOI relative to untreated | long Amplicon bp | GOI Ave. Ct | HPRT1 Ave. Ct | Fold difference in GOI relative to untreated |
| Mock | | 40.0 | 25.5 | 1 | | 40.0 | 25.5 | 1 |
| 4825853 | 141 | 26.5 | 25.7 | 13981 | 993 | 32.4 | 25.1 | 143 |
| Mock | | 40.0 | 25.5 | 1 | | 40.0 | 25.5 | 1 |
| 4825811 | 162 | 23.9 | 25.5 | 71179 | 948 | 27.5 | 25.5 | 5564 |
| Mock | | 40.0 | 25.5 | 1 | | 40.0 | 25.5 | 1 |
| 4825790 | 125 | 25.5 | 25.6 | 24556 | 839 | 29.6 | 25.2 | 1114 |
| Mock | | 40.0 | 25.5 | 1 | | 40.0 | 25.5 | 1 |
| 4825791 | 127 | 24.4 | 26.1 | 78118 | 895 | 26.0 | 25.4 | 15042 |
| Mock | | 40.0 | 25.5 | 1 | | 40.0 | 25.5 | 1 |
| 4825852 | 143 | 21.8 | 25.7 | 360074 | 777 | 22.9 | 25.2 | 113697 |

Example 3

Immunogenicity Testing of HBV Vaccine

All of the antigens were constructed in multi-deleted *gorilla* adenovectors and produced to generate research materials for experimentation as well as pre-GMP stocks that can move to GMP manufacture for clinical studies (FIG. 6).

Optimum plasmid concentration for dendritic cell transfection is determined. The ability of different antigen designs to activate T cells from chronic PHBV patients is assessed. The immunogenicity of antigen design on HBV infected patient samples is assessed. The in vivo testing plan is to conduct in vivo immunogenicity studies in mice (e.g., single administration studies, repeat administration studies, including a "boost at home" proof of feasibility, route of administration (IM vs SC)), and mouse model of chronic HBV infection and eventually HCC.

Monocyte-derived dendritic cells are generated with GM-CSF and IL-4 according to standard protocol. The monocyte-derived dendritic cells are infected with different HBV antigen constructs and incubated with the vectors for 24 hours at 37° C. The cells are washed and matured overnight with 10 ng/ml rhuTNF-α. The cell maturation is assessed by flow cytometry (CD40, CD80, CD83, CD86, HLA-DR). Cytokine production is assessed for IL-1β, TNF-α, IL-6, IL-12p40, and MCP1. The monocyte-derived dendritic cells are co-cultured with autologous T cells for 10 days 1:10 ratio. Exogenous rhuIL-2 (200 U/ml), rhuIL-7 and rHuIL-15 (10 ng/ml) are added on day 3, 5 and 7. Cytokine secretions for IFN-γ, TNF-α, CXCL-10, CXCL-9, IL-10, IL-6, IL-4, IL-5, IL-12p70, and MCP1 are assessed. Activation markers for T cells are CD25, CD69, CD45RA, CD45RO, PD1, CTLA-4, TIGIT, and LAG3. Antigen design with the most immunogenicity based on dendritic cells and T cell activation is selected, and the immunogenicity of the antigen design on HBV infected patient samples is assessed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The present application claims benefit to U.S. Provisional Application No. 62/639,354 filed Mar. 6, 2018, which is incorporated herein by reference in its entirety.

EMBODIMENTS

E1. A non-naturally occurring polynucleotide encoding a polypeptide comprising at least one or more immune response-inducing hepatitis B virus (HBV) polypeptides.

E2. The polynucleotide of E1, wherein said one or more HBV polypeptides comprises an HBV Core peptide.

E3. The polynucleotide of E2, wherein said HBV Core peptide has any one of the Core peptide sequences as shown in Table 3.

E4. The polynucleotide of any one of E1 to E3, wherein said one or more HBV polypeptides comprises an HBV Surface peptide.

E5. The polynucleotide of E4, wherein said HBV Surface peptide has any one of the Surface peptide sequences as shown in Table 3.

E6. The polynucleotide of any one of E1 to E5, wherein said one or more HBV polypeptides comprises an HBV Pol peptide.

E7. The polynucleotide of E6, wherein said HBV Pol peptide has any one of the Pol peptide sequences as shown in Table 3.

E8. The polynucleotide of any one of E1 to E7, wherein said one or more HBV polypeptides comprises an HBV HBSP/HBx peptide.

E9. The polynucleotide of E8, wherein said HBV HBSP/HBx peptide has any one of the HBSP/HBx peptide sequences as shown in Table 3.

E10. The polynucleotide of any one of E1 to E9, wherein said one or more HBV polypeptides comprises a KK linker.

E11. The polynucleotide of E10, wherein said KK linker connects any one of the peptide sequences as shown in Table 3 to any other peptide sequences as shown in Table 3.

E12. A polynucleotide comprising the polynucleotide of any one of E1 to E11, further comprising one or more polynucleotides encoding a gene switch system for inducible control of heterologous gene expression, wherein heterologous gene expression is regulated by said gene switch system; and, wherein said heterologous gene comprises the polynucleotide of any one of E1 to E11.

E13. The polynucleotide of any one of E1 to E12, wherein said gene switch system is an ecdysone receptor-based (EcR-based) gene switch system.

E14. The polynucleotide of any one of E1 to E13, wherein said one or more HBV polypeptides is for use in a vaccine.

E15. A vector comprising the polynucleotide of any one of E1 to E14.

E16. The vector of E15, wherein said vector is an adenoviral vector.

E17. The vector of E16, wherein said adenoviral vector is a *gorilla* adenoviral vector.

E18. A method of regulating the expression of a heterologous gene in a cell, the method comprising: introducing into said cell one or more polynucleotides that comprise (i) an repressible or inducible gene switch, and (ii) a heterologous immune response-inducing gene, wherein expression of said heterologous immune response-inducing gene is regulated by said gene switch, wherein said heterologous immune response-inducing gene encodes at least one of one or more HBV polypeptides; and exposing said cell to a compound in an amount sufficient to repress or induce expression of said heterologous immune response-inducing gene.

E19. The method of E18, wherein said target cell is a mammalian cell.

E20. The method of E18 or E19, wherein said gene switch comprises a ligand binding domain derived from at least one of an ecdysone receptor (EcR), a ubiquitous receptor, an orphan receptor 1, an NER-1, a steroid hormone nuclear receptor 1, a retinoid X receptor interacting protein-15, a liver X receptor β, a steroid hormone receptor like protein, a liver X receptor, a liver X receptor α, a farnesoid X receptor, a receptor interacting protein 14, and a farnesol receptor.

E21. A vector, wherein said vector comprises a polynucleotide that encodes at least one HBV peptide, wherein said vector is an adenoviral vector.

E22. A vector, wherein said vector comprises a polynucleotide that encodes at least one HBV peptide, wherein said vector is an adenoviral vector, wherein said adenoviral vector is a *gorilla* adenoviral vector.

E23. A polypeptide construct, wherein said polypeptide construct comprises an HBV HBx domain and at least one of an HBV Pol domain, an HBV Core domain, an HBV pre-Core domain or an HBV Surface domain.

E24. A polypeptide construct, wherein said polypeptide construct comprises a pre-Core domain and at least one of an HBV Pol domain, an HBV HBx domain or an HBV Surface domain.

E25. The polypeptide construct of E23 or E24, wherein said HBV HBx domain has a sequence as shown in SEQ ID NO: 98.

E26. The polypeptide construct of any one of E23 to E25, wherein said HBV Pol domain comprises a deletion of at least one amino acid as compared to a wildtype HBV Pol domain.

E27. The polypeptide construct of E26, wherein said deletion comprises a deleted portion of said wildtype HBV Pol domain, wherein said deleted portion comprises at least one of amino acids 538-544 or amino acids 710-742.

E28. The polypeptide construct of E27, wherein said deleted portion comprises both of amino acids 538-544 and amino acids 710-742.

E29. The polypeptide construct of E28, wherein said HBV Pol domain has a sequence as shown in SEQ ID NO: 99.

E30. The polypeptide construct of any one of E23 to E29, wherein said HBV Surface domain comprises at least one of a PreS1 domain, a PreS2 domain and an S domain.

E31. The polypeptide construct of E30, wherein said HBV Surface domain comprises an HBV S domain.

E32. The polypeptide construct of E30 or E31, wherein said HBV Surface domain has a sequence as shown in SEQ ID NO: 100.

E33. The polypeptide construct of any one of E24 to E32, wherein said polypeptide construct further comprises an HBV Core domain.

E34. The polypeptide of E23 or E33, wherein said polypeptide construct comprises a Core portion, wherein said Core portion comprises said HBV Core domain and said HBV pre-Core domain.

E35. The polypeptide construct of E34, wherein said Core portion has a sequence as shown in SEQ ID NO: 101.

E36. The polypeptide construct of E23 or E33, wherein said polypeptide construct comprises each of SHB(Env), HBeAg, HBx, and Pol domains.

E37. The polypeptide construct of E36, wherein said polypeptide construct comprises a structure, from N-terminus to C-terminus, of said SHB(Env), HBeAg, HBx, and Pol domains.

E38. The polypeptide construct of E36 or E37, wherein said SHB(Env) domain has a sequence as shown in SEQ ID NO: 102.

E39. The polypeptide construct of E36 or E37, wherein said HBeAg domain has a sequence as shown in SEQ ID NO: 103.

E40. The polypeptide construct of E36 or E37, wherein said HBx domain has a sequence as shown in SEQ ID NO: 104.

E41. The polypeptide construct of E36 or E37, wherein said Pol domain has a sequence as shown in SEQ ID NO: 105.

E42. The polypeptide construct of E36 or E37, wherein said polypeptide construct has a sequence as shown in SEQ ID NO: 106.

E43. The polypeptide construct of E36 or E37, further comprising a rigid linker.

E44. The polypeptide construct of E36 or E37, wherein said polypeptide has a sequence as shown in SEQ ID NO: 112.

E45. A polypeptide construct, wherein said polypeptide construct comprises one or more HBV HBx linkers and at least one of a Core domain, a Surface domain and a Pol domain, wherein one of said Core domain, said Surface domain and said Pol domain is connected to another of said Core domain, said Surface domain and said Pol domain by said one or more HBx linkers.

E46. The polypeptide construct of E45, wherein said Surface domain comprises at least one of an HBV PreS1 domain, an HBV PreS2 domain and an HBV S domain.

E47. The polypeptide construct of E45 or E46, wherein said one or more HBV HBx linkers comprises multiple HBV HBx linkers.

E48. The polypeptide construct of E47, wherein at least two of said multiple HBV HBx linkers differ in an amino acid sequence.

E49. The polypeptide construct of any one of E45 to E48, wherein said HBV HBx linker has a sequence as shown in any one of HBx-1, HBx-2, HBx-3, HBx-4, HBx-5 or HBx-6 of Table 3.

E50. The polypeptide construct of any one of E45 to E49, wherein said Core domain is adjacent to said Surface domain.

E51. The polypeptide construct of E50, wherein said Surface domain comprises a PreS1 domain.

E52. The polypeptide construct of E50 or E51, wherein said Surface domain is connected to said Core domain by one of said one or more HBx linkers.

E53. The polypeptide construct of any one of E45 to E52, wherein said Pol domain is adjacent to a Surface domain.

E54. The polypeptide construct of E53, wherein said Surface domain comprises at least one of a PreS1 domain, a PreS2 domain and an S domain.

E55. The polypeptide construct of E54, wherein said Surface domain comprises said PreS1 domain, and an N-terminal portion of said Pol domain is adjacent to said PreS1 domain.

E56. The polypeptide construct of E55, wherein said N-terminal portion of said Pol domain is connected to said PreS1 domain by one of said one or more HBx linkers.

E57. The polypeptide construct of E56, wherein said Surface domain comprises said PreS2 domain, and an N-terminal portion of said Pol domain is adjacent to said PreS2 domain.

E58. The polypeptide construct of E57, wherein said N-terminal portion of said Pol domain is connected to said PreS2 domain by one of said one or more HBx linkers.

E59. The polypeptide construct of E58, wherein said Surface domain comprises said PreS2 domain, and a C-terminal portion of said Pol domain is adjacent to said PreS2 domain.

E60. The polypeptide construct of E59, wherein said C-terminal portion of said Pol domain is connected to said PreS2 domain by one of said one or more HBx linkers.

E61. The polypeptide construct of E60, wherein said Surface domain comprises said S domain, and a C-terminal portion of said Pol domain is adjacent to said S domain.

E62. The polypeptide construct of E61, wherein said C-terminal portion of said Pol domain is connected to said S domain by one of said one or more HBx linkers.

E63. The polypeptide construct of any one of E45 to E62, wherein said polypeptide construct has a sequence as shown in SEQ ID NO: 107.

E64. A polypeptide construct comprising an ankyrin-like repeat domain and one or more HBV peptides.

E65. The polypeptide construct of E64, wherein said ankyrin-like repeat protein is a human ankyrin-like repeat protein.

E66. The polypeptide construct of E64 or E65, wherein said one or more HBV peptides has a sequence as shown in any one of the amino acid sequences of Table 3.

E67. The polypeptide construct of any one of E64 to E66, wherein said one or more HBV peptides comprises one or more of a Core peptide, a Surface peptide, a Pol peptide and an HBSP/HBx peptide.

E68. The polypeptide construct of E67, wherein said one or more HBV peptides comprises a Core peptide, and said Core peptide has a sequence as shown in any one of the Core amino acid sequences of Table 3.

E69. The polypeptide construct of E67, wherein said one or more HBV peptides comprises a Surface peptide, and said Surface peptide has a sequence as shown in any one of the Surface amino acid sequences of Table 3.

E70. The polypeptide construct of E67, wherein said one or more HBV peptides comprises a Pol peptide, and said Pol peptide has a sequence as shown in any one of the Pol amino acid sequences of Table 3.

E71. The polypeptide construct of E67, wherein said one or more HBV peptides comprises an HBSP/HBx peptide, and said HBSP/HBx peptide has a sequence as shown in any one of the HBSP/HBx amino acid sequences of Table 3.

E72. The polypeptide construct of any one of E65 to E71, wherein said polypeptide construct has a sequence as shown in SEQ ID NO: 108.

E73. A polypeptide construct, wherein said polypeptide construct comprises at least two HBV amino acid sequences as shown in Table 3, wherein said at least two HBV amino acid sequences are connected by a peptide linker, wherein said peptide linker is a KK linker.

E74. The polypeptide construct of E73, wherein said comprises at least two HBV amino acid sequences comprise at least one of a Core peptide, a Surface peptide, a Pol peptide and an HBSP/HBx peptide as shown in Table 3.

E75. The polypeptide construct of E73 or E74, wherein said at least two HBV amino acid sequences comprise each of the amino acid sequences as shown in Table 3.

E76. The polypeptide construct of E75, wherein said each of the amino acid sequences is connected to another of said each of the amino acid sequences by said KK linker.

E77. The polypeptide construct of any one of E73 to E75, wherein said polypeptide construct has a sequence as shown in SEQ ID NO: 109.

E78. The polypeptide construct of any one of E23 to E77 for use in a vaccine.

E79. A polynucleotide encoding the polypeptide construct of any one of E25 to E78.

E80. A vector comprising the polynucleotide of E79.

E81. The vector of E80, wherein said vector is an adenoviral vector.

E82. The vector of E81, wherein said adenoviral vector is a *gorilla* adenoviral vector.

SEQUENCES

Provided herein is a representative list of certain sequences included in embodiments provided herein (Table 6).

TABLE 6

Polynucleotide/Amino Acid Sequences

| SEQ ID NO: | Description |
|---|---|
| 1 | Adenovirus pIX fragment nucleotides |
| 2 | Adenovirus DNA polymerase fragment nucleotides |
| 3 | Adenovirus penton base protein fragment nucleotides |
| 4 | Adenovirus hexon protein fragment nucleotides |
| 5 | Adenovirus fiber protein fragment nucleotides |
| 6 | Adenovirus pIX nucleotides |
| 7 | Adenovirus DNA polymerase nucleotides |
| 8 | Adenovirus penton base protein nucleotides |
| 9 | Adenovirus hexon protein nucleotides |
| 10 | Adenovirus fiber protein nucleotides |
| 11 | Adenovirus pIX protein fragment |
| 12 | Adenovirus DNA polymerase fragment |
| 13 | Adenovirus penton base protein fragment |
| 14 | Adenovirus hexon protein fragment |
| 15 | Adenovirus fiber protein fragment |
| 16 | Adenovirus pIX amino acids |
| 17 | Adenovirus DNA polymerase amino acids |

TABLE 6-continued

Polynucleotide/Amino Acid Sequences

| SEQ ID NO: | Description |
|---|---|
| 18 | Adenovirus penton base protein |
| 19 | Adenovirus hexon protein |
| 20 | Adenovirus fiber protein |
| 21 | Adenovirus vector nucleotide sequences |
| 22 | Adenovirus vector nucleotide sequences |
| 23 | Adenovirus vector nucleotide sequences |
| 24 | Adenovirus vector nucleotide sequences |
| 25 | Adenovirus vector nucleotide sequences |
| 26 | IL-2 core promoter |
| 27 | IL-2 minimal promoter |
| 28 | IL-2 enhancer and promoter variant |
| 29 | L-2 enhancer and promoter variant |
| 30 | (NF-κB)$_1$-IL2 promoter variant |
| 31 | (NF-κB)$_3$-IL2 promoter variant |
| 32 | (NF-κB)$_6$-IL2 promoter variant |
| 33 | 1X NFAT response elements-IL2 promoter variant |
| 34 | 3X NFAT response elements-IL2 promoter variant |
| 35 | 3X NFAT response elements-IL2 promoter variant |
| 36 | 6X NFAT response elements-IL2 promoter variant |
| 37 | 6X NFAT response elements-IL2 promoter variant |
| 38 | 6X NFAT response elements-IL2 promoter variant |
| 39 | 6X NFAT response elements-IL2 promoter variant |
| 40 | human EEF1A1 promoter variant |
| 41 | human EEF1A1 promoter variant |
| 42 | human EEF1A1 promoter and enhancer |
| 43 | human UBC promoter |
| 44 | synthetic minimal promoter 1 |
| 61 | GCAd-RTS-IL12 design 1 |
| 62 | GCAd-RTS-IL12 design 2 |
| 63 | GCAd-RTS-IL12 design 3 |
| 98 | HBV HBx domain of HBV design 1 |
| 99 | HBV Pol domain of HBV design 1 |
| 100 | HBV Surface (Env1) domain of HBV domain 1 |
| 101 | HBV Core domain of HBV design 1 |
| 102 | SHB(Env) domain |
| 103 | HBeAg domain |
| 104 | HBx domain |
| 105 | Pol domain |
| 106 | HBV design 1 |
| 107 | HBV design 2 |
| 108 | HBV design 3 |
| 109 | HBV design 4 |
| 112 | HBV design 5 |

SEQUENCE LISTING

```
Sequence total quantity: 148
SEQ ID NO: 1            moltype = DNA  length = 30
FEATURE                 Location/Qualifiers
misc_feature            1..30
                        note = Adenovirus pIX fragment nucleotides
source                  1..30
                        mol_type = other DNA
                        organism = synthetic construct
SEQUENCE: 1
agctctttgg tggcgagcgg cgcggcctct                                              30

SEQ ID NO: 2            moltype = DNA  length = 439
FEATURE                 Location/Qualifiers
misc_feature            1..439
                        note = Adenovirus DNA polymerase fragment nucleotides
source                  1..439
                        mol_type = other DNA
                        organism = synthetic construct
SEQUENCE: 2
aacatcaata cctcaaagtc atggtcaggg acactttcgc cctcacccac acctccctcc    60
gcaaggcggc gcaggcctac gcgctgcccg tggagaaggg ctgttgcccc taccaggccg   120
tcaaccagtt ctacatgcta ggctcttacc gttcggacac ggacgggttt cccctccaag   180
agtactggaa agaccgcgaa gagttcgtcc tcaaccgcga gctgtggaaa aagaagggg    240
```

```
aggataagta tgacatcatc cgcgagaccc tcgactactg cgcgctcgac gtccaggtca    300
ccgccgagct ggtgcacaag ctgcgcgagt cctacgcctc cttcgtcagg gactcggtgg    360
gcttgcaaga agcaagcttc aacgtcttcc agcggcccac catctcctcc aactcccatg    420
ccatcttcag gcagatcgc                                                 439

SEQ ID NO: 3            moltype = DNA   length = 34
FEATURE                 Location/Qualifiers
misc_feature            1..34
                        note = Adenovirus penton base protein fragment nucleotides
source                  1..34
                        mol_type = other DNA
                        organism = synthetic construct
SEQUENCE: 3
actgaggctg cggctaaggc tgaggtcgaa gcca                                 34

SEQ ID NO: 4            moltype = DNA   length = 45
FEATURE                 Location/Qualifiers
misc_feature            1..45
                        note = Adenovirus hexon protein fragment nucleotides
source                  1..45
                        mol_type = other DNA
                        organism = synthetic construct
SEQUENCE: 4
ataggtgtgg atgccacaca ggcgggagat aaccctatat atgct                    45

SEQ ID NO: 5            moltype = DNA   length = 30
FEATURE                 Location/Qualifiers
misc_feature            1..30
                        note = Adenovirus fiber protein fragment nucleotides
source                  1..30
                        mol_type = other DNA
                        organism = synthetic construct
SEQUENCE: 5
gtagcaggcc ccctagctgt ggccaatggc                                     30

SEQ ID NO: 6            moltype = DNA   length = 399
FEATURE                 Location/Qualifiers
misc_feature            1..399
                        note = Adenovirus pIX nucleotides
source                  1..399
                        mol_type = other DNA
                        organism = synthetic construct
SEQUENCE: 6
atgagcgaca ccggcaacag ctttgatgga agcatctttta gccctatct gacagtgcgc    60
atgcctcact gggctggagt gcgtcagaat gtgatgggtt ccaacgtgga tggacgcccc   120
gttctgcctt caaattcgtc tacaatggcc tacgcgaccg tgggaggaac tccgctggac   180
gccgcgacct ccgccgccgc ctccgccgcc gccgcagcat ggctacggac                240
ctttacagct ctttggtggc gagcggcgcg gcctctcgcg cgtctgctcg ggatgagaaa   300
ctgaccgctc tgctgcttaa actggaagac ttgacccggg agctgggtca actgacccag   360
caggtctcca gcttgcgtga gagcagcctt gcctccccc                           399

SEQ ID NO: 7            moltype = DNA   length = 3168
FEATURE                 Location/Qualifiers
misc_feature            1..3168
                        note = Adenovirus DNA polymerase nucleotides
source                  1..3168
                        mol_type = other DNA
                        organism = synthetic construct
SEQUENCE: 7
atggacagct ccaatgtgcg cgatgtcgtc atcaaactcc gcccgccgag cgccgagatc     60
tggacctgcg gctctcgcgg cgtggtggtc tgctccacca tcgccctcca ggagacagat   120
gctggcggcc agacaaccaa agtagaagac caccagccac acgggacccc aggcggggga   180
cttagattcc cgctgcgctt cctcgtcaga ggtcgccagg ttcacctcgt gcaagatata   240
caacccgtgc agcgctgcca gtactgcggt cgcttttaca aaagccagca cgagtgctcg   300
gcccgcagac gggacttcta cttttcaccac atcaacagca atcctccaa ctggtggcgg   360
gagatccagt tcttcccgat cggctctcat cctcgcacgg agcgcctctt tgtcacctac   420
gatgtagaga cctacacttg gatgggagcc tttggcaagc agctcgtgcc cttcatgctg   480
gtcatgaaac tgggggggcga cgaggctctg gtcgccgccg cgcgcgaccct cgcccgagag   540
ctcagatggg acccctggga gaaagacccc ctcaccttct actgcatcct ccccgaaaag   600
atggccgtgg ggcgacagtt cagaaccttc cgcgaccgcc tgcagaccct catggcccgc   660
gacctctggc gatccttcct ggcggccaac cctcacttgc aagactggc cctggaggag   720
cacggcctgg aatcgcccga ggagctcacc tacgaggaac tcaaaaagct cccctccatc   780
aagggccagc ccgcttttttt ggagctctac atcgtgggcc acaacataaa cggctttgac   840
gagatcgtcc tggccgccca ggtcatcaac aaccgctcct cggtcccagg gccctttcgc   900
atcaccagaa acttcatgcc tcgagcgggg aagatcctct tcaatgacct cactttctg   960
ctgcccaacc cgcgctccaa aaagcgcacg gactacaccc tgtgggaaca gggcggctgc  1020
gatgacacag acttcaaaca tcaataccctc aaagtcatgg tcaggacac tttcgcctc  1080
acccacacct ccctccgcaa ggcggcgcag gcctacgcgc tgcccgtgga aagggctgt   1140
tgccctacc aggccgtcaa ccagttctac atgctaggct cttaccgttc ggacacggac  1200
```

```
gggtttcccc tccaagagta ctggaaagac cgcgaagagt tcgtcctcaa ccgcgagctg  1260
tggaaaaaga aggggggagga taagtatgac atcatccgcg agaccctcga ctactgcgcg  1320
ctcgacgtcc aggtcaccgc cgagctggtg cacaagctgc gcgagtccta cgcctccttc  1380
gtcagggact cggtgggctt gcaagaagca agcttcaacg tcttccagcg gcccaccatc  1440
tcctccaact cccatgccat cttcaggcag atcgccttcc gcgccgagcg ccccagcgtc  1500
accaacctcg ggcccaacat gctggccccc tcccacgagc tctatgacta cgtgcgcgcc  1560
agcatccgcg ggggcgctg ctaccccacc tacctcggca tcctcaggga acccctgtac  1620
gtgtatgaca tctgcggcat gtacgcctcc gcgctcaccc accccatgcc ctggggcccg  1680
cccctcaacc cctacgagcg cgcgctcgcc gcccgcgaat ggcagcgggc tctggacatg  1740
caagcttgca agatcgacta cttttgacccg cgcttgctcc ccggggtctt caccatcgac  1800
gcggaccccc caaacgagga ccagctggac cccctacccc ccttctgctc gcgcaagggc  1860
ggccgcctct gctggaccaa cgagcgcctg cgcggcgagg tcgccaccag cgtcgacatg  1920
gtcaccctgc acaaccgagg ctggagggtg cgcctaatcc cagacgagcg caccaccgtc  1980
ttccccgagt ggaagtcgt ggccgcgag tacgtgcaac tcaacatcgc ggccaaggag  2040
cgagccgacc gcgacaaaaa ccagaccctg cgctccatcg ccaagctgct ctccaacgcc  2100
ctctacgggt cgttcgccac caagcttgac aacaaaaaaa tagtgttttc tgaccagatg  2160
gacccaggta ccctcaaagg tatcacctcc ggacaggtga acatcaaatc ctcctcatt  2220
ttagaaactg acaacctgag cgctgaggtc atgcccgcct tcgagaggga atacttaccc  2280
cagcagctgg ccctcgcaga cagcgatgcg gaagagagtg aagatgaaag gcgcccccac  2340
ccctttata ccccccgtc gggaacccc ggtcacgtgt cctacaccta caagccaatc  2400
acttttctgg acgcggagga ggggacatg tgcctgcaca ccctggagaa ggtggacccg  2460
ctagtggaca acgaccgcta cccctcccac gtggcctcctc tcgtcctggc ctggacgggg  2520
gccttcgtct cagagtggtc agagtttctc tacgaggagg acagaggcac tccgctggaa  2580
gacaggcccc tgaagtcggt ctacggggac acggacagcc tcttcgtcac cgagaaggga  2640
caccgcctca tggagagccg aggtaagaaa cgcatcaaaa agcatggggg caacctggtt  2700
tttgacctg accgcccgga gctcacttgg ctggtggaat gcgagacggt ctgcgcttcc  2760
tgcggcgcgg acgcctactc cccagagtcc gtgtttctcg ctcccaagct ctacgccctg  2820
aagagctgc agtgccctc gtgcggcgcc acctccaagg gaaagctccg cgccaagggg  2880
cacgccgccg agggtctcga ctacgagacc atggtcaaat gctacctggc cgacgcgcag  2940
ggcgaagagc ggcagcgatt cagcaccagc agaaccagcc tcaagcgcac cctggccagc  3000
gcccaacccg gagcgcaccc cttcaccgtg acccagacca ccctgacgag gaccctgcgc  3060
ccatggaagg acatgactct ggccccgctg gacgcccatc ggctggtgcc ctacagcgaa  3120
agccgcccca cccgcgaaa cgaggagatc tgctggatcg agatgccg              3168

SEQ ID NO: 8           moltype = DNA  length = 1974
FEATURE                Location/Qualifiers
misc_feature           1..1974
                       note = Adenovirus penton base protein nucleotides
source                 1..1974
                       mol_type = other DNA
                       organism = synthetic construct
SEQUENCE: 8
atgcggcgcg cggcgatgtt cgaggagggg cctccccct cttacgagag cgcgatgggg   60
atttctcctg cggcgcccct gcagcctccc tacgtgcctc ctcggtacct gcaacctaca  120
gggggagaa atagcatctg ttactctgag ctgcagcccc tgtacgatac caccagactg  180
tacctggtgg acaacaagtc cgcggacgtg gcctccctga actaccagaa cgaccacagc  240
gattttttga ccacggtgat ccaaaaacaac gacttcaccc caaccgaggc cagcacccag  300
accataaaacc tggataacag gtcgaactgg ggcggcgacc tgaagaccat cttgcacacc  360
aacatgccca acgtgaacga gttcatgttc accaactctt ttaaggcgcg ggtgatggtg  420
gcgcgcgagc aggggaggc gaagtacgag tgggtggact tcacgctgcc cgagggcaac  480
tactcagaga ccatgactct cgacctgatg aacaatgcga tcgtgaaaca ctatctggaa  540
gtgggcaggc agaacgggt gaaggaaagc gatatcgggg tcaagtttga caccagaaac  600
ttccgtctgg gctgggaccc cgtgaccggg ctggtcatgc cggggggtcta caccaacgag  660
gcctttcatc ccgacatagt gcttctgccc ggctgtgggg tggacttcac ccagagccgg  720
ctgacaacc tgctgggcat tcgcaagcgg cagccttcc aggaggtt caagatcacc  780
tatgaggatc tgaaggggg caacattccc gcgctccttg atctggacgc ctacgaggag  840
agcttgaaac ccgaggagag cgctggcgac agcggcgaga gtggcgagga gcaagccggc  900
ggcggtggcg gcgcgtcgt agaaaacgaa agtacgcccg cagtggcggc ggacgctgcg  960
gaggtcgagc cggaggccat gcagcaggac gcagaggagg gcgcacagga gggcgcgcag 1020
aaggacatga acgatgggga gatcaggga gacacattcg ccaccccggg cgaagaaaaa 1080
gaggcagagc cggcggcggc ggcgacggcg gaggccgaaa ccgaggttga ggcagaggca 1140
gagccccgaga ccgaagttat ggaagacatg aatgatggag aacgtagggg cgacacgttc 1200
gccacccggg gcgaagagaa ggcggcgag gcagaagccg cggctgagga ggcggctgcg 1260
gctgcggagc agactgaggc tgcggctaag gctgaggtca aagcaatgt tgcggttgag 1320
gctcaggctg aggaggaggc ggcggctgaa gcagttaagg aaaaggccca ggcagagcag 1380
gaagagaaaa aacctgtcat tcaacctcta aagaagata gcaaaagcg cagttacaac 1440
gtcatcgagg gcagcacctt tacccagtac cgcagctggt acctggcgta caactacggc 1500
gacccggtca aggggtgcg ctcgtggacc ctgctctgca cgccggacgt cacctgcggc 1560
tccgagcca tgtactggtc gctgccgaac atgatgcaag acccggtgac cttccgctcc 1620
acgcggcagg ttagcaactt cccggtggtg ggcgccgaac tgctgccgt gcactccaag 1680
agttttaca acgagcaggc cgtctactcc cagctgatcc gccaggccac ctctctgacc 1740
cacgtgttca atcgctttcc cgagaaccag attttggcgc gccgccggc ccccaccatc 1800
accaccgtga gtgaaaacgt tcctgccctc acagatcacg gacgctacc gctgcgcaac 1860
agcatctcag gagtccagcg agtgaccatt actgacgcg gacgcggac ctgccctac 1920
gtttacaagg ccttgggcat agtctcgccg cgcgtcctct ccagtcgcac tttt        1974

SEQ ID NO: 9           moltype = DNA  length = 2877
FEATURE                Location/Qualifiers
misc_feature           1..2877
```

|  | note = Adenovirus hexon protein nucleotides |
| --- | --- |
| source | 1..2877 |
|  | mol_type = other DNA |
|  | organism = synthetic construct |

SEQUENCE: 9

```
atggcgaccc catcgatgat gcctcagtgg tcgtacatgc acatctcggg ccaggacgct   60
tcggagtacc tgagccccgg gctggtgcag ttcgcccgcg ccacagacac ctacttcaac  120
atgagtaaca agttcaggaa ccccactgtg gcgcccaccc acgatgtgac cacggaccgg  180
tcgcagcgcc tgacgctgcg gttcatcccc gtggatcggg aggacaccgc ctactcttac  240
aaggcgcggt tcacgctggc cgtgggcgac aaccgcgtgc tggacatggc ctccacttac  300
tttgacatca gggggggtgct ggacagggggc cccaccttca gccctactc gggtactgcc  360
```
(Note: minor reading uncertainties in some positions)

```
tacaactccc tggcccccaa gggcgctccc aattcttgcg agtgggaaca agatgaacca   420
gctcaggcag caatagctga agatgaagaa gaacttgaag aagaacaagc tcaggacgaa   480
caggcgccca ctaagaaaac ccatgtatac gcccaggcac ctctttctgg tgaaaaaatt   540
actaaggatg gtttgcaaat aggtgtggat gccacacagg cgggagataa ccctatatat   600
gctgataaaa cattccaacc cgaacctcag ataggtgagt ctcagtggaa cgaggctgat   660
gccacagtag caggaggcag agtcttaaaa aagaccaccc ctatgagacc ttgctatgga   720
tcctatgcca aacctactaa tgccaatggc ggtcaaggga tcatggtggc caatgatcag   780
ggagcgcttg aatctaaagt tgagatgcaa ttttctcca ccacaacgtc tcttaatgta   840
agggaaggtg aaaacaatct tcagccaaaa gtagtgctat acagcgaaga tgttaacttg   900
gaatcccctg acactcattt gtcttacaaa cctaaaaagg atgacaccaa ctctaaaatc   960
atgttgggtc agcaagccat gcccaacaga cccaacctca ttgcttttag ggacaacttt  1020
attggactta tgtactacaa cagcacaggc aacatgggaa tgctggcagg acaggcctcc  1080
cagctaaacg ctgtggtaga cttgcaagac agaaacacag agctgtcata ccaactgatg  1140
cttgattcca ttggagacag atcaagatac ttttccatgt ggaaccaggc agtggacagc  1200
tatgacccag atgtcagaat cattgaaacc atgggggttg aagatgagct gcccaactat  1260
tgctttcccc tgggcggtat tggaattaca gacacatacc agtgcataaa accaaccgca  1320
gctgctaata acactacatg gtctaaggat gaagaattta gtgatcgcaa tgaaataggg  1380
gtgggaaaca acttcgccat ggagatcaac atccaggcca acctctggag gaacttcctc  1440
tatgcgaacg tggggctcta cctgccagac aagctcaagt acaaccccac caacgtggac  1500
atctctgaca accccaacac ctatgactac atgaacagcc gtgtggtggc tcccggcctg  1560
gtggactgct ttgtcaatgt gggagccagg tggtccctgg actacatgga caacgtcaac  1620
cccttcaacc accaccgcaa tgcgggtctg cgctaccgct ccatgatcct gggcaacggg  1680
cgctacgtgc ccttccacat tcaggtgccc cagaagttct ttgccatcaa gaacctcctc  1740
ctcctgccgg gctcctacac ttacgagtgg aacttcagga aggatgtcaa catggtcctg  1800
cagagctctc tggcaatga ccttaggtgt gacggggcca gcatcaagtt tgacagcgtc  1860
accctctatg ctaccttctt ccccatggct cacaacaccg cctccacgct cgaggccatg  1920
ctgaggaacg acaccaacga ccagtccttc aatgactacc tctctggggc caacatgggcc  1980
tacccatcc ccgccaaggc caccaacgtg cccatctcca ttccctcgg caactgggcc  2040
gccttcagag ctgggccttt acccgccttt aagaccaagg aaaaccccct cctgggctcg  2100
ggttttgacc cctactttgt ctactcggga tccatcccct acctggatgg caccttctac  2160
ctcaaccaca cttttaagaa gatatccatc atgtatgact cctccgtcag ctggccgggc  2220
aatgaccgcc tgctcacccc caatgagttc gaggtcaagc gcgcggtgga cgccgaggggc  2280
tacaacgtgg cccagtgcaa catgaccaag gactggttcc tggtgcagat gctggccaac  2340
tacaacatag ctaccaggg cttctacatc ccagagagct acaaggacag gatgtactcc  2400
ttcttcagaa atttccaacc catgagcagg caggtggtgg acgagaccaa atacaaggac  2460
tatcagcagt ttggcatcac tcaccagcac aacaactgga agttcgttga ctacctggct  2520
cccaccatgc gcgaggggca ggcctacccc gccaacttcc cctacccgtt gataggcaaa  2580
accgcggtcg acagcgtcac ccagaaaaag ttcctctgcg accgcaccct ctggcgcatc  2640
cccttctcta gcaacttcat gtccatgggt gcgctcacgg acctgggcca gaacctgctc  2700
tatgccaact ccgcccatgc gctggacatg acttttgagg tggacccat ggacgagccc  2760
acccttctct atattgtgtt tgaagtgttc gacgtggtca gagtgcacca gccgcaccgc  2820
ggtgtcatcg agaccgtgta cctgcgcacg cccttctcgg ccggcaacgc caccacc    2877
```

| SEQ ID NO: 10 | moltype = DNA length = 1749 |
| --- | --- |
| FEATURE | Location/Qualifiers |
| misc_feature | 1..1749 |
|  | note = Adenovirus fiber protein nucleotides |
| source | 1..1749 |
|  | mol_type = other DNA |
|  | organism = synthetic construct |

SEQUENCE: 10

```
atgaaacgcg cgagatcgtc tgacgagacc ttcaaccccg tgtacccta cgataccgag   60
atcgctccga cttctctttcc ctccttacc cctcccttg tgtcatccgc aggaatgcaa  120
gaaaatccag ctggggtgct gtccctgcac ttgtcagagc cccttaccac ccacaatggg  180
gccctgactc taaaaatggg gggcggcctg accctggaca aggaagggaa tctcacttcc  240
caaaacatca ccagtgtcga tccccctctc aaaaaaagca agaacaacat cagccttcag  300
accgccgcac ccctcgccgt cagctccggg gccctaacac tttttgccac tccccccta  360
gcggtcagtg gtgacaacct tactgtgcag tctcaggccc ctctcactt ggaagactca  420
aaactaactc tggccaccaa aggaccccta actgtgtccg aaggcaaact tgcctagaa  480
acagaggctc cctgcatgc aagtgacagc agcagcctgg gcttagcgt tacggcccca  540
cttagcatta caatgacag cctaggacta gatctgcagg caccattgt ctctcaaaat  600
ggaaaactgg ctctaaatgt agcaggcccc ctagctgtgg ccaatggcat taatgctttg  660
acagtaggca caggcaaagg tattggtcta aatgaaacca gcactcactt gcaagcaaag  720
ttggtcgccc cctaggcttt gataccaat ggcaacatta gctaagcgt tgcaggaggc  780
atgagactaa ataatgacac acttatacta gatgtaaact accctttga agctcaaggc  840
caactaagtc taagagtggg ccagggtccg ctgtatatag attctagcag ccataacctg  900
accattgat gccttagagg attatacata acatcgtcta ataaccaaac cggtctagag  960
gccaacataa aactaacaaa aggccttgtc tatgatggaa atgccatagc agtcaatgtt 1020
```

```
ggtcaaggat tgcaatacag cactactgcc acatcggaag gtgtgtatcc tatacagtct    1080
aagataggtt tgggaatgga atatgatacc aacggagcca tgatgacaaa actaggctct    1140
ggactaagct ttgacaattc aggagccatt gtagtgggaa acaaaaatga tgacaggctt    1200
actctgtgga ctacaccaga cccatctcct aactgtagaa tttattctga aaaagatact    1260
aaactaacct tggtgctgac taagtgtggc agccaaatcc taggcacagt atctgccctt    1320
gctgtcagag gcagccttgc gcccatcact aatgcatcca gcatagtcca aatatttcta    1380
agatttgatg aaaatggact attgatgagc aactcatcgc tagacggtga ttactggaat    1440
tacagaaatg gggactccac taatagcaca ccatatacaa atgcagtagg ctttatgcct    1500
aatctagcag cctatcctaa aggtcaggct acagctgcaa aaagcagtat tgtaagccag    1560
gtatacatgg atggtgacac tactaaacct ataacactaa aaataaactt caatggctct    1620
gatgaaacaa cagaaaatac ccctgttagt aaatattcca tgacattctc atggagctgg    1680
cccaccgcaa gctacatagg ccacactttt gcaacaaact cttttacttt ctcctacatc    1740
gcccaagaa                                                             1749

SEQ ID NO: 11           moltype = AA   length = 10
FEATURE                 Location/Qualifiers
REGION                  1..10
                        note = Adenovirus pIX protein fragment
source                  1..10
                        mol_type = protein
                        organism = synthetic construct
SEQUENCE: 11
SSLVASGAAS                                                             10

SEQ ID NO: 12           moltype = AA   length = 147
FEATURE                 Location/Qualifiers
REGION                  1..147
                        note = Adenovirus DNA polymerase fragment
source                  1..147
                        mol_type = protein
                        organism = synthetic construct
SEQUENCE: 12
KHQYLKVMVR DTFALTHTSL RKAAQAYALP VEKGCCPYQA VNQFYMLGSY RSDTDGFPLQ     60
EYWKDREEFV LNRELWKKKG EDKYDIIRET LDYCALDVQV TAELVHKLRE SYASFVRDSV    120
GLQEASFNVF QRPTISSNSH AIFRQIA                                        147

SEQ ID NO: 13           moltype = AA   length = 15
FEATURE                 Location/Qualifiers
REGION                  1..15
                        note = Adenovirus penton base protein fragment
source                  1..15
                        mol_type = protein
                        organism = synthetic construct
SEQUENCE: 13
KTEAAAKAEV EANVA                                                      15

SEQ ID NO: 14           moltype = AA   length = 15
FEATURE                 Location/Qualifiers
REGION                  1..15
                        note = Adenovirus hexon protein fragment
source                  1..15
                        mol_type = protein
                        organism = synthetic construct
SEQUENCE: 14
IGVDATQAGD NPIYA                                                      15

SEQ ID NO: 15           moltype = AA   length = 15
FEATURE                 Location/Qualifiers
REGION                  1..15
                        note = Adenovirus fiber protein fragment
source                  1..15
                        mol_type = protein
                        organism = synthetic construct
SEQUENCE: 15
LNVAGPLAVA NGINA                                                      15

SEQ ID NO: 16           moltype = AA   length = 133
FEATURE                 Location/Qualifiers
REGION                  1..133
                        note = Adenovirus pIX amino acids
source                  1..133
                        mol_type = protein
                        organism = synthetic construct
SEQUENCE: 16
MSDTGNSFDG SIFSPYLTVR MPHWAGVRQN VMGSNVDGRP VLPSNSSTMA YATVGGTPLD     60
AATSAAASAA AATARSMATD LYSSLVASGA ASRASARDEK LTALLLKLED LTRELGQLTQ    120
QVSSLRESSL ASP                                                       133

SEQ ID NO: 17           moltype = AA   length = 1056
```

```
FEATURE                 Location/Qualifiers
REGION                  1..1056
                        note = Adenovirus DNA polymerase amino acids
source                  1..1056
                        mol_type = protein
                        organism = synthetic construct
SEQUENCE: 17
MDSSNVRDVV IKLRPPSAEI WTCGSRGVVV CSTIALQETD AGGQTTKVED HQPHGTPGGG    60
LRFPLRFLVR GRQVHLVQDI QPVQRCQYCG RFYKSQHECS ARRRDFYPHH INSQSSNWWR   120
EIQFFPIGSH PRTERLFVTY DVETYTWMGA FGKQLVPFML VMKLGGDEAL VAAARDLARE   180
LRWDPWEKDP LTFYCITPEK MAVGRQFRTF RDRLQTLMAR DLWRSFLAAN PHLQDWALEE   240
HGLESPEELT YEELKKLPSI KGQPRFLELY IVGHNINGFD EIVLAAQVIN NRSSVPGPFR   300
ITRNFMPRAG KILFNDLTFS LPNPRSKKRT DYTLWEQGGC DDTDFKHQYL KVMVRDTFAL   360
THTSLRKAAQ AYALPVEKGC CPYQAVNQFY MLGSYRSDTD GFPLQEYWKD REEFVLNREL   420
WKKKGEDKYD IIRETLDYCA LDVQVTAELV HKLRESYASF VRDSVGLQEA SFNVFQRPTI   480
SSNSHAIFRQ IAFRAERPQR TNLGPNMLAP SHELYDYVRA SIRGGRCYPT YLGILREPLY   540
VYDICGMYAS ALTHPMPWGP PLNPYERALA AREWQRALDM QACKIDYFDP RLLPGVFTID   600
ADPPNEDQLD PLPPFCSRKG GRLCWTNERL RGEVATSVDM VTLHNRGWRV RLIPDERTTV   660
FPEWKCVARE YVQLNIAAKE RADRDKNQTL RSIAKLLSNA LYGSFATKLD NKKIVFSDQM   720
DPGTLKGITS GQVNIKSSSF LETDNLSAEV MPAFEREYLP QQLALADSDA EESEDERAPT   780
PFYTPPSGTP GHVSYTYKPI TFLDAEEGDM CLHTLEKVDP LVDNDRYPSH VASFVLAWTR   840
AFVSEWSEFL YEEDRGTPLE DRPLKSVYGD TDSLFVTEKG HRLMESRGKK RIKKHGGNLV   900
FDPDRPELTW LVECETVCAS CGADAYSPES VFLAPKLYAL KSLQCPSCGA TSKGKLRAKG   960
HAAEGLDYET MVKCYLADAQ GEERQRFSTS RTSLKRTLAS AQPGAHPFTV TQTTLTRTLR  1020
PWKDMTLAPL DAHRLVPYSE SRPNPRNEEI CWIEMP                            1056

SEQ ID NO: 18           moltype = AA  length = 658
FEATURE                 Location/Qualifiers
REGION                  1..658
                        note = Adenovirus penton base protein
source                  1..658
                        mol_type = protein
                        organism = synthetic construct
SEQUENCE: 18
MRRAAMFEEG PPPSYESAMG ISPAAPLQPP YVPPRYLQPT GGRNSICYSE LQPLYDTTRL    60
YLVDNKSADV ASLNYQNDHS DFLTTVIQNN DFTPTEASTQ TINLDNRSNW GGDLKTILHT   120
NMPNVNEFMF TNSFKARVMV AREQGEAKYE WVDFTLPEGN YSETMTLDLM NNAIVEHYLK   180
VGRQNGVKES DIGVKFDTRN FRLGWDPVTG LVMPGVYTNE APHPDIVLLP GCGVDFTQSR   240
LSNLLGIRKR QPFQEGFKIT YEDLKGGNIP ALLDLDAYEE SLKPEESAGD SGESGEEQAG   300
GGGGASVENE STPAVAADAA EVEPEAMQQD AEEGAQEGAQ KDMNDGEIRG DTFATRGEEK   360
EAEAAAAATA EAETEVEAEA EPETEVMEDM NDGERRGDTF ATRGEEKAAE AEAAAEEAAA   420
AAAKTEAAAK AEVEANVAVE AQAEEEAAAE AVKEKAQAEQ EEKKPVIQPL KEDSKKRSYN   480
VIEGSTFTQY RSWYLAYNYG DPVKGVRSWT LLCTPDVTCG SEQMYWSLPN MMQDPVTFRS   540
TRQVSNFPVV GAELLPVHSK SFYNEQAVYS QLIRQATSLT HVFNRFPENQ ILARPPAPTI   600
TTVSENVPAL TDHGTLPLRN SISGVQRVTI TDARRRTCPY VYKALGIVSP RVLSSRTF    658

SEQ ID NO: 19           moltype = AA  length = 959
FEATURE                 Location/Qualifiers
REGION                  1..959
                        note = Adenovirus hexon protein
source                  1..959
                        mol_type = protein
                        organism = synthetic construct
SEQUENCE: 19
MATPSMMPQW SYMHISGQDA SEYLSPGLVQ FARATDTYFN MSNKFRNPTV APTHDVTTDR    60
SQRLTLRFIP VDREDTAYSY KARFTLAVGD NRVLDMASTY FDIRGVLDRG PTFKPYSGTA   120
YNSLAPKGAP NSCEWEQDEP AQAAIAEDEE ELEEEQAQDE QAPTKKTHVY AQAPLSGEKI   180
TKDGLQIGVD ATQAGDNPIY ADKTFQPEPQ IGESQWNEAD ATVAGGRVLK KTTPMRPCYG   240
SYAKPTNANG GQGIMVANDQ GALESKVEMQ FFSTTTSLNV REGENNLQPK VVLYSEDVNL   300
ESPDTHLSYK PKKDDTNSKI MLGQQAMPNR PNLIAFRDNF IGLMYYNSTG NMGVLAGQAS   360
QLNAVVDLQD RNTELSYQLM LDSIGDRSRY FSMWNQAVDS YDPDVRIIEN HGVEDELPNY   420
CFPLGGIGIT DTYQCIKPTA AANNTTWSKD EEFSDRNEIG VGNNFAMEIN IQANLWRNFL   480
YANVGLYLPD KLKYNPTNVD ISDNPNTYDY MNKRVVAPGL VDCFVNVGAR WSLDYMDNVN   540
PFNHHRNAGL RYRSMILGNG RYVPFHIQVP QKFFAIKNLL LLPGSYTYEW NFRKDVNMVL   600
QSSLGNDLRV DGASIKFDSV TLYATFFPMA HNTASTLEAM LRNDTNDQSF NDYLSGANML   660
YPIPAKATNV PISIPSRNWA AFRGWAFTRL KTKETPSLGS GFDPYFVYSG SIPYLDGTFY   720
LNHTFKKISI MYDSSVSWPG NDRLLTPNEF EVKRAVDGEG YNVAQCNMTK DWFLVQMLAN   780
YNIGYQGFYI PESYKDRMYS FFRNFQPMSR QVVDETKYKD YQAIGITHQH NNSGFVGYLA   840
PTMREGQAYP ANFPYPLIGK TAVDSVTQKK FLCDRTLWRI PFSSNFMSMG ALTDLGQNLL   900
YANSAHALDM TFEVDPMDEP TLLYIVFEVF DVVRVHQPHR GVIETVYLRT PFSAGNATT   959

SEQ ID NO: 20           moltype = AA  length = 583
FEATURE                 Location/Qualifiers
REGION                  1..583
                        note = Adenovirus fiber protein
source                  1..583
                        mol_type = protein
                        organism = synthetic construct
SEQUENCE: 20
```

```
MKRARSSDET FNPVYPYDTE IAPTSVPFLT PPFVSSAGMQ ENPAGVLSLH LSEPLTTHNG    60
ALTLKMGGGL TLDKEGNLTS QNITSVDPPL KKSKNNISLQ TAAPLAVSSG ALTLFATPPL   120
AVSGDNLTVQ SQAPLTLEDS KLTLATKGPL TVSEGKLVLE TEAPLHASDS SSLGLSVTAP   180
LSINNDSLGL DLQAPIVSQN GKLALNVAGP LAVANGINAL TVGTGKGIGL NETSTHLQAK   240
LVAPLGFDTN GNIKLSVAGG MRLNNDTLIL DVNYPFEAQG QLSLRVGQGP LYVDSSSHNL   300
TIRCLRGLYI TSSNNQTGLE ANIKLTKGLV YDGNAIAVNV GQGLQYSTTA TSEGVYPIQS   360
KIGLGMEYDT NGAMMTKLGS GLSFDNSGAI VVGNKNDDRL TLWTTPDPSP NCRIYSEKDT   420
KLTLVLTKCG SQILGTVSAL AVRGSLAPIT NASSIVQIFL RFDENGLLMS NSSLDGDYWN   480
YRNGDSTNST PYTNAVGFMP NLAAYPKGQA TAAKSSIVSQ VYMDGDTTKP ITLKINFNGI   540
DETTENTPVS KYSMTFSWSW PTASYIGHTF ATNSFTFSYI AQE                     583

SEQ ID NO: 21          moltype = DNA   length = 32739
FEATURE                Location/Qualifiers
misc_feature           1..32739
                       note = Adenovirus vector nucleotide sequences
source                 1..32739
                       mol_type = other DNA
                       organism = synthetic construct
SEQUENCE: 21
catcatcaat aatataccctt attttggatt gtggccaata tgataatgag gtgggcgggg    60
agaggcgggg cggtgacgt aggacgcgcg agtagggttg ggaggtgtgg cggaagtgtg   120
gcatttgcaa gtgggaggag ctcacatgca agcttccgtc gcggaaaatg tgacgttttt   180
gatgagcgcc gcctacctcc ggaagtgcca attttcgcgc gcttttcacc ggatatcgta   240
gtaattttgg gcgggaccat gtaagatttg gccattttcg cgcgaaaagt gaaacgggga   300
agtgaaaact gaataatagg gcgttagtca tagcgcgtaa tatttaccga gggccgaggg   360
acctttgaccg attacgtgga ggactcgccc aggtgttttt tacgtgaatt tccgcgttcc   420
gggtcaaagt ctccgttttt attgtcaccg tcatttgacg cggagggtat ttaaacccgc   480
tgcgctcctc aagaggccac tcttgagtgc cagcgagaag agttttctcc tctgctccgc   540
ttcggtgatc gaaaaatgag acacatagcc tgcactccgg tcttttgtc cggtcgggcg   600
gcggccgagc ttttggacgc tttgatcaat gatgtcctaa gcgatgattt tccgtctact   660
acccacttta gcccacctac tcttcacgaa ctgtacgatc tggatgtact ggtggatgtg   720
aacgatccca acgaggaggc ggttctgcg ttttttcccg agtctgcgct gttggccgct   780
caggagggat ttgacctaca cactccgccg cctattttag agtctccgct gccggagccc   840
agtggtatac cttatatgcc tgaactgctt cccgaagtgg tagacctgac ctgccacgag   900
cctgtctttc cgcccagcga cgatgagggt gagcttttg ttttagactt tgctgagata   960
cctgggcacg gttgcaggtc ttgtgcatat catcagaggg ttaccggaga ccccgaggtt  1020
aagtgttcgc tgtgctatat gaggatgacc tcttcctta tctacagtaa gttttttgtct  1080
aggtgggctt ttgggtaggt gggttttgtg tcagaacagg tgtaaacgtt gcttgtgttt  1140
tttgtacctg taggtccggt gtccgagcca gacccggagc cgaccgcga tcccgagccg  1200
gatcccgagc ctcctcgcag gacaaggaaa ctaccttcca ttctgtgcaa gtctcagaca  1260
cctgtaagga ccagcgaggc agacagcacc gactctggca cttctacctc tcccctgaa   1320
attcacccag tggttcctct gggtatacat aaacctgttg ctgttaaagt ttgcgggcga  1380
cgccctgcag tacagtgcat tgaggacttg cttcacgatc ccgaggaacc ttttggacttg  1440
agccttaaac gccctaggca ataaaccccca cctaagtaat aaaaccccacc taagtaataa  1500
accctgccgc ccttggttat tgagatgacg cccaatgttt gcttttgaat gacttcatgt  1560
gtgtaataaa agtgagtgtg atcatagtc tcttgtttgt ctgggcgggg cttaaggta  1620
tataagtctc ttggggctaa aacttggttac acttgaccccc aatggaggcg tgggggtgct  1680
tggaggagtt tgcggacgtg cgccgtttgc tggacgagag ctctagcaat acctatacta  1740
tttggaggta tctgtggggc tctactcagg ccaagttggt ttccagaatt aagcaggatt  1800
acaagtgcga ttttgaagag cttttttagtt cctgcggtga gcttttgcaa tccttgaatc  1860
tgggccatca ggctatttc caggaaaagg ttctctcgac tttggatttt tccactcccg  1920
ggcgcaccgc cgcttgtgtg gcttttgtgt cttttgtgca agataaatg agcgaggaga  1980
cccacctgag tcacggctac gtactggatt tcatggcgat ggctctttgg aggggctcaca  2040
acaaatggaa gattcagaag gaactgtacg gttccgccct acgtcgtcca cttctgtcgc  2100
gacaggggct gaggtttccc gaccatcggc agcatcagaa tctggaagac gagtcggagg  2160
agcgagcgga ggagaagatc agcttgagag ccggcctgga ccctcctcag gaggaatgaa  2220
tctcccgcag gtggttgacc tgtttccaga actgagacgg gtcctgacta tcagggagga  2280
tggtcagttt gtgaagaagt ttaagaggga tcggggtgag ggagatgatg aggcggctag  2340
caatttagct tttagtctga tgactcgcca ccgaccggaa tgtattacct atcagcagat  2400
taaggagagt tgtgccaacg agctggatct tttgggtcag agtatgca tagaacagct  2460
taccacttac tggcttcagc ctggggatga ttggaagag gcgatcaggg tgtatgcaaa  2520
ggtgccctg cggcccgatt gcaagtataa gattactaag tttggtaata ttagaaactg  2580
ctgctatatt tctgggaacg gggccgaagt ggagatagat actcaggaca gggtggcttt  2640
taggtgttgc atgataaaca tgtgccccgg gatactgggg atgatgggga tggtattcat  2700
gaatgtgagg tttacggggc caactttaa tggcacgggtg ttcatgggga acaccaactt  2760
gctcctgcat ggtgcgagtt tctatgggtt taataacacc tgtataagg cctgaccga   2820
tgtaaaggtt cgaggttgtt ccttttatag ctgttgaaag gcggtggtgt gtcgccctaa  2880
aagcaggggt tctgtgaaaa aatgcttgtt tgaaaggtgc accttaggca tcctctctga  2940
gggcaactcc agggtgcgcc ataatgtggc ttcgaactgg ttgcttca tgcaagtgaa  3000
gggggtgagc gttatcaagc ataactcggt gtgtggaaac tgcgaggatc gcgcctccca  3060
gatgctgacc tgcttgatg gcaactgtca cctgttgaag accattcata taagcagcca  3120
ccccagaaag gcctggcccg tgtttgagca taacatcttg acccgctgct ccttgcatct  3180
gggggtcagg agggtatgt tcctgcctta ccagtgtaac tttagccaca ctaaaatcct  3240
gctggaaccc gagtgcatga ccaaggtcag cctgaatggt tgttgatg tgactctgaa  3300
aatctggaag gtgctgaggt atgatgagac caggaccagg tgccgaccct gcgagtgcgg  3360
cggcaagcac atgagaaatc agcctgtgat gttggatgtg accgaggagc ttaggcctga  3420
ccatctggtc ctggcctgca ccagggcgga gtttgggtct agcgatgagg ataccgattg  3480
aggtgggtaa ggtgcgtg gctagaaggg tggggcgtgt ataaattggg ggtctaaggg  3540
tctctctgtt ttgtcttgca acagccgccg ccatgagcga caccggcaac agctttgatg  3600
```

```
gaagcatctt tagccsctat ctgacagtgc gcatgcctca ctgggctgga gtgcgtcaga   3660
atgtgatggg ttccaacgtg gatggacgcc ccgttctgcc ttcaaattcg tctacaatgg   3720
cctacgcgac cgtgggagga actccgctgg acgccgcgac ctccgccgcc gcctccgccg   3780
ccgccgcgac cgcgcgcagc atggctacgg acctttacag ctctttggtg gcgagcggcc   3840
cggcctctcg cgcgtctgct cgggatgaga aactgaccgc tctgctgctt aaactggaag   3900
acttgacccg ggagctgggt caactgaccc agcaggtctc cagcttgcgt gagagcagcc   3960
ttgcctcccc ctaatggccc ataatataaa taaaagccag tctgtttgga ttaagcaagt   4020
gtatgttctt tatttaactc tccgcgcgcg gtaagcccgg gaccagcggt ctcggtcgtt   4080
tagggtgcgg tggattcttt ccaacacgtg gtacaggtgg ctctgatgt ttagatacat   4140
gggcatgagt ccatccctgg ggtggaggta gcaccactgc agagcttcgt gctcggggt   4200
ggtgttgtat atgatccagt cgtagcagga gcgctgggcg tggtgctgaa aaatgtcctt   4260
aagcaagagg cttatagcta gggggaggcc cttggtgtaa gtgtttacaa atctgctcag   4320
ttgggagggg tgcatccggg gggatataat gtgcatcttg gactggattt ttaggttggc   4380
tattgttccca cccagatccc ttctgggatt catgttgtgc aggaccacca gcacggtata   4440
tccagtgcac ttgggaaatt tatcgtggag cttagacggg aatgcatgga agaacttgga   4500
gacgcccttg tggcctccca gattttccat acattcgtcc atgatgatgg caatgggccc   4560
gtgggaagct gcctgagcaa aaatgttcct gggatcgctc acatcgtagt tatgttccag   4620
ggtgaggtca tcataggaca tctttacgaa tcgggggcgg agggtcccgg actgggggat   4680
gatggtaccc tcgggccccg gggcgtagtt ccctcacag atctgcatct cccaggcttt   4740
catttcagag ggagggatca tatccacctg cggagcgatg aaaaacacag tttctggcgc   4800
aggggagatt aactgggatg agagcaggtt tctgagcagc tgtgactttc cacagccggt   4860
gggcccatat atcacgccta tcaccggctg cagctggtag ttaagagagc tgcagctgcc   4920
gtcctcccgg agcagggggg ccacctcgtt cagcatatcc ctgacgtgga tgttctccct   4980
gaccaattcc gccagaaggc gctcgccgcc cagcgaaagc agctcttgca aggaagcaaa   5040
atttttcagc ggttttaggc cgtcggccgt gggcatgttt ttcagcgtct gggtcagcag   5100
ttccagcctg tcccacagct cggtgatgtc ctctacggca tctcgatcca gcagatctcc   5160
tcgtttcgcg ggttggggcg gctttcgctg tagggcacca gccgatgggc gtccagcggg   5220
gccagagtca tgtccttcca tgggcgcagg gtcctcgtca gggtggtctg ggtcacggtg   5280
aaggggtgcg ctccggggttg ggcgctggcc agggtgcgct tgaggctggt tctgctggtg   5340
ctgaatcgct gccgctcttc gccctgccgcg tcggccaggt agcatttgac catgtctcg   5400
tagtcgagac cctcggcggc gtgcccctg gcgcggaagt ttcccttgga ggtggccgg   5460
cacgaggggc actgcaggct cttcagggcg tagagcttgg gagcgagaaa cacggactct   5520
ggggagtagg cgtccgcgcc gcaggaagcg cagaccgtct cgcattccac cagccaagtg   5580
agctccggc ggtcagggtc aaaaaccagg ttgccccat gcttttgat gcgttcttt   5640
cctcggctct ccatgaggcg gtgtcccttc tcggtgacga agaggctgtc cgtgtcccg   5700
tagaccgact tcagggggcct gtcttccagc ggagtgcctc tgtcctcctc gtagagaaac   5760
tctgaccact ctgagacgaa ggcccgcgtc caggccagga cgaaggaggc cacgtgggag   5820
gggtagcggt cgttgtccac tagcgggtcc accttctcca gggtgtgcag gcacatgtcc   5880
ccctcctccg cgtccagaaa agtgattggc ttgtaggtgt aggacacgtg accgggggat   5940
cccgacgggg gggtataaaaa gggggtgggc gcccttcat cttcactctc ttccgcatcg   6000
ctgtctgcga gggccagctg ctgggtaag tattccctct cgaaggcggg catgacctca   6060
gcgctcaggt tgtcagtttc taaaaatgag gaggatttga tgttcacctg tccggaggtg   6120
ataccttga gggtacctgg gtccatctgg tcagaaaaca ctatttttt gttgtcaagc   6180
ttggtggcga acgacccgta gaggggcgttg gagagcagct tggcgatgga gcgcagggtc   6240
tggttttttgt cgcggtcggc tcgctccttg gccgcgatgt tgagttgcac gtactcgcgg   6300
gccacgcact tccactcggg gaagacgtg gtgcgctcgt ctgggattag gcgcaccctc   6360
cagcctcggt tgtgcagggt gaccatgtgc acgctggtgc cgacctcgcc gcaggcgc   6420
tcgttggtcc agcagaggcg gccgcccttg cgcgagcaga agggggggtag ggggtccagc   6480
tggtcctcgt ttgggggggtc cgcgtcgatg gtgaagaccc cggggagcaa gcgcgggtca   6540
aagtagtcga tcttgcaagc ttgcatgtcc agagcccgct gccattcgcg ggcggcgagc   6600
gcgcgctcgt aggggttgag gggcggggcc cagggcatgg ggtgggtgag cgcggaggcg   6660
tacatgccgc agatgtcata cacgtacagg ggttccctga ggatgccgag gtaggtgggg   6720
tagcagcgcc cccgcgggat gctgcgcgc acgtagtcat agagctcgtg ggaggggcc   6780
agcatgttgg gcccgaggtt ggtgcgctgg gggcgctcgg cgcggaaggc gatctgcctg   6840
aagatggcat gggagttgga ggagatggtg ggccgctgga agacgttgaa gcttgcttct   6900
tgcaagccca ccgagtccct gacgaaggag gcgtaggact cgcgcagctt gtgcaccagc   6960
tcggcggtga cctggacgtc gagcgcgcag tagtcgaggg tctcgcggat gatgtcatac   7020
ttatcctccc ccttcttttt ccacagctcg cggttgagga cgaactcttc gcggtctttc   7080
cagtactctt ggaggggaaa cccgtccgtg tccgaacggt aagagcctag catgtagaac   7140
tggttgacgg cctggtaggg gcaacagccc ttctccacgg gcagcgcgta ggcctgcgcc   7200
gccttgcgga gggaggtgtg ggtgagggcg aaagtgtccc tgaccatgac tttgaggtat   7260
tgatgtttga agtctgtgtc atcgcagccg ccctgttccc acagggtgta gtccgtgcgc   7320
ttttttggagc gcgggttggg cagggagaag gtgaggtcat tgaagaggat cttccccgct   7380
cgaggcatga agtttctggt gatgcgaaag ggccctgagc ccgaggagcg gttgttgatg   7440
acctgggcgg ccaggacgat ctcgtcaaag ccgtttatgt tgtgcccac gatgtagagc   7500
tccaaaaagc ggggctggcc cttgatggag gggagctttt tgattcctc gtaggtgagc   7560
tcctcggcg attccaggcc gtgctcctcc agggcccagt cttgcaagtg agggttggcc   7620
gccaggaagg atcgccagag gtcgcgggcc atgagggtct gcaggcggtc gcggaaggtt   7680
ctgaactgtc gccccacggc catcttttcg gggtgatgc agtagaaggt gaggggtct   7740
ttctcccagg ggtccatct gagctctcgg gcgaggtcgc gcgggcggc gaccagagcc   7800
tcgtcgcccc ccagttccat gaccagcatg aagggcacga gctgcttgcc aaaggctccc   7860
atccaagtgt aggtctctac atcgtaggtg acaaagaggc gctccgtgcg aggatgagag   7920
ccgatcggga agaactggat ctcccgccac cagtggaggg attggctgtt gatgtggtga   7980
aagtagaagt ccgtctgcg ggccgagcac tcgtgtgc tttgtaaaa gcgaccgcag   8040
tactggcagc gctgcacggg ttgtatatct tgcacgaggt gaacctgcg acctctgacg   8100
aggaagcgca gcgggaatct aagtccccg cctgggtcc cgtgtggctg gtggtcttct   8160
actttggtta tctggccgcc agcatctgtc tcctggaggg cgatggtgga gcagaccacc   8220
acgccgcgag agccgcaggt ccagatctcg gcgctcggcg ggcggagttt gatgacgaca   8280
tcgcgcacat tggagctgtc catggtctcc agctcccgcg gcggcaggtc agctgggagt   8340
```

```
tcctggaggt tcacctcgca gagacgggtc aaggcgcggg cagtgttgag atggtatctg   8400
atttcaaggg gcgtgttggc ggcggagtcg atggcttgca ggaggccgca gccccggggg   8460
gccacgatgg ttccccgcgg ggcgcgaggg gaggcggaag ctgggggtgt gttcagaagc   8520
ggtgacgcgg gcgggccccc ggaggtaggg ggggttccgg ccccacaggc atgggcggca   8580
ggggcacgtc ttcgccgcgc gcgggcaggg gctggtgctg gctccgaaga gcgcttgcgt   8640
gcgcgacgac gcgacggttg gtgtcctgta tctgacgcct ctgagtgaag accacgggtc   8700
ccgtgacctt gaacctgaaa gagagttcga cagaatcaat ctcggcatcg ttgacagcgg   8760
cctggcgcag gatctcctgc acgtcgcccg agttgtcctg gtaggcgatc tctgccatga   8820
actgctcgat ctcttcttcc tggagatctc ctcgtccggc gcgctccacg gtggccgcag   8880
ggtcgttgga gatgcgaccc atgagctgtg agaaggcgtt gagcccgccc tcgttccaga   8940
cccggctgta gaccacgccc ccctcggcgt cgcgagcgcg catgaccacc tgggccaggt   9000
tgagctccac gtgtcgcgtg aagacggcgt agttgcgcag gcgctggaaa aggtagttca   9060
gggtggtggc ggtgtgctcg gcgacgaaga agtacatgac ccagcgccgc aacgtggatt   9120
cattgatgtc ccccaaggcc tccaggcgct ccatgcgctc gtagaagtcc acggcgaagt   9180
tgaaaaactg ggagttgcga gcggacacgg tcaactcctc ctccagaaga cggatgagct   9240
cggcgacagt gttgcgcacc tcgcgctcga aggccacggg gggcgcttct tcctcttcca   9300
cctcttcttc catgatcgct tcttcttctt cctcagccgg gacgggaggg ggcggcggcc   9360
gcggggggagg ggcgcggcgg cggcggccgg gcaccgggag gcggtcgatg aagcgctcga   9420
tcatctcccc ccgcatgcgg cgcatggtct cggtgacggc gcggccgttc tcccgggggc   9480
gcagctcgaa gacgccgcct ctcatctcgc cgcggggcga gcggccgtga ggtagcgaga   9540
cggcgctgac tatgcatctt aacaattgct gtgtaggtac accgccgagg gacctgattg   9600
agtccagatc caccggatcc gaaaacctt t ggaggaaagc gtctatccag tcgcagtcgc   9660
aaggtaggct gagcaccgtg gcgggcgggg gcggtctgg agagttcctg gcggagatgc   9720
tgctgatgat gtaattaaag taggcggtct tgagaaggcg gatggtggac aggagccacca  9780
tgtctttggg tccggcctgt tggatgcgga ggcggtcggc catgccccag gcctcgttct   9840
gacaccgggc caggtctttg tagtagtctt gcatgagtct ttccaccggc acctcttctc   9900
cttcctcttc tccatctcgc cggtggtttc tcgcgccgtc catgcgcgtg acccaaagc   9960
ccctgagcgg ctgcagcagg gccaggtcgg cgaccacgcg ctcggccaag atggcctgct  10020
gcacctgagt gagggtcctc tcgaagtcat ccatgtccac gaagcggtgg taggcgcccg  10080
tgttgatggt gtaggtgcag ttggccatga cggaccagtt gacggtctgg tgtcccggct  10140
gcgagagctc cgtgtaccgc aggcgcgaga aggcgcggga atcgaacacg tagtcgttgc  10200
aagtccgcac cagatactgg tagcccacca ggaagtgcgg cggaggttgg cgatagaggg  10260
gccagccgctg ggtggcgggg gcgccgggcg ccaggtcttc cagcatgagg cggtggtatc  10320
cgtagatgta cctggacatc caggtgatgc cggcggcggt ggtggtggcg cgcgcgtagt  10380
cgcggacccg gttccagatg ttttcgcaggg gcgagaagtg ttccatggtc ggcacgctct  10440
ggccggtgag gcgcgcgcag tcgttgacgc tctatacaca cacaaaaacg aaagcgttta  10500
cagggctttc gttctgtagc ctggaggaaa gtaaatgggt tgggttgcgg tgtgccccgg  10560
ttcgagacca agctgagctc ggccggctga agccgcagct aacgtggtat tggcagtccc  10620
gtctcgacce aggccctgta tcctccagga tacggtcgag gcccttttg ctttcttggg  10680
caagcgcccg tggcgcgatc tgggatagat ggtcgcgatg agaggacaaa gcgggctcgc  10740
ttccgtagtc tggagaaaca atcgccaggg ttgcgttgcg gcgtaccccg gttcgagccc  10800
ctatggcggc ttgaatcggc cggaaccgcg gctaacgagg gccgtggcag ccccgtcctc  10860
aggaccccga cagccgactt ctccagttac gggagcgagc ccctttttgt tttttatttt  10920
tagatgcatc ccgtgctgcg gcagatgcgc ccctcgcccc ggcccgatca gcagcagcaa  10980
cagcaggcat gcagaccccc ctctcccctt tccgccccgg tcaccacggc cgcggcggcc  11040
gtgtcggcg cggggggcgc gctggagtca gatgagccac cgcggcggcg acctaggcag  11100
tatctggact tggaagaggg cgagggactg gcgcggctgg gggcgaactc tccagagcgc  11160
cacccgcggg tgcagttgaa aagggacgcg cgcgaggcgt acctgccgcg gcagaacctg  11220
tttcgcgacc gcgggggcga ggagcccgag gagatgcgag actgcaggtt ccaagcgggg  11280
cgcgagctgg ggcgcgggct ggacagacag cgcctgctgc gcgaggagga ctttgagccc  11340
gacaccgaga cgggcatcag ccccgcgcgc gcgcacgtag ccgcggccga cctggtgacc  11400
gcctacgagc agacggtaaa ccaggagcgc aacttccaaa agagcttcaa caaccacgtg  11460
cgcacgctgg tggcgcgcga ggaggtgacc ctgggtctca tgcatctgtg ggacctggtg  11520
gaggcgatcg tgcagaaccc cagcagcaag ccccctgaccg cgcagctgtt cctggtggtg  11580
cagcacaga gggacaacga ggccttcagg gaggcgctgc tgaacatcac cgagccggag  11640
gggcgctggc tcctggacct gataaacatc ctgcagagca tagtggtgca ggagcgcagc  11700
ctgagcctgg ccgagaaggt ggcggccatc aactactcta tgctgagcct gggcaagttc  11760
tacgcccgca agatctacaa gacccctac gtgcccatag acaaggaggt gaagatagac  11820
agcttctaca tgcgcatggc gctgaaggtg ctgaccctga gcgacgacct gggagtgtac  11880
cgcaacgagc gcatccacaa ggcctgtgagc gccagccggc ggcgcgagct gagcgaccgc  11940
gagctgatgc acagtctgca gcgcgcgctg accggcgcgg gcgagggcga cagggaggtc  12000
gagtcctact tcgacatggg ggccgacctg cactggcagc cgagccgccc cgccctggag  12060
gcggcggggg cgtacggcgg cccctgggcg gccgatgacc aggaagagga ggactatgag  12120
ctagaggagg gcgagtacct ggaggactga cctggctggt ggtgttttgg tatagatgga  12180
agatccgaac gtggcggacc cggcggtccg ggcggcgctg caaagccagc cgtccggcat  12240
taactcctct gacgactggg ccgcggcat gggtcgcatc atggcccctga ccgcgcgcaa  12300
cccccgaggct tcaggcagc agcctcaggc caaccggctg gcggccatct tggaagcggt  12360
agtgcccgcg cgctccaacc ccacccacga gaaggtgctg gccatagtca acgcgctggc  12420
ggagagcagg gccatccgcg ggacgaggc cggactgggt tacgatgcgc tctgcagcg  12480
ggtggcgcgg tacaacacgc gcaacgtgca gaccaacctg gaccgcctgg tgacggacgt  12540
gcgcgaggcc gtggcgcagc gcgagcgctt gcatcaggac ggtaacctgg gctcgctggt  12600
ggcgctaaac gccttcctca gcacccagcc ggccaacgta ccgcggggc aggaggacta  12660
caccaacttt ttgagcgcgc tgcggctgat ggtgaccgag gtccctcaga gcgaggtgta  12720
ccagtcgggg cccgactact tcttccagac cagcagagg gcgttgcaaa ccgtgaacct  12780
gagccaggct ttcaagaacc tgccggggct gtggggagtg aaggcgccca ccggcgaccg  12840
ggctacggtg tccagcctgc taaccccaa ctcgcgcctg ctgctgctgc tgatcgcgcc  12900
cttcacggac agcgggagcg tctcgcggga gacctatctg ggccacctgc tgacgctgta  12960
ccgcgaggcc atcgggcagg cgcaggtgga cgagcacacc ttccaagaga tcaccagcgt  13020
gagccacgcg ctggggcagg aggacacggg cagcctgcag gcgaccctga actacctgct  13080
```

```
gaccaacagg cggcagaaga ttcccacgct gcacagcctg acccaggagg aggagcgcat  13140
cttgcgctac gtgcagcaga gcgtgagcct gaacctgatg cgcgacgacg tgacgcccag  13200
cgtggcgctg gacatgaccg cgcgcaacat ggaaccgggc atgtacgcct cccaccggcc  13260
gtttatcaac cgcctgatgg actacttgca tcgggcggcg gccgtgaacc ccgagtactt  13320
cactaatgcc attctgaatc cccactggat gcccctccg ggtttctaca acggggactt  13380
tgaggtgccc gaggtcaacg acgggttcct ctgggatgac atggatgaca gtgtgttctc  13440
acccaacccg ctgcgcgccg cgtctctgcg attgaaggag ggctctgaca gggaaggacc  13500
gaggagtctg gcctcctccc tggctctggg agcggtgggc gccacgggcg cggcggcgcg  13560
gggcagtagc cccttcccca gcctggcaga ctctctgaac agcgggcggg tgagcaggcc  13620
ccgcttgcta ggcgaggagg agtatctgaa caactccctg ctgcagcccg cgagggacaa  13680
gaacgctcag cggcagcagt ttcccaacaa tgggatagag agcctggtgg acaagatgtc  13740
cagatggaag acgtatgcgc aggagtacaa ggagtgggag gaccgccagc cgcggccctt  13800
gccgccccct aggcagcgct ggcagcggcg cgcgtccaac cgccgctgga ggcaggggcc  13860
cgaggacgat gatgactctg cagatgcag cagcgtgttg gacctgggcg ggcgagcggg aa  13920
cccttttcg cacctgcgcc cacgcctggg caagatgttt taaaagaaaa aaaaaataaa  13980
actcaccaag gccatggcga cgagcgttgg ttttttgttc ccttccttag tatgcggcgc  14040
gcggcgatgt tcgaggaggg gcctccccc tcttacgaga gcgcgatggg gatttctcct  14100
gcggcgcccc tgcagcctcc ctacgtgcct cctcggtacc tgcaacctac aggggggaga  14160
aatagcatct gttactctga gctgcagccc ctgtacgata ccaccagact gtacctggtg  14220
gacaacaagt ccgcggacgt ggcctccctg aactaccaga acgaccacag cgattttttg  14280
accacggtga tccaaaacaa cgacttcacc ccaaccgagg ccagcaccca gaccataaac  14340
ctggataaca ggtcgaactg gggcggcgac ctgaagacca tcttgcacac caacatgccc  14400
aacgtgaacg agttcatgtt caccaactct tttaaggcgc gggtgatggt ggcgcgcgag  14460
caggggggagg cgaagtacga gtgggtggac ttcacgctgc ccgagggcaa ctactcagag  14520
accatgactc tcgacctgat gaacaatgcg atcgtggaac actatctgaa agtgggcagg  14580
cagaacgggg tgaaggaaag cgatatcggg gtcaagtttg acaccagaaa cttccgtctg  14640
ggctgggacc ccgtgaccgg gctggtcatg ccggggggtct acaccaacga ggcctttcat  14700
cccgacatag tgcttctgcc cggctgtggg gtggacttca cccagagccg gctgagcaac  14760
ctgctggca ttcgcaagcg gcagccttc caggagggtt tcaagatcac ctatgaggat  14820
ctgaagggg gcaacattcc cgcgctcctt gatctgacg cctacgagga gcttgaaa  14880
cccgaggaga gcgctggcga cagcggcgag agtggcgagg agcaagccgg cggcggtggc  14940
ggcgcgtcgg tagaaaacga aagtacgccc gcagtggcgg cggacgctgc ggaggtcgag  15000
ccggaggcca tgcagcagga cgcagaggag ggcgcacagg agggcgcgca gaaggacatg  15060
aacgatgggg agatcagggg agacacattc gccaccccgg gcgaagaaaa agaggcagag  15120
gcggcgcccc cggcgacggc ggaggccgaa accgaggttg aggcagaggc agagcccgag  15180
accgaagtta tggaagacat gaatgatgga gaacgtaggg gcgacacgtt cgccaccccgg  15240
ggcgaagaga aggcggcgga ggcagaagcc gcggctgagg aggcggctgc ggctgcggcc  15300
aagactgagg ctgcggctaa ggctgaggtc gaagccaatg ttgcgtttga ggctcaggct  15360
gaggagaggc cggcggctga agcagttaag gaaaaggccc aggcagagca gggaagagaaa  15420
aaacctgtca ttcaacctct aaaagaagat agcaaaaagc gcagttacaa cgtcatcgag  15480
ggcagcacct ttacccagta ccgcagctgg tacctggcgt acaactacgg cgacccggtc  15540
aaggggggtgc gctcgtggac cctgctctgc acgccggacg tcacctgcgg ctccgagcag  15600
atgtactggt cgctgccgaa catgatgcaa gacccggtgc cttccgctc cacgcggcag  15660
gttagcaact tcccggtggt gggcgccgaa ctgctgcccg tgcactccaa gagtttttac  15720
aacgagcagg ccgtctactc ccagctgatc cgccaggcca cctctctgac ccacgtgttc  15780
aatcgctttc ccgagaacca gattttggcg cgcccgccgg ccccaccat caccaccgtg  15840
agtgaaaacg ttcctgccct cacagatcac gggacgctac ggctgcgcaa cagcatctca  15900
ggagtccagc gagtgaccat tactgacgcc agacgccgga cctgccccta cgtttacaag  15960
gccttgggca tagtctcgcc gcgcgtcctc tccagtcgca cttttaaaa cacatctacc  16020
cacacgttcc aaaatcatgt ccgtactcat ctcacccagc aacaacaccg gctggggct  16080
gcgcgcgccc agcaagatgt ttggagggggcc gaggaagcgc tccgaccagc acccctgtgcg  16140
cgtgcgcggc cactaccgcg cgccctgggg agcgcacaag cgcgggcgca cagggcgcac  16200
cactgtggac gacgtcattg actccgtagt ggagcaagcg cgccactaca cacccggcgc  16260
gccgaccgcc cccgccgtgt ccaccgtgga ccaggcgatc gaaagcgtgg tacagggcgc  16320
gcggcactat gccaaccta aaagtcgccg ccgccgcgtg ccgccgcc atcgccggag  16380
accccgggcc accgccgccg cgcgccttac taaggctctg ctcaggcgcg ccaggcgaac  16440
tggccaccgg gccgccatga gggcgcacg gcgggctgcc gctgccgcaa gcgtcgtggc  16500
cccgcggcac cgaaggcgcg cggccgctgc cgccgccgcc gccatttcca gcttggcctc  16560
gacgcggcgc ggtaacatat actgggtgcg cgactcggta accggcacgc gggtaccgt  16620
gcgcttccgc ccccgcgga attagcacaa gacaacatac acactgagtc tcctgctgtt  16680
gtgtatccca gcggcgaccg tcagcagcgg cgacatgtcc aagcgcaaaa ttaaagaaga  16740
gatgctccag gtcatcgcgc cggagatcta tgggcccccg aagaaggagg aggatgatta  16800
caagccccgc aagctaaagc gggtcaaaaa gaaaagaaa gatgatgatg acgaggcggt  16860
ggagttttgtc cgccgcatgg cacccaggcg ccccgtgcag ttggccgcag aaggcgggga  16920
gcgcgttttg cgcccggca ccgcggtggt cttcacgccc ggcgagcgct ccacgcgcac  16980
tttcaagcgg gtgtacgatg aggtgtacgg cgacgaggac ctgttggagc aggccaacca  17040
gcgctttggg gagtttgcat atgggaaacg gccccgcgag agtctaaaag aggacctgct  17100
ggcgctaccg ctggacgagg gcaatccac cccgagtctg aagccggtaa ccctgcaaca  17160
ggtgctgcct ttgagcgcgc cagcagca taagctggagg ttgaagcgcg aagcggggga  17220
cctggcgccc accgtgcagt tgatggtgcc caagcggcag aagctggagg acgtgctgga  17280
gaaaatgaaa gtagagcccg ggatccagcc cgagatcaag gtccgcccca tcaagcaggt  17340
ggcgcccggc gtgggagtcc agaccgtgga cgttaggatt cccacggagg agatggaaac  17400
ccaaaccgcc actccctctt cggcggccag cgccaccacc ggcaccgctt cggtagaggt  17460
gcagacgaac cccttgctac ccgccaccgc tgttgccgcc ccgcgcggg  17520
gcgcaagaga aattatccag cggccagcgc gctcatgccc cagtacgcac tgcatccatc  17580
catcgtgccc accccggct accgcgggta ctcgtaccgc ccgcgcagat cagccggcac  17640
tcgcggccgc cgccgccgtg cgaccacaac cagccgccgc cgtcgccgcc gccgccagcc  17700
agtgctgacc ccgtgtctg taaggaaggt ggctcgctcg gggagcacgc tggtggtgcc  17760
cagagcgcgc taccacccca gcatcgttta aagccggtct ctgtatggtt cttgcagata  17820
```

```
tggccctcac ttgtcgcctc cgcttcccgg tgccgggata ccgaggaaga actcaccgcc   17880
gcagaggcat ggccggcagc ggtctccgcg gcggccgtcg ccatcgccgg cgcgcaaaaa   17940
gcaggcgcat gcgcggcggt gtgctgcctc tgctaatccc gctaatcgcc gcggcgatcg   18000
gtgccgtacc cggatcgcc tccgtggccc tgcaggcgtc ccagaaacgt tgactcttgc    18060
aaccttgcaa gcttgcattt tttggaggaa aaataaaaaa aagtctagac tctcacgctc   18120
gcttggtcct gtgactattt tgtagaaaaa aagatggaag acatcaactt tgcgtcgctg   18180
gccccgcgtc acggctcgcg cccgttcatg ggagactgga cagatatcgg caccagcaat   18240
atgagcggtg gcgccttcag ctggggcagt ctgtggagcg gccttaaaaa ttttggttcc   18300
accattaaga actatggcaa caaagcgtgg aacagcagca cgggccagat gctgagagac   18360
aagttgaaag agcagaactt ccaggagaag gtggcgcagg gcctggcctc tggcatcagc   18420
gggtggtgg acatagctaa ccaggccgtg cagaaaaaga taaacagtca tctgaccccc     18480
cgtcctcagg tggaggaaat gcctccagcg atggagacgg tgtctcccga gggcaaaggc   18540
gaaaagcgcc cgcggcccga cagagaagag accctggtgt cacacaccga ggagccgccc   18600
tcttacgagg aggcagtcaa ggccggcctg cccaccactc gccccatagc ccccatggcc   18660
accggtgtgg tgggccacag gcaacacact cccgcaacac tagatctgcc ccgccgtcc    18720
gagccgccgc gccagccaaa ggcggcgacg gtgcccgctc cctccacttc cgccgccaac   18780
agagtgcccc tgcgccgcgc cgcgagcggc ccccgggcct cgcgagttag cggcaactgg   18840
cagagcacac tgaacagcat cgtgggcctg ggagtgagga gtgtgaagcg ccgccgttgc   18900
tactgaatga gcaagctagc taacgtgttg tatgtgtgta tgcgtcctat gtcgccgcca   18960
gaggagctgt tgagccgccg gcgccgtctg cactccagcg aatttcaaga tggcgacccc   19020
atcgatgatg cctcagtggt cgtacatgca catctcgggc caggacgctt cggagtacct   19080
gagccccggg ctggtgcagt tcgcccgcgc cacagcaccc tacttcaaca tgataacaa    19140
gttcaggaac cccactgtgg cgcccaccca cgatgtgacc acgaccggt cgcagcgcct    19200
gacgctgcgg ttcatccccg tggatcggga ggacaccgcc tactcttaca aggcgcggtt   19260
cacgctggcc gtgggcgaca accgcgtgct ggacatggcc tccacttact ttgacatcag   19320
ggggtgctg gacaggggcc ccaccttcaa gccctactcg ggtactgcct acaactccct    19380
ggcccccaag ggcgctccca attcttgcga gtgggaacaa gatgaaccag ctcaggcagc   19440
aatagctgaa gatgaagaag aacttgaaga agaacaagct caggacgaac aggcgcccac   19500
taagaaaacc catgtatacg cccaggcacc tctttctggt gaaaaaatta ctaaggatgg   19560
tttgcaaata ggtgtggatg ccacacaggc gggagataac cctatatatg ctgataaaac   19620
attccaaccc gaacctcaga taggtgagtc tcagtggaac gaggctgatg ccacagtagc   19680
aggaggcaga gtcttaaaaa agaccacccc tatgagacct tgctatggat cctatgccaa   19740
acctactaat gccaatggcg tcaagggat catggtggcc aatgatcagg gagcgcttga    19800
atctaaagtt gagatgcaat tttctccac cacaacgtct cttaatgtaa gggaaggtga    19860
aaacaatctt cagccaaaag tagtgctata cagcgaagat gttaacttgg aatccctga    19920
cactcatttg tcttacaaac ctaaaaagga tgacaccaac tctaaaatca tgtttgggtca   19980
gcaagccatg cccaacagac caacctcat tgcttttagg gacaaccttta ttggacttat   20040
gtactacaac agcacaggca acatgggagt gctggcagga caggcctccc agctaaacgc   20100
tgtggtagac ttgcaagaca gaaacacaga gctgtcatac caactgatgc ttgattccat   20160
tggagacaga tcaagatact tttccatgtg gaaccaggca gtggacagct atgcccaga    20220
tgtcagaatc attgaaaacc atgggggttga agatgagctg cccaactatt gctttcccct   20280
gggcggtatt ggaattacag acacatacca gtgcataaaa ccaaccgcag ctgctaataa   20340
cactacatgg tctaaggatg aagaatttag tgatcgcaat gaaatagggg tgggaaacaa   20400
cttcgccatg gagatcaaca tccaggccaa cctctggagg aacttcctct atgcgaacgt   20460
ggggctctac ctgccagaca agctcaagta caacccccacc aacgtggaca tctctgacaa   20520
ccccaacacc tatgactaca tgaacaagcg tgtggtggct cccggcctgg tggactgctt   20580
tgtcaatgtg ggagccaggt ggtccctgga ctacatggac aacgtcaacc cctttcaacca   20640
ccaccgcaat gcgggtctgc gctaccgctc catgatcctg ggcaacgggc gctacgtgcc   20700
cttccacatt caggtgcccc agaagttctt tgccatcaag aacctcctcc tcctgccggg   20760
ctcctacact tacgagtgga cttcaggaa ggatgtcaac atggtcctgc agagctctct    20820
gggcaatgac cttagggtgg acggggccag catcaagttt gacagcgtca ccctctatgc   20880
taccttcttc cccatggctc acaacaccgc ctccacgctc gaggccatgc tgaggaacga   20940
caccaacgac cagtccttca tgactacct ctctggggcc aacatgctct accccatccc    21000
cgccaaggcc accaacgtgc ccatctccat tccctctcgc aactgggccg ccttcagagg   21060
ctgggccttt acccgcctta agaccaagga aaccccctc ctgggctggg gttttgaccc    21120
ctactttgtc tactcgggat ccatcccca cctggatggc accttctacc tcaaccacac   21180
ttttaagaag atatccatca tgtatgactc ctccgtcagc tggccgggca atgaccgcct   21240
gctcaccccc aatgagttcg aggtcaagcg cgccgtggac ggcgagggct acaacgtggc   21300
ccagtgcaac atgaccaagg actggttcct ggtgcagatg ctggccaact acaacatagg   21360
ctaccagggc ttctacatcc cagagagcta caaggacaag atgtactcct tcttcagaaa   21420
tttccaaccc atgagcaggc aggtggtgga cgagaccaaa tacaaggact atcaggccat   21480
tggcatcact caccagcaca acaactcggg attcgtgggc tacctggctc caccatgcg    21540
cgaggggcag gcctaccccg ccaacttccc ctacccgttg ataggcaaaa ccgcggtcga   21600
cagcgtcacc cagaaaagt tcctctgcga ccgcaccctc tggccgcatcc cttctctag     21660
caacttcatg tccatgggtg cgctcacgga cctgggccag aacctgctct atgccaactc   21720
cgcccatgcg ctgacatga cttttgaggt ggacccatg gacgagccca ccttctcta     21780
tattgtgttt gaagtgttcg acgtggtcag agtgcaccag ccgcaccgcg tgtcatcga    21840
gaccgtgtac ctgcgcacgc ccttctcggc cggcaacgcc accaacccttaag gagacagcgc  21900
cgccgcctgc atgacgggtt ccaccgagca agagctcagg ggccatccga gagcctgg     21960
atgcggaccc tattttttgg gcacctatga caaacgcttc ccgggcttca tctcccgaga   22020
caagctcgcc tgcgccatcg tcaacacggc ccgcgcgag accgggggcg tgcactggct    22080
ggcctttggc tgggacccgc gctccaaaac ctgctacctc ttcgacccct ttggcttctc   22140
cgatcagcgc ctcagacaga tctatgagtt tgagtacaga gggctgctgc gccgcagcgc   22200
gcttgcctcc tcgccccacc gctgcatcac ccttgagaag tccaccgagg tgctgcaagg   22260
gccccactcg gccgcctgcg gtctcttctg ctgcatgttt ttgcacgcct ttgtgcgctg   22320
gccccagagt cccatggatc gcaacccac catgaacttg ctcaagggag tgcccaacgc   22380
catgctccag agcccccagg tccagcccac cctgcgccac aaccaggaac agctctaccg   22440
cttcctggag cgcacctccc ctacttccg cagtcacagc gcgcacatcc ggggggccac   22500
ctcttcctgc cacttgcaag aaaacatgca agacggaaaa tgatgtacag ctcgcttttt   22560
```

```
aataaatgta aagactgtgc actttattta tacacgggct cttctggtt atttattcaa  22620
caccgccgtc gccatctaga aatcgaaagg gttctgccgc gcgtcgccgt gcgccacggg  22680
cagagacacg ttgcgatact ggaagcggct cgcccactta aactcgggca ccaccatgcg  22740
gggcagtggt tcctcgggga agttctcgcc ccacagggtg cgggtcagct gcagcgcgct  22800
caggaggtcg ggagccgaga tcttgaagtc gcagttgggc ccggaaccct gcgcgcgcga  22860
gttgcggtac acgggggttgc agcactggaa caccagcagg gccggattat gcacgctggc  22920
cagcaggctc tcgtcgctga tcatgtcgct gtccagatcc tccgcgttgc tcagggcgaa  22980
cggggtcatc ttgcagacct gcctgcccag gaaaggcggc agcccgggct tgccgttgca  23040
gtcgcagcgc aggggcatca gcaggtgccc gcggcccgac tgcgcctgcg ggtacagcgc  23100
gcgcatgaag gcttcgatct gcctgaaagc cacctgcgtc ttggctccct ccgaaaagaa  23160
catcccacag gacttgctgg agaactggtt cgcgggacag ctggcatcgt gcaggcagca  23220
gcgcgcgtcg gtgttggcga tctgcaccac gttgcgaccc caccggttct tcactatctt  23280
ggccttggaa gcctgctcct tcagcgcgcg ctggccgttc tcgctggtca catccatctc  23340
tatccacctgc tccttgttga tcatgtttgt accgtgcaga cacttcaggt cgccctccgt  23400
ctgggtgcag cggtgctccc acagcgcgca accgtgggc tcccaatttt tgtgggtcac  23460
ccccgcgtag gcctgcaggt aggcctgcaa gaagcgcccc atcatggcca caaaggtctt  23520
ctggctcgta aaggtcagct gcaggccgcg atgctcttcg ttcagccagg tcttgcagat  23580
ggcggccagc gcctcggtct gctcgggcag catcctaaaa tttgtcttca ggtcgttatc  23640
cacgtggtac ttgtccatca tggcgcgcgc cgcctccatg cccttctccc aggcggacac  23700
catgggcagg cttaggggt ttatcacttc caccggcgag gacaccgtac tttcgatttc  23760
ttcttcctcc ccctcttccc ggcgcgcgcc cacgctgctg cgcgctctca ccgcctgcac  23820
caaggggtcg tcttcaggca agcgccgcac cgagcgcttg ccgcccttga cctgcttaat  23880
cagcaccggc gggttgctga agcccaccat ggtcagcgcc gcctgctctt cttcgtcttc  23940
gctgtctacc actatctctg gggaagggct tctccgctct gcggcggcgc gcttctttt  24000
tttcttggga gcggccgtga tggagtccgc cacggcgacg gaggtcgagg gcgtggggct  24060
ggggtgcgc ggtaccaggg cctcgtcgcc tccgactct tcctctgact ccaggcgcg  24120
gcggagtcgc ttctttggg gcgcgcgcgt cagcggcggc ggagacgggg acggggacgg  24180
ggacgggacg ccctccacag ggggtggtct tcgcgcagac ccgcgccgc gctcggggt  24240
cttctcgagc tggtcttggt cccgactggc cattgtatcc tcctcctcct aggcagagag  24300
acataaggag tctatcatgc aagtcgaaa ggaggagagc ttaaccaccc cctctgagac  24360
cgccgatgcg cccgccgtcg ccgtcgcccc cgctgccgcc gacgcgcccg ccacaccgga  24420
cgacaccccc gcggaccccc ccgccgacgc accctgtcc gaggaagcgg ccgtggagca  24480
ggacccgggc tttgtctcgg cagaggagga tttgcgagag gaggaggata aggagaagaa  24540
gccctcagtg ccaaaagatg ataaagagca agacgagcga gacgcagatg cacacccaggg  24600
tgaagtcggg cgggggacg gagggcatga cggcgccgac tacctagacg aagggaacga  24660
cgtgctcttg aagcacctgc atcgtcagtg cgccattgtt tgcgacgctc tgcaggagcg  24720
cagcgaagtc cccctcagcg tggcggaggt cagccacgcc tacgagctca gcctcttctc  24780
ccccgggtg cccccccgcc gccgcgaaa cggcacatgc gagcccaacc cgcgcctcaa  24840
cttctaccc gccttttgtgg tacccgaggt cctggccacc tatcacatct tctttcaaaa  24900
ttgcaagatc cccctctcgt gccgcgccaa ccgtagccgc gccgataaga tgctggccct  24960
gcgccagggc gaccacatac ctgatatcgc cgctttggaa gatgtaccaa agatcttcga  25020
gggtctgggt cgcaacgaga agcgggcagc aaactctctg caacaggaaa acagcgaaaa  25080
tgagagtcac accgggggtac tggtggagct cgagggcgac aacgcccgcc tggcggtggt  25140
caagcgcagc atcgaggtca cccactttgc ctaccccgcg ctaaacctgc cccccaaagt  25200
catgaacgcg gccatggacg ggctgatcat gcgccgcggc cggcccctcg ctccagatgc  25260
aaacttgcat gaggagaccg aggacggcca gcccgtggtc agcgacgagc agctggcgcg  25320
ctggctggag accgcggacc ccgccgaact ggaggagcgg gcaagatga tgatggccgt  25380
ggtgctggtc accgtagagc tggagtgtct gcagcgcttc ttcggcgacc ccgagatgca  25440
gagaaaggtc gaggagaccc tgcactacac cttccgccag ggctacgtgc gccaggcttg  25500
caagatctcc aacgtggagc tcagcaacct ggtgtcctac ctgggcatct tgcatgaaga  25560
ccgcctgggg cagagcgtgc tgcactccac cctgcgcggg gaggcgcgc gcgactacgt  25620
gcgcgactgc gtttacctct tcctctgcta cacctggcag acggccatgg gggtctggca  25680
gcagtgcctg gaggagcgca acctcaagga gctggagaag ctcctgcagc gcgcgctcaa  25740
agatctctgg acgggctaca acgagcgctc ggtggccgcc gcgctggccg acctcatctt  25800
ccccgagcgc ctgctcaaaa ccctccagca ggggctgccc gacttcacca gccaaagcat  25860
gttgcaaaac ttcaggaact ttatcctgga gcgttctggc atcctacccg ccacctgctg  25920
cgccctgccc agcgactttg tccccctcgt gtaccgcgag tgcccccgc cgctgtgggg  25980
tcactgctac ctgttccaac tggccaacta cctgtcctac cacgcggacc tcatggagga  26040
ctccagcggc gaggggctca tggagtccga ctgccgctgc aacctctgca cgccccaccg  26100
ctccctggtc tgcaacaccc aactgctcag cgagagtcag attatcggta ccttcgagct  26160
acagggtccg tcctcctcag acgagaagtc cgccggctccg gggctaaaac tcactccggg  26220
gctgtggact tccgcctacc tgcgcaaatt tgtacctgaa gactaccacg cccacgagat  26280
caggttttac gaagaccaat cccgcccgcc caaggcggag ctgaccgcct gcgtcatcac  26340
ccaggcgag atcctaggcc aattgcaagc catccaaaaa gcccgccaag acttttgct  26400
gaagaagggt cgggggggtgt atctggaccc ccagtcgggt gaggagctca cccggttcc  26460
cccgctgccg ccgccgcggg accttgcttc ccaggataag catcgccatg gctcccagaa  26520
agaagcagca gcggccgcca ctgccgccac cccacatgct ggaggaagag gaggaatact  26580
gggacagtca ggcagaggag gttcggacg aggaggagc ggagacggag atggaagagt  26640
gggaggagga cagcttagac gaggaggctt ccgaagccga agggcagca gcaacaccgt  26700
caccctcggc cgcagccccc tcgcaggcgc cccgaagtc cgctcccagc atcagcagca  26760
acagcagcgc tataacctcc gctcctccac cgccgcgacc cacggccgac cgcagaccca  26820
accgtagatg ggacaccacc ggaaccgggg ccggtaagtc ctccgggaga ggcaagcaag  26880
cgcagcgcca aggctaccgc tcgtggcgcg ctcacaagaa cgccatagtc gcttgcttgc  26940
aagactggg ggggaacatc tccttcgcc gccgcttcct gctcttccac cacggtgtgg  27000
ccttccccg taacgtcctg cattactacc gtcatctcta cagcccctac tgcggcggca  27060
gtgagccaga gacggtcggc ggcggcgcg gcgcccgttt cggcgcctag aagaccag  27120
ggcaagactt cagccaagaa actcgcgcg ccgcggcga acgcggtcgc gggggccctg  27180
cgcctgacgg tgaacgaacc cctgtcgacc cgcgaactga ggaaccgaat cttccccact  27240
ctctatgcca tcttccagca gagcagaggg caggatcagg aactgaaagt aaaaaacagg  27300
```

```
tctctgcgct ccctcacccg cagctgtctg tatcacaaga gcgaagacca gcttcggcgc  27360
acgctggagg acgctgaggc actcttcagc aaatactgcg cgctcactct taaggactag  27420
ctccgcgccc ttctcgaatt taggcgggaa cgcctacgtc atcgcagcgc cgccgtcatg  27480
agcaaggaca ttcccacgcc atacatgtgg agctatcagc cgcagatggg actcgcggcg  27540
ggcgcctccc aagactactc cacccgcatg aactggctca gtgccgaccg acacatgatc  27600
tcacaggtta atgatatccg cacccatcga aaccaaatat tggtggagca ggcggcaatt  27660
accaccacgc cccgcaataa tcccaacccc agggagtggc ccgcgtccct ggtgtatcag  27720
gaaattcccg gccccaccac cgtactactt ccgcgtgatt cccaggccga agtccaaatg  27780
actaactcag gggcacagct cgcgggcggc tgtcgtcaca gggtgcggcc tcctcgccag  27840
ggtataactc acctggagat ccgaggcaga ggtattcagc tcaacgacga gtcggtgagc  27900
tcctcgctcg gtctcagacc tgacgggacc ttccagatag ccggagccgg ccgatcttcc  27960
ttcacgcccc gccaggcgta cctgactctg caaagctcgt cctcggcgcc gcgctcgggc  28020
ggcatcggga ctctccagtt cgtgcaggag tttgtgccct cggtctactt caaccccttc  28080
tcgggctctc ccggtcgcta cccggaccag ttcatctcga actttgacgc cgcgagggac  28140
tcggtggacg gctacgactg aatgtcgggt ggaccggtg cagagcaact tcgcctgaag  28200
cacctcgacc actgccgccg ccctcagtgc tttgcccgct gtcagaccgg tgagttccag  28260
tacttttccc tgcccgactc gcacccggac ggccccggcgc acggggtgcg cttttttcatc  28320
ccgagtcagg tgcgctctac cctaatcagg gagtttaccg cccgtcccct actggcggag  28380
ttggaaaagg ggccttctat cctaaccatt gcctgcatct gctctaaccc tggattgcac  28440
caagatcttt gctgtcattt gtgtgctgag tataataaag gctgagatca gaatctactc  28500
gggctcctgt cgccatcctg tcaacgccac cgtccaagcc cggcccgatc agcccgaggt  28560
gaacctcacc tgcggtctgc accggcgcct gaggaaatac ctagcttgt actacaacag  28620
cactcccttt gtggtttaca acagctttga ccaggacgg gtctcactga gggataacct  28680
ctcgaacctg agctactcca tcaggaagaa cagcaccctc gagctactc ctccttacct  28740
gcccgggact taccagtgtg tcaccggtcc ctgcacccac acccacctgt tgatcgtaaa  28800
cgatctcttc ccgagaacag acctcaataa atcctcttcg cagttcccca gaacaggagg  28860
tgagctcagg aaaccccggg taaagaaggg tggacgagag ttaacacttg tggggttttct  28920
ggtgtatgtg acgctggtgg tggctctttt gattaaggct tttccttcca tgtctgaact  28980
ctccctcttc ttttatgaac aactcgacta gtgctaacgg gaccctaccc aacgaatcgg  29040
gattgaatat cggtaaccag gttcagttt cacttttcata gtcctcttcc  29100
tgctagtgct gtcgcttctg tgcctgcgga tcggggctg ctgcatccac gtttatatct  29160
ggtgctggct gtttagaagg ttcggagacc atcgcaggta gaataaacat gctgctgctt  29220
accctctttg tcctggcgct ggccgccagc tgccaagcct tttccgaggc tgactttata  29280
gagcccccagt gtaatgtgac tttaaagcc catgcacagc gttgtcatac tataatcaaa  29340
tgtgccaccg aacacgatga ataccttatc cagtataaag ataaatcaca caaagtggca  29400
cttgttgaca tctggaaacc cgaagacct tggaataca atgtgaccgt tttccagggt  29460
gacctcttca aaatttacaa ttacactttc ccatttgacc agatgtgtga ctttgtcatg  29520
tacatggaaa agcagcacaa gctgtggcct ccgactcccc agggctgtgt ggaaaatcca  29580
ggctctttct gcatgatctc tctctgtgta actgtgctgg cactaatact cacgcttttg  29640
tatatcagat ttaaatcaag gcaaagcttc attgatgaaa agaaaatgcc ttaatcgctt  29700
tcacgcttga ttgctaacac cgggtttta tccgcagaat gattggaatc accctactaa  29760
tcacctccct ccttgcgatt gcccatgggt tggaacgaat cgaagtccct gtgggggcca  29820
atgttaccct ggtggggcct gtcggcaatg ctacattaat gtgggaaaaa tatactaaaa  29880
atcaatgggt ctcttactgc actaacaaaa atagccacaa gcccagagcc atctgcgatg  29940
ggcaaaatct aaccttgatt gatgttcaat tgctggatgc gggctactat tatgggcagc  30000
tgggtacaat gattaattac tggagacccc acagagatta catgctccac gtagtaaagg  30060
gtcccttag cagcccaccc actaccacct ctactacccc cactaccacc actactccca  30120
ccaccagcac tgccgcccag cctcctcata gcagaacaac cacttttatc aattccaagt  30180
cccactccc ccacattgcc ggcgggcct ccgcctcaga ctccgaaacc accgagatct  30240
gcttctgcaa atgctctgac gccattgccc aggatttgga agatcacgag gaagatgagc  30300
atgacttcgc agatgcatgc caggcatcag agccagaagc gctgccggtg gccctcaaac  30360
agtatgcaga cccccacacc accccccgacc ttcctccacc ttcccagaag ccaagtttcc  30420
tgggggaaaa tgaaactctg cctctctcca tactcgctct gacatctgtt gctatgttga  30480
ccgctctgct ggtgcttcta tgctctatat gctacctgat ctgctgcaga aagaaaaat  30540
ctcacggca tgctcaccag cccctcatgc acttcccta ccctccagag ctgggcgacc  30600
acaaacttta agtctgcagt aactatctgc ccatccttg tcagtcgaca gcgatgagcc  30660
ccactaatct aacggcctct ggactacaa catcgtctct taatgagacc accgctcctc  30720
aagacctgta cgatggtgtc tccgcgctgg ttaaccagtg ggatcacctg gcatatggt  30780
ggctcctcat aggagcagtg accctgtgcc taatcctggt ctggatcatc tgctgcatca  30840
aaagcagaag acccaggcgg cggcccatct acaggccctt tgtcatcaca cctgaagatg  30900
atgatgacac cacttccagg ctgcagaggc taaagcagct actcttctct tttacagcat  30960
ggtaaattga atcatgcctc gcattttcat ctacttgtct ctccttccac ttttttctggg  31020
ctcttctaca ttggccgctg tgtcccacat cgaggtagac tgcctcacgc ccttcacagt  31080
ctacctgctt ttcggctttg tcatctgcac cttttgtctgc agcgttatca ctgtagtgat  31140
ctgcttcata cagtgcatcg actacgtctg cgtcgcgggtg gcttactta gacaccaccg  31200
ccagtatcgc aacagggaca tagcggctct cctaagactt gtttaaaatc atggccaaat  31260
taactgtgat tggtcttctg atcatctgct gcgtcctagc cgccgattggg actcaagctc  31320
ctaccaccac cagcgctccc agaaagagac atgtatcctg cagcttcaag cgtccctgga  31380
atataccccca atgctcttact gatgaacctg aaatctcttc ggcttggtac ttcagcgtca  31440
ccgcccttct tatcttctgc agtacgcgtta ttgcccttgc catctaccct tcccttgacc  31500
tgggctggaa tgctgtcaac tctatggaat atcccacctt cccagaacca gacctgccag  31560
acctggttgt tctaaacgcg tttcctcctc ctgctcccgt tcaaaatcag tttcgcccte  31620
cgtccccac gcccactgag gtcagctact taatctaac aggcggagat gactgaaaac  31680
ctagactag aaatggacgg tctctgcagc gagcaacgca cactagagag gcgccggcaa  31740
aaagagctcg agcgtcttaa acaagagctc caagacgcgg tggccataca ccagtgcaaa  31800
aaaggtgtct tctgtctggt aaaacaggcc acgctcacct atgaaaaaac aggtgacacc  31860
caccgcctag gatacaagct gcccacacag cgccaaaagt tcgccctcat gataggcgaa  31920
caaccoatca ccgtgaccca gcactccgtg gagacagaag gctgcataca tgctcccctgt  31980
aggggcgctg actgcctcta caccttgatc aaaaccctct gcggtctcag agaccttatc  32040
```

```
cctttcaatt aatcataact gtaatcaata aaaaatcact tacttgaaat ctgatagcaa  32100
gcctctgtcc aatttttttca gcaacacttc cttccctcc tcccaactct ggtactctag  32160
gcgcctccta gctgcaaact tcctccacag tctgaaggga atgtcagatt cctcctcctg  32220
tccctccgca cccacgatct tcatgttgtt gcagatgaaa cgcgcgagat cgtctgacga  32280
gaccttcaac cccgtgtacc cctacgatac cgagatcgct ccgacttctg tccctttcct  32340
taccctccc tttgtgtcat ccgcaggaat gcaagaaaat ccagctgggg tgctgtccct  32400
gcacttgtca gagcccctta ccacccacaa tggggccctg actctaaaaa tgggggcgg  32460
cctgaccctg gacaaggaag ggaatctcac ttcccaaaac atcaccagtg tcgatcccc  32520
tctcaaaaaa agcaagaaca acatcagcct tcagaccgcc gcaccoctcg ccgtcagctg  32580
cggggccta acacttttg ccactccccc cctagcggtc agtggtgaca accttactgt  32640
gcagtctcag gcccctctca ctttggaaga ctcaaaacta actctggcca ccaaaggacc  32700
cctaactgtg tccgaaggca aacttgtcct agaaacaga                        32739

SEQ ID NO: 22         moltype = DNA  length = 32739
FEATURE               Location/Qualifiers
misc_feature          1..32739
                      note = Adenovirus vector nucleotide sequences
source                1..32739
                      mol_type = other DNA
                      organism = synthetic construct
SEQUENCE: 22
catcatcaat aatataccttt attttggatt gtggccaata tgataatgag gtgggcgggg  60
agaggcgggg cgggtgacgt aggacgcgcg agtaggggttg ggaggtgtgg cggaagtgtg  120
gcatttgcaa gtgggaggag ctcacatgca agcttccgtc gcggaaaatg tgacgttttt  180
gatgagcgcc gcctacctcc ggaagtgcca attttcgcgc gcttttcacc ggatatcgta  240
gtaattttgg gcgggaccat gtaagatttg gccattttcg ccgcaaaagt gaaacgggga  300
agtgaaaact gaataatagg gcgttagtca tagcgcgtaa tatttaccga gggccgaggg  360
actttgaccg attacgtgga ggactcgccc aggtgttttt tacgtgaatt tccgcgttcc  420
gggtcaaagt ctccgttttt attgtcaccg tcatttgacg cggagggtat ttaaacccgc  480
tgcgctcctc aagaggccac tcttgagtgc cagcgagaag agttttctcc tctgctccgc  540
ttcggtgatc gaaaaatgag acacatagcc tgcactccgg gtcttttgtc cggtcgggcg  600
gcggccgagc ttttggacgc tttgatcaat gatgtcctaa gcgatgattt tccgtctact  660
acccactttaa gcccacctac tcttcacgaa ctgtacgatc tggatgtact ggtggatgtg  720
aacgatccca acgaggaggc ggtttctgcg ttttttcccg agtctgcgct gttggccgct  780
caggagggat ttgacctaca cactccgccg cctattttag agtctccgct gccggagccc  840
agtggtatac cttatatgcc tgaactgctt cccgaagtgg tagacctgac ctgccacgag  900
cctggctttc cgcccagcga cgatgagggt gagccttttg ttttagactt tgctgagata  960
cctgggcacg gttgcaggtc ttgtgcatat catcagaggg ttaccggaga ccccgaggtt  1020
aagtgttcgc tgtgctatat gaggatgacc tcttcctta tctacagtaa gttttttgtct  1080
aggtgggctt ttgggtaggt gggttttgtg tcagaacagg tgtaaacgtt gcttgtgttt  1140
tttgtacctg taggtccggt gtccgagcca gacccggagc ccgaccgcga tcccgagccg  1200
gatcccgagc ctcctcgcag gacaaggaaa ctaccttcca ttctgtgcaa gtctcagaca  1260
cctgtaagga ccagcgagga gacagcacc gactctgaca cttctaccctc tcccccttgaa  1320
attcacccag tggttcctct gggtatacat aaacctgttg ctgttaaagt ttgcgggcga  1380
cgccctgcag tacagtgcat tgaggacttg cttcacgatc ccgaggaacc tttgacttg   1440
agccttaaac gcctaggca ataaacccca cctaagtaat aaaccccacc taagtaataa  1500
accctgccgc ccttggttat tgagatgacg cccaatgttt gcttttgaat gacttcatgt  1560
gtgtaataaa agtgagtgtg atcataggtc tcttgtttgt ctgggcgggg cttaaggta   1620
tataagtctc ttggggctaa acttggttac acttgacccc aatggaggcg tgggggtgct  1680
tggaggagtt tgcggacgtg cgccgtttgc tggacgagag ctctagcaat acctatacta  1740
tttggaggta tctgtgggc tctactcagg ccaagttggt ttcagaatt aagcaggatt  1800
acaagtgcga ttttgaagag cttttttagtt cctgcggtga gcttttgcaa tccttgaatc  1860
tgggccatca ggctattttc caggaaaagg ttctctcgac tttggatttt tccactcccg  1920
ggcgcaccgc cgcttgtgtg gcttttgtgt cttttgtgca agataaatgg agcgaggaga  1980
cccacctgag tcacggctac gtactggatt tcatggcgat gctcttttgg agggctcaca  2040
acaaatggaa gattcagaag gaactgtacg gttccgccct acgtcgtcca cttctgtcgc  2100
gacaggggct gaggtttccc gaccatcggc agcatcagaa tctggaagac gagtcggagg  2160
agcgagcgga ggagaagatc agcttgagag ccggcctgga ccctcctcag gaggaatgaa  2220
tctcccgcag gtgttgtacc tgtttccaga actgagacgg gtcctgacta tcagggagga  2280
tggtcagttt gtgaagaagt ttaagaggga tcgggggtga ggagatgatg aggcggctag  2340
caatttagct tttagtctga tgactcgcca ccgaccggaa tgtattacct atcagcagat  2400
taaggagagt tgtgccaacg agctggatct tttgggtcag aagtatagca tagaacagct  2460
taccacttac tggcttcagc ctggggatga tgggaagag gcgatcaggg tgtatgcaaa  2520
ggtggccctg cggccccgatt gcaagtataa gattactgag ttggttaata ttagaaactg  2580
ctgctatatt tctgggaacg gggccgaagt ggagatagat actcaggaca gggtggcttt  2640
taggtgttgc atgataaaca tgtgcccgg gatactgggg atggatgggg tggtattcat  2700
gaatgtgagg tttacgggcc ccaactttaa tggcacggtg ttcatgggca acaccaactt  2760
gctcctgcat ggtgcgagtt tctatgggtt taataacacc tgtatagagg cctgaccga   2820
tgtaaaggtt cgaggtgtt cctttatag ctgttggaag gcggtggtgt gtcgccctaa   2880
aagcagggt tctgtgaaaa aatgcttgtt tgaaaggtgc accttaggca tcctctctga  2940
gggcaactcc agggtgcgcc ataatgtggc ttcgaactgc ggttgcttca tgcaagtgaa  3000
ggggggtgagc gttatcaagc ataactcggt gtgtggaaac tgcgaggatc gcgcctccca  3060
gatgctgacc tgctttgatg gcaactgtca cctgttgaag accattcata taagcagcca  3120
ccccagaaag gcctggccccg tgtttgagca taacactctt accccgctgc ctttgcatct  3180
gggggtcagg agggggtatgt tcctgcctta ccagtgtaac tttagccaca ctaaaatcct  3240
gctgaacccc agtgcatga ccaaggtcag cctgaatggt gtgtttgatg tgactctgaa  3300
aatctggaag gtgctgaggt atgatgagac caggaccagg tgccgaccct gcgagtgcgg  3360
cggcaagcac atgagaaatc agcctgtgat gttggatgtg accgagagc ttaggcctga  3420
ccatctggtg ctggcctgca ccagggccga gtttgggtct agcgatgagg ataccgattg  3480
```

-continued

```
aggtgggtaa ggtgggcgtg gctagaaggg tggggcgtgt ataaattggg ggtctaaggg   3540
tctctctgtt ttgtcttgca acagccgccg ccatgagcga caccggcaac agctttgatg   3600
gaagcatctt tagcccctat ctgacagtgc gcatgcctca ctgggctgga gtgcgtcaga   3660
atgtgatggg ttccaacgtg gatggacgcc ccgttctgcc ttcaaattcg tctacaatgg   3720
cctacgcgac cgtgggagga actccgctgg acgccgcgac ctccgccgcc gcctccgccg   3780
ccgccgcgac cgcgcgcagc atggctacgg acctttacag ctctttggtg gcgagcggcg   3840
cggcctctcg cgcgtctgct cgggatgaga aactgaccgc tctgctgctt aaactggaag   3900
acttgacccg ggagctgggt caactgaccc agcaggtctc cagcttgcgt gagagcagcc   3960
ttgcctcccc ctaatggccc ataatataaa taaaagccag tctgtttgga ttaagcaagt   4020
gtatgttctt tatttaactc tccgcgcgcg gtaagcccgg gaccagcggt ctcggtcgtt   4080
tagggtgcgg tggattcttt ccaacacgtg gtacaggtgg ctctggatgt ttagatacat   4140
gggcatgagt ccatccctgg ggtggaggta gcaccactgc agagcttcgt gctcgggggt   4200
ggtgttgtat atgatccagt cgtagcagga gcgctgggcg tggtgctgaa aaatgtcctt   4260
aagcaagagg cttatagcta gggggaggcc cttggtgtaa gtgtttacaa atctgctcag   4320
ttgggagggg tgcatccggg gggatataat gtgcatcttg gactggattt ttaggttggc   4380
tatgttccca cccagatccc ttctgggatt catgttgtgc aggaccacca gcacggtata   4440
tccagtgcac ttgggaaatt tatcgtggag cttagacggg aatgcatgga agaacttgga   4500
gacgcccttg tggcctccca gattttccat acattcgtcc atgatgatgg caatgggccc   4560
gtgggaagct gcctgagcaa aaatgtttct gggatcgctc acatcgtagt tatgttccag   4620
ggtgaggtca tcataggaca tctttacgaa tcggggggcgg agggtcccgg actgggggat   4680
gatggtaccc tcgggccccg gggcgtagtt cccctcacag atctgcatct cccaggcttt   4740
catttcagag ggagggatca tatccacctg cggagcaggg aaaaacacag tttctggcgc   4800
agggggagatt aactgggatg agagcaggtt tctgagcagc tgtgactttc cacagccggt   4860
gggcccatat atcacgccta tcaccggctg cagctggtag ttaagagagc tgcagctgcc   4920
gtcctcccgg agcagggggg ccacctcgtt cagcatatcc ctgacgtgga tgttctccct   4980
gaccaattcc gccagaaggc gctcgccgcc cagcgaaagc agctcttgca aggaagcaaa   5040
atttttcagc ggttttaggc cgtcggccgt gggcatgttt ttcagcgtct gggtcagcag   5100
ttccagcctg tcccacagct cggtgatgtg ctctacggca tctcgatcca gcagatctcc   5160
tcgtttcgcg ggttggggcg gctttcgctg tagggcacca gccgatgggc gtccagcggg   5220
gccagagtca tgtccttcca tgggcgcagg gtcctgctga gtcggtgggc ggtcacggtg   5280
aaggggtgcg ctccggggttg ggcgctggcc agggtgcgct tgaggctggt tctgctggtg   5340
ctgaatcgct gccgctcttc gccctgcgcg tcggccaggt agcatttgac catggtctcg   5400
tagtcgagac cctcggcggc gtgccccttg gcgcggagct ttcccttgga ggtggcgccg   5460
cacgaggggc actgcaggct cttcagggcg tagagccttgg gagcgagaaa cacggactct   5520
ggggagtagg cgtccgcgcc gcaggaagcg cagaccgtct cgcattccac cagccaagtg   5580
agctccgggc ggtcagggtc aaaaaccagg ttgcccccat gctttttgat gcgtttctta   5640
cctcggctct ccatgaggcg gtgtcccttc tcggtgacga agaggctgtc cgtgtccccg   5700
tagaccgact tcaggggcct gtcttccagc ggagtgcctc tgtcctcctc gtagagaaac   5760
tctgaccact ctgagacgaa ggcccgcgtc caggccagga cgaaggaggc cacgtgggag   5820
gggtagcggt cgttgccacc tagcgggtcc accttctcca gggtgtgcag gcacatgtcc   5880
ccctcctccg cgtccagaaa agtgattggc ttgtaggtgt aggacacgtg accgggggtt   5940
cccgacgggg gggtataaaa gggggtgggc gccctttcat cttcactctc ttccgcatcg   6000
ctgtctgcga gggccagctg ctgggggtaag tattccctct gcaaggcggg catgacctca   6060
gcgctcaggt tgtcagtttc taaaaatgag gaggatttga tgttcacctg tccggaggtg   6120
ataccttgta gggtacctgg gtccatctgg tcagaaaaca ctattttttt gttgtcaagc   6180
ttggtggcga acgacccgta gagggcgttg gagagcagct tggcgatgga gcgcagggtc   6240
tggttttttgt cgcggtcggc tcgctccttg gccgcagtgt tgagttgcac gtactgcggg   6300
gccacgcact tccactcggg gaagacggtg gtgcgctcgt ctgggattag gcgcaccctc   6360
cagcctcggt tgtgcagggt gaccatgtcg acgctggtgg cgacctcgcc gcgcaggcgc   6420
tcgttggtcc agcagaggcg gccgcccttg cgcgagcaga aggggggtag ggggtccagc   6480
tggtcctcgt ttggggggtc cgcgtcggatg gtgaagaccc tggggagcaa gcgcgggtca   6540
aagtagtcga tcttgcaagc ttgcatgtcc agagcccgct gccattcgcg ggcggcgagc   6600
gcgcgctcgt aggggttgag gggcgggccc cagggcatgg ggtgggtgag cgcggaggcg   6660
tacatgccgc agatgtcata cacgtacagg ggttccctga ggatgccgag gtaggtgggg   6720
tagcagcgcc ccccgcggat gctggcgcgc acgtagtcat agagctcgtg ggagggggcc   6780
agcatgttgg gcccgaggtt ggtgcgctgg gggcgctcgg cgcggaaggc gatctgcctg   6840
aagatggcat gggagttgga ggagatggtg ggccgctgga agacgttgaa gcttgcttct   6900
tgcaagccca ccgagtccct gacgaaggag gcgtaggact cgcgcagctt gtgcaccagc   6960
tcggcggtga cctggacgtc gagcgcgcag tagtcgaggg tctcgcggat gatgtcatac   7020
ttatcctccc ccttcttttt ccacagctcg cggttgagca cgaactcttc gcggtctttc   7080
cagtactctt ggagggggaaa cccgtccgtg tccgaacggt aagagcctag catgtagaac   7140
tggttgacgg cctggtaggg gcaacagccc ttctccacgg gcagcgcgta ggcctgcgcc   7200
gccttgcgga gggaggtgtg ggtgagggcg aaagtgtccc tgaccatgac tttgaggtat   7260
tgatgtttga agtctgtgtc atcgcagccg ccctgttccc agtgatcgca gtccgtgctg   7320
tttttggagc gcgggttggg cagggagaag gtgaggtcat tgaagaggat cttccccgct   7380
cgaggcatga agtttctggt gatgcgaaag ggccctggga ccgaggagcg gttgttgatg   7440
acctgggcgg ccaggacgat ctcgtcaaag ccgtttatgt tgtggcccac gatgtagagc   7500
tccaaaaagc ggggctggcc cttgatggag gggagcttt tgagttcctc gtaggtgagc   7560
tcctcgggcg attccaggcc gtgctcctcc agggcccagt cttgcaagtg agggttggcc   7620
gccaggaagg atcgccagag gtcgcggggcc atgagggtct gcaggcggtc gcggaaggtt   7680
ctgaactgtc gccccacggc catctttttcg ggggtgatgc agtagaaggt gaggggtct   7740
ttctcccagg ggtccatct gagctctcgg gcgaggtcgc gcgcggcggc gaccagagcc   7800
tcgtcgcccc ccagtttcat gaccagcatg aagggcacga gctgcttgcc aaaggctccc   7860
atcaagtgt aggtctctac atcgtaggtg acaaagaggc actccgtgcg aggatgagag   7920
ccgatcggga agaactggat ctcccgccac cagttggagg attggctgtt gatgtggtga   7980
aagtagaagt cccgtctgcg ggccgagcac tcgtgctggc ttttgtaaaa gcgaccgcag   8040
tactggcagc gctgcacggg ttgtatatct tgcacgaggt gaacctggcg acctctgacg   8100
aggaagcgca gcgggaatct aagtccccg cctgggggtcc cgtgtggctg gtggtcttct   8160
actttggttg tctggccgcc agcatctgtc tcctggaggg cgatggtgga gcagaccacc   8220
```

```
acgccgcgag agccgcaggt ccagatctcg gcgctcggcg ggcggagttt gatgacgaca    8280
tcgcgcacat tggagctgtc catggtctcc agctcccgcg gcggcaggtc agctgggagt    8340
tcctggaggt tcacctcgca gagacgggtc aaggcgcggg cagtgttgag atggtatctg    8400
atttcaaggg gcgtgttggc ggcggagtcg atggcttgca ggaggccgca gccccggggg    8460
gccacgatgg ttccccgcgg ggcgcgaggg gaggcggaag ctgggggtgt gttcagaagc    8520
ggtgacgcgg gcgggccccc ggaggtaggg ggggttccgg ccccacaggc atgggcggca    8580
ggggcacgtc ttcgccgcgc gcgggcaggg gctggtgctg gctccgaaga gcgcttgcgt    8640
gcgcgacgac gcgacggttg gtgtcctgta tctgacgcct ctgagtgaag accacgggtc    8700
ccgtgacctt gaaccctgaaa gagagttcga cagaatcaat ctcggcatcg ttgacagcgg    8760
cctggcgcag gatctcctgc acgtcgcccg agttgtcctg gtaggcgatc tctgccatga    8820
actgctcgat ctcttcttcc tggagatctc ctcgtccggc gcgctccacg gtggccgcca    8880
ggtcgttgga gatgcgaccc atgagctgtg agaaggcgtt gagcccgccc tcgttccaga    8940
cccggctgta gaccacgccc ccctcggcgt cgcgagcgcg catgaccacc tgggccaggt    9000
tgagctccac gtgtcgcgtg aagacggcgt agttgccgag gcgctggaaa aggtagttca    9060
gggtggtggc ggtgtgctcg gcgacgaaga agtacatgac ccagcgccgc aacgtggatt    9120
cattgatgtc ccccaaggcc tccaggcgct ccatggcctc gtagaagtcc acggcgaagt    9180
tgaaaaactg ggagttgcga gcggacacgg tcaactcctc ctccagaaga cggatgagct    9240
cggcgacagt gttgcgcacc tcgccgctcga aggccacggg gggcgcttct tcctcttcca    9300
cctcttcttc catgatcgct tcttcttctt cctcagccgg gacgggaggg ggcggcggcg    9360
gcggggagg ggcggcggcgg cggcggcggc gcaccgggag gcggtcgatg aagcgctcga    9420
tcatctcccc ccgcatgcgg cgcatggtct cggtgacggc gcggccgttc tcccgggggc    9480
gcagctcgaa gacgccgcct ctcatctcgc cgcggggcgg gcgccgtga ggtagcgaga    9540
cggcgctgac tatgcatctt aacaattgct gtgtaggtac accgccgagg gacctgattg    9600
agtccagatc caccggatcc gaaaaccttt ggaggaaagc gtctatccag tcgcagtcgc    9660
aaggtaggct gagcaccgtg gcgggcgggg gcgggtctgg agagttcctg gcggagatgc    9720
tgctgatgat gtaattaaag taggcggtct tgagaaggcg gatggtggac aggagcacca    9780
tgtctttggg tccggcctgt tggatgcgga ggcggtcggc catgcccag gcctcgttct    9840
gacaccggcg caggtctttg tagtagtctt gcatgagtct ttccaccggc acctcttctc    9900
cttcctcttc tccatctcgc cggtggttc tcgcgccgcc catgcgcgtg accccaaagc    9960
ccctgcagcg gctgcagcagg gccaggtcgg cgaccacgcg ctcggccaag atggcctgct   10020
gcacctgagt gaggggtcctc tcgaagtcat ccatgtccac gaagcggtgg taggcgcccg   10080
tgttgatggt gtaggtgcag ttggccatga cggaccagtt gacggtctgg tgtcccggct   10140
gcgagagctc cgtgtaccgc aggcgcgaga aggcgcggga atcgaacacg tagtcgttgc   10200
aagtccgcac cagatactgg tagcccacca ggaagtgcgg cggaggttgg cgatagaggg   10260
gccagcgctg ggtggcgggg gccgccgggc ccaggtcttc cagcatgagg cggtggtatc   10320
cgtagatgta cctggacatc caggtgatgc cggcggcggt ggtggtggcg cgcgcgtagt   10380
cgcggacccg gttccagatg tttcgcaggg gcgagaagtg ttccatggtc ggcacgctct   10440
ggccggtgag gcgcgcgcag tcgttgacgc tctatacaca cacaaaaacg aaagcgttta   10500
cagggcttc gttctgtagc ctggaggaaa gtaaatgggt tgggttgcgg tgtgcccgg    10560
ttcgagacca agctgagctc ggccggctga agccgcagct aacgtggtat tggcagtccc   10620
gtctcgaccc aggccctgta tcctccagga tacggtcgag agcccttttg ctttcttggc   10680
caagcgcccg tggcgcgatc tgggatagat ggtcgcgatg agaggacaaa agcggctcgc   10740
ttccgtagtc tggagaaaca atcgccaggg ttgcgttgcg gcgctaccccg gttcgagccc   10800
ctatggcggc ttgaatcggc cggaaccgcg gctaacgagg gccgtggcag ccccgtcctc   10860
aggacccgc cagccgactt ctccagttac gggagcgagc cccttttgtt ttttatttt    10920
tagatgcatc ccgtgctgcg gcagatgcgc ccctcgcccc ggcccgatca gcagcagcaa   10980
cagcaggcat gcagaccccc ctctcccctt tccgccccgg tcaccacgc ccgggcgggcc   11040
gtgtcgggcg cgggggggcgc gctggagtca gatgagccac cgcggcgcg acctaggcag   11100
tatctggact tggaagaggg cgagggactg gcgcggctgg gggcgaactc tccagagcgc   11160
cacccgcggg tgcagttgaa aagggacgcg cgcgaggcgt acctgccgcg gcagaacctg   11220
tttcgcgacc gcgggggcgg ggagcccgag gagatgcgag actgcaggtt ccaagcgggg   11280
cgcgagctgc ggcgcgggct ggacagacag cgcctgctgc gcgaggagga ctttgagccc   11340
gacacgcaga cgggcatcag ccccgcgcgc gcgcacgtag ccgcggccga cctggtgacc   11400
gcctacgagc agacgtaaa ccaggagcgc aacttccaaa agagcttcaa caaccacgtg   11460
cgcacgctgg tggcgcgcga ggaggtgacc ctgggtctca tgcatctgtg ggacctggtg   11520
gaggcgatcg tgcagaaccc cagcagcaag cccctgaccg cgcagctgtt cctggtggtg   11580
cagcacagca gggacaacga ggccttcagg gaggcgctgc tgaacatcac cgagccggag   11640
gggcgctggc tcctggacct gataaacatc ctgcagagca tagtggtgca ggagcgcagc   11700
ctgacctgg ccgagaaggt ggcggccatc aactactcta tgctgagcct gggcaagttc   11760
tacgcccgca agatctacaa gaccccctac gtgcccatag acaaggaggt gaagatagac   11820
agcttctaca tgcgcatggc gctgaaggtg ctgaccctga gcgacgacct gggagtgtac   11880
cgcaacgagc gcatccacaa ggccgtgagc gccagccggc ggcgcgagct gagcgaccgc   11940
gagctgatgc acagtctgca gcgcgcgctg accggcgcgg gcgagggcga cagggaggtc   12000
gagtcctact tcgacatggg ggccgacctg cactggcag cgccccggag tgtgctgcag   12060
gcggcggggg cgtacggcgg cccctggcg gccgatgacc aggaaggaga ggactatgag   12120
ctagaggagg gcgagtacct ggaggactga cctggctggt ggtgttttgg tatagatgca   12180
agatccgaac gtgcggacc cggcggtccg ggcggcgctg caaagccagc cgtccggcat   12240
taactcctct gacgactggg ccgcggccat gggtcgcatc atggccgcat ccgcgcgcaa   12300
ccccgaggct tcaggcagc agcctcaggc caaccggtgg gcgccatct tggaagcgt    12360
agtgccgcg cgctccaacc ccacccacga gaaggtgctg gccatagtca acgcgctggc   12420
ggagagcagg gccatccgcg cggacgaggc cggactggtg tacgatcgcg tgctgcagcg   12480
ggtggcgcgg tacaacagcg gcaacgtgca gaccaacctg gaccgcctgg tgacggacgt   12540
gcgcgaggcc gtggcgcagc gcgagcgctt gcatcaggac ggtaacctgg gctcgctggt   12600
ggcgctaaac gccttcctca gcaccagcc ggccaacgta ccgcggagcc aggaggacta   12660
caccaacttt ttgagcgcgc tgcggctgat ggtgaccgag gtccctcaga gcgaggtgta   12720
ccagtcgggg cccgactact tcttccagac cagcagacag ggcttgcaaa ccgtgaacct   12780
gagccaggct ttcaagaacc tgcgggggct gtggggagtg aaggcgccca ccggcgaccg   12840
ggctacggtg tccagcctgc taacccccaa ctcgcgcctg ctgctgctgc tgatcgcgcc   12900
cttcacggac agcgggagcg tctcgcggga gacctatctg ggccacctgc tgacgctgta   12960
```

```
ccgcgaggcc atcgggcagg cgcaggtgga cgagcacacc ttccaagaga tcaccagcgt   13020
gagccacgcg ctggggcagg aggacacggg cagcctgcag gcgaccctga actacctgct   13080
gaccaacagg cggcagaaga ttcccacgct gcacagcctg acccaggagg aggagcgcat   13140
cttgcgctac gtgcagcaga gcgtgagcct gaacctgatg cgcgacgcg tgacgcccag    13200
cgtgcgctg gacatgaccg cgcgcaacat ggaaccgggc atgtacgcct cccaccggcc    13260
gtttatcaac cgcctgatgg actacttgca tcgggcggcg gccgtgaacc ccgagtactt   13320
cactaatgcc attctgaatc cccactggat gccccctccg ggtttctaca acggggactt   13380
tgaggtgccc gaggtcaacg acgggttcct ctgggatgac atggatgaca gtgtgttctc   13440
acccaacccg ctgcgcgccg cgtctctgcg attgaaggag ggctctgaca gggaaggacc   13500
gaggagtctg gcctcctccc tggctctggg agcggtgggc gccacgggcg cggcggcgcg   13560
gggcagtagc cccttcccca gcctggcaga ctctctgaac agcgggcggg tgagcaggcc   13620
ccgcttgcta ggcgaggagg agtatctgaa caactccctg ctgcagcccg cgagggacaa   13680
gaacgctcag cggcagcagt ttcccaacaa tgggatagag agcctggtgg acaagatgtc   13740
cagatggaag acgtatgcgc aggagtacaa ggagtgggga gaccgccagc gcgggccctt   13800
gccgcccct aggcagcgct ggcagcggcg cgcgtccaac cgccgctgga ggcaggggcc    13860
cgaggacgat gatgactctg cagatgacag cagcgtgttg gacctgggcg ggagcgggaa   13920
ccccttttcg cacctgcgcc cacgcctggg caagatgttt taaaagaaaa aaaaaataa    13980
aactccaccaa ggccatggcc acgagcgttg gtttttttgtt cccttcctta gtatgcggcg  14040
cgcggcgatg ttcgaggagg ggcctccccc ctcttacgag agcgcgatgg ggatttctcc   14100
tgcggcgccc ctgcagcctc cctacgtgcc tcctcggtac ctgcaaccta cagggggag    14160
aaatagcatc tgttactctg agctgcagcc cctgtacgat accaccagac tgtacctggt   14220
ggacaacaag tccgcggacg tggcctcct gaactaccag gcgatttttt                14280
gaccacggtg atccaaaaca acgacttcac cccaaccgag gccagcaccc agaccataaa   14340
cctggataac aggtcgaact ggggcggcga cctgaagacc atcttgcaca ccaacatgcc   14400
caacgtgaac gagttcatgt tcaccaactc tttttaaggcg cgggtgatgg tggcgcgcga   14460
gcaggggag gcgaagtacg agtgggtgga cttcccgctg cccgagggca actactcaga    14520
gaccatgact ctcgacctga tgaacaatgc gatcgtggaa cactatctga agtgggcag    14580
gcagaacggg gtgaaggaaa gcgatatcgg ggtcaagttt gacaccagaa acttccgtct    14640
gggctggac cccgtgaccg ggctggtcat gccgggggtc tacaccaacg aggcctttca    14700
tcccgacata gtgcttctgc ccggctgtgg ggtggacttc acccagagcc ggctgagcaa   14760
cctgctgggc attcgcaagc ggcagccttt ccaggagggt ttcaagatca cctatgagga   14820
tctgaagggg ggcaacattc ccgcgctcct tgatctggac gcctacgagg agagcttgaa   14880
acccgaggag agcgctggcg acagcggcga gagtggcgag gagcaagccg gcggcggtgg   14940
cggcgcgtcg gtagaaaacg aaagtacgcc cgcagtggcg gcggacgctg cggaggtcga   15000
gccgagcgac atgcagcagg acgcagagga gggcgcacag gagggcgcgc agaaggacat   15060
gaacgatggg gagatcaggg gagacacatt cgccacccgg ggcgaagaaa agaggcaga    15120
ggcggcggcg gcggcgacgg cggaggccga aaccgaggtt gaggcagagg cagagcccga   15180
gaccgaagtt atgaagaca tgaatgatgg agaacgtagg ggcgacacgt tcgccaccccg    15240
gggcgaagag aaggcggcgg aggcagaagc cgcggctgga ggcggcggcg cggctgcgga   15300
caagactgag gctgcggcta aggctgaggt cgaagccaat gttgcggttg aggctcaggc   15360
tgaggaggag gcggcggctg aagcagttaa ggaaaaggcc caggcagagc aggaagagaa   15420
aaaacctgtc attcaacctc taaaagaaga tagcaaaaag cgcagttaca acgtcatcga   15480
gggcagcacc tttacccagt accgcagctg gtacctggca tacaactacg gcgacccggt   15540
caaggggggtg cgctcgtgga ccctgctctg cacgccggac gtcacctgcg gctccgagca   15600
gatgtactgg tcgctgccga acatgatgca agacccggtg accttccgct ccacgcggca   15660
ggttagcaac ttcccggtgg tgggcgccga actgctgccc gtgcactcca agagttttta   15720
caacgagcag gccgtctact cccagctgat ccgccaggcc acctctctga cccacgtgtt   15780
caatcgcttt cccgagaacc agatttttggc gcgcccgccg gcccccacca tcaccaccgt   15840
gagtgaaaac gttcctgccc tcacagatca cgggacgcta ccgctgcgca acagcatctc   15900
aggagtccga cgagtgacca ttactgacgc cagacgccgg acctgcccct acgtttacaa   15960
ggccttgggc atagtctcgc cgcgcttcct ctccagtcgc acttttttaaa acacatctac   16020
ccacacgttc caaaatcatg tccgtactca tctcacccag caacaacacc ggctggggc    16080
tgcgcgcgcc cagcaagatg tttggagggg cgaggaagcg ctccgaccag caccctgtgc   16140
gcgtgcgcgg ccactaccgc gcgccctggg gagcgcacaa gcgcgggcgc acagggcgca   16200
ccactgtgga cgacgtcatt gactccgtag tggagcaggc cgccactac acacccggcg    16260
cgccgaccgc ccccgccgtg tccaccgtgg accaggcgat cgaaagcgtg gtacagggcg   16320
cgcggcacta tgccaacctt aaaagtcgcc gccgccgcgt ggccgccgc catcgccgga    16380
gaccccgggc caccgccgcc gcgcgcctta ctaaggctct gctcaggcgc gccaggcgaa   16440
ctggccaccg ggccgcatg agggccggac ggcgggctgc cgctgccgca agcgtcgtgg     16500
ccccgcgggc acgaaggcgc ggggccgctg cgcgccgcgc cgccatttcc agcttggcct   16560
cgacgcggcg cggtaacata tactgggtgc gcgactcggt aaccggcacg cgggtacccg   16620
tgcgcttttcg ccccccgcgg aattagcaca agacaacata cacactgagt ctcctgctgt   16680
tgtgtatccc agcggcgacc gtcagcagcg gcgacatgtc caagcgcaaa attaaagaag   16740
agtgctcca ggtcatcgcg ccggagatct atgggccccc gaagaaggag gaggatgatt     16800
acaagccccg caagctaaag cgggtcaaaa agaaaaagaa agatgatgat gacgaggcgg   16860
tggagtttgt ccgccgcatg gcacccaggc gccccgtgca gtggaagggc cggcgcgtgc   16920
agcgcgtttt gcgccccggc accgcggtgg tcttcacgcc cggcgagcgc tccacgcgca   16980
ctttcaagcg ggtgtacgat gaggtgtacg gcgacgagga cctgttggga caggccaacc   17040
agcgcttttg ggagtttgca tatgggaaac ggccccggga ggtctaaaa gaggacctgc    17100
tggcgctacc gctggacgag ggcaatccca ccccgagtct gaagccggta acctgcaac    17160
aggtgctgcc tttgagcgcg cccgagcagc ataagcgagg gttgaagcgc gaaggcgggg   17220
acctggcgcc caccgtgcag ttgatggtgc ccaagcggca gaagctggag gacgtgctgg   17280
agaaaatgaa agtagagccc gggatccagc ccgagatcaa ggtccgcccc atcaagcagg   17340
tggcgctggg ccgtggggat gtcgttaggat tccacgtggg gagatggaaa                17400
cccaaaccgg cactccctct tcggcggcca gcgccaccac cggcaccgct tcggtagagg   17460
tgcagacgga ccctggcta cccgccaccg ctgttgccgc cgccgccccc cgttcgcgcg     17520
ggcgcaagag aaaattatcca gcggccacgc gctcatgcc ccagtacgca ctgcatccat     17580
ccatcgtgcc caccccggc tacgcgggt actcgtaccg cccgcgcaga tcagccggca      17640
ctcgcggccc ccgccgccgt gcgaccacaa ccagccgccg ccgtcgccgc cgccgccagc    17700
```

```
cagtgctgac ccccgtgtct gtaaggaagg tggctcgctc ggggagcacg ctggtggtgc   17760
ccagagcgcg ctaccacccc agcatcgttt aaagccggtc tctgtatggt tcttgcagat   17820
atggccctca cttgtcgcct ccgcttcccg gtgccgggat accgaggaag aactcaccgc   17880
cgcagaggca tggcgggcag cggtctccgc ggcggccgtc gccatcgccg gcgcgcaaaa   17940
agcaggccga tgccgggcgg tgtgctgcct ctgctaatcc cgctaatcgc cgccggcgatc  18000
ggtgccgtac ccgggatcgc ctccgtggcc ctgcaggcgt cccagaaacg ttgactcttg   18060
caaccttgca agcttgcatt ttttggagga aaaaataaaa aaaagtcta gactctcacg    18120
ctcgcttggt cctgtgacta ttttgtagaa aaaagatgg aagacatcaa ctttgcgtcg    18180
ctggccccgc gtcacggctc cgcccgttc atgggagact ggacagatat cggcaccagc    18240
aatatgagcg gtggcgcctt cagctgggc agtctgtgga gcggccttaa aaatttttggt   18300
tccaccatta agaactatgg caacaaagcg tggaacagca gcacgggcca gatgctgaga   18360
gacaagttga aagagcagaa cttccaggag aaggtggcgc agggcctggc ctctggcatc    18420
agcggggtgg tggacatagc taaccaggcc gtgcagaaaa agataaacag tcatctggac    18480
ccccgtcctc aggtggagga aatgcctcca gcgatggaga cggtgtctcc ggagggcaaa    18540
ggcgaaaagc gcccgcggcc cgacagaaga gagaccctgg tgtcacacac cgaggagccg   18600
ccctcttacg aggaggcagt caaggccggc ctgcccacca ctcgccccat agcccccatg    18660
gccaccggtg tggtgggcca caggcaacac actcccgcaa cactagatct gccccgccg    18720
tccgagccgc cgcgccagcc aaaggcgcg acggtgcccg ctccctccac ttccgccgcc    18780
aacagagtgc ccctgcgccg cgccgcgagc ggccccggg cctcgcgagt tagcggcaac    18840
tggcagagca cactgaacag catcgtgggc ctgggagtga ggagtgtgaa gcgccgccgt    18900
tgctactgaa tgagcaagct agctaacgtg ttgtatgtgt gtatgcgtcc tatgtcgccg    18960
ccagaggagc tgttgagccg ccggcgccgt ctgcactcca gcgaattca agatggcgac   19020
cccatcgatg atgcctcagt ggtcgtacat gcacatctcg ggccaggacg cttcggagta   19080
cctgagcccc gggctggtgc agttcgcccg cgccacagac acctacttca acatgagtaa   19140
caagttcagg aaccccactg tggcgcccac ccacgatgtg accacggacc ggtcgcagcg   19200
cctgacgctg cggttcatcc ccgtggatcg ggaggacacc gctactctt acaaggcgcg    19260
gttcacgctg gccgtgggcg acaaccgcgt gctggacatg gcctccactt actttgacat    19320
caggggggtg ctggacaggg gccccacctt caagccctac tcgggtactg cctacaactc    19380
cctggccccc aagggcgctc ccaattcttg cgagtgggaa caagatgaac cagctcaggc    19440
agcaatagct gaagatgaag aagaacttga agaagaacaa gctcaggacg aacaggcgcc    19500
cactaagaaa acccatgtat acgcccaggc acctctttct ggtgaaaaaa ttactaagga    19560
tggtttgcaa ataggtgtgg atgccacaca ggcgggagat aaccctatat atgctgataa    19620
aacattccaa cccgaacctc agataggtga gtctcagtgg aacgaggctg atgccacagt    19680
agcaggagge agagtcttaa aaaagaccac ccctatgaga ccttgctatg gatcctatgc    19740
caaacctact aatgcccaatg gcggtcaagg gatcatggtg gccaatgatc agggagcggc   19800
tgaatctaaa gttgagatgc aatttttctc caccacaacg tctcttaatg taagggaagg    19860
tgaaaacaat cttcagccaa agtagtgct atacagcgaa gatgttaact tggaatcccc    19920
tgacactcat ttgtcttaca aacctaaaaa ggatgacacc aactcataaa tcatgttggg    19980
tcagcaagcc atgcccaaca gacccaacct cattgctttt agggacaact ttattggact    20040
tatgtactac aacagcacag gcaacatggg agtgctggca ggacaggcct cccagctaaa   20100
cgctgtggta gacttgcaag acagaaacac agagctgtca taccaactga tgcttgattc   20160
cattggagac agatcaagat acttttccat gtggaaccag gcagtggaca gctatgaccc   20220
agatgtcaga atcattgaaa accatgggt tgaagatgaa ctgcccaact attgcttcc     20280
cctgggcgt attggaatta cagacacata ccagtgcata aaaccaaccg cagctgctaa    20340
taacactaca tggtctaagg atgaagaatt tagtgatcgc aatgaaatag gggtgggaaa    20400
caacttcgcc atgagatcca acatccaggc caacctctgg aggaacttcc tctatgccaa    20460
cgtgggggtc tacctgccag acaagctcaa gtacaacccc accaacgtgg acatctctga    20520
caacccaac acctatgact acatgaacaa cgcgtgtggtg gctcccggcc tggtggactg    20580
ctttgtcaat gtgggagcca ggtggtccct ggactacatg gacaacgtca accccttcaa    20640
ccaccaccgc aatgcgggtc tgcgctaccg ctccatgatc ctgggcaacg ggcgctacgt    20700
gcccttccac atcaggtgc cccagaagtt cttgccatc aagaacctcc tcctcctccc    20760
gggctcctac acttacgagt ggaacttcag gaaggatgtc aacatggtcc tgcagagctc   20820
tctgggcaat gaccttaggg tggacggggc cagcatcaag tttgcagcg tcaccctcta    20880
tgctaccttc ttccccatgg ctcacaacac cgcctcacg ctcgaggcca tgctgaggaa    20940
cgacaccaac gaccagtcct tcaatgacta cctctctggg gccaacatgc tctaccccat    21000
ccccgccaag gccaccaacg tgcccatctc cattccctct cgcaactggg ccgccttcag    21060
aggctgggcc tttacccgcc ttaagaccaa ggaaaccccc tccctgggct cgggttttga    21120
cccctacttt gtctactcgg gatccatccc ctacctggat ggcaccttct acctcaacca    21180
cacttttaag aagatatcca tcatgtatga ctcctccgtc agctggccgg gcaatgaccg    21240
cctgctcacc cccaatgagt tcgaggtcaa gcgcgcgtg gacggcgagg gctacaacgt    21300
ggcccagtgc aacatgacca aggactggtt cctggtgcag atgctggcca actacaaacat    21360
aggctaccag ggcttctaca tcccagagag ctacaaggac aggatgtact ccttcttcag    21420
aaatttccaa cccatgagca ggcaggtggt ggacgagacc aaatacaagg actatcaggc    21480
cattggcatc actcaccagc acaacaactc gggattcgtg gactacctgg ctcccaccat    21540
gcgcgagggg caggcctacc ccgccaactt cccctacccg ttgataggca aaaccgcggt    21600
cgacagcgtc cccagaaaa agttcctctg cgaccgcacc ctctgcgca tccccttctc    21660
tagcaacttc atgtccatgg gtgcgctcac ggacctgggc cagaacctgc tctatgccaa    21720
ctccgcccat gcgctggaca tgactttga ggtggacccc atggacgagc ccacccttct    21780
ctatattgtg tttgaagtgt tcgacgtggt cagatgcac cagcacgcc gcgtgtcat    21840
cgagaccgtg tacctgcgca cgccccttct ggccggcaac gccaccacct aaggagacag    21900
cgccgccgcc tgcatgacgg gttccaccga gcaagagctc agggccatcg ccagagacct    21960
gggatgcgga cccctatttt tgggcaccta tgacaaacgc ttcccgggct tcatctcccg    22020
agacaagctc gcctgcgcca tcgtcaacac ggccgcgcgc gagaccgggg gcgtgcactg    22080
gctgccttt ggctgggacc cgcgctccaa aacctgctac ctcttggctt cccgatcag    22140
cgcctcagac agatctatga gttgagtac gaggggctgc tgcgccgcag                22200
cgcgcttgcc tcctcgcccg accgctgcat caccttgag aagtccaccg agaccgtgca    22260
ggggcccac tcggccgcct gcggtctctt ctgctgcatg tttttgcacg cctttgtgcg    22320
ctggccccag agtccatgg atcgcaaccc caccatgaac ttgctcaagg gagtgccaa    22380
cgccatgctc cagagccccc aggtccagcc cacccctgcc cacaaccagg aacagctcta    22440
```

```
ccgcttcctg gagcgccact cccctactt ccgcagtcac agcgcgcaca tccgggggc    22500
cacctctttc tgccacttgc aagaaaaaat gcaagacgga aaatgatgta cagctcgctt    22560
tttaataaat gtaaagactg tgcactttat ttatacacgg gctctttctg gttatttatt    22620
caacaccgcc gtcgccatct agaaatcgaa agggttctgc cgcgcgtcgc cgtgcgccac    22680
gggcagagac acgttgcgat actggaagcg gctcgccgac ttaaactcgg gcaccaccat    22740
gcggggcagt ggttcctcgg ggaagttctc gccccacagg gtgcgggtca gctgcagcgc    22800
gctcaggagg tcgggagccg agatcttgaa gtcgcagttg gggccggaac cctgcgcgcg    22860
cgagttgcgg tacacggggt tgcagcactg gaacaccagc agggccggat tatgcacgct    22920
ggccagcagg ctctcgtcgc tgatcatgtc gctgtccaga tcctccgcgt tgctcagggc    22980
gaacgggtc atcttgcaga cctgcctgcc caggaaaggc ggcagcccgg gcttgccgtt    23040
gcagtcgcag cgcaggggca tcagcaggtg cccgcggccc gactgcgcct gcgggtacag    23100
cgcgcgcatg aaggcttcga tctgcctgaa agccacctgc gtcttggctc cctccgaaaa    23160
gaacatccca caggacttgc tggagaactg gttcgcggga cagctggcat cgtgcaggca    23220
gcagcgcgcg tcggtgttgg cgatctgcac cacgttgcga cccaccggt tcttcactat    23280
cttggccttg gaagcctgct ccttcagcgc gcgctggccg ttctcgctgg tcacatccat    23340
ctctatcacc tgctccttgt tgatcatgtt tgtaccgtgc agacacttca ggtcgccctc    23400
cgtctgggtg cagcggtgct cccacagcgc gcaaccggtg ggctcccaat ttttgtgggt    23460
cacccccgca taggcctgca ggtaggcctg caagaagcgc cccatcatgg ccacaaaggt    23520
cttctggctc gtaaaggtca gctgcaggcc gcgatgctct tcgttcagcc aggtcttgca    23580
gatggcggcc agcgcctcgg tctgctcggg cagcatccta aaatttgtct tcaggtcgtt    23640
atccacgtgg tacttgtcca tcatggccgcg cgccgcctcc atgcccttct cccaggcgga    23700
caccatgggc aggcttaggg ggtttatcac ttccaccgge gaggacaccg tactttcgat    23760
ttcttcttcc tccccctctt cccgggcgcg ccccacgctg ctgcgcgctc tcaccgcctg    23820
caccaagggg tcgtcttcag gcaagcgccg caccgagcgc ttgccgccct tgacctgctt    23880
aatcagcacc ggcgggttgc tgaagcccac catggtcagc gccgcctgct cttcttcgtc    23940
ttcgctgtct accactatct ctggggaagg gcttctccgc tctgcggcgg cgcgcttctt    24000
ttttttcttg ggagcggccg tgatggagtc cgccacgcgc acggaggtcg agggcgtggg    24060
gctgggggtg cgcggtacca gggcctcgtc gccctcggac tcttcctctg actccaggcg    24120
gcggcggagt cgcttctttg ggggcgcgcg cgtcagcggc ggcggagacg gggacgggga    24180
cggggaccgg acgccctcca caggggtgg tcttcgcgga gacccgcggc cgcgctcggg    24240
ggtcttctcg agctggtctt ggtcccgact ggccattgta tcctcctcct cctaggcaga    24300
gagacataag gagtctatca tgcaagtcga aaggaggag agcttaacca ccccctctga    24360
gaccgccgat gcgcccgccg tcgccgtcgc ccccgctgcc gccgacgcgc cgccacacc    24420
gagcgacacc cccgcggacc ccccgcccga cgcaccctg ttcgaggaag cggccgtgga    24480
gcaggacccg ggctttgtct cggcagagga ggatttgcga gaggaggag ataaggagaa    24540
gaagcccctca gtgccaaaag atgataaga gcaagacgag cacgacgcag atgcacacca    24600
gggtgaagtc gggcggggg acggaggca tgacggcgcc gactacctag acgaagggaa    24660
cgacgtgctc ttgaagcacc tgcatcgtca gtgcgccatt gtttgcgacg ctctgcagga    24720
gcgcagcgaa gtgcccctca gcgtgcggga ggtcagccac gcctacgac tcagcctctt    24780
ctccccccgg gtgccccccc gccgccgcga aaacgcaca tgcgagccca acccgcgcct    24840
caacttctac cccgcctttg tggtacccga ggtcctggcc acctatcaca tcttctttca    24900
aaattgcaag atccccctct cgtgccgcgc caaccgtagc cgcgccgata agatgctggc    24960
cctgcgccag ggcgaccaca tacctgatat cgccgctttg gaagatgtac caaagatctt    25020
cgagggtctg ggtcgcaacg agaagcgggc agcaaactct ctgcaacagg aaaacagcga    25080
aaatgagagt cacaccgggg tactggtgga gctcgagggc gacaacgccc gcctggcggt    25140
ggtcaagcgc agcatcgagg tcaccacctt tgcctacccc gcgctaaacc tgcccccaa    25200
agtcatgaac gcgccatgg acgggcgtat catgcgccgc gccccctcgc tccaga    25260
tgcaaacttg catgaggaga ccgaggacgg ccagcccgtg gtcagcgacg agcagctggc    25320
gcgctggctg gagaccgcgg accccgccga actggaggag cggcgcaaga tgatgatggc    25380
cgtggtgctg gtcaccgtag agctggagtg tctgcagcgc ttcttcggcg accccgagat    25440
gcagagaaag gtcgaggaga ccctgcacta caccttccgg cagggctacg tgcgccagga    25500
ttgcaagatc tccaacgtgg agctcagcaa cctggtgtcc tacctgggca tcttgcatga    25560
gaaccgcctc gggcagagcg tgctgcactc caccctgcgc ggggaggcgc gccgcgacta    25620
cgtgcgcgac tgcgttacc tcttcctctg ctacacctgg cagacggcca tggggtctg    25680
gcagcagtgc ctgaggagc gcaacctcaa ggagctgaag aagctcctgc agcgcgcgtt    25740
caaagatctc tggacgggct acaacgagcg ctcggtggcc gccgcgctgg ccgacctcat    25800
cttccccgag cgcctgctca aaaaccctcca gcaggggctg cccgacttca ccagccaaag    25860
catgttgcaa aacttcagga actttatcct ggagcgttct ggcatcctac ccgccacctg    25920
ctgcgccctg cccagcgact ttgtccccct cgtgtaccgc gagtgcccc cgccgctgg    25980
gggtcactgc tacctgttcc aactggccaa ctacctgtcc taccacgcgg acctcatgga    26040
ggactccagc ggcgaggggc tcatggagtg ccactgccgc tgcaacctct gcacgcccca    26100
ccgctccctg gtctgcaaca cccaactgct cagcgagagt cagattatcg gtaccttcga    26160
gctacagggt ccgtcctcct cagacgagaa gtccgcggct ccggggctaa aactcactcc    26220
ggggctgtgg acttccgcct acctgcgcaa atttgtacct gaagactacc acgccacga    26280
gatcaggtttt tacgaagacc aatcccgccc gccaagcg gagctgaccg cctgcgtcat    26340
cacccagggc gagatcctag gccaattgca agccatccaa aaagcccgcc aagactttt    26400
gctgaagaag ggtcgggggg tgtatctgga ccccagtcg ggtgaggagc tcaacccggt    26460
tcccccgctg ccgccgccgc gggccttgc ttcccaggat aagcatccca atggctccca    26520
gaaagaagca gcagcggccg ccactgccgc cacccacat gctggaggaa gaggaggaat    26580
actgggacag tcaggcagag gagggttttcgg acgaggagga gccggagacg gagatggaag    26640
agtgggagga ggacagctta gacgaggagg cttccgaagc cgaagaggca gacgcaacac    26700
cgtcaccctc ggccgcagcc cctcgcagg cgcccccgaa gtccgctccc agcatcagca    26760
gcaacagcag cgctataacc tccgctcctc caccgccgcg acccacgcc gaccgcagac    26820
ccaaccgtag atgggacacc accggaaccg gggccgtaa gtctccggg agaggcacga    26880
aagcgcagcc ccaaggctac cgctcgtggc gcgctcacaa gaacgccata gtcgcttgct    26940
tgcaagactg cggggggaac atctccttcg cccgccgctt cctgctcttc caccacggtg    27000
tggccttccc ccgtaacgtc ctgcattact accgtcatct ctacagcccc tactgcggcg    27060
gcagtgagcc agagacggtc ggcggcggcg gcggcgcccg tttcggcgcc taggaagacc    27120
cagggcaaga cttcagccaa gaaactcgcg gcggccgcgg cgaacgcggt cgcggggcc    27180
```

```
ctgcgcctga cggtgaacga accccgtgcg accgcgaac tgaggaaccg aatcttcccc    27240
actctctatg ccatcttcca gcagagcaga gggcaggatc aggaactgaa agtaaaaaac    27300
aggtctctgc gctccctcac ccgcagctgt ctgtatcaca agagcgaaga ccagcttcgg    27360
cgcacgctgt aggacgctga ggcactcttc agcaaatact gcgcgctcac tcttaaggac    27420
tagctccgcg cccttctcga atttaggcgg gaacgcctac gtcatcgcag cgccgccgtc    27480
atgagcaagg acattccac gccatacatg tggagctatc agccgcagat gggactcgcg    27540
gcgggcgcct cccaagacta ctccaccgc atgaactggc tcagtgccgg cccacacatg    27600
atctcacagg ttaatgatat ccgcacccat cgaaaccaaa tattggtgga gcaggcggca    27660
attaccacca cgccccgcaa taatcccaac cccagggagt ggcccgcgtc cctggtgtat    27720
caggaaattc ccggcccac caccgtacta cttccgcgtg attccaggc cgaagtccaa    27780
atgactaact caggggcaca gctcgcgggc ggctgtcgtc acagggtgcg gcctcctcgc    27840
cagggtataa ctcacctgga gatccgaggc agaggtattc agctcaacga cgagtcggtg    27900
agctcctcgc tcggtctcag acctgacggg accttccaga tagccggagc cggccgatct    27960
tccttcacgc cccgccaggc gtacctgact ctgcaaagct cgtcctcggc gccgcgctcg    28020
ggcggcatcg ggactctcca gttcgtgcag gagtttgtgc cctcggtcta cttcaaccc    28080
ttctcgggct ctcccggtcg ctacccggac cagttcatct cgaactttga cgccgcgagg    28140
gactcggtgg acggctacga ctgaatgtcg ggtggacccg gtgcagagca acttcgcctg    28200
aagcacctcg accactgccg cgccctcag tgctttgccc gctgtcagac cggtgagttc    28260
cagtacttt ccctgcccga ctcgcacccg gacggcccgg cgcacgggt gcgcttttt    28320
atcccgagtc aggtgcgctc taccctaatc agggagttta ccgcccgtcc cctactggcg    28380
gagttggaaa aggggcctc tatcctaacc attgcctgca tctgctctaa ccctggattg    28440
caccaagatc tttgctgtca tttgtgtgct gagtataata aaggctgaga tcagaatcta    28500
ctcgggctcc tgtcgccatc ctgtcaacgc caccgtccaa gcccggcccg atcagcccga    28560
ggtgaacctc acctgcggtc tgcaccggcg cctgaggaaa tacctagctt ggtactacaa    28620
cagcactccc tttgtggttt acaacagctt tgaccaggac ggggtctcac tgagggataa    28680
cctctcgaac ctgagctact ccatcaggaa gaacagcacc ctcgagctac ttcctcctta    28740
cctgccgggg acttaccagt gtgtcaccgg tccctgcacc cacacccacc tgttgatcgt    28800
aaacgactct cttccgagaa cagacctcaa taactcctct tcgcagttcc ccagaacagg    28860
aggtgagctc aggaaacccc gggtaaagaa gggtggacga gagttaacac ttgtggggtt    28920
tctggtgtat gtgacgctgg tggtggctct tttgattaag gcttttcctt ccatgtctga    28980
actctccctc ttcttttatg aacaactcga ctagtgctaa cgggacccta cccaacgaat    29040
cgggattgaa tatcggtaac caggttgcag tttcacttt gattaccttc atagtcctct    29100
tcctgctagt gctgtcgctt ctgtgcctgc ggatcggggg ctgctgcatc cacgtttata    29160
tctggtgctg gctgtttaga aggttcggag accatcgcag gtagaataaa catgctgcg    29220
cttaccctct ttgtcctggc gctgccgcc agctgccaag ccttttccga ggctgacttt    29280
atagagcccc agtgtaatgt gacttttaaa gcccatgcac agcgttgtca tactataatc    29340
aaatgtgcca ccgaacacga tgaataccct atccagtata aagataaatc acacaaagtg    29400
gcacttgttg acatctggaa acccgaagac cctttggaat acaatgtgac cgtttttccag    29460
ggtgacctct tcaaaattta caattacact ttcccatttg accagatgtg tgactttgtc    29520
atgtacatgg aaaagcagca caagctgtgg cctccgactc cccagggctg tgtggaaaat    29580
ccaggctctt tctgcatgat ctctctctgt gtaactgtgc tggcactaat actcacgctt    29640
ttgtatatca gatttaaatc aaggcaaagc ttcattgatg aaaagaaaat gccttaatcg    29700
cttccacgct tgattgctaa caccggggttt ttatccgcag aatgattgga atcacctac    29760
taatcacctc cctccttgcg attgcccatg ggttggaacg aatcgaagtc cctgtggggg    29820
ccaatgttac cctggtgggg cctgtcggca atgctacatt aatgtgggaa aaatatacta    29880
aaaatcaatg ggtctcttac tgcactaaca aaaatagcca caagcccaga gccatctgcg    29940
atgggcaaaa tctaaccttg attgatgttc aattgctgga tgcgggctac tattatgggc    30000
agctgggtac aatgattaat tactggagac cccacagaga ttacatgctc cacgtagtaa    30060
agggtcccct tagcagccca cccactacca cctctactac cccactaccc accactactc    30120
ccaccaccag cactgccgcc cagcctcctc atagcagaac aaccacttt atcaattcca    30180
agtcccactc cccccacatt gccggcgggc cctccgcctc agactccgaa accaccgaga    30240
tctgcttctg caaatgctct gacgccattg cccaggattt ggaagatcac gaggaagatg    30300
agcatgactt cgcagatgca tgccaggcat cagagccaga agcgctgccg gtggccctca    30360
aacagtatgc agaccccac accaccccg accttcctcc accttcccag aagccaagtt    30420
tcctggggga aaatgaaact ctgcctctct ccatactcgc tctgacatct gttgctatgt    30480
tgaccgctct gctggtgctt ctatgctcta tatgctacct gatctgctgc agaaagaaaa    30540
aatctcacgg ccatgctcac cagccccctca tgcacttccc ttaccctcca gagctgggcg    30600
accacaaact ttaagtctgc agtaactatc tgcccatccc ttgtcagtcg acagcgatga    30660
gccccactaa tctaacggcc tctggactta caacatcgtc tcttaatgag accaccgctc    30720
ctcaagacct gtacgatggt gtctccgcgc tggttaacca gtgggatcac ctgggcatat    30780
ggtggctcct cataggagca gtgacccgt gcctaatcct ggtctggatc atctgctgca    30840
tcaaaagcag aagacccagg cggcggccca tctacaggcc ctttgtcatc acacctgaag    30900
atgatgatga caccacttcc aggctgcaga ggctaaagca gctactcttc tcttttacag    30960
catggtaaat tgaatcatgc ctcgcatttt catctacttg tctctcctc cacttttct    31020
gggctcttct acattggccg ctgtgtccca catcgaggta gactgcctca cgcccttcac    31080
agtctacctg cttttcggct ttgtcatctg caccttggtc tgcagcgtta tcactgtagt    31140
gatctgcttc atacagtgca tcgactacgt ctgcgtgcgg tggcttact ttagacacca    31200
ccccagtat cgcaacaggg acatagcggc tctcctaaga cttgtttaaa atcatggcca    31260
aattaactgt gattggtctt ctgatcatct gtgcgtcct agccgcgatt gggactcaag    31320
ctcctaccac caccagcgct cccagaaaga gacatgtatc ctgcagcttc aagcgtccct    31380
ggaatatacc ccaatgcttt actgatgaac ctgaaatctc tttggcttgg tacttcagcg    31440
tcaccgccct tcttatcttc tgcagtacgg ttattgccct tgccatctac ccttcccttg    31500
acctgggctg gaatgctgtc aactctatgg aatatcccac cttcccagaa ccagacctgc    31560
tccttggt tgttctaaac gcgttttcctc ctcctgctcc cgttcaaaat cagtttttgt    31620
ctccgtcccc cacgcccact gaggtcagct actttaatct aacaggcgga gatgactgaa    31680
aacctagacc tagaaatgga cggtctctgc agcgagcaac gcacactaga gaggcgccgg    31740
caaaaagagc tcgagcgtct taaacaagag ctccaagacg cggtgccat acaccagtgc    31800
aaaaaaggtg tcttctgtct ggtaaaacag gccacgctca cctatgaaaa aacaggtgac    31860
acccaccgcc taggatacaa gctgcccaca cagcgccaaa agttcgccct catgataggc    31920
```

```
gaacaaccca tcaccgtgac ccagcactcc gtggagacag aaggctgcat acatgctccc   31980
tgtaggggcg ctgactgcct ctacaccttg atcaaaaccc tctgcggtct cagagacctt   32040
atcccttttca attaatcata actgtaatca ataaaaaatc acttacttga aatctgatag   32100
caagcctctg tccaattttt tcagcaacac ttccttcccc tcctcccaac tctggtactc   32160
taggcgcctc ctagctgcaa acttcctcca cagtctgagg ggaatgtcag attcctcctc   32220
ctgtccctcc gcacccacga tcttcatgtt gttgcagatg aaacgcgcga gatcgtctga   32280
cgagaccttc aaccccgtgt accectacga taccgagatc gctccgactt ctgtcccttt   32340
ccttacccct cccttttgtgt catccgcagg aatgcaagaa aatccagctg gggtgctgtc   32400
cctgcacttg tcagagcccc ttaccaccca caatggggcc ctgactctaa aaatgggggg   32460
cggcctgacc ctggacaagg aagggaatct cacttcccaa aacatcacca gtgtcgatcc   32520
ccctctcaaa aaaagcaaga acaacatcag ccttcagacc gccgcacccc tcgccgtcag   32580
ctccggggcc ctaacacttt ttgccactcc cccctagcg gtcagtggtg acaaccttac    32640
tgtgcagtct caggcccctc tcactttgga agactcaaaa ctaactctgg ccaccaaagg   32700
accccctaact gtgtccgaag gcaaacttgt cctagaaac                         32739

SEQ ID NO: 23          moltype = DNA   length = 32739
FEATURE                Location/Qualifiers
misc_feature           1..32739
                       note = Adenovirus vector nucleotide sequences
source                 1..32739
                       mol_type = other DNA
                       organism = synthetic construct
SEQUENCE: 23
ataatatacc ttattttgga ttgtggccaa tatgataatg aggtgggcgg ggagaggcgg   60
ggcgggtgac gtaggacgcg cgagtagggt tgggaggtgt ggcggaagtg tggcatttgc   120
aagtgggagg agctcacatg caagcttccg tcgcggaaaa tgtgacgttt ttgatgagcg   180
ccgcctacct ccggaagtgc caattttcgc gcgcttttca ccggatatcg tagtaatttt   240
gggcgggacc atgtaagatt tggccatttt cgcgcgaaaa gtgaaacggg gaagtgaaaa   300
ctgaataata gggcgttagt catagcgcgt aatatttacc gagggccgag ggactttgac   360
cgattacgtg gaggactcgc ccaggtgttt tttacgtgga tttccgcgtt ccgggtcaaa   420
gtctccgttt ttattgtcac cgtcatttga cgcggagggt atttaaaccc gctgcgctcc   480
tcaagaggcc actcttgagt gccagcgaga agagttttct cctctgctcc gcttcggtga   540
tcgaaaaatg agacacatag cctgcactcc gggtctttg tccggtcggg cggcggccga    600
gcttttggac gctttgatca atgatgtcct aagcgatgat tttccgtcta ctacccactt   660
tagcccacct actcttcacg aactgtacga tctggatgtt ctggtggatg tgaacgatcc   720
caacgaggag gcggtttctg cgttttttcc cgagtctgcg ctgttggccg ctcaggaggg   780
atttgaccta cacactccgc cgcctatttt agagtctccg ctgccggagc ccagtggtat   840
accttatatg cctgaactgc ttcccgaagt ggtagacctg acctgccacg agcctggctt   900
tccgcccagc gacgatgagg gtgagccttt tgttttagac tttgctgaga tacctgggca   960
cggttgcagg tcttgtgcat atcatcagag ggttaccgga gaccccgagg ttaagtgttc   1020
gctgtgctat atgaggatga cctcttcctt tatctacagt aagttttgt ctaggtgggc    1080
ttttggggtag gtgggttttg tgtcagaaca ggtgtaaacg ttgcttgtgt tttttgtacc   1140
tgtaggtccg gtgtccgagc cagacccgga gcccgaccgc ggatcccga                1200
gcctcctcgc aggacaagga aactaccttc cattctgtgc aagtctcaga cacctgtaag   1260
gaccagcgag gcagacagca ccgactctgg cacttctacc tctcccctg aaattcaccc    1320
agtggttcct ctgggtatac ataaacctgt tgctgttaaa gtttgcgggc gacgccctgc   1380
agtacagtgc attgaggact tgcttcacga tcccgaggaa cctttggact tgagccttaa   1440
acgcccctagg caataaaaccc cacctaagta ataaaccccca cctaagtaat aaaccctgcc   1500
gcccttggtt attgagatga cgcccaatgt ttgcttttga atgacttcat gtgtgtaata   1560
aaagtgagtg tgatcatagg tctcttgttt gtctgggcgg ggcttaaggg tatataagtc   1620
tcttgggct aaacttggtt acacttgacc ccaatgaagg cgtgggggtg cttggaggag    1680
tttgcgacg tgcgccgttt gctgacgag agctctagca ataccatac tatttggagg      1740
tatctgtggg gctactactca ggccaagttg gtttccagaa ttaagcagga ttacaagtgc   1800
gatttttgaag agcttttttag ttcctgcggt gagcttttgc aatccttgaa tctgggccat   1860
caggctatt tccaggaaaa ggttctctcg actttggatt tttccactcc cgggcgcacc   1920
gccgcttgtg tggcttttgt gtcttttgtg caagatcaaat ggagcgagga gacccacctg   1980
agtcacggct acgtactgga tttcatggcg atggctcttt ggagggctca caacaaatgg   2040
aagattcaga aggaactgta cggttccgcc ctacgtcgtc cacttctgtc gcgacagggg   2100
ctgaggtttc ccgaccatcg gcagcatcag aatctgaaga acgagtcgga ggagcgagcg   2160
gaggagagaa tcagcttgag agccggcctg gaccctcctc aggaggaatg aatctccgag   2220
aggtggttga cctgtttcca gaactgagac gggtcctgac tatcagggag gatggtcagt   2280
ttgtgaagaa gtttaagagg gatcggggtg agggagatga tgaggcggct agcaatttag   2340
cttttagtct gatgactcgc caccgaccgg aatgtattac ctatcagcag attaaggaga   2400
gttgtgccaa cgagctggat cttttgggtc agaagtatag catgaacag cttaccactt    2460
actggcttca gcctggggat gattgggaag aggcgatcga ggtgtatgca aaggtggccc   2520
tgcggcccga ttgcaagtat aagattacta agttggttaa tattagaaac tgctgctata   2580
tttctgggaa cggggccgaa gtggagatag atactcagga cagggtggct tttaggtgtt   2640
gcatgataaa catgtggccc gggatactgg ggatgatga ggtggtattc atgaatgtga     2700
ggtttacggg ccccaacttt aatggcacgg tgttcatggg caacaccaac ttgctcctgc   2760
atggtgcgag tttctatggg tttaataaca cctgtataga ggcctggacc gatgtaaagg   2820
ttcgaggttg ttccttttat agctgttgga aggcggtggt gtgtcgccct aaaagcaggg   2880
gttctgtgaa aaaatgcttg tttgaaaggt gcacttagg catcctctct gagggcaact   2940
ccagggtgcg ccataatgtg gcttcgaact gcggttgctt catgcaagtg aaggggtga    3000
gcgttatcaa gcataatcg gtgtgtgaa actgcgagga cgcctccc cagatgctga    3060
cctgctttga tggcaactgt cacctgttga agaccattca tataagcagc accccagaa     3120
aggcctggcc cgtgtttgag cataacatct tgacccgctg ctccttgcat ctgggggtca   3180
ggagggggtat gttcctgcct taccagtgta actttagcca cactaaaaatc ctgctggaac   3240
ccgagtgcat gaccaaggtc agcctgaatg gtgtgtttga tgtgactctg aaaatctgga   3300
aggtgctgag gtatgatgag accaggacca ggtgccgacc ctgcgagtgc ggcggcaagc   3360
```

```
acatgagaaa tcagcctgtg atgttggatg tgaccgagga gcttaggcct gaccatctgg   3420
tgctggcctg caccagggcc gagtttgggt ctagcgatga ggataccgat tgaggtgggt   3480
aaggtgggcg tggctagaag ggtggggcgt gtataaattg ggggtctaag ggtctctctg   3540
ttttgtcttg caacagccgc cgccatgagc gacaccggca acagctttga tggaagcatc   3600
tttagcccct atctgacagt gcgcatgcct cactgggctg gagtgcgtca gaatgtgatg   3660
ggttccaacg tggatggacg ccccgttctg ccttcaaatt cgtctacaat ggcctacgcg   3720
accgtgggag gaactccgct ggacgccgcg acctccgccg ccgcctccgc cgccgccgcg   3780
accgcgcgca gcatggctac ggacctttac agctctttgg tggcgagcgg cgcggcctct   3840
cgcgcgtctg ctcgggatga gaaactgacc gctctgctgc ttaaactgga agactttgacc  3900
cgggagctgg gtcaactgac ccagcaggtc tccagcttgc gtgagagcag ccttgcctcc   3960
ccctaatggc ccataatata aataaaagcc agtctgtttg gattaagcaa gtgtatgttc   4020
tttatttaac tctccgcgcg cggtaagccc gggaccagcg gtctcggtcg tttagggtgc   4080
ggtggattct ttccaacacg tggtacaggt ggctctggat gtttagatac atgggcatga   4140
gtccatccct gggggtggagg tagcaccact gcagagcttc gtgctcgggg gtggtgttgt   4200
atatgatcca gtcgtagcag gagcgctggg cgtggtgctg aaaaatgtcc ttaagcaaga   4260
ggcttatagc tagggggagg cccttggtgt aagtgtttac aaatctgctc agttgggagg   4320
ggtgcatccg ggggatata atgtgcatct tggactggat ttttaggttg gctatgttcc    4380
cacccagatc ccttctggga ttcatgttgt gcaggaccac cagcacggta tatccagtgc   4440
acttgggaaa tttatcgtgg agcttagacg ggaatgcatg gaagaacttg gagacgccct   4500
tgtggcctcc cagattttcc atacattcgt ccatgatgat ggcaatgggc ccgtgggaag   4560
ctgcctgagc aaaaatgttt ctgggatcgc tcacatcgta gttatgttcc agggtgaggt   4620
catcatagga catctttacg aatcggggc ggagggtccc ggactggggg atgatggtac    4680
cctcgggccc cggggcgtag ttcccctcac agatctgcat ctcccaggct ttcatttcag   4740
agggagggat catatccacc tgcggagcga tgaaaaacac agtttctggc gcaggggaga   4800
ttaactggga tgagagcagg tttctgagca gctgtgactt ccacagccg gtgggcccat    4860
atatcacgcc tatcaccggc tgcagctggt agttaagaga gctgcagctg ccgtcctccc   4920
ggagcagggg ggccacctcg ttcagcatat ccctgacgtg gatgttctcc ctgaccaatt   4980
ccgcagaag gcgctcgccg cccagcgaaa gcagctcttg caaggaagca aaatttttca    5040
gcggttttag gccgtcggcc gtgggcatgt ttttcagcgt ctgggtcagc agttccagcc   5100
tgtccacacg ctcggtgatg tgctctacgg catctcgatc cagcagatct cctcgtttcg   5160
cgggttgggg cggctttcgc tgtagggcac cagccgatgg gcgtccagcg gggccagagt   5220
catgtccttc catgggcgca gggtcctcgt cagggtggtc tgggtcacgg tgaaggggtg   5280
cgctccgggt tgggcgctgg ccagggtgcg cttgaggctg gttctgctgg tgctgaatcg   5340
ctgccgctct tcgccctgcg cgtcggccag gtagcatttg accatggtct cgtagtcgag   5400
accctcggcg gcgtgcccct tggcgcggag ctttccttg gaggtggcgc cgcacgaggg   5460
gcactgcagg ctcttcaggg cgtagagctt gggagcgaga aacacggact ctggggagta   5520
ggcgtccgcg ccgcaggaag cgcagaccgt ctcgcattcc accagccaag tgagctccgg   5580
gcggtcaggg tcaaaaacca ggttgccccc atgcttttg atgcgtttct tacctcggct    5640
ctccatgagg cggtgtccct tctcggtgac gaagaggctg tccgtgtccc cgtagaccga   5700
cttcaggggc ctgtcttcca gcggagtgcc tctgtcctcc tcgtagagaa actctgacca   5760
ctctgagacg aaggcccgcg tccaggccag gacgaaggag gccacgtggg aggggtagcg   5820
gtcgttgtcc actagcgggt ccaccttctc cagggtgtgc aggcacatgt ccccctcctc   5880
cgcgtccaga aaagtgattg gcttgtaggt gtaggacacg tgaccgggga ttcccgacgg   5940
gggggtataa aaggggggtgg gcgccccttc atcttcactc tcttccgcat cgctgtctgc   6000
gagggccagc tgctggggta agtattccct ctcgaaggcg ggcatgacct cagcgctcag   6060
gttgtcagtt tctaaaaatg aggaggattt gatgttcacc tgtccggagg tgatacccttt  6120
gagggtacct gggtccatct ggtcagaaaa cactattttt ttgttgtcaa gcttggtggc   6180
gaacgacccg tagagggcgt tggagagcag cttggcgatg gagcgcaggg tctggttttt   6240
gtcgcggtcg gctcgctcct tggccgcgat gttgagttgc acgtactcgc gggccacgca   6300
cttccactcg gggaagacgg tggtgcgctc gtctgggatt aggcgcaccc tccagcctcg   6360
gttgtgcagg gtgaccatgt cgacgctggt ggcgacctcg ccgcgcagcc gtcgttggt    6420
ccagcagagg cggccgccct tgcgcgagca gaaggggggt aggggtcca gctggtcctc    6480
gtttgggggg tccgcgtcga tggtgaagac cccggggagc aagcgcgggt caaagtagtc   6540
gatcttgcaa gcttgcatgt ccagagcccg ctgccattcg cgggcggcga gcgcgcgctc   6600
gtaggggttg aggggcgggc cccagggcat ggggtgggtg agcgcgggca cgtacatgcc   6660
gcagatgtca tacacgtaca ggggttccct gaggatgccg aggtaggtgg ggtagcagcc   6720
ccccccgcgg atgctggcgc gcacgtagtc atagagctcg tgggaggggg ccagcatgtt   6780
gggcccgagg ttggtgcgct ggggcgctc ggcgcggaag gcgatctgcc tgaagatggc    6840
atgggagttg gaggagatgg tgggccgctg gaagacgttg aagcttgctt cttgcaagcc   6900
caccgagtcc ctgacgaagg aggctagga ctcgcgcagc ttgtgcacca gctcggcggt    6960
gacctggacg tcgagcgcgc agtagtcgag ggtctcgcgg atgatgtcat acttatcctc   7020
cccttctttt ttccacagct cgcggttgag gacgaactct tcgcggtctt tccagtactc   7080
ttggagggaa aacccgtccg tgtccgaacg gtaagagcct agcatgtaga actggttgac   7140
ggcctggtag gggcaacagc ccttctccac gggcagcgcg taggcctgcg ccgccttgcg   7200
gagggaggtg tgggtgaggg cgaaagtgtc cctgaccatg actttgaggt attgatgttt   7260
gaagtctgtg tcatcgcagc cgccctgttc ccacagggtg tagtccgtgc gcttttggga   7320
gcgcgggttg ggcagggaga aggtgaggtc attgaagagg atcttcccg ctcgaggcat    7380
gaagtttctg gtgatgcgaa agggccctgg gaccgaggag cggttgttga tgacctggc    7440
ggccaggacg atctcgtcaa agccgtttat gttgtggccc acgatgtaga gctccaaaaa   7500
gcggggctgg cccttgatgg aggggagctt tttgagttcc tcgtaggtga gctcctcgga   7560
cgattccagg ccgtgctcct ccagggccca gtcttgcaag tgagggttgg ccgccaggaa   7620
ggatcgccag aggtcgcggg ccatgagggt ctgcaggcgg tcgcggaagg ttctgaactg   7680
tcgccccacg gccatctttt cggggtgat gcagtagaag gtgaggggt cttttctccca    7740
gggtcccat ctgagctctc gggcgaggtc gcgcgcagag cctcgtcgg                7800
ccccagtttc atgaccagca tgaagggcac gagctgcttg ccaaaggctc ccatccaagt   7860
gtaggtctct acatcgtagg tgacaaagag gcgctccgtg cgaggatgag agccgatcgg   7920
gaagaactgg atctcccgcc accagttgga ggattggctg ttgatgtggt gaaagtagaa   7980
gtcccgtctg cgggccgagc actcgtgctg gcttttgtaa aagcgaccgc agtactggca   8040
gcgctgcacg ggttgtatat cttgcacgag gtgaacctgg cgacctctga cgaggaagcg   8100
```

```
cagcgggaat ctaagtcccc cgcctggggt cccgtgtggc tggtggtctt ctactttggt  8160
tgtctggccg ccagcatctg tctcctggag ggcgatggtg gagcagacca ccacgccgcg  8220
agagccgcag gtccagatct cggcgctcgg cgggcggagt ttgatgacga catcgcgcac  8280
attggagctg tccatggtct ccagctcccg cggcggcagg tcagctggga gttcctggag  8340
gttcacctcg cagagacggg tcaaggcgcg ggcagtgttg agatggtatc tgatttcaag  8400
gggcgtgttg gcggcggagt cgatggcttg caggaggccg cagccccggg gggccacgat  8460
ggttccccgc ggggcgcgag gggaggcgga agctgggggt gtgttcagaa gcggtgacgc  8520
gggcgggccc ccggaggtag gggggggttcc ggccccacag gcatgggcgg caggggcacg  8580
tcttcgccgc gcgcgggcag gggctggtgc tggctccgaa gagcgcttgc gtgcgcgacg  8640
acgcgacggt tggtgtcctg tatctgacgc ctctgagtga agaccacggg tcccgtgacc  8700
ttgaacctga aagagagttc gacagaatca atctcggcat cgttgacagc ggcctggcgc  8760
aggatctcct gcacgtcgcc cgagttgtcc tggtaggcga tctctgccat gaactgctcg  8820
atctcttctt cctggagatc tcctcgtccg gcgcgctcca cggtggccgc caggtcgttg  8880
gagatgcgac ccatgagctg tgagaaggcg ttgagcccgc cctcgttcca gacccggctg  8940
tagaccacgc cccctcggc gtcgcgagcg cgcatgacca cctgggccag gttgagctcc  9000
acgtgtcgcg tgaagacggc gtagttgcgc aggcgctgga aaaggtagtt cagggtggtg  9060
gcggtgtgct cggcgacgaa gaagtacatg acccagcgcc gcaacgtgga ttcattgatg  9120
tcccccaagg cctccaggcg ctccatggcc tcgtagaagt ccacggcgaa gttgaaaaac  9180
tgggagttgc gagcggacac ggtcaactcc tcctccagaa gacgcgatgag ctcggcgaca  9240
gtgttgcgca cctcgcgctc gaaggccacg ggggcgctt cttcctcttc cacctcttct  9300
tccatgatcg cttcttcttc ttcctcagcc gggacgggag gggcgggccgg cggcggggga  9360
ggggcgggcg ggcggccgcg ggcaccggg aggcggtcga tgaagcgctc gatcatctcc  9420
ccccgcatgc ggcgcatggt ctcggtgacg gcgcggccgt tctcccgggg gcgcagctcg  9480
aagacgccgc ctctcatctc gccgcggggc gagcggccgt gaggtagcga gacggcgctg  9540
actatgcatc ttaacaattg ctgtgtaggt acaccgccga gggacctgat tgagtccaga  9600
tccaccggat ccgaaaacct ttggaccgaaa gcgtctatcc agtcgcagtc gcaaggtagg  9660
ctgagcaccg tggcgggcgg gggcgggtct ggagagttcc tggcggagat gctgctgatg  9720
atgtaattaa agtaggcggt cttgagaagg cggatggtgg acaggagcac catgtctttg  9780
ggtccggcct gttggatgcg gaggcggtcg gccatgcccc aggcctcgtt ctgacaccgg  9840
cgcaggtctt tgtagtagtc ttgcatgagt cttttccaccg gcacctcttc tccttcctct  9900
tctccatctc gccggtggtt tctcgcgccg cccatgcgcg tgaccccaaa gcccctgagc  9960
ggctgcagca gggccaggtc ggcgaccacg cgctcggcca agatggcctg ctgcacctga 10020
gtgagggtcc tctcgaagtc atccatgtcc acgaagcggt ggtaggcgcc cgtgttgatg 10080
gtgtaggtgc agttggccat gacggaccag ttgacggtct ggtgtcccgg ctgcgagagc 10140
tccgtgtacc gcaggcgcga gaaggcgcgg gaatcgaaca cgtagtcgtt gcaagtccga 10200
accagatact ggtagcccac caggaagtgc ggcggaggtt ggcgatagag gggccagcgc 10260
tgggtggcgg gggcgccggg cgccaggtct tccagcatga ggcggtggta tccgtagatg 10320
tacctggaca tccaggtgat gccggcgcg gtggtggtgg cgcgcgcgta gtcgcggacc 10380
cggttccaga tgtttcgcag gggcgacaaag tgttccatgg tcggcacgct ctggccggtg 10440
aggcgcgcgc agtcgttgac gctctataca cacacaaaaa cgaaagcgtt tacagggctt 10500
tcgttctgta gcctggagga aagtaaatgg gttgggttgc ggtgtgcccc ggttcgagac 10560
caagctgagc tcggccggct gaagccgcag ctaacgtggt attggcagtc ccgtctcgac 10620
ccaggccctg tatcctccag gatacgtcg agagcccttt tgctttcttg gccaagcgcn 10680
cgtggccgca tctgggatag atggtcgcga tgagggaca aaagcggctc gcttccgtag 10740
tctggagaaa caatcgccag ggttgcgttg cggcgtaccc cggttcgagc ccctatggcg 10800
gcttgaatcg gccggaaccg cggctaacga gggccgtggc agccccgtcc tcaggacccc 10860
gccagccgac ttctccagtt acgggagcga gcccctttg ttttttattt tttagatgca 10920
tcccgtgctg cggcagatgc gcccctcgcc ccggcccgat cagcagcagc aacagcaggc 10980
atgcagaccc ccctctcccc tttccgcccc ggtcaccacg gccgcggcgg ccgtgtcggg 11040
cgcgggggc gcgctggagt cagatgagcc accgcggcgg cgacctaggc agtatctgga 11100
cttgaagag ggcgagggac tggcgggct ggggcgaaac tctccagagc gccaccgcg 11160
ggtgcagttg aaaagggacg cgcgcgaggc gtacctgccg cggcagaacc tgtttcgcga 11220
ccgcggggc gaggagcccg aggagatgcg agactcagg ttccaagcgg ggcgcgagct 11280
gcggcgcggg ctgacagac agcgcctgct gcgcgaggag gactttgagc ccgacacgca 11340
gacgggcatc agccccgcgc gcgcgcacgt agccgccggc gacctggtga ccgcctacga 11400
gcagacggta aaccaggagc gcaacttcca aaagagcttc aacaaccacg tgcgcacgct 11460
ggtggcgcgc gaggaggtga ccctgggtct catgcatctg tgggacctgg tggaggcgat 11520
cgtgcagaac cccagcagca agccctgac cgcgcagctg ttcctggtgg tgcagcacag 11580
cagggacaac gaggccttca gggaggcgct gctgaacatc accgagccgg aggggcgctg 11640
gctcctggac ctgataaaca tcctgcagag catagtggtg caggagcgca gcctgagcct 11700
ggccgagaag gtggcggcca tcaactactc tatgctgagc ctgggcaagt tctacgcccg 11760
caagatctac aagaccccct acgtgccat agacaaggag gtgaagatag acagcttcta 11820
catgcgcatg gcgctgaagg tgctgaccct gagcgacgac ctgggagtgt accgcaacga 11880
gcgcatccac aaggccgtga gcgcagccg gcggcgccga ctgacgcacc gcgagctgat 11940
gcacagtctg cagcgcgcgc tgaccggcgc gggcgagggc gacagggagg tcgagtccta 12000
cttcgacatg ggggccgacc tgcactggca gccgagccgc cgcgccctgg aggcggcggg 12060
ggcgtacggc ggcccctgg cggccgatga ccaggaagag gaggactatg agctagagga 12120
gggcgagtac ctgaggact gacctggctg gtggtgtttt ggtatagatg caagatccga 12180
acgtggccga ccccggccgc tgcaaagcgc tgcgtccggc attaactcct 12240
ctgacgactg ggccgcggcc atgggtcgca tcatgccct gaccgcgcgc aaccccgagg 12300
ctttcaggca gcagcctcag gccaaccggc tggcggccat cttggaagcg gtagtgcccg 12360
cgcgctccaa ccccacccac gagaaggtgc tggccatagt caacgcgctg gcggagcagca 12420
gggccatccg cgcggacgag gccggactgg tgtacgatgc gctgctgcag cggtggcgc 12480
aacagcaccg gcaacgtg cagaccaacc tggacggac gtgcgagcg 12540
ccgtggcgca gcgcgagcgc ttgcatcagg acgtaacct gggctcgctg gtggcgctaa 12600
acgccttcct cagcacccag ccggccaacg taccgcgggg gcaggaggac tacaccaact 12660
ttttgagcgc gctgcggctg atggtgaccg aggtccctca gagcgaggtg taccagtcgg 12720
ggcccgacta cttcttccag accagcagac agggcttgca aaccgtgaac ctgagccagg 12780
cttttcaagaa cctgcggggg ctgtggggag tgaaggcgcc caccggcgac cgggctacgg 12840
```

```
tgtccagcct gctaacccc  aactcgcgcc tgctgctgct gctgatcgcg cccttcacgg  12900
acagcgggag cgtctcgcgg gagacctatc tgggccacct gctgacgctg taccgcgagg  12960
ccatcgggca ggcgcaggtg gacgagcaca ccttccaaga gatcaccagc gtgagccacg  13020
cgctgggca  ggaggacacg ggcagcctgc aggcgaccct gaactacctg ctgaccaaca  13080
ggcggcagaa gattcccacg ctgcacagcc tgacccagga ggaggagcgc atcttgcgct  13140
acgtgcagca gagcgtgagc ctgaacctga tgcgcgacgg cgtgacgccc agcgtggcgc  13200
tggacatgac cgcgcgcaac atggaaccgg gcatgtacgc ctcccaccgg ccgtttatca  13260
accgcctgat ggactacttg catcgggcgg cggccgtgaa ccccgagtac ttcactaatg  13320
ccattctgaa tccccactgg atgcccctc  cgggtttcta caacggggac tttgaggtgc  13380
ccgaggtcaa cgacgggttc ctctgggatg acatgatga  cagtgtgttc tcacccaacc  13440
cgctgcgcgc cgcgtctctg cgattgaagg agggctctga cagggaagga ccgaggagtc  13500
tggcctcctc cctggctctg ggagcggtgg gcgccacggg cgcggcggcg cggggcagta  13560
gcccctcc  cagcctggca gactctctga acagcgggcg ggtgagcagg cccgcttgc   13620
taggcgagga ggagtatctg aacaactccc tgctgcagcc cgcgagggac aagaacgctc  13680
agcggcagca gtttcccaac aatgggatag agagcctggt ggacaagatg tccagatgga  13740
agacgtatgc gcaggagtac aaggagtggg aggaccgcca gccgcggccc ttgccgcccc  13800
ctaggcagcg ctggcagcgg cgcgcgtcca accgccgctg gaggcagggg cccgaggacg  13860
atgatgactc tgcagatgac agcagcgtgt tggacctggg cgggagcggg aaccccttct  13920
cgcacctgcg ccccacgcctg ggcaagatgt tttaaaagaa aaaaaaata aaactcacca  13980
aggccatggc gacgagcgtt ggttttttgt tcccttcctt agtatgcggc gcgcggcgat  14040
gttcgaggag gggcctcccc cctcttacga gagcgcgatg gggatttctc ctgcggcgcc  14100
cctgcagcct cccctacgtgc ctcctcggta cctgcaacct acaggggga  gaaatagcat  14160
ctgttactct gagctgcagc ccctgtacga taccaccaga ctgtacctgg tggacaacaa  14220
gtccgcggac gtggcctccc tgaactacca gaacgaccac agcgattttt tgaccacggt  14280
gatccaaaac aacgacttca ccccaaccga ggccagcacc cagaccataa acctggataa  14340
caggtcgaac tggggcggcg acctgaagac catcttgcac accaacatgc ccaacgctca  14400
cgagttcatg ttcaccaact cttttaaggc gcgggtgatg gtgcgcgcgc agcaggggga  14460
ggcgaagtac gagtgggtgg acttcacgct gcccgagggc aactactcag agaccatgac  14520
tctcgacctg atgaacaatg cgatcgtgga acactatctg aaagtgggca ggcagaacgg  14580
ggtgaaggaa agcgatatcg gggtcaagtt tgacaccaga aacttccgtc tgggctggga  14640
ccccgtgacc gggctggtca tgcggggggt ctacaccaac gaggcctttc atcccgacat  14700
agtgcttctg cccggctgtg gggtggactt cacccagagc cggctgagca acctgctggg  14760
cattcgcaag cggcagcctt tccaggaggg tttcaagatc acctatgagg atctgaaggg  14820
gggcaacatt cccgcgctcc ttgatctgga cgcctacgag gagagcttga aacccgagga  14880
gagcgctggc gacagcggcg agagtggcga ggagcaagcc ggcgggcggtg gcggcgcgtc  14940
ggtagaaaac gaaagtacgc ccgcagtggc ggcggacgct gcggaggtcg agccggaggc  15000
catgcagcag gacgcagagg agggcgcaca ggagggcgcg cagaaggaca tgaacgatgg  15060
ggagatcagg ggagacacat tcgccacccg gggcgaagaa aaagaggcag aggcggcggc  15120
gggcgcgacg gcggaggccg aaaccgaggt tgaggcagga gcagacccg  agaccgaagt  15180
tatggaagac atgaatgatg gagaacgtag gggcgacacg ttcgccaccc ggggcgaaga  15240
gaaggcggcg gaggcagaag ccggcctga  ggaggcggct gcggctgcgg ccaagactga  15300
ggctgcggct aaggctgagg tcgaagccaa tgttgcggtt gaggctcagg ctgaggagga  15360
ggcggcggct gaagcagtta aggaaaaggc ccaggcagga caggaagaga aaaaacctgt  15420
cattcaacct ctaaaagaag atagcaaaaa gcgcagttac aacgtcatcg agggcagcac  15480
cttttacccag taccgcagct ggtacctggc gtacaactac ggcgacccgg tcaagggggt  15540
gcgctcgtgg accctgctct gcacgccgga cgtcacctgc ggctccgagc agatgtactg  15600
gtcgctgcga aacatgatgc aagacccggt gaccttccgc tccacgcggc aggttagcaa  15660
cttcccggtg gtgggcgccg aactgctgcc cgtgcactcc aagagttttt acaacgagca  15720
ggccgtctac tcccagctga tccgccaggc cacctctctg acccacgtgt caatcgctt   15780
tcccgagaac cagattttgg cgcgcccgcc ggcccccacc atcaccaccg tgagtgaaaa  15840
cgttcctgcc ctcacagatc acgggacgct accgctgccc aacagcatct caggagtcca  15900
gcgagtgacc attactgacg ccagacgccg gacctgcccc tacgtttaca aggccttggg  15960
catagtctcg ccgcgcgtcc tctccagtcg cacttttaa  aacacatcta cccacacgtt  16020
ccaaaatcat gtccgtactc atctcaccca gcaacaacac cggctggggg ctgcgcgcgc  16080
ccagcaagat gttttggaggg gcgaggaagc gctccgacca gcaccctgtg cgcctgtgcg  16140
gccactaccg cgcgccctgg ggagcgcaca agcgcgggcg cacagggcgc accactgtgg  16200
acgacgtcat tgactccgta gtggagcaag cgcgccacta cacacccggc gcgccgaccg  16260
cccccgccgt gtccaccgtg gaccaggcga tcgaaagcgt ggtacagggc gcgcggcact  16320
atgccaacct taaaagtcgc cgccgcgcg  tggcccgccg ccatccgcgg agaccccgag  16380
ccaccgccgc cgcgcgcctt actaaggctc tgctcaggca cgccaggcga actggccacc  16440
gggccgccat gagggccgca cggcgggctg ccgctgccgc aagcgtcgtg gccccgcggg  16500
cacgaaggcg cgcggccgct gccgccgccg ccgccatttc cagcttggcc tcgacgcggc  16560
gcggtaacat atactgggtg cgcgactcgg taaccgcac gcgggtaccc gtgcgcttc   16620
gcccccgcg  gaattagcac aagacaacat cacactgga  tctcctgctg ttgtgtatcc  16680
cagcggcgac cgtcagcagc ggcgacatgt ccaagcgcaa aattaaagaa gagatgctcc  16740
aggtcatcgc gccggagatc tatgggcccc gaagaaggga ggaggatgat tacaagcccc  16800
gcaagctaaa gcgggtcaaa aagaaaaaga aagatgatga tgacgaggcg gtggagtttg  16860
tccgccgcat ggacacccagg cgcccctgc  agtggaaggg ccggcgcgtg cagcgcgttt  16920
tgcgccgcag caccgcggtg gtcttcacgc cggcgacgag ctccacgcgc acttcaagc   16980
gggtgtacga tgaggtgtac cgcgacgagg acctgttgga gcaggccaac cagcgctttg  17040
gggagtttgc atatgggaaa cggccccgcg agagtctaaa agaggacctg ctggcgctac  17100
cgctggacga gggcaatccc accccgagtc tgaagccggt aaacctgcaa caggtgctgc  17160
ctttgagcgc gcccagcgag cataagcgag ggttgaagcg cgaaggcggg gacctggcgc  17220
tggcgca  cgttgatgtg ccaaggcgg agaagctgga gaggaaatga  17280
ccaccgtgca gttgatggtg ccaaggcggc agaagctgga gaggaaatga  17280
aagtagagcc cggatccag  cccgagatca aggtccgccc catcaagcag gtggcgcccg  17340
gcgtgggagt ccagaccgtg gacgttagga ttcccacgga ggagatggaa acccaaaccg  17400
ccactccctg ttcggcggcc agcgccacca ccggcaccgc ttcggtagag gtgcagacgg  17460
accccctggct acccgccacc gctgttgccg ccgccgccct ccgttcgcgc gggcgcaaga  17520
gaaattatcc agcggccagc gcgctcatgc cccagtacgc actgcatcca tccatcgtgc  17580
```

```
ccacccccgg ctaccgcggg tactcgtacc gcccgcgcag atcagccggc actcgcggcc   17640
gccgccgccg tgcgaccaca accagccgcc gccgtcgccg ccgccgccag ccagtgctga   17700
cccccgtgtc tgtaaggaag gtggctcgct cggggagcac gctggtggtg cccagagcgc   17760
gctaccaccc cagcatcgtt taaagccggt ctctgtatgg ttcttgcaga tatgccctc    17820
acttgtcgcc tccgcttccc ggtgccggga taccgaggaa gaactcaccg ccgcagaggc   17880
atggcgggca gcggtctccg cggcggccgt cgccatcgcc ggcgcgcaaa aagcaggcgc   17940
atgcgccggc gtgtgctgcc tctgctaatc ccgctaatcg ccgcggcgat cggtgccgta   18000
cccgggatcg cctccgtggc cctgcaggcg tcccagaaac gttgactctt gcaaccttgc   18060
aagcttgcat tttttggagg aaaaataaaa aaagtctag actctcacgc tcgcttggtc    18120
ctgtgactat tttgtagaaa aaaagatgga agacatcaac tttgcgtcgc tggccccgcg   18180
tcacggctcg cgcccgttca tgggagactg gacagatatc ggcaccagca atatgagcgg   18240
tggcgccttc agctggggca gtctgtggag cggccttaaa aattttggtt ccaccattaa   18300
gaactatggc aacaaagcgt ggaacagcag cacgggcag atgctgagag acaagttgaa    18360
agagcagaac ttccaggaga aggtggcgca gggcctgacc tctgccatca gcgggggtggt 18420
ggacatagct aaccaggccg tgcagaaaaa gataaacagt catctggacc cccgtcctca   18480
ggtgaggaa atgcctccag cgatggagac ggtgtctccc gagggcaaag gcgaaaagcg    18540
cccgcggccc gacagagaag agaccctggt gtcacacacc gaggagccgc cctcttacga   18600
ggaggcagtc aaggccggcc tgcccaccac tcgcccata gccccatgg ccaccggtgt     18660
ggtgggccac aggcaacaca ctcccgcaac actagatctg cccccgccgt ccgagccgcc   18720
gcgcagcca aaggcggcga cggtgcccgc tccctccact tccgccgcca acagagtgcc    18780
cctgcgccgc gccgcgagcg gccccgggc ctcgcgagtt agcggcaact ggcagagcac    18840
actgaacagc atcgtgggcc tgggagtgag gagtgtgaag cgccgccgtt gctactgaat   18900
gagcaagcta gctaacgtgt tgtatgtgtg tatgcgtcct atgtcgccgc cagaggagct   18960
gttgagccgc cggcgccgtc tgcactccag cgaatttcaa gatggcgacc ccatcgatga   19020
tgcctcagtg gtcgtacatg cacatctcgg gccaggacgc ttcggagtac ctgagccccg   19080
ggctggtgca gttcgcccgc gccacagaca cctacttcaa catgagtaac aagttcagga   19140
accccactgt ggcgcccacc cacgatgtga ccacggaccg gtcgcagcgc ctgacgctgc   19200
ggttcatccc cgtggatcgg gaggacaccg cctactctta caaggcgcgg ttcacgctgg   19260
ccgtgggcga caaccgcgtg ctggacatgg cctccactta ctttgacatc agggggtgc    19320
tggacagggg ccccaccttc aagccctact cgggtactgc ctacaactcc ctggccccca   19380
agggcgctcc caattcttgc gagtgggaac aagatgaacc agctcaggca gcaatagctc   19440
aagatgaaga agaacttgaa gaagaacaag ctcaggacga caggcgccc actaagaaaa     19500
cccatgtata cgcccaggca cctctttctg gtgaaaaaat tactaaggat ggtttgcaaa   19560
taggtgtgga tgccacacag gcgggagata accctatata tgctgataaa acattccaac   19620
ccgaacctca gataggtgag tctcagtgga acgaggctga tgccacagta gcaggagca    19680
gagtcttaaa aaagaccacc cctatgagac cttgctatgg atcctatgcc aaacctacta   19740
atgccaatgg cggtcaaggg atcatggtgg ccaatgatca gggagcgctt gaatctaaag   19800
ttgagatgca attttctcc accacaacgt ctcttaatgt aagggaaggt gaaaacaatc     19860
ttcagccaaa agtagtgcta tacagcgaag atgttaactt ggaatcccct gacactcatt   19920
tgtcttacaa acctaaaaag gatgacacca actctaaaat catgtttgggt cagcaagcca   19980
tgcccaacag acccaacctc attgcttta gggacaactt tattggactt atgtactaca    20040
acagcacagg caacatggga gtgctggcag acaggcctc ccagctaaac gctgtggtag     20100
acttgcaaga cagaaacaca gagctgtcat accaactgat gcttgattcc attggagaca   20160
gatcaagata cttttccatg tggaaccagg cagtggacag ctatgaccca gatgtccagaa  20220
tcattgaaaa ccatggggtt gaagatgagc tgcccaacta ttgctttccc ctgggcggta   20280
ttggaattac agacacatac cagtgcataa aaccaaccgc agctgctaat aacactacat   20340
ggtctaagga tgaagaattt agtgatcgca atgaaatagg ggtgggaaac aacttcgcca   20400
tggagatcaa catccaggcc aacctctgga ggaacttcct ctatgcgaac gtggggctct   20460
acctgccaga caagctcaag tacaacccca ccaacgtgga catctctgac aaccccaaca   20520
cctatgacta catgaacaag cgtgtggtgg ctcccggcct ggtggactgc tttgtcaatg   20580
tgggagccag gtggtccctg gactacatgg acaacgtcaa cccccttcaac caccaccgca   20640
atgcgggtct gcgctaccgc tccatgatcc tgggcaacgg cgctacgtg cccttccaca    20700
ttcaggtgcc ccagaagttc tttgccatca gaaacctcct cctcctgccg ggctcctaca   20760
cttacgagtg gaacttcagg aaggatgtca acatggtcct gcagagctct ctgggcaatg   20820
accttagggt ggacggggcc agcatcaagt ttgacagcgt cacccctctat gctaccttct   20880
tcccatggc tcacaacacc gcctccacgc tcgaggccat gctgaggaac gacaccaacg    20940
accagtcctt caatgactac ctctctgggg ccaacatgct ctaccccatc cccgccaagg   21000
ccaccaacgt gcccatctcc attccctctc gcaactgggc cgccttcaga ggctgggcct   21060
ttacccgcct taagaccaag gaaacccccct ccctgggctc gggttttgac ccctacttg    21120
tctactcggg atccatcccc tacctgatg gcacccttcta cctcaaccac acttttaaga   21180
agatatccat catgtatgac tcctccgtca gctggcgggg caatgaccgc ctgctcaccc   21240
ccaatgagtt cgaggtcaag cgcgccgtgg acggcgaggg ctacaacgtg cccagtgca    21300
acatgaccaa ggactggttc ctggtgcaga tgctggccaa ctacaacata ggctaccagg   21360
gcttctacat cccagagagc tacaaggaca ggatgtactc cttccttgaa aatttccaaa   21420
ccatgagcag gcaggtggtg gacgagacca atacaaggga ctatcaggcc attggcatca   21480
ctcaccagca caacaactcg ggattcgtgg gctacctggc tccaccatg cgcgaggggc    21540
aggcctaccc cgccaacttc ccctaccgt tgataggcaa aaccgcggtc gacagcgtca    21600
cccagaaaaa gttcctctgc gaccgcacca tctggcgcat cccttctct agcaacttca   21660
tgtccatggg tgcgctcacg gacctgggcc agaacctgct ctatgccaac tccgccatg    21720
cgctggacat gacttttgag gtggacccca tggacagcc cacccttctc tatattgtgt    21780
ttgaagtgtt cgacgtggtc agagtgcacc agccgcaccg cggtgtcatc gagaccgtgt   21840
acctgcgcac gccttctcg gccggcaacg ccaccaccta aggagacagc gccgccgcct    21900
gcatgacggg ttcaccgag caagagctca gggcatcgc cagagacctg ggatgcggac     21960
cctattttt gggcacctat gacaaacgct tcccgggctt catctcccga gacaagctgg   22020
cctgcgccat cgtcaacacg gccgcgcgcg agaccggggg cgtgcactgg ctggcctttg   22080
gctgggaccc gcgctccaaa acctgctacc tcttcgaccc ctttggcttc tccgatcagc   22140
gcctcagaca gatctatgag tttgagtacg aggggctgct gcgccgcagc gcgcttgcct   22200
cctcgcccga ccgctgcatc accccttgaga agtccaccga accgtgcag gggcccact     22260
cggccgcctg cggtctcttc tgctgcatgt ttttgcacgc ctttgtgcgc tggccccaga   22320
```

```
gtcccatgga tcgcaacccc accatgaact tgctcaaggg agtgcccaac gccatgctcc   22380
agagccccca ggtccagccc accctgcgcg acaaccagga acagctctac cgcttcctgg   22440
agcgccactc cccctacttc cgcagtcaca gcgcgcacat ccgggggggcc acctctttct   22500
gccacttgca agaaaacatg caagacgaaa aatgatgtac agctcgcttt ttaataaatg   22560
taaagactgt gcactttatt tatacacggg ctctttctgg ttatttattc aacaccgccg   22620
tcgccatcta gaaatcgaaa gggttctgcc gcgcgtcgcc gtgcgccacg ggcagagaca   22680
cgttgcgata ctggaagcgg ctcgcccact taaactcggg caccaccatg cggggcagtg   22740
gttcctcggg gaagttctcg ccccacaggg tgcgggtcag ctgcagcgcg ctcaggaggt   22800
cgggagccga gatcttgaag tcgcagttgg ggccggaacc ctgcgcgcgc gagttgcggt   22860
acacggggtt gcagcactgg aacaccagca gggccggatt atgcacgctg gccagcaggc   22920
tctcgtcgct gatcatgtcg ctgtccagat cctccgcgtt gctcagggcg aacgggtca   22980
tcttgcagac ctgcctgccc aggaaaggcg gcagcccggg cttgccgttg cagtcgcagc   23040
gcaggggcat cagcaggtgc ccgcggcccg actgcgcctg cgggtacagc gcgcgcatga   23100
aggcttcgat ctgcctgaaa gccacctgcg tcttggctcc ctccgaaaag aacatcccac   23160
aggacttgct ggagaactgg ttcgcgggac agctggcatc gtgcaggcag cagcgcgcgt   23220
cggtgttggc gatctgcacc acgttgcgac cccaccggtt cttcactatc ttggccttgg   23280
aagcctgctc cttcagcgcg cgctggccgt tctcgctggt cacatccatc tctatcacct   23340
gctccttgtt gatcatgttt gtaccgtgca gacacttcag gtcgccctcc gtctgggtgc   23400
agcggtgctc ccacagcgcg caaccggtgg gctcccaatt tttgtgggtc accccgcgt   23460
aggcctgcag gtaggcctgc aagaagcgcc ccatcatggc cacaaaggtc ttctggctcg   23520
taaaggtcag ctgcaggccg cgatgctctt cgttcagcca ggtcttgcag atggcggcca   23580
gcgcctcggt ctgctcgggc agcatcctaa aatttgtctt caggtcgtta tccacgtggt   23640
acttgtccat catggcgcgc gccgcctcca tgccctcc caggcggac accatgggca   23700
ggcttagggg gttatcact tccaccggcg aggacaccgt actttcgatt tcttcttcct   23760
cccctcttc ccgcgcgcg cccacgctgc tgcgcgctct caccgcctgc accaagggt   23820
cgtcttcagg caagcgccgc aaccgagcgct tgccgccta gacctgctta atcagcaccg   23880
gcgggttgct gaagcccacc atggtcagcg ccgcctgctc ttcttcgtct tcgctgtcta   23940
ccactatctc tggggaaggg cttctccgct ctgcggcggc gcgcttctt tttttcttgg   24000
gagcggccgt gatggagtcc gccacggcga cggaggtcga gggcgtgggg ctggggtgc   24060
gcggtaccag ggcctcgtcg ccctcggact cttcctctga ctccaggcag cggcggagtc   24120
gcttcttgg gggcgcgcgc gtcaggcggc gcggagacgg ggacgggac ggggacgagc   24180
cgccctccac aggggtggt cttgcgcag acccgcggcc gcgtcgggg gtcttctcga   24240
gctggtcttg gtcccgactg gccattgtat cctcctcctc ctaggcagag agacataagg   24300
agtctatcat gcaagtcgag aaggaggaga gcttaaccac ccctctgag accgccgatg   24360
cgcccgccgt cgccgtcgcc cccgctgccg ccgacgccgg cccacaccg agcgacaccc   24420
ccgcggaccc ccccgccgac gcacccctgt tcgaggaagc ggccgtggag caggaccgg   24480
gctttgtctc ggcagaggag gatttgcgag aggaggagga taaggagaag aagccctcag   24540
tgccaaaaga tgataaagag caagacgagc acgacgcaga tgcacaccag ggtgaagtcg   24600
ggcggggga cggagggcat gacggcgccg actacctaga cgaagggaac gacgtgctct   24660
tgaagcacct gcatcgtcag tgcgccattg tttgcgacgc tctgcaggag cgcagcgaag   24720
tgcccctcag cgtggcggag gtcagccacg cctacgagct cagcctcttc tcccccggg   24780
tgcccccccg ccgccgcgaa aacggcacat gcgagcccaa cccgcgcctc aacttctacc   24840
ccgcctttgt ggtacccgag cctatccacat cttctttcaa aattgcaaga   24900
tcccctctc gtgccgcgcc aaccgtagcc gcgccgataa gatgctggcc ctgcgccagg   24960
gcgaccacat acctgatatc gccgctttgg aagatgtacc aaagatcttc gagggtctgg   25020
gtcgcaacga gaagcgggca gcaaactctc tgcaacagga aaacagcgaa aatgagagtc   25080
acaccggggt actggtggag ctcgagggcg acaacgccg cctggcggtg gtcaagcgca   25140
gcatcgaggt cacccacttt gcctaccccg cgctaaacct gccccccaaa gtcatgaacg   25200
cggccatgga cgggctgatc atgcgccgcg gccggcccct cgctccagat gcaaacttgc   25260
atgaggagac cgaggacggc cagccgtgg tcagcgacga gcagctggcg cgctggctgg   25320
agaccgcgga ccccgccgaa ctggaggagc ggcgcaagat gatgatggcc gttggtgctg   25380
tcaccgtaga gctggagtgt ctgcagcgct tcttcggcga ccccgagatg cagagaaagg   25440
tcgaggagac cctgcactac accttccgcc agggctacgt gcgccaggct tgcaagatct   25500
ccaacgtgga gctcagcaac ctggtgtcct acctgggcat cttgcatgag aaccgcctcg   25560
ggcagagcgt gctgcactcc accctgcgtg gggaggccgg ccgcgactac gtgcgcgact   25620
gcgtttacct cttcctctgc tacacctggc agacggccat ggggtctgg cagcagtgcc   25680
tggaggagcg caacctcaag gagctggaga agctcctgca gcgcgcgctc aaagatctct   25740
ggacgggcta caacgagcgc tcggtggccg ccgcgctggc cgacctcatc ttccccgagc   25800
gcctgctcaa aaccctccag caggggctgc ccgacttcac cagccaaagc atgttgcaaa   25860
acttcaggaa ctttatcctg gagcgttctg gcatcctacc cgccacctgc tgcgccctgc   25920
ccagcgactt tgtcccccctc gtgtaccgcg agtgcccccc gccgctgtgg ggtcactgct   25980
acctgttcca actggccaac tacctgtcct accacgcgga cctcatggag gactccagcg   26040
gcgagggct catggagtgc cactgccgct gcaacctctg cacgcccac cgctccctgg   26100
tctgcaacac ccaactgctc agcgagagtc agattatcga tacctttcgag ctacaggtc   26160
cgtcctcctc agacgagaag tccgcggctc cggggctaaa actcactccg ggctgtgaa   26220
cttccgccta cctgcgcaaa tttgtacctg aagactacca cgcccacgag atcaggtttt   26280
acgaagacca atcccgcccg cccaaggcgg agctgaccgc ctgcgtcatc cccagggcg   26340
agatcctagg ccaattgcaa gccatccaaa agcccgcca agacttttgt ctgaagaagg   26400
gtcgggggt gtatctgcgac cccagtcgg gtgaggagct caacccggtt ccccgctgc   26460
cgccgccgcg ggaccttgct tcccaggata agcatcgca tggctcccag aaagaagcag   26520
cagcggccgc cactgccgcc accccacatg ctggaggaag aggaggaata ctgggacagt   26580
caggcagagg aggtttcgga cgaggaggag ccggagacgg agatgaaga gtgggaggag   26640
gacagcttag acgaggaggc ttccgaagcc gaagaggcag acgcaacacc gtcacccctcg   26700
gccgcagccc cctcgcaggc gccccgaag caatcagcag caacagcagc   26760
gctataacct ccgctcctcc accgccgcga cccacgccg accgcagacc caaccgtaga   26820
tgggacacca ccggaaccgg ggccggtaag tcctccggga gaggcaagca agcgcagcgc   26880
caaggctacc gctcgtggcg cgctcacaag aacgccatag tcgcttgctt gcaagactgc   26940
gggggaaca tctccttcgc ccgccgcttc ctgctcttcc accacggtgt ggccttccc   27000
cgtaacgtcc tgcattacta ccgtcatctc tacagcccct actgcggcgg cagtgagcca   27060
```

```
gagacggtcg gcggcggcgg cggcgcccgt ttcggcgcct aggaagaccc agggcaagac  27120
ttcagccaag aaactcgcgg cggccgcggc gaacgcggtc gcggggcgcc tgcgcctgac  27180
ggtgaacgaa cccctgtcga cccgcgaact gaggaaccga atcttcccca ctctctatgc  27240
catcttccag cagagcagag ggcaggatca ggaactgaaa gtaaaaaaca ggtctctgcg  27300
ctccctcacc cgcagctgtc tgtatcacaa gagcgaagac cagcttcggc gcacgctgga  27360
ggacgctgag gcactcttca gcaaatactg cgcgctcact cttaaggact agctccgcgc  27420
ccttctcgaa tttaggcggg aacgcctacg tcatcgcagc gccgccgtca tgagcaagga  27480
cattcccacg ccatacatgt ggagctatca gccgcagatg ggactcgcgg cgggcgcctc  27540
ccaagactac tccacccgca tgaactggct cagtgccggc ccacacatga tctcacaggt  27600
taatgatatc cgcacccatc gaaaccaaat attggtggag caggcggcaa ttaccaccac  27660
gccccgcaat aatcccaacc ccagggagtg gcccgcgtcc ctggtgtatc aggaaattcc  27720
cggcccccacc accgtactac ttccgcgtga ttcccaggcc gaagtccaaa tgactaactc  27780
aggggcacag ctcgcgggcg gctgtcgtca cagggtgcgg cctcctcgcc agggtataac  27840
tcacctggag atccgaggca gaggtattca gctcaacgac gagtcggtga gctcctcgct  27900
cggtctcaga cctgacggga ccttccagat agccggagcc ggccgatctt ccttcacgcc  27960
ccgccaggcc tacctgactc tgcaaagctc gtcctcggcg ccgcgctcgg gcggcatcgg  28020
gactctccag ttcgtgcagg agtttgtgcc ctcggtctac ttcaacccct tctcgggctc  28080
tcccgctcgc tacccggacc agttcatctc gaactttgac gccgcgaggg actcggtgga  28140
cggctacgac tgaatgtcgg gtggaccgg tgcagagcaa cttcgcctga agcacctcga  28200
ccactgccgc cgcccttcagt gctttgcccg ctgtcagacc ggtgagttcc agtacttttc  28260
cctgcccgac tcgcacccgg acggcccggc gcacggggtg cgcttttttca tcccgagtca  28320
gtgcgctct accctaatca gggagtttac gccccgtccc ctactggcgg agttggaaaa  28380
ggggccttct atcctaacca ttgcctgcat ctgctctaac cctggattgc accaagatct  28440
ttgctgtcat ttgtgtgctg agtataataa aggctgagat cagaattcac tcgggctcct  28500
gtcgccatcc tgtcaacgcc accgtccaag cccggcccga tcagcccgag gtgaacctca  28560
cctgcggtct gcaccggcgc ctgaggaaat acctagcttg tgactacaac agcactcctt  28620
ttgtggttta caacagcttt gaccaggacg gggtctcact gagggataac ctctcgaacc  28680
tgagctactc catcaggaag aacagcaccc tcgagctact tcctccttac ctgcccggga  28740
cttaccagtg tgtcaccggt ccctgcaccc acacccacct gttgatcgta aacgactctc  28800
ttccgagaac agacctcaat aactcctctt cgcagttccc cagaacagga ggtgagctca  28860
ggaaaccccg ggtaaagaag ggtggacgag agttaacact tgtgggggttt ctggtgtatg  28920
tgacgctggt ggtggctctt ttgattaagg cttttccttc catgtctgaa ctctccctct  28980
tcttttatga acaactcgac tagtgctaac gggaccctac ccaacgaatc gggattgaat  29040
atcggtaacc aggttgcagt ttcacttttg attaccttca tagtcctctt cctgctagtg  29100
ctgtcgcttc tgtgcctgcg gatcggggc tgctgcatcc acgtttatat ctggtgctgg  29160
ctgtttagaa ggttcggaga ccatcgcagg tagaataaac atgctgctgc ttaccctctt  29220
tgtcctggcg ctggccgcca gctgccaagc cttttcgag gctgacttta tagagcccca  29280
gtgtaatgtg acttttaaag cccatgcaca gcgttgtcat actataatca aatgtgccac  29340
cgaacacgat gaataccta tccagtataa agataaatca acaaagtgg cacttgttga  29400
catctgaaa cccgaagacc ctttggaata caatgtgacc gttttccagg gtgacctctt  29460
caaaatttac aattacactt tcccatttga ccagatgtgt gactttgtca tgtacatgga  29520
aaagcagcac aagctgtggc ctccgactcc ccagggctgt gtggaaaatc caggctcttt  29580
ctgcatgatc tctctctgtg taactgtgct ggcactaata ctcacgcttt tgtatatcag  29640
atttaaatca aggcaaagct tcattgatga aagaaaatg ccttaatcgc tttcacgctt  29700
gattgctaac accgggtttt tatccgcaga atgattggaa tcaccctact aatcacctcc  29760
ctccttgcga ttgcccatgg gttggaacga atcgaagtcc ctgtgggggc caatgttacc  29820
ctggtgggac ctgtcggcaa tgctacatta atgtgggaaa aatatactaa aaatcaatgg  29880
gtctcttact gcactaacaa aaatagccac aagcccagag ccatctgcga tgggcaaaat  29940
ctaaccttga ttgatgttca attgctggat gcgggctact attatgggca gctgggtaca  30000
atgattaatt actggagacc ccacagagat tacatgctcc acgtagtaaa gggtcccctt  30060
agcagcccac ccactaccac ctctactacc cccactaccca ccactactcc caccaccagc  30120
actgccgccc agcctcctca tagcagaaca accacttttta tcaattccaa gtccactcc  30180
cccccacattg ccggcgggcc ctcgcctca gactccgaaa ccaccgagat ctgcttctgc  30240
aaatgctctg acgccattgc ccaggatttg gaagatcacg aggaagatga gcatgacttc  30300
gcagatgcat gccaggcatc agagccagaa gcgctgcggg tggccctcaa acagtatgca  30360
gaccccacaa ccaccccga ccttcctcca ccttcccaga agccaagttt cctgggggaa  30420
aatgaaactc tgcctctctc catactgctc ctgacatctg ttgctatgtt gaccgctctg  30480
ctggtgcttc tatgctctat atgctacctg atctgctgca gaaagaaaaa atctcacggc  30540
catgctcacc agcccctcat gcacttccct taccctccag agctgggcga ccacaaactt  30600
taagtctgca gtaactatct gcccatccct tgtcagtcga cagcgatgag ccccactaat  30660
ctaacgccct ctggacttac aacatcgtct cttaatgaga ccaccgctcc tcaagacctg  30720
tacgatggtg tctccgcgct ggttaaccag tgggatcacc tgggcatatg gtggctcctc  30780
ataggagcag tgacctgtg cctaatcctg gtctggatca tctgctgcat caaaagcaga  30840
agacccaggc gcggcccat ctacagggcc ttttgtcatca caactgaaga tgatgatgac  30900
accacttcca ggctgcagag gctaaagcag ctactcttct cttttacagc atggtaaatt  30960
gaatcatgcc tcgcatttttc atctacttgt ctctccttcc actttttctg ggctcttcta  31020
cattggccgc tgtgtcccac atcgaggtag actgcctcac gcccttcaca gtctacctgc  31080
ttttcggctt tgtcatctgc accttttgtct gcagcgtatt cactgtagtg atctgcttca  31140
tacagtgcat cgactacgtc tgcgtgcggg tggcttactt tagacaccac cccagtatc  31200
gcaacaggga catagcggct ctcctaagac ttgttttaaaa tcatggccaa attaactgtg  31260
attggtcttc tgatcatctg ctgcgtccta gccgcgattg ggactcaagc tcctaccacc  31320
accagcgctc ccagaaagag acatgtatcc tgcagcttca gcgtccctg gaatatacc  31380
caatgctttta ctgatgaacc tgaaatctct ttggcttggt acttcagcgt caccgccctt  31440
cttatcttct gcagtacggt tattgccctt gccatctacc cttccttga cctgggctgg  31500
aatgctgtca actctatgga atatcccacc ttcccagaac cagacctgcc agacctggtt  31560
gttctaaacg cgtttcctcc tcctgctccc gttcaaaatc agtttcgccc tccgtcccc  31620
acgcccactg aggtcagcta ctttaatcta acaggcggag atgactgaaa acctagacct  31680
agaaatggac ggtctctgca gcgagcaacg cacactagag aggcgccggc aaaaagagct  31740
cgagcgtctt aaacaagagc tccaagacgc ggtggccata caccagtgca aaaaaggtgt  31800
```

```
cttctgtctg gtaaaacagg ccacgctcac ctatgaaaaa acaggtgaca cccaccgcct   31860
aggatacaag ctgcccacac agcgccaaaa gttcgccctc atgataggcg aacaacccat   31920
caccgtgacc cagcactccg tggagacaga aggctgcata catgctccct gtaggggcgc   31980
tgactgcctc tacaccttga tcaaaaccct ctgcggtctc agagaccttg tcccttcaa    32040
ttaatcataa ctgtaatcaa taaaaaatca cttacttgaa atctgatagc aagcctctgt   32100
ccaatttttt cagcaacact tccttcccct cctcccaact ctggtactct aggcgcctcc   32160
tagctgcaaa cttcctccac agtctgaagg gaatgtcaga ttcctcctcc tgtccctccg   32220
cacccacgat cttcatgttg ttgcagatga acgcgcgag atcgtctgac gagaccttca    32280
accccgtgta cccctacgat accgagatcg ctccgacttc tgtcccttc cttaccctg     32340
cctttgtgtc atccgcagga atgcaagaaa atccagctgg ggtgctgtcc ctgcacttgt   32400
cagagcccct tacacccac aatgggggcc tgactctaaa aatgggggc ggcctgaccc     32460
tggacaagga agggaatctc acttcccaaa acatcaccag tgtcgatccc cctctcaaaa   32520
aaagcaagaa caacatcagc cttcagaccg ccgcacccct cgccgtcagc tccggggccc   32580
taacacttttt tgccactccc ccctcagcgg tcagtggtga caaccttact gtgcagtcgt   32640
aggcccctct cactttggaa gactcaaaac taactctggc caccaaagga cccctaactg   32700
tgtccgaagg caaacttgtc ctagaaacag aggctcccc                          32739

SEQ ID NO: 24            moltype = DNA   length = 32739
FEATURE                  Location/Qualifiers
misc_feature             1..32739
                         note = Adenovirus vector nucleotide sequences
source                   1..32739
                         mol_type = other DNA
                         organism = synthetic construct
SEQUENCE: 24
ataatatacc ttattttgga ttgtggccaa tatgataatg aggtgggcgg ggagaggcgg   60
ggcgggtgac gtaggacgcg cgagtagggt tgggaggtgt ggcggaagtg tggcatttgc  120
aagtgggagg agctcacatg caagcttccg tcgcggaaaa tgtgacgttt ttgatgagcg  180
ccgcctacct ccggaagtgc caattttcgc gcgcttttca ccggatatcg tagtaatttt  240
gggcggaacc atgtaagatt tggccatttt cgcgcgaaaa gtgaacggtg gaagtgaaaa  300
ctgaataata gggcgttagt catagcgcgt aatatttacc gagggccgag ggactttgac  360
cgattacgtg gaggactcgc ccaggtgttt tttacgtgaa tttccgcgtt ccgggtcaaa  420
gtctccgttt ttattgtcac cgtcatttga cgcggagggt atttaaaccc gctgcgctcc  480
tcaagaggcc actcttgagt gccagcgaga agagttttct cctctgctcc gttcggtga   540
tcgaaaaatg agacacatag cctgcactcc gggtctttg tccggtcggg cggcggccga  600
gcttttggac gctttgatca atgatgtcct aagcgatgat tttccgtcta ctacccactt  660
tagcccacct actcttcacg aactgtacga tctggatgta ctggtggatg tgaacgatcc  720
caacgaggag gcggtttctg cgtttttttc cgagtctgcg ctgttggccg ctcaggaggg  780
atttgaccta cacactccgc cgcctatttt agagtctcgg ctgccggacc ccagtggtat  840
acctatatg cctgaactgc ttcccgaagt ggtagacctg acctgccacg agcctggctt   900
tccgcccagc gacgatgagg gtgagccttt tgtttagac tttgctgaga tacctgggca   960
cggttgcagg tcttgtgcat atcatcagag ggttaccgga gacccgagg ttaagtgttc   1020
gctgtcgtat atgaggatga cctcttcctt tatctacagt aagttttttct ctaggtgggc 1080
tttgggtag gtgggttttg tgtcagaaca ggtgtaaacg ttgcttgtgt tttttgtacc   1140
tgtaggtccg cgtgtccgagc cagacccgga gcccgaccgc gatcccgagc cggatcccga  1200
gcctcctcgc aggacaagga aactaccttc cattctgtgc aagtctcaga cacctgtaag  1260
gaccagccgag gcagacagca ccgactctgg cacttctacc tctccccctg aaattcaccc  1320
agtggttcct ctgggtatac ataaacctgt tgctgttaaa gtttgcgggc gacgccctgc  1380
agtacagtgc attgaggact tgcttcacga tcccgaggaa cctttggact tgagccttaa  1440
acgccctagg caataaaccc cacctaagta ataaacccca cctaagtaat aaaccctgcc  1500
gcccttggtt attgagatga cgcccaatgt ttgcttttta atgactttcat gtgtgtaata  1560
aaagtgagtg tgatcatagg tctcttgttt gtctgggcgg ggcttaaggg tatataagtc  1620
tcttggggct aaacttggtt acacttgacc ccaatggagg cgtgggggtg cttgaggag   1680
tttgcggacg tgcgccgttt gctggacgag agctctagca ataccatac tatttggagg  1740
tatctggtgg gctctactca ggccaagttg gtttccagaa ttaagcagga ttacaagtgc  1800
gattttgaag agcttttag ttcctgcggt gagcttttgc aatccttgaa tctgggccat   1860
caggctattt tccaggaaaa ggttctctcg actttggatt tttccactcc cgggcgcacc   1920
gccgcttgtg tggcttttgt gtcttttgtg caagataaat ggagcgagga gacccacctg  1980
agtcacggct acgtactgga tttcatggcg atggctcttt ggagggctca caacaaatgg  2040
aagattcaga aggaactgta cggttccgcc ctacgtcgtc cacttctgtc gcgacagggg  2100
ctgagggtttc ccgaccatcg gcagcatcag aatctgaag acgagtcgga ggagcgagcg  2160
gaggagaaga tcagcttgag agccggcctg gaccctcctc aggaggaatg aatctcccgc   2220
aggtggttga cctgtttcca gaactgagac gggtcctgac tatcagggag gatggtcagt   2280
ttgtgaagaa gtttaagagg gatcggggtg agggagatag tgaggcggct agcaattag   2340
ctttttagtct gatgactcgc caccgaccgg aatgtattac ctatcagcag attaaggaga   2400
gttgtgccaa cgactggatt cttttgggtc agaagtatag catagaacag cttaccactt   2460
actgcttca gcctggggat gattgggaag aggcgatcag ggtgtatgca aaggtgggcc   2520
tgcggcccga ttgcaagtat aagattacta agttggttaa tattagaaac tgctgctata   2580
ttttctgggaa cgggggcgaa gtggagatag atactcagga cagggtggct tttaggtgtt   2640
gcatgataaa catgtggccc gggatactgg ggatggatgg ggtggtattc atgaatgtga   2700
ggtttacggg ccccaacttt aatgcacgg tgttcatggg caacaccaac ttgctcctgc   2760
atggtgcgag tttctatggg tttaataaca cctgtataga ggcctggacc gatgtaaagg   2820
ttcgaggttg ttcctttat agctgttgga aggcggtggt gtgtcgccct aaaagcaggg   2880
gttctgtgga aaatggt tttgaaaggt gcaccttagg catcctctct gagggcaact    2940
ccagggtgcg ccataatgtg gcttcgaact gcgcgttgctt catgcaagtg aagggggtag  3000
gcgttatcaa gcataactcg gtgtgtgaa actgcgagga tcgcgcctcc cagatgctga  3060
cctgctttga tggcaactgt caccgtgtga agaccattca tataagcagc caccccagaa  3120
aggcctggcc cgtgtttgag cataaactct tgacccgctg ctccttgcat ctgggggtca  3180
ggaggggtat gttcctgcct taccagtgta acttagccaa cactaaaatc ctgctggaac  3240
```

```
ccgagtgcat gaccaaggtc agcctgaatg gtgtgtttga tgtgactctg aaaatctgga  3300
aggtgctgag gtatgatgag accaggacca ggtgccgacc ctgcgagtgc ggcggcaagc  3360
acatgagaaa tcagcctgtg atgttggatg tgaccgagga gcttaggcct gaccatctgg  3420
tgctggcctg caccagggcc gagtttgggt ctagcgatga ggataccgat tgaggtgggt  3480
aaggtgggcg tggctagaag ggtggggcgt gtataaattg ggggtctaag ggtctctctg  3540
ttttgtcttg caacagccgc cgccatgagc gacaccggca acagctttga tggaagcatc  3600
tttagcccct atctgacagt gcgcatgcct cactgggctg gagtgcgtca gaatgtgatg  3660
ggttccaacg tggatggacg ccccgttctg ccttcaaatt cgtctacaat ggcctacgcg  3720
accgtgggag gaactccgct ggacgccgcg acctccggcc ccgcctccgc cgccgccgcg  3780
accgcgcgca gcatggctac ggaccttac agctctttgg tggcgagcgg cgcggcctct  3840
cgcgcgtctg ctcgggatga gaaactgacc gctctgctgc ttaaactgga agacttgacc  3900
cgggagctgg gtcaactgac ccagcaggtc tccagcttgc gtgagagcag ccttgcctcc  3960
ccctaatggc ccataatata aataaaagcc agtctgtttg gattaagcaa gtgtatgttc  4020
tttatttaac tctccgcgcg cggtaagccc gggaccagcc gtctcggtcg tttagggtgc  4080
ggtggattct ttccaacacg tggtacaggt ggctctggat gtttagatac atgggcatga  4140
gtccatccct ggggtggagg tagcaccact gcagagcttc gtgctcgggg gtggtgttgt  4200
atatgatcca gtcgtagcag gagcgctggg cgtggtgctg aaaaatgtcc ttaagcaaga  4260
ggcttatagc taggggagg cccttggtgt aagtgtttaa aaatctgctc agttgggagg  4320
ggtgcatccg gggggatata atgtgcatct tggactggat ttttaggttg gctatgttcc  4380
cacccagatc ccttctggga ttcatgttgt gcaggaccac cagcacggta tatccagtgc  4440
acttgggaaa tttatcgtgg agcttagacg ggaatgcatg gaagaacttg gagacgccct  4500
tgtggcctcc cagattttcc atacattcgt ccatgatgat gcaatggcc ccgtgggaag  4560
ctgcctgagc aaaaatgttt ctgggatcgc tcacatcgta gttatgttcc agggtgaggt  4620
catcatagga catctttacg aatcgggggc ggagggtccc ggactggggg atgatggtac  4680
cctcgggccc cggggcgtag ttcccctcac agatctgcat ctcccaggct ttcatttcag  4740
agggagggat catatccacc tgcggagcga tgaaaaacac agtttctggc gcaggggaga  4800
ttaactggga tgagagcagg tttctgagca gctgtgactt tccacagccg gtgggccat  4860
atatcacgcc tatcaccggc tgcagctggt agttaagaga gctgcagctg ccgtcctccc  4920
ggagcagggg ggccacctcg ttcagcatat ccctgacgtg gatgttctcc ctgaccaatt  4980
ccgccagaag gcgctccgcg cccagcagaa gcagctcttg caaggaagca aaattttca  5040
gcggttttag gccgtcggcc gtgggcatgt ttttcagcgt ctgggtcagc agttccagcc  5100
tgtcccacag ctcggtgatg tgctctacgt catctcgatc cagcagatct cctcgtttcg  5160
cgggttgggg cggcttttcgc tgtagggcac cagccgatgg gcgtcagcg gggccagagt  5220
catgtccttc catgggcgca gggtcctcgt cagggtggtc tgggtcacgg tgaaggggtg  5280
cgctccgggt tgggcgctgg ccagggtgcg cttgaggctg gttctgctgg tgctgaatcg  5340
ctgccgctct tcgccctgcg cgtcggccag gtagcatttg accatggtct cgtagtcgag  5400
accctcggcg gcgtgcccct tggcgcggag ctttcccttg gaggtggcgc cgcacgaggg  5460
gcactgcagg ctcttcaggg cgtagagctt gggagcgaga acacggact ctggggagta  5520
ggcgtccgcg ccgcaggaag cgcagaccgt ctcgcattcc accagccaag tgagctccgg  5580
gcggtcaggg tcaaaaacca ggttgccccc atgcttttg atgcgtttct tacctcggct  5640
ctccatgagg cggtgtccct tctcggtgac gaagaggctg tccgtgtccc cgtagaccga  5700
cttcaggggc ctgtcttcca gcggagtgcc tctgtcctcc tcgtagagaa actctgacca  5760
ctctgagacg aaggcccgcg tccaggccag gacgaaggag gccacgtggg aggggtagcg  5820
gtcgttgtcc actagcgggt ccaccttctc cagggtgtgc aggcacatgt ccccctcctc  5880
cgcgtccaga aaagtgattg gcttgtaggt gtaggcacg tgaccggggg ttcccgacgg  5940
gggggtataa aaggggtgg gcgcccttc atcttcactc tcttccgcat cgctgtctgc  6000
gagggccagc tgctggggta agtattccct ctcgaaggcg gcatgacct cagcgctcag  6060
gttgtcagtt tctaaaaatg aggaggattt gatgttcacc tgtccggagg tgatacccttt  6120
gagggtacct gggtccatct ggtcagaaaa cactatttt ttgttgtcaa gcttggtggc  6180
gaacgacccg tagagggcgt tggagagcag cttggcgatg gagcgcaggg tctggttttt  6240
gtcgcggtcg gctcgctcct tggccgcgat gttgagttgc acgtactcgc gggccacgca  6300
cttccactcg gggaagacgg tggtgcgctc gtctgggatt aggcgcaccc tccagcctcg  6360
gttgtgcagg gtgaccatgt cgacgctggt ggcgacctcg ccgcgcaggc gctcgttggt  6420
ccagcagagg cggccgccct tgcgcgagca gaaggggggt aggggtcca gctggtcctc  6480
gtttggggg tccgcgtcga tggtgaagac cccggggagc aagcgcgggt caaagtagtc  6540
gatcttgcaa gcttgcatgt ccagagcccg ctgccattcg cgggcggcga gcgcgcgctc  6600
gtaggggttg aggggcgggc cccagggcat ggggtgggtg agcgcggagg cgtacatgcc  6660
gcagatgtca tacacgtaca ggggttccct gaggatgccg aggtaggtgg ggtagcagcg  6720
ccccccgcgg atgctggcgc gcacgtagtc atagagctgg tgggaggggg ccagcatgtt  6780
gggcccgagg ttggtgcgct gggggcgctc ggcgcggaag gcgatctgcc tgaagatggc  6840
atgggagttg gaggagatgg tgggccgctg gaagacgttg aagcttgctt cttgcaagcc  6900
caccgagtcc ctgacgaagg aggcgtagga ctcgcgcagc ttgtgcacca gctcggcggt  6960
gacctggacg tcgagcgcgc agtagtcgag ggtctcgcgg atgatgtcat acttatcctc  7020
cccttcttt ttccacagct cgcggtttgag gacgaactct tccagtactc  7080
ttggagggga aacccgtccg tgtccgaacg gtaagagcct agcatgtaga actggttgac  7140
ggcctggtag gggcaacagc ccttctccac gggcagcgcg taggcctgcg ccgccttgcg  7200
gagggaggtg tgggtgaggg cgaaagtgtc cctgaccatg actttgaggt attgatgttt  7260
gaagtctgtg tcatcgcagc cgccctgttc ccacagggtg tagtccgtgc gcttttttgga  7320
gcgcgggttg ggcagggaga agtgaggtc attgaagagg atcttccccg ctcgaggcat  7380
gaagtttctg gtgatgcgaa agggccctgg gaccgaggag cggttgttga tgacctgggc  7440
ggccaggacg atctcgtcaa agccgtttat gttgtggccc acgatgtaga gctccaaaaa  7500
gcgggctgg cccttgatgg aggggagctt tttgagttcc tcgtaggtga gctcctcggg  7560
cgattccagg ccgtgctcct ccagggccca gtcttgcaag tgagggttgg ccgccaggaa  7620
ggatcgccag aggtcgcggg ccatgaggat ctgcagggtg tcgccgaagg ttctgaactg  7680
tcgcccacg gccatctttt cggggggtgat gcagtagaag gtgagggggt cttttctccca  7740
gggggtcccat ctgagctctc gggcgaggtc gcgcgcggcg gcgaccagag cctcgtcgcc  7800
ccccagttc atgaccagca tgaagggcac gagctgcttg ccaaaggctc ccatccaagt  7860
gtaggtctct acatcgtagg tgacaaagag gcgctccgtg cgaggatgag agccgatcgg  7920
gaagaactgg atctcccgcc accagttgga ggattggctg ttgatgtggt gaaagtagaa  7980
```

-continued

```
gtcccgtctg cgggccgagc actcgtgctg gcttttgtaa aagcgaccgc agtactggca    8040
gcgctgcacg ggttgtatat cttgcacgag gtgaacctgg cgacctctga cgaggaagcg    8100
cagcgggaat ctaagtcccc cgcctggggt cccgtgtggc tggtggtctt ctactttggt    8160
tgtctggccg ccagcatctg tctcctggag ggcgatggtg gagcagacca ccacgccgcg    8220
agagccgcag gtccagatct cggcgctcgg cgggcgagct ttgatgacga ctcgcgcac    8280
attggagctg tccatggtct ccagctcccg cggcggcagg tcagctggga gttcctggag    8340
gttcacctcg cagagacggg tcaaggcgcg ggcagtgttg agatggtatc tgatttcaag    8400
gggcgtgttg gcggcggagt cgatggcttg caggaggccg cagcccccggg gggccacgat    8460
ggttccccgc ggggcgcgag gggaggcgga agctgggggt gtgttcagaa gcggtgacgc    8520
gggcgggccc ccggaggtag ggggggttcc ggccccacag gcatgggcgg caggggcacg    8580
tcttcgccgc gcgcgggcag gggctggtgc tggctccgaa gagcgcttgc gtgcgcgacg    8640
acgcgacggt tggtgtcctg tatctgacgc ctctgagtga agaccacggg tcccgtgacc    8700
ttgaacctga aagagagttc gacagaatca atctcggcat cgttgacagc ggcctggcgc    8760
aggatctcct gcacgtcgcc cgagttgtcc tggtaggcga tctctgccat gaactgctca    8820
atctcttctt cctggagatc tcctcgtccg gcgcgctcca cggtggccgc caggtcgttg    8880
gagatgcgac ccatgagctg tgagaaggcg ttgagcccgc cctcgttcca gacccggctg    8940
tagaccacgc ccccctcggc gtcgcagcgc cgcatgacca cctgggccag gttgagctcc    9000
acgtgtcgcg tgaagacggc gtagttgcgc aggcgctgga aaaggtagtt caggggtggtg    9060
gcggtgtgct cggcgacgaa gaagtacatg acccagcgcc gcaacgtgga ttcattgatg    9120
tcccccaagg cctccaggcg ctccatggcc tcgtagaagt ccacggcgaa gttgaaaaac    9180
tgggagttgc gagcggacac ggtcaactcc tcctccagaa gacggatgag ctcggcgaca    9240
gtgttgcgca cctcgcgctc gaaggccacg gggggcgctt cttcctcttc cacctcttct    9300
tccatgatcg cttcttcttc ttcctcagcc gggacggagg ggggcggcgg cggcggggga    9360
ggggcggggc ggcggcggcg gcgcaccggg aggcggtcga tgaagcgctc gatcatctcc    9420
ccccgcatgc ggcgcatggt ctcggtgacg gcgcggccgt tctcccgggg gcgcagctcg    9480
aagacgccgc ctctcatctc gccgcggggc gagcggccgt gaggtagcga gacggcggtg    9540
actatgcatc ttaacaattg ctgtgtaggt acaccgccga gggacctgat tgagtccaga    9600
tccaccggat ccgaaaaacct ttggaggaaa gcgtctatcc agtcgcagtc gcaaggtagg    9660
ctgagcaccg tggcgggcgg gggcgggtct ggagagttcc tggcggagat gctgctgatg    9720
atgtaattaa agtaggcggt cttgaaggg cggatgggga acaggagcac catgtctttg    9780
ggtccggcct gttggatgcg gaggcggtcg gccatgcccc aggcctcgtt ctgacaccgg    9840
cgcaggtctt tgtagtagtc ttgcatgagt ctttccaccg gcacctcttc tcttcctct    9900
tctccatctc gccggtggtt tctgcgccg cccatgcgcg tgaccccaaa gcccctgagc    9960
ggctgcagca gggccaggtc ggcgaccacg cgctccgcca agatggcctg ctgcacctga   10020
gtgagggtcc tctcgaagtc atccatgtcc acgaagcggt ggtaggcgcc cgtgttgatg   10080
gtgtaggtgc agttggccat gacgaccag ttgacggtct ggtgtcccgg ctgcgagagc   10140
tccgtgtacc gcaggcgcga gaaggcgcgg gaatcgaaca cgtagtcgtt gcaagtccgc   10200
accagatact ggtagcccac caggaagtgc ggccggaggtt ggcgatagag gggccagcgc   10260
tgggtggcgg gggcgccggg cgccaggtct tccagcatga ggcggtggta tccgtagatg   10320
tacctggaca tccaggtgat gccggcggcg gtggtggtgg cgcgcgcgta gtcgcggacc   10380
cggttccaga tgtttcgcag gggcgagaag tgttccatgg tcggcacgct ctggccggtg   10440
aggcgcgcgc agtcgttgac gctctataca cacacaaaaa cgaaagcgtt tacagggctt   10500
tcgttctgta gcctggagga aagtaaatgg gttgggttgc gtgcccc ggttcgagac   10560
caagctgagc tcggccggct gaagccgcag ctaacgtggt attggcagtc ccgtctcgac   10620
ccaggccctg tatcctccag gatacggtcg agagcccttt tgctttcttg gccaagcgcc   10680
cgtgcgcgca tctgggatag atggtcgcga tgagaggaca aaagcggctc gcttccgtag   10740
tctggagaaa caatcgccca ggttgcgttg cggcgtaccc cggttcgagc ccctatggcg   10800
gcttgaatcg gccggaaccg cggctaacga gggccggtggc agcccgtcc tcaggacccc   10860
gccagccgac ttctccagtt acgggagcga gccccttttg ttttttattt tttagatgca   10920
tcccgtgctg cggcagatgc gccctcgcc ccggcccgat cagcagcagc aacagcaggc   10980
atgcagaccc ccctctcccc tttccgcccc ggtcaccacg gccgcggcgg ccgtgtcgga   11040
cgcgggggggc gcgctggagt cagatgagcc accggcggg cgacctaggc agtatctgaa   11100
cttgaaagag ggcgagggac tggcgcggct ggggggcgaac tctccagagc gccaccgcg   11160
ggtgcagttg aaaagggacg cgcgcgaggc gtacctgccg cggcagaacc tgtttcgcga   11220
ccgcgggggcg gaggagcccg aggagatgcag agactgcagg ttccaagcgg ggcgcgagct   11280
gcggcgcggg ctggacagac agcgcctgct gcgcgaggag gactttgagc ccgacacgca   11340
gacgggcatc agcccgcgc gcgcgcacgt agccgcggcc gacctggtga ccgcctacga   11400
gcagacggta aaccaggagc gcaacttcca aaagagcttc aacaaccacg tgcgcacgct   11460
ggtgcgcgcg gaggaggtga ccctgggtct catgcatctg tgggacctgg tgaggcgat   11520
cgtgcagaac cccagcagca gccccttgac cgcgcagctg ttcctggtgg tgcagcacag   11580
cagggacaac gaggccttca gggaggcgct gctgaacatc accgagcggg aggggcgctg   11640
gctcctggac ctgataaaca tcctgcagag catagtggtg caggagcgca gcctgagcct   11700
ggccgagaag gtggcggcca tcaactactc tatgctgagc ctgggcaagt tctacgcccg   11760
caagatctac aagacccct acgtgccat agacaaggag gtgaagatag acagcttcta   11820
catgcgcatg gcgctgaagg tgctgaccct gagcgacgac ctgggagtgt accgcaacga   11880
gcgcatccac aaggccgtga gcgccagccg cggcgcgag ctgagcgacc gcgagctgat   11940
gcacagtctg cagcgcgcgc tgaccggcgc gggcgagggc acagggagg tcgagtccta   12000
cttcgacatg ggggccgacc tgcactggca gccgagccgc cgcgccctgg aggcggcggg   12060
ggcgtacggc ggcccccctgg cggccgatga ccaggaagga ggactatg agctagagga   12120
gggcgagtac ctggaggact gacctggctg gtgtgttttt ggtatagatg caagatccga   12180
acgtggcgga cccgccggtc cggcggcgc tgcaaagcca gccgtccggc attaactcct   12240
ctgacgactg ggccgcggcc atgggtcgca tcatggccct gaccgcgcgc aaccccgagg   12300
cttttcaggca gcagcctcag gccaaccggc tggcggcat cttggaagcg gtagtgcccg   12360
cgcgctccaa ccccacccac gagaaggtgc tggccatagt caacgcgctg gcggagagca   12420
gggccatccg cgcggacgag gccggactgg tgtacgatgc gctgctgcag cgggtggcgc   12480
ggtacaacag cggcaacgtg cagaccaacc tggaccgcct ggtgacggac gtgcgcgagg   12540
ccgtggcgca gcgcgagcgc ttgcatcagg acggtaacct gggctcgctg gtggcgctaa   12600
acgccttcct cagcacccag ccggccaacg taccgcgggg gcaggaggac tacaccaact   12660
ttttgagcgc gctgcggctg atggtgaccg aggtccctca gagcgaggtg taccagtcgg   12720
```

```
ggcccgacta cttcttccag accagcagac agggcttgca aaccgtgaac ctgagccagg   12780
cttttcaagaa cctgcggggg ctgtggggag tgaaggcgcc caccggcgac cgggctacgg   12840
tgtccagcct gctaaccccc aactcgcgcc tgctgctgct gctgatcgcg cccttcacgg   12900
acagcgggag cgtctcgcgg gagacctatc tgggccacct gctgacgctg taccgcgagg   12960
ccatcggcca ggcgcaggtg gacgagcaca ccttccaaga gatcaccagc gtgagccagg   13020
cgctggggca ggaggacacg ggcagcctgc aggcgaccct gaactacctg ctgaccaaca   13080
ggcggcagaa gattcccacg ctgcacagcc tgacccagga ggaggagcgc atcttgcgct   13140
acgtgcagca gagcgtgagc ctgaacctga tgcgcgacgg cgtgacgccc agcgtggcgc   13200
tggacatgac cgcgcgcaac atggaaccgg gcatgtacgc ctcccaccgg ccgtttatca   13260
accgcctgat ggactacttg catcggcgg cggccgtgaa ccccgagtac ttcactaatg   13320
ccattctgaa tccccactgg atgccccctc cgggtttcta caacgggac tttgaggtgc   13380
ccgaggtcaa cgacgggttc ctctgggatg acatggatga cagtgtgttc tcacccaacc   13440
cgctgcgcgc cgcgtctctg cgattgaagg agggctctga cagggaagga ccgaggagtc   13500
tggcctcctc cctggctctg ggagcggtgg gcgccaccgg cgcgccggcg cggggcagta   13560
gccccttccc cagcctggca gactctctga acagcggggcg ggtgagcagg ccccgcttgc   13620
taggcgagga ggagtatctg aacaactccc tgctgcagcc cgcgagggac aagaacgctc   13680
agcggcagca gtttcccaac aatgggatag agagcctggt ggacaagatg tccagatgga   13740
agacgtatgc gcaggagtac aaggagtggg aggaccgcca tgccggccc ttgccgcccc   13800
ctaggcagcg ctggcagcgg cgcgcgtcca accgccgctg gaggcagggg cccgaggacg   13860
atgatgactc tgcagatgac agcagcgtgt tggacctggg cgggagcggg aacccctttt   13920
cgcacctgcg cccacgcctg ggcaagatgt tttaaaagaa aaaaaaaat aaaactcacc   13980
aaggccatgg cgacgagcgt tggttttttg ttcccttcct tagtatgcgg cgcgcggcga   14040
tgttcgagga ggggcctccc ccctcttacg agagcgcgat ggggatttct cctgcggcgc   14100
ccctgcagcc tccctacgtg cctcctcggt acctgcaacc tacagggggg agaaatagca   14160
tctgttactc tgagctgcag cccctgtacg ataccaccag actgtacctg gtggacaaca   14220
agtccgcgga cgtggcctcc ctgaactacc agaacgacca cagcgattt ttgaccacgg   14280
tgatccaaaa caacgacttc accccaaccg aggccagcac ccagaccata aacctggata   14340
acaggtcgaa ctgggcggc gacctgaaga ccatcttgca caccaacatg cccaacgtga   14400
acgagttcat gttcaccaac tcttttaagg cgcgggtgat ggtggcgcgc gagcagggg   14460
aggcgaagta cgagtgggtg gacttcacgc tgcccgaggg caactactca gagaccatga   14520
ctctcgacct gatgaacaat gcgatcgtgg aacactatct gaaagtgggc aggcagaacg   14580
gggtgaagga aagcgatatc ggggtcaagt ttgacaccag aaacttccgt ctgggctggg   14640
accccgtgac cgggctggtc atgccgggg tctacaccaa cgaggccttt catcccgaca   14700
tagtgcttct gcccggctgt ggggtggact tcacccagag ccggctgagc aacctgctgg   14760
gcattcgcaa gcggcagcct ttcaggaagg gtttcaagat cacctatgag gatctgaagg   14820
ggggcaacat tcccgcgctc cttgatctgg acgcctacga ggagagcttg aaacccgagg   14880
agagcgctgg cgacagcggc gagagtgcgc aggagcaagc cggcggcggt ggcggcgcgt   14940
cggtagaaaa cgaaagtacg cccgcagtgg cggcggacgc tgcggaggtc gagccggagg   15000
ccatgcagca ggacgcagag gagggcgcac aggagggcgc gcagaaggac atgaacgatg   15060
gggagatcag gggagacaca ttcgccaccc ggggcgaaga aaaagaggca gaggcggcgg   15120
cggcggcgac ggcggaggcc gaaaccgagg ttgaggcaga ggcagagccc gagaccgaag   15180
ttatggaaga catgaatgat ggagaacgta ggggcgacac gttcgccacc cggggcgaag   15240
agaaggcggc ggaggcagaa gccgcggctg aggaggcgc tgcggctgcg gccaagactg   15300
aggctgcggc taaggctgag gtcgaagcca atgttgcggt tgaggctcag gctgaggagg   15360
aggcggcggc tgaagcagtt aaggaaaagg cccaggcaga gcaggaagag aaaaaacctg   15420
tcattcaacc tctaaaagaa gatagcaaaa agcgcagtta caacgtcatc gagggcagca   15480
cctttaccca gtaccgcagc tggtacctgg cgtacaacta caaagacccg gtcaaggggg   15540
tgcgctcgtg gacccgctct tgcacgccgg acgtcacctg cggctccgag cagatgtact   15600
ggtcgctgcc gaacatgatg caagaccccgg tgaccttccg ctccacgcgg caggttagca   15660
acttcccggt ggtgggcgcc gaactgctgc ccgtgcactc caagagtttt tacaacgagc   15720
aggccgtcta ctcccagctg atccgccagg ccacctctct gacccacgtg ttcaatcgct   15780
ttcccgagaa ccagattttg gcgcgcccgc cggccccac catcaccacc gtgagtgaaa   15840
acgttcctgc cctcacagat cacgggacgc taccgctgcg caacagcatc tcaggagtcc   15900
agcgagtgac cattactgac gccagacgcc ggacctgccc ctacgtttac aaggccttgg   15960
gcatagtctc gccgcgcgtc ctctccagtc gcactttta aaacacatct acccacacgt   16020
tccaaaatca tgtccgtact catctcaccc agcaacaaca ccggctgggg gctcgcgcgg   16080
cccagcaaga tgtttggagg ggcgaggaag cgctccgacc agcaccccgt gcgcgtcgcg   16140
ggccactacc gcgcgccctg gggagcgcac aagcgcgggc gcacaggggcg caccactgtg   16200
gacgacgtca ttgactccgt agtggacaga gcgcgccact acacaccegg cgccgccgc   16260
gcccccgccg tgtccaccgt ggaccaggcg atcgaaagcg tggtacaggg cgcgcggcac   16320
tatgccaacc ttaaaagtcg ccgccgccgc gtgcccgcc gccatcgccg gagacccgg   16380
gccaccgccg ccgcgcgcct tactaaggct ctgctcaggc gcgccaggcg aactggccac   16440
cgggccgcca tgagggccgc acggcgggct gccgctgccc caagcgtcgt ggccccgcgg   16500
gcacgaaggc gcgcggccgc tgccgccgcc ccgccattt ccagcttggc ctcgacgcgg   16560
cgcggtaaca tatactgggt gcgcgactcg gtaaccggca cgcgggtacc cgtgcgcttt   16620
cgcccccgc ggaattagca caagacaaca tacacactga gtctcctgct gttgtgtatc   16680
ccagcggcga ccgtcagcag cggcgacatg tccaagcgca aaattaaaga agagatgctc   16740
caggtcatcg cgccggagat ctatgggccc ccgaagaagg aggaggatga ttacaagccc   16800
cgcaagctaa agcgggtcaa aaagaaaaag aagatgtacg agcgtcagag tgtcgcgctt   16860
gtccgccgca tggcacccag gcgccccgtg cagtggaagg gccgcgcgt gcagcgcgtt   16920
ttgcgccccg gcaccgcggt ggtcttcacg cccggcgagc gctccacgcg cactttcaag   16980
cgggtgtacg atgaggtgta cggcgacgag gacctgttgg agcaggccaa ccagcgcttt   17040
gggagtttg catatgggaa acggcccgc gagagtctaa aagaggacct gctggcgcta   17100
ccgctgggca gggcaatcc caccccgagt ctgaagcgat taaccctgca acaggtgctg   17160
cctttgagcg cgcccagcga gcataagcga gggttgaagc gcgaaggcgg gacctggcg   17220
cccaccgtgc agttgatggt gcccaagcgg cagaagctgg aggacgtgct ggagaaaatg   17280
aaagtagagc ccgggatcca gcccgagatc aaggtccgcc ccatcaagca ggtggcgccc   17340
ggcgtgggag tccagaccgt ggacgttagg attcccacgg aggagatgga aacccaaacc   17400
gccactccct cttcggcggc cagcgccacc accggcaccg cttcggtaga ggtgcagacg   17460
```

```
gaccoctggc tacccgccac cgctgttgcc gccgccgccc cccgttcgcg cgggcgcaag   17520
agaaattatc cagcggccag cgcgctcatg ccccagtacg cactgcatcc atccatcgtg   17580
cccaccccg gctaccgcgg gtactcgtac cgcccgcgca gatcagccgg cactcgcggc    17640
cgccgccgcc gtgcgaccac aaccagccgc cgccgtcgcc gccgccgcca gccagtgctg   17700
accccgtgt ctgtaaggaa ggtggctcgc tcggggacga cgctggtggt gcccagagcg    17760
cgctaccacc ccagcatcgt ttaaagccgg tctctgtatg gttcttgcag atatggccct   17820
cacttgtcgc ctccgcttcc cggtgccggg ataccgagga agaactcacc gccgcagagg   17880
catggcgggc agcggtctcc gcggcggccg tcgccatcgc cggcgcgcaa aaagcaggcg   17940
catgcgcggc ggtgtgctgc ctctgctaat cccgctaatc gccgcggcga tcggtgccgt   18000
acccgggatc gcctccgtgg ccctgcaggc gtcccagaaa cgttgactct tgcaaccttg   18060
caagcttgca ttttttggag gaaaaaataa aaaaaaagtc tagactctca cgctcgcttg   18120
gtcctgtgac tattttgtag aaaaaaagat ggaagacatc aactttgcgt cgctggcccc   18180
gcgtcacggc tcgcgcccgt tcatgggaga ctggacagat atcggcacca gcaatatgag   18240
cggtggcgcc ttcagctggg gcagtctgtg gagcggcctt aaaaattttg gttccaccat   18300
taagaactat ggcaacaaag cgtggaacag cagcacgggc cagatgctga gagacaagtt   18360
gaaagagcag aacttccagg agaaggtggc cagggcctg gcctctggca tcagcggggt    18420
ggtggacata gctaaccagg ccgtgcagaa aaagataaac agtcatctgg acccccgtcc   18480
tcaggtggag gaaatgcctc cagccgatgga gacggtgtct cccgagggca aaggcgaaaa   18540
gcgcccgcgg cccgacagag aagagaccct ggtgtcacac accgaggagc cgccctctta   18600
cgaggaggca gtcaaggccg gcctgcccac cactcgcccc atagcccca tggccaccgg    18660
tgtggtgggc cacaggcaac acactcccgc aacactagat ctgcccccgc cgtccgagcc   18720
gccgcgccag ccaaaggccg cgacggtgcc cgctccctcc acttccgccg ccaacagagt   18780
gcccctgcgc cgcgccgcga gcggccccg ggctcgcga gttagcggca actggcagag     18840
cacactgaac agcatcgtgg gcctgggagt gaggagtgtg aagcgccgcc gttgctactg   18900
aatgagcaag ctagctaacg tgttgtatgt gtgtatgcgt cctatgtcgc cgccagagga   18960
gctgttgagc cgccgggcgcc gtctgcactc cagcgaattt caagatgcg acccccatcga 19020
tgatgcctca gtggtcgtac atgcacatct cgggccagga cgcttcggag tacctgagcg   19080
ccgggctggt gcagttcgcc cgcgccacag acacctactt caacatgagt aacaagttca   19140
ggaaccccac tgtggcgccc acccacgatg tgaccacgga ccggtcgcag cgcctgacgc   19200
tgcggttcat ccccgtggat cgggaggaca ccgcctactc ttacaaggcg cggttcacgc   19260
tggccgtggg cgacaaccgc gtgctggaca tggcctccac ttactttgac atcagggggg   19320
tgctggacag gggccccacc ttcaagccct actcgggtac tgcctacaac tccctggccc   19380
ccaagggcgc tcccaattct tgcgagtggg aacaagatga accagctcag gcagcaatag   19440
ctgaagatga agaagaactt gaacaagaac aagctcagga cgaacaggcg cccactaaga   19500
aaacccatgt atacgcccag gcacctcttt ctggtgaaaa aattactaag gatggtttgc   19560
aaataggtgt ggatgccaca caggcgggag ataaccctat atatgctgat aaaacattcc   19620
aacccgaacc tcagataggt gagtctcagt ggaacgaggc tgatgccaca gtagcaggag   19680
gcagagtctt aaaaaagacc accctatga gaccttgcta tggatcctat gccaaaccta    19740
ctaatgccaa tggcggtcaa gggatcatgg tggccaatga tcaggagcg cttgaatcta    19800
aagttgagat gcaattttct tccaccacaa cgtctcttaa tgtaagggaa ggtgaaaaca   19860
atcttcagcc aaaagtagtg ctatacacgg aagatgttaa cttggaatcc cctgacactc   19920
atttgtctta caaacctaaa aaggatgaca ccaactctaa aatcatgttg ggtcagcaag   19980
ccatgcccaa cagacccaac ctcattgctt ttagggacaa ctttattgga cttatgtact   20040
acaacagcac aggcaacatg ggagtgctgg caggacaggc ctcccagcta aacgctgtgg   20100
tagacttgca agacagaaac acagagctgt cataccaact gatgcttgat tccattggag   20160
acagatcaag atacttttcc atgtggaacc aggcagtgga cagctatgac ccagatgtca   20220
gaatcattga aaccatggg gttgaagatg agctgcccaa ctattgcttt ccccctgggcg   20280
gtattggaat tacagacaca taccagtgca taaaaccaac cgcagctgct aataacacta   20340
catggtctaa ggatgaagaa tttagtgatc gcaatgaaat aggggtggga aacaacttcg   20400
ccatggagat caacatccag gccaacctct ggaggaactt cctctatgcg aacgtggggc   20460
tctacctgcc agacaagctc aagtacaacc ccaccaagcc tgacatctct gacaacccca   20520
acacctatga ctacatgaac aagcgtgtgg tggctcccgg cctggtggac tgctttgtca   20580
atgtgggagc caggtggtcc ctggactaca tggacaacgt caaccccttc aaccaccacc   20640
gcaatgcggg tctgcgctac cgctccatga tcctgggcaa cgggcgctac gtgcccttcc   20700
acattcaggt gccccagaag ttctttgcca tcaagaacct cctcctgctc ccgggctcct   20760
acacttacga gtggaacttc aggaaggatg tcaacatgat cctgcagagc tctctgggca   20820
atgaccttag ggtggacggg gccagcatca gtttgacag cgtcaccctc tatgctacct   20880
tcttccccat ggctcacaac accgcctcca cgctcgaggc catgctgagg aacgacacca   20940
acgaccagtc cttcaatgac tacctctctg gggccaacat gctctacccc atcccccgca   21000
aggccaccaa cgtgcccatc tccattccct ctcgcaactg gccgccttc agaggctggg    21060
cctttacccg ccttaagacc aaggaaaccc cctccctggg ctcgggtttt gacccctact   21120
ttgtctactc gggatccatc ccctacctgg atggcacctt ctacctcaac cacactttta   21180
agaagatatc catcatgtat gactcctccg tcagctggcc gggcaatgac cgcctgctca   21240
cccccaatga gttcgaggtc aagcgcgccg tggacgggcg aggctacaac gtggccagt    21300
gcaacatgac caaggactgg ttcctggtgc agatgctggc caactacaac ataggctacc   21360
agggcttcta catcccagag agctacaagg acaggatgta ctccttcttc agaaatttcc   21420
aacccatgag caggcaggtg gtggacgaga ccaaatacaa ggactatcag gccattggca   21480
tcactcacca gcacaacaac tcgggattcg tgggctacct ggctcccacc atgcgcgagg   21540
ggcaggccta ccccgccaac ttcccctacc cgttgatagg caaaaccgcg gtcgacagcg   21600
tcacccagaa aaagttcctc tgcgaccgca ccctctggcg catccccttc tctagcaact   21660
tcatgtccat gggtgcgctc acggacctgg gccagaacct gctctatgcc aactccgccc   21720
atgcgctgga catgactttt gaggtggacc ccatggacga gcccaccctt ctctatattg   21780
tgtttgaagt gttcgacgtg gtcagagtgc accagccgca ccgggtgtc atcgagaccg    21840
tgtacctgcg cacgcccttc taggcagca acgcaccgc ctaaggagac agcgcccgga    21900
cctgcatgac gggttccacc gagcaagagc tcagggccat cgccagagac ctgggatgcg   21960
gaccctattt tttgggcacc tatgacaaac gcttcccggg cttcatctcc cgagacaagc   22020
tcgcctgcgc catcgtcaac acggccgcgc gcgagaccgg gggcgtgcac tggctggcct   22080
ttgggctggga cccgcgctcc aaaacctgct acctcttcga cccctttggc ttctccgatc   22140
agcgcctcag acagatctat gagtttgagt acgaggggct gctgcgccgc agcgcgcttg   22200
```

```
cctcctcgcc cgaccgctgc atcacccttg agaagtccac cgagaccgtg caggggcccc 22260
actcggccgc ctgcggtctc ttctgctgca tgttttgca cgcctttgtg cgctggcccc 22320
agagtcccat ggatcgcaac cccaccatga acttgctcaa gggagtgccc aacgccatgc 22380
tccagagccc ccaggtccag cccacccctgc gccacaacca ggaacagctc taccgcttcc 22440
tggagcgcca ctccccctac ttccgcagtc acagcgcgca catccggggg gccacctctt 22500
tctgccactt gcaagaaaac atgcaagacg gaaaatgatg tacagctcgc ttttaataa 22560
atgtaaagac tgtgcacttt atttatacac gggctctttc tggttattta ttcaacaccg 22620
ccgtcgccat ctagaaatcg aaagggttct gccgcgcgtc gccgtgcgcc acgggcagag 22680
acacgttgcg atactggaag cggctcgccc acttaaactc gggcaccacc atgcggggca 22740
gtggttcctc ggggaagttc tcgccccaca gggtgcgggt cagctgcagc gcgctcagga 22800
ggtcgggagc cgagatcttg aagtcgcagt tggggccgga accctgcgcg cgcgagttgc 22860
ggtacacggg gttgcagcac tggaacacca gcagggccgg attatgcacg ctggccagca 22920
ggctctcgtc gctgatcatg tcgctgtcca gatcctccgc gttgctcagg gcgaacgggg 22980
tcatcttgca gacctgcctg cccaggaaag gcggcagccg gggcttgccg ttgcagtcgc 23040
agcgcagggg catcagcagg tgcccgcggc ccgactgcgc ctgcgggtac agcgcgcgca 23100
tgaaggcttc gatctgcctg aaagccacct gcgtcttggc tccctccgaa aagaacatcc 23160
cacaggactt gctggagaac tggttcgcgg gacagctggc atcgtgcagg cagcagcgcg 23220
cgtcggtgtt ggcgatctgc accacgttgc gaccccaccg gttcttcact atcttggcct 23280
tggaagcctg ctccttcagc gcgcgctggc cgttctcgct ggtcacatcc atctctatca 23340
cctgctcctt gttgatcatg tttgtaccgt gcagacactt caggtcgccc tccgtctggg 23400
tgcagcggtg ctcccacagc gcgcaaccgg tgggctccca attttgtgg gtcaccccg 23460
cgtaggcctg caggtaggcc tgcaagaagc gcccccatcat ggccacaaag gtcttctggc 23520
tcgtaaaggt cagctgcagg ccgcgatgct cttcgttcag ccaggtcttg cagatggcgg 23580
ccagcgcctc ggtctgctcg ggcagcatcc taaaatttgt cttcaggtcg ttatccacgt 23640
ggtacttgtc catcatggcg cgcgccgcct ccatgcccct ctcccaggcg gacaccatgg 23700
gcaggcttag ggggtttatc acttccaccg gcgaggacac cgtactttcg atttcttctt 23760
cctcccctc ttcccggcgc gcgcccacgc tgctgcgcgc tctcaccgcc tgcaccaagg 23820
ggtcgtcttc aggcaagcgc cgcaccgagc gcttgccgcc cttgacctgc ttaatcagca 23880
ccggcgggtt gctgaagccc accatggtca gcgccgcctg ctcttcttcg tcttcgctgt 23940
ctaccactat ctctggggaa gggcttctcc gctctgcggc ggcgccgcttc tttttttct 24000
tgggagcggc cgtgatggag tccgccacgg cgacggaggt cgagggcgtg gggctggggg 24060
tgcgcggtac caggggcctcg tcgccctcgg actcttcctc tgactccagg cggcggcgga 24120
gtcgcttctt tgggggcgcg cgcgtcagcg gcggcggaga cggggacggg gacggggacg 24180
ggacgccctc cacaggggt ggtcttgcg cagacccgcg gccgcgctcg ggggtcttct 24240
cgagctggtc ttggtcccga ctggccattg tatcctcctc ctcctaggca gagagacata 24300
aggagtctat catgcaagtc gagaaggagg agagcttaac caccccctct gagaccgccg 24360
atgcgcccgc cgtcgccgtc gccccgctg ccgccgacgc gcccgccaca ccgagcgaca 24420
cccccgcgga cccccccgcc gacgcacccc tgttcgagga gcggccgtg gagcaggacc 24480
cgggctttgt ctcggcagag gaggatttgc gagaggagga ggataaggag aagaagccct 24540
cagtgccaaa agatgataaa gagcaagacg agcacgacg agatgcacac cagggtgaag 24600
tcgggcgggg ggacggaggg catgacgcg ccgactacct agacgaaggg aacgacgtgc 24660
tcttgaagca cctgcatcgt cagtgcgcca ttgtttgcga cgctctgcag gagcgcagcg 24720
aagtgcccct cagcgtggcg gaggtcagcc acgcctacga gctcagcctc ttctcccccc 24780
gggtgccccc ccgccgccgc gaaaacggca catgcgagcc caacccgcgc ctcaacttct 24840
accccgcctt tgtggtaccc gaggtcctgg ccacctatca catcttcttt caaaattgca 24900
agatccccct ctcgtgccgc gccaaccgta gccgcgcgca taagatgctg gccctgcgcc 24960
agggcgacca catacctgat atcgccgctt tggaagatgt accaaagatc ttcgagggtc 25020
tgggtcgcaa cgagaagcgg gcagcaaact ctctgcaaca ggaaaacagc gaaaatgaga 25080
gtcacaccgg ggtactggtg gagctcgagg gcgacaacgc ccgcctggcg gtggtcaagc 25140
gcagcatcga ggtcacccac tttgcctacc ccgcgctaaa cctgcccccc aaagtcatga 25200
acgcggccat ggacgggctg atcatgcgcc gcggccggcc cctcgctcca gatgcaaact 25260
tgcatgagga gaccgaggac ggccagcccg tggtcagcga cgagcagctg gcgcgctggc 25320
tggagaccgc ggaccccgcc gaactggagg agcggcgcaa gatgatgatg gccgtggtgc 25380
tggtcaccgt agagctggag tgtctgcagc gcttcttcgg cgaccccgag atgcagagaa 25440
aggtcagga gaccctgcac tacaccttcc gccagggcta cgtgcgccag gcttgcaaga 25500
tctccaacgt ggagctcagc aacctggtgt cctacctggg catcttgcat gagaaccgcc 25560
tcgggcagag cgtgctgcac tccacccctgc gcggggaggc gcgccgcgac tacgtgcgcg 25620
actgcgttta cctcttcctc tgctacacct ggcagacggc catgggggtc tggcagcagt 25680
gcctggaaga gcgcaaactc aaggagctgg agaagtcct gcagcgcgcg ctcaaagatc 25740
tctggacggg ctacaacgag cgctcggtgg ccgccgcgct ggccgacctc atcttccccg 25800
agcgcctgct caaaaccctc cagcaggggc tgcccgactt caccagccaa agcatgttgc 25860
aaaacttcag gaactttatc ctggagcgtt ctggcatcct acccgccacc tgctgcgccc 25920
tgcccagcga ctttgtcccc ctcgtgtacc gcgagtgccc ccgccgctg tggggtcact 25980
gctacctgtt ccaactggcc aactacctgt cctaccacgc gggcttcgca gggactccca 26040
gcggcgaggg gctcatggag tgccactgcc gctgcaacct ctgcacgccc accgctcccc 26100
tggtctgcaa cacccaactg ctcagcgaga gtcagattat cggtaccttc gagctacagg 26160
gtccgtcctc ctcagacgag aagtccgcgg ctccggggct aaaactcact ccggggctgt 26220
ggacttccgc ctacctgcgc aaatttgtac ctgaagacta ccacgcccac gagatcaggt 26280
tttacgaaga ccaatcccgc ccgcccacgg cggagctgac cgcctgcgtc atcacccagg 26340
gcgagatcct aggccaattg caagccatcc aaaaagcccg ccaagacttt ttgctgaaga 26400
agggtcgggg ggtgtatctg gaccccagt cgggtgagga gctcaacccg ttccccccgc 26460
tgccgccgcc gcgggacctt gcttccagg ataagcatcg ccatggctcc cagaaagaag 26520
cagcagcggc cgccactgcc gccaccccac atgctggagg aagaggagga atactgggac 26580
agtcaggag aggagtttc ggacgaggag gagccgagga agagtgggaa 26640
gaggacagct tagacgagga ggcttccgaa gccgaagagg cagacgcaac accgtcaccc 26700
tcggccgcag cccctcgca ggcgccccg aagtccgctc ccagcatcag cagcaacagc 26760
agcgctataa cctccgctcc tccaccgccg cgacccacgg ccgaccgcag acccaaccgt 26820
agatgggaca ccaccggaac cggggccggt aagtcctccg ggagaggcaa gcaagcgcag 26880
cgccaaggct accgctcgtg gcgcgctcac aagaacgcca tagtcgcttg cttgcaagac 26940
```

```
tgcgggggga acatctcctt cgcccgccgc ttcctgctct tccaccacgg tgtggccttc    27000
ccccgtaacg tcctgcatta ctaccgtcat ctctacagcc cctactgcgg cggcagtgag    27060
ccagagacgg tcggcggcgg cggcggcgcc cgtttcggcg cctaggaaga cccagggcaa    27120
gacttcagcc aagaaactcg cggcggccgc ggcgaacgcg gtcgcggggg ccctgcgcct    27180
gacggtgaac gaaccccctgt cgacccgcga actgaggaac cgaatcttcc ccactctcta    27240
tgccatcttc cagcagagca gagggcagga tcaggaactg aaagtaaaaa acaggtctct    27300
gcgctccctc acccgcagct gtctgtatca caagagcgaa gaccagcttc ggcgcacgct    27360
ggaggacgct gaggcactct tcagcaaata ctgcgcgctc actcttaagg actagctccg    27420
cgcccttctc gaatttaggc gggaacgcct acgtcatcgc agcgccgccg tcatgagcag    27480
ggacattccc acgccataca tgtggagcta tcagccgcag atgggactcg cggcgggcgc    27540
ctcccaagac tactccaccc gcatgaactg gctcagtgcc ggcccacaca tgatctcaca    27600
ggttaatgat atccgcaccc atcgaaacca aatattggtg gagcaggcgg caattaccac    27660
cacgcccgc aataatccca accccaggga gtggcccgcg tccctggtgt atcaggaaat    27720
tcccgcccc accaccgtac tacttccgcg tgattccgca gccgaagtcc aaatgactaa    27780
ctcaggggca cagctcgcgg gcggctgtcg tcacagggtg cggcctcctc gccagggtat    27840
aactcacctg gagatccgag gcagaggtat tcagctcaac gacgagtcgg tgagctcctc    27900
gctcggtctc agacctgacg ggaccttcca gatagccgga gccggccgat cttccttcac    27960
gccccgccag gcgtacctga ctctgcaaag ctcgtcctcg gcgccgcgct cgggcgggcat    28020
cgggactctc cagttcgtgc aggagtttgt gccctcggtc tacttcaacc ccttctcggg    28080
ctctcccggt cgctacccgg accagttcat ctcgaacttt gacgccgcga gggactcggt    28140
ggacggctac gactgaatgt cgggtggacc cggtgcagag caacttcgcc tgaagcacct    28200
cgaccactgc cgccgccctc atgtgctttgc ccgctgtcaa gccggtggtt tccagtactt    28260
ttccctgccc gactcgcacc cggacggccc ggcgcacggg gtgcgcttt tcatcccgag    28320
tcaggtcgcg tctaccctaa tcagggagtt taccgcccgt ccctactgg cggagttgga    28380
aaaggggcct tctatcctaa ccattgcctg catctgctct aaccctggat tgcaccaaga    28440
tctttgcgct cattgtgtg ctgagtataa taaaggctga gatcagaatc tactcgggct    28500
cctgtcgcca tcctgtcaac gccaccgtcc aagcccggcc cgatcagccc gaggtgaacc    28560
tcacctgcgg tctgcaccgg cgcctgagga aatacctagc ttggtactac aacagcactc    28620
cctttgtggt ttacaacagc tttgaccagg acggggtctc actgagggat aacctctcga    28680
acctgagcta ctccatcagg aagaacagca ccctcgagct acttcctcct tacctgcccg    28740
ggacttacca gtgtgtcacc ggtccctgca cccacaccca cctgttgatc gtaaacgact    28800
ctcttccgag aacagacctc aataactcct cttcgcagtt ccccagaaca ggaggtgagc    28860
tcaggaaacc ccgggtaaag aagggtggac gagagttaac acttgtgggg tttctggtgt    28920
atgtgacgct ggtggtgggct cttttgatta aggcttttcc ttccatgtct gaactcctcc    28980
tcttctttta tgaacaactc gactagtgct aacgggaccc tacccaacga atcgggattg    29040
aatatcggta accaggttgc agtttcactt ttgattacct tcatagtcct cttcctgcta    29100
gtgctgtcgc ttctgtgcct gcggatcggg ggctgctgca tccacgttta tatctggtgc    29160
tggctgttta gaaggttcgg agaccatcgc aggtagaata aacatgctgc tgcttaccct    29220
cttgtcctg gcgctggccg ccagctgcca agccttttcc gaggctgact ttatagagcc    29280
ccagtgtaat gtgacttttaa aagcccatgc acagcgttgt catactataa tcaaatgtgc    29340
caccgaacac gatgaatacc ttatccagta taaagataaa tcacacaaag tggcacttgt    29400
tgacatctgg aaacccgaag acccttttgga atacaatgtg accgttttcc agggtgacct    29460
cttcaaaatt tacaattaca cttttcccatt tgaccagatg tgtgactttg tcatgtacat    29520
ggaaaagcag cacaagctgt ggcctccgac tccccagggc tgtgtggaaa atccaggctc    29580
tttctgcatg atctctctct gtgtaactgt gctggcacta atactcacgc ttttgtatat    29640
cagatttaaa tcaaggcaaa gcttcattga tgaaagaaa atgccttaat cgctttcacg    29700
cttgattgct aacaccgggt tttatccgc agaatgattg gaatcaccct actaatcacc    29760
tccctccttg cgattgccca tgggttggaa cgaatcgaag tccctgtggg ggccaatgtt    29820
accctggtgg ggcctgtcgg caatgctaca ttaatgtggg aaaaatatac taaaatcaa    29880
tgggtctctt actgcactaa caaaaatagc cacaagccca gagccatctg cgatgggcaa    29940
aatctaacct tgattgatgt tcaattgctg gatgcgggct actattatgg gcagctgggt    30000
acaatgatta attactggag accccacaga gattacatgc tccacgtagt aaagggtccc    30060
cttagcagcc caccccactac cacctctact accccccacta ccaccactac tcccaccacc    30120
agcactgccg cccagcctcc tcatagcaga acaaccactt ttatcaattc caagtccccac    30180
tccccccaca ttgccggcgg gcctccgcc tcagactccg aaaccaccga gatctgcttc    30240
tgcaaatgct ctgacgccat tgcccaggat ttggaagatc acgaggaaga tgagcatgac    30300
ttcgcagatg catgccaggc atcagagcca aagcgctgc cggtggccct caaacagtat    30360
gcagaccccc acaccacccc cgaccttcct ccaccttccc agaagccaag tttcctgggg    30420
gaaaatgaaa tctgcctct ctccatactc gctctgacat ctgttgctat gttgaccgct    30480
ctgctggtgc ttctatgctc tatatgctac ctgatctgct gcagaagaa aaaatctcac    30540
ggccatgctc accagcccct catgcacttc ccttacccttc cagagctggg cgaccacaaa    30600
ctttaagtct gcagtaacta tctgcccatc ccttgtcagt cgacagcgat gagcccact    30660
aatctaacgg cctctggact tacaaacatcg tctcttaatg agaccaccgc tcctcaagac    30720
ctgtacgatg gtgtctccgc gctggttaac cagtgggatc acctgggcat atggtggtct    30780
ctcataggag cagtgacccct gtgcctaatc ctggtctgga tcatctgctg catcaaaagc    30840
agaagaccca ggcggcggcc catctacagg ccctttgtca tcacacctga agatgatgat    30900
gacaccactc caggctgca gaggctaaag cagctactct tctctttac agcatggtaa    30960
attgaatcat gcctcgcatt ttcatctact tgtctctcct tccactttttt ctgggctctt    31020
ctacattggc cgctgtgtcc cacatcgagg tagactcctt cacgcccttc acagtctacc    31080
tgcttttcgg ctttgtcatc tgcacctttg tctgcagcgt tatcactgta gtgatctgct    31140
tcatacagtg catcgactac gtctgcgtgc gggtggctta cttagacac caccccagt    31200
atcgcaacag ggacatagcg gctctcctaa gacttgttta aaatcatggc caaattaact    31260
gtgattggtc ttctgatcat ctgctgcgtc ctagccgcga ttgggactca agtcctacc    31320
accaccgcag ctcccagaaa gagacatgta tcctgcgact tcaagcgtca ctgaaatata    31380
ccccaatgct ttactgatga acctgaaatc tctttggctt ggtacttcag cgtcaccgcc    31440
cttcttatct tctgcagtac ggttattgcc cttgccatct accttccct tgacctgggc    31500
tggaatgctg tcaactctat ggaatatccc accttcccag aaccagacct gcagacctg    31560
gttgttctaa acgcgtttcc tcctcctgct cccgttcaaa atcagtttcg ccctccgtcc    31620
cccacgccca ctgaggtcag ctactttaat ctaacaggcg gagatgactg aaaacctaga    31680
```

```
cctagaaatg gacggtctct gcagcgagca acgcacacta gagaggcgcc ggcaaaaaga   31740
gctcgagcgt cttaaacaag agctccaaga cgcggtggcc atacaccagt gcaaaaaagg   31800
tgtcttctgt ctggtaaaac aggccacgct cacctatgaa aaaacaggtg acacccaccg   31860
cctaggatac aagctgccca cacagcgcca aaagttcgcc ctcatgatag gcgaacaacc   31920
catcaccgtg acccagcact ccgtggagac agaaggctgc atacatgctc cctgtagggg   31980
cgctgactgc ctctacacct tgatcaaaac cctctgcggt ctcagagacc ttatcccttt   32040
caattaatca taactgtaat caataaaaaa tcacttactt gaaatctgat agcaagcctc   32100
tgtccaattt tttcagcaac acttccttcc cctcctccca actctggtac tctaggcgcc   32160
tcctagctgc aaacttcctc cacagtctga agggaatgtc agattcctcc tcctgtccct   32220
ccgcacccac gatcttcatg ttgttgcaga tgaaacgcgc gagatcgtct gacgagacct   32280
tcaaccccgt gtaccctac gataccgaga tcgctccgac ttctgtccct ttccttaccc   32340
ctcccttgt gtcatccgca ggaatgcaag aaaatccagc tggggtgctg tccctgcact   32400
tgtcagagcc ccttaccacc cacaatgggg ccctgactct aaaaatgggg ggcggcctga   32460
ccctggacaa ggaagggaat ctcacttccc aaaacatcac cagtgtcgat cccctctca    32520
aaaaaagcaa gaacaacatc agccttcaga ccgccgcacc cctcgccgtc agctccgggg   32580
ccctaacact ttttgccact ccccccctag cggtcagtgg tgacaacctt actgtgcagt   32640
ctcaggcccc tctcactttg gaagactcaa aactaactct ggccaccaaa ggaccccttaa  32700
ctgtgtccga aggcaaactt gtcctagaaa cagaggctc                          32739

SEQ ID NO: 25            moltype = DNA    length = 32739
FEATURE                  Location/Qualifiers
misc_feature             1..32739
                         note = Adenovirus vector nucleotide sequences
source                   1..32739
                         mol_type = other DNA
                         organism = synthetic construct
SEQUENCE: 25
catcatcaat aatataccctt attttggatt gtgccaata tgataatgag gtgggcgggg    60
agaggcgggg cggtgacgt aggacgcgcg agtagggttg ggaggtgtgg cggaagtgtg    120
gcatttgcaa gtgggaggag ctcacatgca agcttccgtc gcggaaaatg tgacgttttt   180
gatgagcgcc gcctacctcc ggaagtgcca attttcgcgc gcttttcacc ggatatcgta   240
gtaattttgg gcgggaccat gtaagatttg gccattttcg cgcgaaaagt gaaacgggga   300
agtgaaaact gaataatagg gcgttagtca tagtgcgtaa tatttaccga gggccgaggg   360
actttgaccg attacgtgga ggactcgccc aggtgtttct gcttgtgaatt tccgcgttcg   420
gggtcaaagt ctccgtttta ttgtcaccgt catttgacgc ttaggcctga ccatctggtg   480
ctggcctgca ccaggggcga gttttgggtct agcgatgagg ataccgattg aggtgggtaa   540
ggtgggcgtg gctagaaggg tggggcgtgt ataaattggg ggtctaaggg tctctctgtt   600
ttgtcttgca acagccgccg ccatgagcga caccggcaac agctttgatg gaagcatctt   660
tagccctat ctgacagtgc gcatgcctca ctgggctgga gtgcgtcaga atgtgatggg   720
ttccaacgtg gatggacgcc ccgttctgcc ttcaaaattcg tctacaatgg cctacgcgac   780
cgtgggagga actccgctgg acgcgcgac ctccgccgcc gcctccgccg ccgccgcgac   840
cgcgcgcagc atggctacgg acctttacag ctctttggtg gcgagcggcg cggcctctcg   900
cgcgtctgct cgggatgaga aactgaccgc tctgctgctt aaactgaccg                960
ggagctgggt caactgaccc agcaggtctc cagcttgcgt gagagcagcc ttgcctccca   1020
ctaatgcccc ataatataaa taaaagccaa tctgtttgga ttaagcaagt gtatgttctt   1080
tatttaactc tccgcgcgcg gtaagcccgg gaccagcggg ctcggtcgtt tagggtgcgg   1140
tggattcttt ccaacacgtg gtacaggtgg ctctggatgt ttagatacat gggcatgagt   1200
ccatccctgg ggtggaggta gcaccactgc agagcttcgt gctcgggggt ggtgttgtat   1260
atgatccagt cgtagcagga gcgctgggcg tggtgctgaa aaatgtcctt aagcaagagg   1320
cttatagcta gggggaggcc cttggtgtaa gtgtttacaa atctgctcag ttgggagggg   1380
tgcatccggg gggatataat gtgcatcttg gactggattt ttaggttggc tatgttccca   1440
cccagatccc ttctgggatt catgttgtgc aggaccacca gcacggtata tccagtgcac   1500
ttgggaaatt tatcgtggag cttagacggg aatgcatgga agaacttgga gacgcccttg   1560
tggcctccca gattttccat acattcgtcc atgatgatgg caatgggccc gtgggaagct   1620
gcctgagcaa aaatgtttct gggatcgctc acatcgtagt tatgttccag ggtgaggtca   1680
tcataggaca tctttacgaa tcggggcgg agggtcccgg actgtgggat gatggtaccc   1740
tcgggccccg gggcgtagtt cccctcacag atctgcatct cccaggcttt catttcagag   1800
ggagggatca tatccacctg cggagcgatg aaaaacacag tttctggcgc aggggagatt   1860
aactgggatg agagcaggtt tctgagcagc tgtgacttc cacagccggt gggcccatat   1920
atcacgccta tcaccggctg cagctggtag ttaagagagc tgcagctgcc gtcctcccgg   1980
agcagggggg ccacctcgtt cagcatatcc ctgacgtgga tgttctccct gaccaattcc   2040
gccagaaggc gctcgccgcc cagcgaaagc agctcttgca aggaagcaaa attttttcagc  2100
ggttttaggc cgtcggccgt gggcatgttt ttcagcgtct gggtcagcag ttccagcctg   2160
tcccacagct cggtgatgtg ctctacggca tcgatccca gcagatctcc tcgtttccga   2220
ggttggggcg gctttcgctg tagggcacca gccgatgggg gtccagcggg ccagagtca    2280
tgtccttcca tgggcgcagg gtcctcgtca gggtggtctg ggtcacggtg aagggggtgcg   2340
ctccggggttg ggcgctggcc agggtgcgct tgaggctggt tctgctggtg ctgaatcgct   2400
gccgctcttc gccctgcgcg tcggccaggt agcatttgac catggtctcg tagtcgagac   2460
cctggggggc gtgcccccttg gcgcggagct tcccttgga ggtggcgcca cacgagggc    2520
actgcaggct cttcagggcg tagagcttgg gagcagagaa cacggactct ggggagtagg   2580
cgtccgcgcc gcaggaagcg cagaccgtct cgcattccac cagccaagtg agctccgggc   2640
ggtcagggtc aaaaaccagg ttgccccat gcttttttgat gcgtttctta cctcggctct   2700
ccatgaggcg gtgtcccttc tcggtgacga agaggctgtc cgtgtccccg tagaccgact   2760
tcagggcgt gtcttccagc ggagtgcctc tgtcctcctc gtagagaaac tctgaccact   2820
ctgagacgaa ggcccgcgtc caggccagga cgaaggaggc cacgtgggag gggtagcggt   2880
cgttgtccac tagcgggtcc accttctcca gggtgtgcag gcacatgtcc cctcctccg    2940
cgtccagaaa agtgattggc ttgtaggtgt aggacacgtg accgggggtt cccgacgggg   3000
gggtataaaa ggggtgggc gcccttcat cttcactctc ttccgcatcg ctgtctgcga    3060
gggccagctg ctggggtaag tattccctct cgaaggcggg catgacctca gcgctcaggt   3120
```

```
tgtcagtttc taaaaatgag gaggatttga tgttcacctg tccggaggtg atacctttga   3180
gggtacctgg gtccatctgg tcagaaaaca ctattttttt gttgtcaagc ttggtggcga   3240
acgacccgta gagggcgttg gagagcagct tggcgatgga gcgcaggtc tggttttttgt   3300
cgcggtcggc tcgctccttg gccgcgatgt tgagttgcac gtactcgcgg gccacgcact   3360
tccactcggg gaagacggtg gtgcgctcgt ctgggattag cgcaccctc cagcctcggt   3420
tgtgcagggt gaccatgtcg acgctggtgg cgacctcgcc gcgcaggcgc tcgttggtcc   3480
agcagaggcg gccgcccttg cgcgagcaga agggggtag ggggtccagc tggtcctcgt   3540
ttgggggtc cgcgtcgatg gtgaagaccc cggggagcaa gcgcgggtca aagtagtcga   3600
tcttgcaagc ttgcatgtcc agagcccgct gccattcgcg ggcggcgagc gcgcgctcgt   3660
aggggttgag gggcgggccc cagggcatgg ggtgggtgag cgcggaggcg tacatgccgc   3720
agatgtcata cacgtacagg ggttccctga ggatgccgag gtaggtgggg tagcagcgcc   3780
ccccgcggat gctggcgcgc acgtagtcat agagctcgtg ggaggggcc agcatgttgg   3840
gcccgaggtt ggtgcgctgg gggcgctcgg cgcggaaggc gatctgcctg aagatggcat   3900
gggagttgga ggagatggtg ggccgctgga agacgttgaa gcttgcttct tgcaagccca   3960
ccgagtccct gacgaaggag gcgtaggact cgccgcagct tgtgccagc tcggcggtga   4020
cctggacgtc gagcgcgcag tagtcgaggg tctcgcggat gatgtcatac ttatcctccc   4080
ccttctttt ccacagctcg cggttgagga cgaactcttc gcggtctttc cagtactctt   4140
ggagggaaa ccgtccgtg tccgaacggt aagagcctag catgtagaac tggttgacgg   4200
cctggtaggg gcaacagccc ttctccacgg gcagcgcgta ggcctgcgcc gccttgcgca   4260
gggaggtgtg ggtgagggcg aaagtgtccc tgaccatgac tttgaggtat tgatgtttga   4320
agtctgtgtc atcgcagccg ccctgttccc acagggtgta gtccgtgcgc ttttttggagc   4380
gcgggttggg cagggagaag gtgaggtcat tgaagaggat cttccccgct cgaggcatga   4440
agtttctggt gatgcgaaag ggccctggga ccgaggagcg gttgttgatg acctgggcgg   4500
ccaggacgat ctcgtcaaag ccgtttatgt tgtggcccac gatgtagagc tccaaaaagc   4560
ggggctggcc cttgatggag gggagctttt tgagttcctc gtaggtgagc tcctcggggcg   4620
attccaggcc gtgctcctcc agggcccagt cttgcaagtg agggttgcc gccaggaagg   4680
atcgccagag gtcgcgggcc atgggggtct gcaggcggtc gcggaaggtt ctgaactgtc   4740
gccccacggc catcttttcg ggggtgatgc agtagaaggt gaggggtct ttctcccagg   4800
ggtcccatct gagctctcgg gcgaggtcgc gcgcggcggc gaccagagcc tcgtcgcccc   4860
ccagtttcat gaccagcatg aagggcacga gctgcttgcc aaaagctccc atccaagtgt   4920
aggtctctac atcgtaggtg acaaagaggc gctccgtgcg aggatgagag ccgatcggga   4980
agaactggat ctcccgccac cagttggagg attggctgtt gatgtggtga aagtagaagt   5040
cccgtctgcg ggccgagcac tcgtgctggc ttttgtaaaa gcgaccgcag tactggcagc   5100
gctgcacggg ttgtatatct tgcacgaggt gaacctggcg acctctgacg aggaagcgca   5160
gcgggaatct aagtcccccg cctgggggtcc cgtgtgggtg gtggtcttct actttggttg   5220
tctggccgcc agcatctgtc tcctggaggg cgatggtgga gcagaccacc acgccgcgag   5280
agccgcaggt ccagatctcg gcgctcggcg ggcggagttt gatgacgaca tcgcgcacat   5340
tggagctgtc catggtctcc agctcccgcg gcggcaggtc agctgggagt tcctggaggt   5400
tcacctgca gagacgggtc aaggcgcggg cagtgttgag atggtatctg atttcaaggg   5460
gcgtgttggc ggcggagtcg atggcttgca ggaggccgca gccccggggg gccacgatgg   5520
ttccccgcgg ggcgcgaggg gaggcggaag ctggggtgt gttcagaagc ggtgacgcgg   5580
gcgggccccc ggaggtaggg ggggttccgg ccccacaggc atgggcggca ggggcacgtc   5640
ttcgccgcgc gcgggcaggg gctggtgctg gctccgaaga gcgcttgct ggcgacgac   5700
gcgacggttg gtgtcctgta tctgacgcct ctgagtgaag accacgggtc ccgtgacctt   5760
gaacctgaaa gagagttcga cagaatcaat ctcggcatcg ttgacagcgg cctggcgcag   5820
gatctcctgc acgtcgcccg agttgtcctg gtaggcgatc tctgccatga actgctcgat   5880
ctcttcttcc tggagatctc ctcgtccggc gcgctccacg gtggccgcca ggtcgttgga   5940
gatgcgaccc atgagctgtg agaaggcgtt gagcccgccc tcgttccaga cccggctgta   6000
gaccacgccc cctcggcgt cgcgagcgcg catgaccacc tgggccaggt tgagctccac   6060
gtgtcgcgtg aagacggcgt agttgcgcag gcgctggaaa aggtagttca gggtggtggc   6120
ggtgtgctcg gcgacgaaga agtacatgac ccagcgccgc aacgtggatt cattgatgtc   6180
ccccaaggcc tccaggcgct ccatggcctc gtagaagtcc acggcgaagt tgaaaaactg   6240
ggagttgcga gcggacacgg tcaactcctc ctccagaaga cggatgagct cggcgacagt   6300
gttgcgcacc tcgcgctcga aggccacggg gggcgcttct tcctcttcca cctcttcttc   6360
catgatcgct tcttcttctt cctcagccgg gacgggaggg ggcgcggcg gggggggagg   6420
ggcgcggcgg cggcggcggc cgcaccggag gcggtcgatg aagcggctcga tcatctcccc   6480
ccgcatgcgg cgcatggtct cggtgacggc gcggccgttc tccgggggc gcagctcgaa   6540
gacgccgcct ctcatctcgc gcgggggcga gcggccgtga ggtagcgaga cggcgctgac   6600
tatgcatctt aacaattgct gtgtaggtac accgccgagg gacctgattg agtccagatc   6660
caccggatcc gaaaacccttt ggaggaaagc gtctatccag tcgcagtcgc aaggtaggct   6720
gagcaccgtg gcgggcgggg gcgggtctgg agagttcctg gcgagatgc tgctgatgat   6780
gtaattaaag taggcggtct tgagaaggcg gatggtggac aggagcacca tgtctttggg   6840
tccggcctgt tggatgcgga ggcggtcggc catgcccag gcctcgttct gacaccggcg   6900
caggtcttg tagtagtctt gcatgagtct tccaccgag acctcttctc cttccttcttc   6960
tccatctcgc cggtggttc tcgcgccgcc catgcgcgtg acccccaaagc ccctgagccg   7020
ctgcagcagg gccaggtcgg cgaccacgcg ctcggccaag atggcctgct gcacctgagt   7080
gagggtcctc tcgaagtcat ccatgtccac gaagcggtgg taggcgcccg tgttgatggt   7140
gtaggtgcag ttggccatga cggaccagtt gacggtctgg tgtcccggct gcgagagctc   7200
cgtgtaccgc aggcgcgaga aggcgcggga atcgaacacg tagtcgttgc aagtccgcac   7260
cagatactgg tagcccacca ggaagtgcgg cggaggttgg cgatagaggg gccagcgctg   7320
ggtggcgggg gcgccgggcg ccaggtcttc cagcatgagg cggtggtatc cgtagatgta   7380
cctgacatc caggtgatgc cggcggcggt ggtggtggcg cgcgcgtagt cgcggacccg   7440
gttccagatg tttcgcaggg gcgagaagtg ttccatggtc ggcacgctct ggccggtgag   7500
gcgcgcgcag gcgttgcgc tctatacaca cacaaaaacg aaagcgttta cagggcttc   7560
gttctgtagc ctggaggaaa gtaaatgggt tgggttgcgg tgtgcccggg ttcgagacca   7620
agctgagctc ggccggctga agccgcagct aacgtggtat tggcagtccc gtctcgaccc   7680
aggccctgta tcctccagga tacggtcgag agccctttg cttctttggc caagcgcccc   7740
tggcgcgatc tgggatagat ggtcgcgatg agaggacaaa agcggctcgc ttccgtagtc   7800
tggagaaaca atcgccaggg ttgcgttgcg gcgtaccccg gttcgagccc ctatggcggc   7860
```

```
ttgaatcggc cggaaccgcg gctaacgagg gccgtggcag ccccgtcctc aggaccccgc  7920
cagccgactt ctccagttac gggagcgagc ccctttgtt ttttatttt tagatgcatc  7980
ccgtgctgcg gcagatgcgc ccctcgcccc ggcccgatca gcagcagcaa cagcaggcat  8040
gcagaccccc ctctcccctt tccgcccgg tcaccacggc cgcggcggcc gtgtcgggcg  8100
cggggggcgc gctggagtca gatgagccac cgcggcggcg acctaggcag tatctggact  8160
tggaagaggg cgagggactg gcgcggctgg gggcgaactc tccagagcgc caccgcggg  8220
tgcagttgaa aagggacgcg cgcgaggcgt acctgccgcg gcagaacctg tttcgcgacc  8280
gcggggcga ggagccgag gagatgcgag actgcaggtt ccaagcgggg cgcgagctgc  8340
ggcgcgggct ggacagacag cgcctgctgc gcgaggagga ctttgagccc gacacgcaga  8400
cgggcatcag cccgcgcgc gcgcacgtag ccgcggccga cctggtgacc gcctacgagc  8460
agacggtaaa ccaggagcgc aacttccaaa agagcttcaa caaccacgtg cgcacgctgg  8520
tggcgcgcga ggaggtgacc ctgggtctca tgcatctgtg ggacctggtg gaggcgatcg  8580
tgcagaaccc cagcagcaag cccctgaccg cgcagctgtt cctggtggtg cagcacagca  8640
gggacaacga ggccttcagg gaggcgctgc tgaacatgca ggaccggag ggggcgctgc  8700
tcctggacct gataaacatc ctgcagagca tagtggtgca ggagcgcagc ctgagcctgg  8760
ccgagaaggt ggcggccatc aactactcta tgctgagcct gggcaagttc tacgcccgca  8820
agatctacaa gaccccctac gtgcccatag acaaggaggt gaagatagac agcttctaca  8880
tgcgcatggc gctgaaggtg ctgaccctga gcgacgacct gggagtgtac gcgaacgagc  8940
gcatccacaa ggccgtgagc gccagccggc ggcgcgacct gagcgaccgc gagctgatgc  9000
acagtctgca gcgcgcgctg accggcgcgg gcgagggcga cagggaggtc gagtcctact  9060
tcgacatggg ggccgacctg cactggcagc cgagccgccg cgcctggag gcggcgggg  9120
cgtacggcgg cccctggcg gccgatgacc aggaagagga ggactatgag ctagaggagg  9180
gcgagtacct ggaggactga cctggctggt ggtgttttgg tatagatgca agatccgaac  9240
gtggcggacc cggcggtccg ggcggcgctg caaagccagc cgtccggcat taactcctct  9300
gacgactggg ccgcggccat gggtcgcatc atggccctga ccgcgcgcaa ccccgaggct  9360
ttcaggcagc agcctcaggc caaccggctg gcggccatct tggaagcggt agtgcccgag  9420
cgctccaacc ccacccacga gaaggtgctg gccatagtca acgcgctggc ggagagcagg  9480
gccatccgcg cggacgaggc cggactggtg tacgatgcgc tgctgcagcg ggtggcgcgg  9540
tacaacagcg gcaacgtgca gaccaacctg gaccgcctgg tgacggacgt gcgcgaggcc  9600
gtggcgcagc gcgagcgctt gcatcaggac ggtaacctgg gctcgctggt ggcgctaaac  9660
gccttcctca gcacccagcc ggccaacgta ccgcggggc aggaggacta caccaacttt  9720
ttgagcgcgc tgcggctgat ggtgaccgag gtccctcaga gcgaggtgta ccagtcgggg  9780
cccgactact tcttccagac cagcagacag ggcttgcaaa ccgtgaacct gagccaggct  9840
ttcaagaacc tgcgggggct gtggggagtg aaggcgccca cccgcgaccg ggctacggtg  9900
tccagcctgc taaccccaa ctcgcgcctc ctgctgctac tgatcgcgcc cttcacggac  9960
agcgggagcg tctcgcggga gacctatctg ggccacctgc tgacgctgta ccgcgaggcc 10020
atcgggcagg cgcaggtgga cgagcacacc ttccaagaga tcaccagcgt gagccacgcg 10080
ctggggcagg aggacacggg cagcctgcag gcgaccctga actacctgct gaccaacagg 10140
cggcagagaa ttcccacgct gcacagcctg acccaggagg aggagcgcat cttgcgctac 10200
gtgcagcaga gcgtgagcct gaacctgatg cgcgacgcg tgacgcccag cgtggcgctg 10260
gacatgaccg cgcgcaacat ggaaccgggc atgtacgcct cccaccggcc gtttatcaac 10320
cgcctgatgg actacttgca tcgggcgcg ccgtgaacc ccgagtactt cactaatgcc 10380
attctgaatc cccactggat gccccctccg ggtttctaca acgggacctt tgaggtgccc 10440
gaggtcaacg acgggttcct ctgggatgac atggatgaca gtgtgttctc acccaacccg 10500
ctgcgcgccc cgtctctgcg attgaaggag ggctctgaca gggaaggacc gaggagtctg 10560
gcctcctccc tggctctggg agcggtgggc gccacgggcg cggcggcgcg gggcagtagc 10620
cccttcccca gcctggcaga ctctctgaac agcggcggg tgacaggcc ccgcttgcta 10680
ggcgaggagg agtatctgaa caactccctg ctgcagcccg cgaggacaa gaacgctcag 10740
cggcagcagt ttcccaacaa tgggatagag agccggtgg acaagatgtc cagatggaag 10800
acgtatgcgc aggagtacaa ggagtgggag gaccgccagc cgcggccctt gccgcccctt 10860
aggcagcgct ggcagcgcg cgcgtccaac cgccgctggg ggcaggggcc cgaggacgat 10920
gatgactctg cagatgacag cagcgtgttg gacctgggcg ggagcgggaa ccccttttcg 10980
cacctgcgcc cacgcctggg caagatgttt aaaagaaaa aaaaataaa actcaccaag 11040
gccatggcga cgagcgttgg ttttttgttc ccttccttag tatgcggcgc gcggcgatgt 11100
tcgagggggg gcctcccccc tcttacgaga gcgcgatggg gatttctcct gcggcgcccc 11160
tgcagcctcc ctacgtgcct cctcggtacc tgcaacctac agggggagaa aatagcatct 11220
gttactctga gctgcagccc ctgtacgata ccaccagact gtacctggtg gacaacaagt 11280
ccgcggacgt ggcctccctg aactaccaga acgaccacag cgatttttg accacgtga  11340
tccaaaacaa cgacttcacc ccaaccgagg ccagcaccca gaccataaac tggataaca  11400
ggtcgaactg gggcggcgac ctgaagacca tcttgcacac caacatgccc aacgtgaacg 11460
agttcatgtt caccaactct tttaaggcgc gggtgatggt ggcgcgcgag cagggggagg 11520
cgaagtacga gtgggtggac ttcacgctgc ccgagggcaa ctactcagag accatgactc 11580
tcgacctgat gaacaatgcg atcgtggaac actatctgaa agtgggcagg cagaacgggg 11640
tgaaggaaag cgatatcggg gtcaagtttg acaccagaaa cttccgtctg gcgtgggcc  11700
ccgtgaccgg gctggtcatg ccgggggtct acaccaacga ggcctttcat ccgacatag  11760
tgcttctgcc cggctgtggg gtggacttca cccagagccg gctgagcaac ctgctgggca  11820
ttcgcaagcg gcagcctttc caggagggtt tcaagatcac ctatgaggat ctgaaggggg  11880
gcaacattcc cgcgctcctt gatctggacg cctacgagga gagcttgaaa cccgaggaga  11940
gcgctggcga cagcggcgag agtggcgagg agcaagccgc cgggcgtggc ggcgcgtcgg  12000
tagaaaacga aagtacgccc gcagtggcgg cggacgctgc ggaggtcgca ccggaggcca  12060
tgcagcagga cgcagaggag ggcgcacagg agggcgcgca gaaggacatg aacgatgggg  12120
agatcagggg agacacattc gccacccggg gcgaagaaaa agaggcagag gcggcggcgg  12180
cggcgacggc ggaggccgaa accgaggttg aggcagaggc agagcccgag accgaagtta  12240
tggaagacat gaatgatgga gaactagggg gcgacacggt cgcacccgg ggcgaagaga  12300
aggcggcgga ggcagaagcc gcggctgagg aggcggctgc ggctgcgcc aagactgagg  12360
ctgcggctaa ggctgaggtc gaagccaatg ttgcggttga ggctcaggct gaggaggagg  12420
cggcggctga agcagttaag gaaaaggccc aggcagagca ggaagagaaa aaacctgtca  12480
ttcaacctct aaaagaagat agcaaaaagc gcagttacaa cgtcatcgag ggcagcacct  12540
ttacccagta ccgcagctgg tacctggcgt acaactacgg cgacccggtc aagggggtgc  12600
```

```
gctcgtggac cctgctctgc acgccggacg tcacctgcgg ctccgagcag atgtactggt    12660
cgctgccgaa catgatgcaa gacccggtga ccttccgctc cacgcggcag gttagcaact    12720
tcccggtggt gggcgccgaa ctgctgcccg tgcactccaa gagttttttac aacgagcagg   12780
ccgtctactc ccagctgatc cgccaggcca cctctctgac ccacgtgttc aatcgctttc    12840
ccgagaacca gattttgcg cgcccgccgg ccccaccat caccaccgtg agtgaaaacg       12900
ttcctgccct cacagatcac gggacgctac cgctgcgcaa cagcatctca ggagtccagc    12960
gagtgaccat tactgacgcc agacgccgga cctgcccta cgtttacaag gccttgggca     13020
tagtctcgcc gcgcgtcctc tccagtcgca cttttttaaaa cacatctacc cacacgttcc   13080
aaaatcatgt ccgtactcat ctcacccagc aacaacaccg gctgggggct gcgcgcgccc    13140
agcaagatgt ttggagggc gaggaagcgc tccgaccagc accctgtgcg cgtgcgcggc     13200
cactaccgcg cgcccgggg agcgcacaag cgcgggcgca cagggcgcac cactgtggac     13260
gacgtcattg actccgtagt ggagcaagcg cgccactaca cacccggcgc gccgaccgcc    13320
cccgccgtgt ccaccgtgga ccaggcgatc gaaagcgtgg tacagggcgc gcggcactat    13380
gccaaccta aaagtcgccg ccgccgcgtg gcccgccgc atcgccggag accccgggcc      13440
accgccgccg cgcgccttac taaggctctg ctcaggcgcg ccaggcgaac tggccaccgg    13500
gccgccatga gggccgcacg gcgggctgcc gctgccgcaa gcgtcgtggc cccgcgggca    13560
cgaaggcgcg cggccgctgc cgccgccgcc gccatttcca gcttggcctc gacgcggcgc    13620
ggtaacatat actgggtgcg cgactcggta accggcacgc ggatacccgt gcgctttcgc    13680
cccccgcgga attagcacaa gacaacatac acactgagtc tcctgctgtt gtgtatccca    13740
gcggcgaccg tcagcagcgg cgacatgtcc aagcgcaaaa ttaaagaaga gatgctccag    13800
gtcatcgcgc cggagatcta tgggcccccg aagaaggagg aggatgatta caagcccgcg   13860
aagctaaagc gggtcaaaaa gaaaaagaaa gatgatgatg acgaggcgct ggagtttgtc    13920
cgccgcatgg cacccaggcg ccccgtgcag tggaagggcc ggcgcgtgca gcgcgttttg    13980
cgccccggca ccgcggtggt cttcacgccc ggcgagcgct ccacgcgcac tttcaagcgg    14040
gtgtacgatg aggtgtacgg cgacgaggac ctgttggagc aggccaacca gcgctttggg    14100
gagtttgcat atgggaaacg gccccgcgag agtctaaaag aggacctgct ggcgctaccg    14160
ctggacgagg gcaatcccac cccgagtctg aagccggtaa ccctgcaaca ggtgctgcct    14220
ttgagcgcgc ccagcgagca taagcgaggg ttgaagcgcg aaggcgggga cctggcgccc   14280
accgtgcagt tgatggtgcc caagcggcag aagctggagg acgtgctgga gaaaatgaaa   14340
gtagagcccg ggatccgacc cgagatcaag gtcccgcca tcaagcaggt ggcgcccggc     14400
gtgggagtcc agaccgtgga cgttaggatt cccacgcgagg agatggaaac ccaaaccgcc    14460
actccctctt cggcggccag cgccaccacc ggcaccgctt cggtagaggt gcagacggac    14520
ccctggctac ccgccaccgc tgttgccgcc ccgccccccc gttcgcgcgg gcgcaagaga    14580
aattatccag cggccagcgc gctcatgccc cagtacgcac tgcatccatc catcgtgccc    14640
acccccggct accgcgggta ctcgtaccgc ccgcgcagat cagccggcac tcgcggccgc    14700
cgccgccgtg cgaccacaac cagccgccgc cgtcgccgcc gccgccagcc agtgctgacc    14760
cccgtgtctg taaggaaggt ggctcgctcg gggagcacgc tggtggtgcc cagagcgcgc    14820
taccacccca gcatcgtttta aagccggtct ctgtatggtt cttgcagata tggccctcac   14880
ttgtcgcctc cgcttcccgg tgccgggata ccgaggaaga actcaccgcc gcagaggcat    14940
ggcgggcagc ggtctccgcg gcggccgtcg ccatcgccgg cgcgcaaaaa gcaggcgcat    15000
gcgcggcggt gtgctgcctc tgctaatccc gctaatcgcc gcggcgatcg gtgccgtacc    15060
cgggatcgcc tccgtggccc tgcaggcgtc ccagaaacgt tgactcttgc aaccttgcaa    15120
gcttgcattt tttggaggaa aaataaaaaa aagtctagac tctcacgctc gcttggtcct    15180
gtgactattt tgtagaaaaa aagatgcaag acatcaactt tgcgtcgctg gccccgcgtc    15240
acggctcgcg cccgttcatg ggagactgga cagatatcgg caccagcaat atgagcggtg    15300
gcgccttcag ctggggcagt ctgtggagcg gccttaaaaa ttttggttcc accattaaga    15360
actatggcaa caaagcgtgg aacagcagca cgggccaagc gctgagagac aagttgaaag    15420
agcagaactt ccaggagaag gtggcgcagg gcctggcctc tggcatcagc gggggtggtgg   15480
acatagctaa ccaggccgtg cagaaaaaga taaacagtca tctggacccc cgtcctcagg    15540
tggaggaaat gcctccagcg atggagacgg tgtctcccga gggcaaaggc gaaaagcgcc    15600
cgcggcccga cagagaagag accctggtgt cacacaccgg ggagccgcc tcttacgagg     15660
aggcagtcaa ggccggcctg cccaccactc gccccatagc cccatggcc accggtgtgg    15720
tgggccacag gcaacacact cccgcaacac tagatctgcc ccgccgtcc gagccgccgc     15780
gccagccaaa ggcggcgacg gtgccgcctc cctccacttc cgccgccaac agagtgcccc    15840
tgcgccgcgc cgcgagcggc ccccgggcct cgcgagttag cggcaactgg cagagcacac    15900
tgaacagcat cgtgggcctg ggagtgagga gtgtgaagcg ccgccgttgc tactgaatga    15960
gcaagctagc taacgtgttg tatgtgtgta tgcgtcctat gtcgccgcca gaggagctgt    16020
tgagccgccg cgcgcgtctg cactccagcg aatttcaaga tggcgacccc atcgatgatg    16080
cctcagtggt cgtacatgca catctgggc caggacgctt cggagtacct gagcccgggg    16140
ctggtgcagt tcgccgcgc cacagacacc tacttcaaca tgactaacaa gttcaggaac    16200
cccactgtgg cgcccaccca cgatgtgacc acggaccggt cgcagcgcct gacgctgcgg    16260
ttcatcccg tggatcggga ggacaccgcc tactcttaca aggcgcggtt cacgctggcc    16320
gtgggcgaca accgcgtgct ggacatggcc tccacttact ttgacatcag gggggtgctg    16380
gacaggcccg ccaccttcaa gccctactcg ggtactgcct acaactccct ggccctccaa    16440
ggcgctccca attcttgcga gtgggaacaa gatgaaccag ctcaggcagc aatagctgaa    16500
gatgaagaag aacttgaaga agaacaagct caggacgaac aggcgcccac taagaaaacc    16560
catgtatacg cccaggcacc tctttctggt gaaaaaatta ctaaggatgg tttgcaaata    16620
ggtgtggatg ccacacaggc gggagataac cctatatatg ctgataaaac attccaaccc    16680
gaacctcaga taggtgagtc tcagtggaac gaggctgagt gccagtagc aggaggcaga    16740
gtcttaaaaa agaccacccc tatgagacct tgctatggat cctatgccaa acctactaat    16800
gccaatggcg gtcaagggat catggtggcc aatgatcagg gagcgcttga atctaaagtt    16860
gagatgcaat ttttctccac cacaacgtct cttaatgtaa gggaaggtga aaacaatctt    16920
cagccaaaag tagtgctata cagcgaagat gttaacttgg aatcccctga cactcatttg    16980
tcttacaaac ctaaaaagga tgacaacaac tctaaaatca tgttgggtca gcaagccatg    17040
cccaacagac ccaacctcat tgcttttagg gacaacttta ttggacttat gtactacaac    17100
agcacaggca catgggagt gctggcagga caggcctccc agctaaacgc tgtggtagac    17160
ttgcaagaca gaaacacaga gctgtcatac caactgatgc ttgattccat ggagacagga    17220
tcaagatact tttccatgtg gaaccaggca gtggacagct atgacccaga tgtcagaatc    17280
attgaaaacc atgggggttga agatgagctg cccaactatt gctttccct gggcggtatt    17340
```

```
ggaattacag acacatacca gtgcataaaa ccaaccgcag ctgctaataa cactacatgg   17400
tctaaggatg aagaatttag tgatcgcaat gaaatagggg tgggaaacaa cttcgccatg   17460
gagatcaaca tccaggccaa cctctggagg aacttcctct atgcgaacgt ggggctctac   17520
ctgccagaca agctcaagta caaccccacc aacgtggaca tctctgacaa ccccaacacc   17580
tatgactaca tgaacaagcg tgtggtggct cccggcctgg tggactgctt tgtcaatgtg   17640
ggagccaggt ggtccctgga ctacatggac aacgtcaacc ccttcaacca ccaccgcaat   17700
gcgggtctgc gctaccgctc catgatcctg ggcaacgggc gctacgtgcc cttccacatt   17760
caggtgcccc agaagttctt tgccatcaag aacctcctcc tcctgccggg ctcctacact   17820
tacgagtgga acttcaggaa ggatgtcaac atggtcctgc agagctctct gggcaatgac   17880
cttagggtgg acggggccag catcaagttt gacagcgtca ccctctatgc taccttcttc   17940
cccatggctc acaacaccgc ctccacgctc gaggccatgc tgaggaacga caccaacgac   18000
cagtccttca atgactacct ctctggggcc aacatgctct accccatccc cgccaaggcc   18060
accaacgtgc ccatctccat tccctctcgc aactgggccg ccttcagagg ctgggccttt   18120
acccgcctta agaccaagga aacccctcc ctgggctccg gttttgaccc ctactttgtc   18180
tactcgggat ccatccccta cctggatggc accttctacc tcaaccacac tttaagaag   18240
atatccatca tgtatgactc ctccgtcagc tggccgggca atgaccgcct gctcaccccc   18300
aatgagttca aggtcaagcg cgccgtggac ggcgagggct acaacgtggc ccagtgcaac   18360
atgaccaagg actggttcct ggtgcagatg ctggccaact acaacatagg ctaccagggc   18420
ttctacatcc cagagagcta caaggacagg atgtactcct tcttcagaaa tttccaaccc   18480
atgagcaggc aggtggtgga cgagaccaaa tacaaggact atcaggccat ggcatcact   18540
caccagcaca acaactcggg attcgtgggc tacctggctc ccaccatgcg cgaggggcag   18600
gcctacccccg ccaacttccc ctacccgttg ataggcaaaa ccggtgtgca cagcgtcaac   18660
cagaaaaagt tcctctgcga ccgcacctc tggcgcatcc ccttctctag caacttcatg   18720
tccatgggtg cgctcacgga cctgggccag aacctgctct atgccaactc cgccatgcg   18780
ctggacatga cttttgaggt ggaccccatg acgagccca cccttctcta tattgtgttt   18840
gaagtgttcg acgtggtcag agtgcaccag ccgcaccgcg gtgtcatcga gaccgtgtac   18900
ctgcgcacgc ccttctcggc cggcaacgcc accacctaag agacagcgc cgccgcctgc   18960
atgacgggtt ccaccgagca agagctcagg gccatcgcca gagacctggg atgcggaccc   19020
tattttttgg gcacctatga caaacgcttc ccgggcttca tctcccgaga caagctcgcc   19080
tgcgccatcg tcaacacggc cgcgcgcgag accggggcg tgcactggct ggcctttggc   19140
tgggaccccgc gctccaaaac ctgctacctc ttcgacccct ttggcttctc cgatcagcgc   19200
ctcagacaga tctatgagtt tgagtacgag gggctgctgc ccgcagcgc gcttgcctcc   19260
tcgcccgacc gctgcatcac ccttgagaag tccaccgaga ccgtgcaggg gccccactcg   19320
gccgcctgcg gtctcttctg ctgcatgttt ttgcacgcct ttgtgcgctg gcccccagagt   19380
cccatggatc gcaaccccac catgaacttg ctcaaggagg tgcccaacgc catgctccag   19440
agcccccagg tccagcccac cctgcgccac aaccaggaac agctctaccg cttcctggag   19500
cgccactccc cctacttccg cagtcacagc gcgcacatcc gggggccccac ctctttctgc   19560
cacttgcaag aaaaatgca agacggaaaa tgatgtacag ctcgcttttt aataaatgta   19620
aagactgtgc actttattta tacacgggct cttttctggtt atttattcaa caccgccgtc   19680
gccatctaga aatcgaaagg gttctgccgc gcgtcgccgt gcgccacggg cagagacacg   19740
ttgcgatact ggaagcggct cgcccactta aactcgggca ccaccatgcg gggcagtggt   19800
tcctcgggga agttctcgcc ccacagggtg cgggtcagct gcagcgcgct caggaggtcg   19860
ggagccgaga tcttgaagtc gcagttgggg ccggaaccct gcgcgcgga gttgcggtac   19920
acggggttgc agcactggaa caccagcagg gccggattat gcacgctggc cagcaggctc   19980
tcgtcgctga tcatgtcgct gtccagatcc tccgcgttgc tcaggggaa cggggtcatc   20040
ttgcagacct gcctgcccag gaaaggcggc agcccgggct tgccgttgca gtcgcagcgc   20100
aggggcatca gcaggtgccc gcggcccgac tgcgcctgcg ggtacagcgc gcgcatgaag   20160
gcttcgatct gcctgaaagc cacctgcgtc ttggctccct ccgaaaagaa catcccacag   20220
gacttgctgg agaactggtt cgcgggacag ctggcatcgt gcaggcagca gcgcgcgtcg   20280
gtgttggcga tctgcaccac gttgcgaccc caccggttct tcactatctt ggccttggaa   20340
gcctgctcct tcagcgcgcg ctgccgttc tcgctggtca catccatctc tatcacctgc   20400
tccttgttga tcatgtttgt accgtgcaga cacttcaggt cgccctccgt ctgggtgcag   20460
cggtgctccc acagcgcgca accggtgggc tcccaatttt tgtgggtcac cccgcgtag   20520
gcctgcaggt aggcctgcaa gaagcgcccc atcatggcca caaggtctt ctggctcgta   20580
aaggtcagct ggcagcgcg atgctcttcg ttcagccagg tcttgcagat ggcggccagc   20640
gcctcggtct gctcgggcag catcctaaaa tttgtcttca ggtcgttatc cacgtgtac   20700
ttgtccatca tggcgcgcgc cgcctccatg cccttctccc aggcggacac catgggcagg   20760
cttagggggt ttatcacttc caccggcgag gacaccgtac tttcgatttc ttcttcctcc   20820
ccctcttccc ggcgcgcgcc cacgctgctg cgcgctctca ccctgcacc caaggggtcg   20880
tcttcaggca agccgccgcac cgagcgcttg ccgccttga cctgcttaat cagcaccggc   20940
gggtgctga agcccaccat ggtcagcgcc gcctgctctt cttcgtcttc gctgtctacc   21000
actatctctg gggaagggct ctccgctct cgggcggcgc gcttctttt ttcttggga   21060
gcggccgtga tggagtccgc cacggcgacg gaggtcgagg gcgtgggct gggggtgcgc   21120
ggtaccaggg cctcgtcgcc ctcggactct tcctctgacg tccaggcggcg cggagtcgg   21180
ttctttgggg gcgcgcgcgt cagcggcggc ggagacgggg acgggacgg ggacgggacg   21240
ccctccacag ggggtggtct tcgcgcagac ccgcggccgc gctcgggggt cttctcgagc   21300
tggtcttggt cccgactggc cattgtatcc tcctcctcct aggcagagag acataaggag   21360
tctatcatgc aagtcgagaa ggaggagagc ttaaccaccc cctctgagac cgccgatgcg   21420
cccgccgtcg ccgtcgcccc cgctgccgcc gacgcgcccg ccacaccgag cgacaccccc   21480
gcggaccccc ccgccgacgc accccctgtt c gaggaagcgg ccgtggagca ggacccgggc   21540
tttgtctcgg cagaggagga tttgcgagag gaggaggata aggagaagaa gccctcagtg   21600
ccaaaagatg ataaagagca agacgagcac gacgcagatg cacaccaggg tgaagtcggg   21660
cggggggacg gagggcatga cggcgccgac tacctagacg aagggaacga cgtgctcttg   21720
aagcacctgc atcgtcagtg cgccattgtt tgcgacgtc tgcaggagcg cagcgaagtg   21780
ccccctcagc tggcgaggt cagccacgcc tacgagctca gcctcttctc ccccgggtg   21840
cccccccgcc gccgcgaaaa cggcacatgc gagcccaacc cgcgcctcaa cttctacccc   21900
gcctttgtgg tacccgaggt cctggccacc tatcacatct tctttcaaaa ttgcaagatc   21960
cccctctcgt gccgcgccaa ccgtagccgc gccgataaga tgctggccct gcgccaggc   22020
gaccacatac ctgatatcgc cgctttggaa gatgtaccaa agatcttcga gggtctggt   22080
```

```
cgcaacgaga agcgggcagc aaactctctg caacaggaaa acagcgaaaa tgagagtcac   22140
accggggtac tggtggagct cgagggcgac aacgcccgcc tggcggtggt caagcgcagc   22200
atcgaggtca cccactttgc ctaccccgcg ctaaacctgc cccccaaagt catgaacgcg   22260
gccatggacg ggctgatcat cgccgcggc cggcccctcg ctccagatgc aaacttgcat    22320
gaggagaccg aggacggcca gcccgtggtc agcgacgagc agctggcgcg ctggctggag   22380
accgcggacc ccgccgaact ggaggagcgg cgcaagatga tgatggccgt ggtgctggtc   22440
accgtagagc tggagtgtct gcagcgcttc ttcggcgacc ccgagatgca gagaaaggtc   22500
gaggagaccc tgcactacac cttccgccag ggctacgtgc gccaggcttg caagatctcc   22560
aacgtggagc tcagcaacct ggtgtcctac ctgggcatct tgcatgagaa ccgcctcggg   22620
cagagcgtgc tgcactccac cctgcgcggg gaggcgcgcc gcgactacgt gcgcgactgg   22680
gtttacctct tcctctgcta cacctggcag acggccatgg gggtctggca gcagtgcctg   22740
gaggagcgca acctcaagga gctggagaag ctcctgcagc gcgcgctcaa agatctctgg   22800
acgggctaca acgagcgctc ggtggccgcc gcgctggccg acctcatctt cccgagcgc   22860
ctgctcaaaa ccctccagca ggggctgccc gacttcacca gccaaagcat gttgcaaaac   22920
ttcaggaact tatcctgga gcgttctggc atcctacccg ccacctgctg cgccctgccc    22980
agcgactttg tcccctcgt gtaccgcgag tgcccccgc cgctgtgggg tcactgctac    23040
ctgttccaac tggccaacta cctgtcctac cacgcggacc tcatggagga ctccagcggc   23100
gaggggctca tggagtgcca ctgccgctgc aacctctgca gccccaccg ctccctggtc    23160
tgcaacaccc aactgctcag cgagagtcag attatcggta ccttcgagct acagggtccg   23220
tcctcctcag acgagaagtc cgcggctccg gggctaaaac tcactccggg gctgtggact   23280
tccgcctacc tgcgcaaatt tgtacctgaa gactaccacg cccacgagat caggttttac   23340
gaagaccaat cccgcccgcc caaggcggag ctgaccgcct gcgtcatcac ccagggcgag   23400
atcctaggcc aattgcaagc catccaaaaa gcccgccaag acttttttgct gaagaagggt   23460
cgggggggtgt atctgaccc ccagtcgggt gaggagctca acccggttcc cccgctgccg   23520
ccgccgcggg accttgcttc ccaggataag catcgccatg gctcccagaa agaagcagca   23580
gcggccgcca ctgccgccac cccacatgct ggaggaagag gaggaatact gggacagtca   23640
ggcagaggag gttcggacg aggaggagc ggagacggag atggaagagt ggggaggagga   23700
cagcttagac gaggaggctt ccgaagccga agaggcagac gcaacaccgt caccctcggc   23760
cgcagcccc tcgcaggcgc ccccgaagtc cgctcccagc atcagcagca acagcagcgc   23820
tataacctcc gctcctccac cgccgcgacc cacggccgac cgcagaccca accgtagatg   23880
ggacaccacc ggaaccgggg ccggtaagtc ctccgggaga ggcaagcaag cgcagcgcca   23940
aggctaccgc tcgtggcgcg ctcacaagaa cgccatagtc gcttgcttgc aagactgcgg   24000
ggggaacatc tccttcgccc gccgcttcct gctcttccac cacggtgtgg ccttccccg    24060
taacgtcctg cattactacc gtcatctcta cagccctac tgcggcggca gtgagccaga    24120
gacggtcggc ggcggcgcg gcgcccgttt cggcgcctag gaagacccag ggcaagactt    24180
cagccaagaa actcgcggcg gccgcggcga acgcggtcgc gggggccctg cgcctgacgt    24240
tgaacgaacc cctgtcgacc cgcgaactga ggaaccgaat cttccccact ctctatgcca    24300
tcttccagca gagcagaggg caggatcagg aactgaaagt aaaaaacagg tctctgcgct   24360
ccctcaccg cagctgtctg tatcacaaga gcgaagacca gcttcggcgc acgctggagg   24420
acgctgaggc actcttcagc aaatactgcg cgctcactct taaggactag ctccgcgccc   24480
ttctcgaatt taggcgggaa cgcctacgtc atcgcagcgc cgccgtcatg agcaaggaca   24540
ttcccacgcc atacatgtgg agctatcagc cgcagatggg actcgcggcg ggcgcctccc   24600
aagactactc cacccgcatg aactggctca gtgccgggcc acacatgatc tcacaggtta   24660
atgatatccg cacccatcga aaccaaatat tggtggagca ggcggcaatt accaccacg    24720
cccgcaataa tcccaacccc agggagtggc ccgcgtccct ggtgtatcag gaaatttccg   24780
gccccaccac cgtactactt ccgcgtgatt cccaggccga agtccaaatg actaactcag   24840
gggcacgct cgcgggcggc tgtcgtcaca gggtgcggcc tcctcgccag ggtataactc   24900
acctggagat ccgaggcaga ggtattcagc tcaacgacga gtcggtgagc tcctcgctcg   24960
gtctcagacc tgacgggacc ttccagatag ccggagccgg ccgatcttcc ttcacgcccc   25020
gccaggcgta cctgactctg caaagctcgt cctcggcgcc gcgctcgggc ggcatcggga   25080
ctctccagtt cgtgcaggag tttgtgccct cggtctactt caacccctc tcggggctcg   25140
ccggtcgcta cccggaccag ttcatctcga actttgacgc cgcgagggac tcggtggacg   25200
gctacgactg aatgtcgggt ggacccggtg cagagcaact tcgcctgaag cacctcgacc   25260
actgccgccg ccctcagtgc tttgcccgct gtcagaccgg tgagttccag tactttccc    25320
tgcccgactc gcaccggac ggcccggcgc acggggtgcg cttttttcatc ccgagtcagg   25380
tgcgctctac cctaatcagg gagtttaccg cccgtcccct actggcgagg ttggaaaagg   25440
ggccttctat cctaaccatt gcctgcatct gctctaaccc tggattgcac caagatcttt    25500
gctgtcattt gtgtgctgag tataataaag gctgagatca gaatctactc gggctcctgt   25560
cgccatcctg tcaacgccac cgtccaagcc cggcccgatc agcccgaggt gaacctcacc   25620
tgcggtctgc accgcgcct gaggaaatac ctagcttggt actacaacag cactcccttt    25680
gtggtttaca acagctttga ccaggacggg gtctcactga gggataacct ctcgaacctg   25740
agctactcca tcaggaagaa cagcaccctc gagctacttc ctccttacct gcccgggact   25800
taccagtgtg tcaccggtcc ctgcacccac acccacctgt tgatcgtaaa cgactctctt   25860
ccgagaacag acctcaataa ctcctcttcg cagttcccca gaacaggagg tgagctcagg   25920
aaacccgggg taagaagggg tggacgagag ttaacacttg tgggtgttct ggtgtatgtg   25980
acgctggtgg tggctctttt gattaaggct tttccttcca tgtctgaact ctccctcttc   26040
ttttatgaac aactcgacta gtgctaacgg gaccctaccc aacgaatcgg gattgaatat   26100
cggtaaccag gttgcagttt cacttttgat taccttcata gtcctcttcc tgctagtgct   26160
gtcgcttctg tgcctgcgga tcggggggctg ctgcatccac gtttatatct ggtgctggct   26220
gtttagaagg ttcggagacc atcgcaggta gaataaacat gctgctgctt accctctttg   26280
tcctggcgct ggccgccagc tgccaagcct tttccgaggc tgactttata gagccccagt   26340
gtaatgtgac ttttaaagcc catgcacagc gttgtcatac tataatcaaa tgtgccaccg   26400
aacacgatga atacccttatc cagtataaag ataaatcaca caaagtggca cttgttgaca   26460
tctggaaacc cgaagaccct tttggaataca atgtgacggt tttccagggt gacctcttca   26520
aaatttacaa ttacacttc ccatttgacc agatgtgtga ctttgtcatg tacatggaaa    26580
agcagcacaa gctgtggcct ccgactcccc agggctgtgt ggaaaatcca ggctcttttct   26640
gcatgatctc tctctgtgta actgtgctgg cactaatact cacgcttttg tatatcgat    26700
ttaaatcaag gcaaagcttc attgatgaaa agaaatgcc ttaatcgctt tcacgcttga    26760
ttgctaacac cgggttttta tccgcagaat gattggaatc accctactaa tcacctccct   26820
```

```
ccttgcgatt gcccatgggt tggaacgaat cgaagtccct gtgggggcca atgttaccct  26880
ggtgggcct gtcggcaatg ctacattaat gtgggaaaaa tatactaaaa atcaatgggt  26940
ctcttactgc actaacaaaa atagccacaa gcccagagcc atctgcgatg ggcaaaatct  27000
aaccttgatt gatgttcaat tgctggatgc gggctactat tatgggcagc tgggtacaat  27060
gattaattac tggagacccc acagagatta catgctccac gtagtaaagg gtcccccttag 27120
cagcccaccc actaccacct ctactacccc cactaccacc actactccca ccaccagcac  27180
tgccgcccag cctcctcata gcagaacaac cacttttatc aattccaagt cccactcccc  27240
ccacattgcc ggcgggccct ccgcctcaga ctccgaaacc accgagatct gcttctgcaa  27300
atgctctgac gccattgccc aggatttgga agatcacgag gaagatgagc atgacttcgc  27360
agatgcatgc caggcatcag agccagaagc gctgccggtg gccctcaaac agtatgcaga  27420
ccccacacc accccgacc ttcctccacc ttcccagaag ccaagtttcc tgggggaaaa  27480
tgaaactctg cctctctcca tactcgtctc tgacatctgtt gctatgttga ccgctctgct  27540
ggtgcttcta tgctctatat gctacctgat ctgctgcaga aagaaaaaat ctcacggcca  27600
tgctcaccag cccctcatgc acttccctta ccctccaggca ctgggcgacc acaaacttta  27660
agtctgcagt aactatctgc ccatcccttg tcagtcgaca gcgatgagcc ccactaatct  27720
aacggcctct ggacttacaa catcgtctct taatgagacc accgctcctc aagacctgta  27780
cgatggtgtc tccgcgctgg ttaaccagtg ggatcacctg gcatatggt ggctcctcat  27840
aggagcagtg accctgtgcc taatcctggt ctggatcatc tgctgcatca aaagcagaag  27900
acccaggcgg cggccatct acaggcctt tgtcatcaca cctgaagatg atgatgacac  27960
cacttccagg ctgcagaggc taaagcagct actcttctct tttacagcat ggtaaattga  28020
atcatgcctc gcattttcat ctacttgtct ctccttccac tttttctggg ctcttctaca  28080
ttggccgctg tgtcccacat cgaggtagac tgcctcaccg ccttcacagt ctacctgctt  28140
ttcggctttg tcatctgcac ctttgtctgc agcgttatca ctgtagtgat ctgcttcata  28200
cagtgcatcg actacgtctg cgtgcgggtg gcttacttta gacaccaccc ccagtatcgc  28260
aacagggaca tagcggctct cctaagactt gtttaaaatc atggccaaat taactgtgat  28320
tggtcttctg atcatctgct gcgtcctagc gcgattggg actcaagctc ctaccaccac  28380
cagcgctccc agaaagagac atgtatcctg cagcttcaag cgtccctgga atataccca  28440
atgctttact gatgaacctg aaatctcttt ggcttggtac ttcagcgtca ccgcccttct  28500
tatcttctgc agtacggtta ttgcccttgc catctaccct tcccttgacc tgggctggaa  28560
tgctgtcaac tctatggaat atcccacctt cccagaacca gacctgccag acctggttgt  28620
tctaaacgcg tttcctcctc ctgctcccgt tcaaaatcag tttcgccctc cgtccccac  28680
gcccactgag gtcagctact ttaatctaac aggcggagat gactgaaaac ctagacctag  28740
aaatggacgt tctctgcagc gagcaacgca cactagagag gcgccggcaa aaagagctcg  28800
agcgtcttaa acaagagctc caagacgcgg tggccataca ccagtgcaaa aaaggtgtct  28860
tctgtctggt aaaacaggcc acgctcacct atgaaaaaac aggtgacacc caccgcctag  28920
gatacaagct gcccacacag cgccaaaagt tcgccctcat gataggcgaa caacccatca  28980
ccgtgaccca gcactccgtg gagacagaag gctgcataca tgctccctgt aggggcgctg  29040
actgcctcta caccttgatc aaaaaccctct gcggtctcag agaccttatc cctttcaatt  29100
aatcataact gtaatcaata aaaaatcact tacttgaaat ctgatagcaa gcctctgtcc  29160
aatttttttca gcaacacttc cttccctctc tcccaactct ggtactctag gcgcctccta  29220
gctgcaaact tcctccacag tctgaaggga atgtcagatt cctcctcctg tccctccgca  29280
cccacgatct tcatgttgtt gcagatgaaa cgcgcgagat cgtctgacga gaccttcaac  29340
cccgtgtacc cctacgatac cgagatcgct ccgacttctg tcccttttct taccccctcc  29400
tttgtgtcat ccgcaggaat gcaagaaaat ccagctgggg tgctgtccct gcacttgtca  29460
gagccccta ccacccacaa tgggccctg actctaaaaa tgggggcgg cctgaccctg  29520
gacaaggaag ggaatctcac ttcccaaaac atcaccagtg tcgatccccc tctcaaaaaa  29580
agcaagaaca acatcagcct tcagacgcc gcacccctcg ccgtcagctc cggggcccta  29640
acactttttg ccactccccc cctagccgtc agtggtgaca accttactgt gcagtctcag  29700
gcccctctca ctttggaaga ctcaaaacta actctggcca ccaaaggacc cctaactgtg  29760
tccgaaggca aacttgtcct agaaacagag gctcccctgc atgcaagtga cagcagcagc  29820
ctgggcctta gcgttacggc cccacttagc attaacaatg acagcctagg actagatctg  29880
caggcaccca ttgtctctca aaatggaaaa ctggctctaa atgtagcagg cccctagct  29940
gtggccaatg gcattaatgc tttgacagta ggcacaggca aagtattgg tctaaatgaa  30000
accagcactc acttgcaagc aaagttggtc gccccctag gctttgatac caatggcaac  30060
attaagctaa gcgttgcagg aggcatgaga ctaaataatg acacacttat actagatgta  30120
aactacccat ttgaagctca aggccaacta agtctaagag tgggccaggg tccgctgtat  30180
gtagattcta gcagccataa cctgaccatt agatgcctta gaggattata cataacatcg  30240
tctaataacc aaaccggtct agaggccaac ataaaactaa caaaaggcct tgtctatgat  30300
ggaaatgcca tagcagtcaa tgttggtcaa ggattgcaat acagcactac tgccacatcg  30360
gaaggtgtgt atcctataca gtctaagata ggtttgggaa tggaatatga taccaacgga  30420
gccatgatga caaaactagg ctctggacta agctttgaca attcaggagc cattgtagtg  30480
ggaaacaaaa atgatgacag gcttactctg tggactacac cagacccatc tcctaactgt  30540
agaatttatt ctgaaaaaga tactaaacta accttggtgt tgactaagtg tggcagccaa  30600
atcctaggca cagtatctgc ccttgctgtc agaggcagcc ttgcgcccat cactaatgca  30660
tccagcatag tccaaaatatt tctaagattt gatgaaaatg gactattgat gagcaactca  30720
tcgctagacg gtgattactg gaattacaga aatgggact ccactaatag cacaccatat  30780
acaaatgcag taggctttat gcctaatcta gcagcctatc ctaaaggtca ggctacagct  30840
gcaaaaagca gtattgtaag ccaggtatac atggatggtg acactactaa acctataaca  30900
ctaaaaataa acttcaatgg cattgatgaa acaacagaaa ataccctgt tagtaaatat  30960
tccatgacat tctcatggag ctggcccacc gcaagctaca taggccacac ttttgcaaca  31020
aactcttttta ctttctccta catcgcccaa gaataaagaa agcacagaga tgcttgtttt  31080
gatttcaaaa ttgtgtgctt ttattttattt tcagcttaca gtatttccag tagtcattcg  31140
aataaagctt aatcaaactg catgagaacc cttcccacata gcttaaatta gcaccagtgc  31200
aagaa aagcctcgag gtcgttgcgc ggccgggatc ggtgatcacc gatccagaca  31260
tgataagata cattgatgag tttggacaaa ccacaactag aatgcagtga aaaaatgct  31320
ttatttgtga aatttgtgat gctattgctt tatttgtaac cattataagc tgcaataaac  31380
aagttcccga atcgcgatcc ggcccgaggc tgtagccgac gatggtgcgc caggagagtt  31440
gttgattcat tgtttgcctc cctgctgcgg tttttcaccg aagttcatgc cagtccagcg  31500
ttttgcagc agaaaagccg ccgacttcgg tttgcggtcg cgagtgaaga tccctttctt  31560
```

```
gttaccgcca acgcgcaata tgccttgcga ggtcgcaaaa tcggcgaaat tccatacctg  31620
ttcaccgacg acggcgctga cgcgatcaaa gacgcggtga tacatatcca gccatgcaca  31680
ctgatactct tcactccaca tgtcggtgta cattgagtgc agcccggcta acgtatccac  31740
gccgtattcg gtgatgataa tcggctgatg cagtttctcc tgccaggcca gaagttcttt  31800
ttccagtacc ttctctgccg tttccaaatc gccgcttttg acataccatc cgtaataacg  31860
gttcaggcac agcacatcaa agagatcgct gatggtatcg gtgtgagcgt cgcagaacat  31920
tacattgacg caggtgatcg gacgcgtcgg gtcgagttta cgcgttgctt ccgccagtgg  31980
cgcgaaatat tcccgtgcac cttgcggacg ggtatccggt tcgttggcaa tactccacat  32040
caccacgctt gggtggtttt tgtcacgcgc tatcagctct ttaatcgcct gtaagtgcgc  32100
ttgctgagtt tccccgttga ctgcctcttc gctgtacagt tctttcggct tgttgcccgc  32160
ttcgaaacca atgcctaaag agaggttaaa gccgacagca gcagtttcat caatcaccac  32220
gatgccatgt tcatctgccc agtcgagcat ctcttcagcg taagggtaat gcgaggtacg  32280
gtaggagttg gccccaatcc agtccattaa tgcgtggtcg tgcaccatca gcacgttatc  32340
gaatcctttg ccacgcaagt ccgcatcttc atgacgacca aagccagtaa agtagaacgg  32400
tttgtggtta atcaggaact gttcgcccct cactgccact gaccggatgc cgacgcgaag  32460
cgggtagata tcacactctg tctgcctttt ggctgtgacg cacagttcat agagataacc  32520
ttcacccggt tgccagaggt gcggattcac cacttgcaaa gtcccgctag tgccttgtcc  32580
agttgcaacc acctgttgat ccgcatcacg cagttcaacg ctgacatcac cattggccac  32640
cacctgccag tcaacagacg cgtggttaca gtcttgcgcg acatgcgtca ccacggtgat  32700
atcgtccacc caggtgttcg gcgtggtgta gagcattac                         32739

SEQ ID NO: 26           moltype = DNA  length = 114
FEATURE                 Location/Qualifiers
misc_feature            1..114
                        note = IL-2 core promoter
source                  1..114
                        mol_type = other DNA
                        organism = synthetic construct
SEQUENCE: 26
acattttgac accccataa tattttcca gaattaacag tataaattgc atctcttgtt     60
caagagttcc ctatcactct ctttaatcac tactcacagt aacctcaact cctg         114

SEQ ID NO: 27           moltype = DNA  length = 55
FEATURE                 Location/Qualifiers
misc_feature            1..55
                        note = IL-2 minimal promoter
source                  1..55
                        mol_type = other DNA
                        organism = synthetic construct
SEQUENCE: 27
tcaagagttc cctatcactc tctttaatca ctactcacag taacctcaac tcctg         55

SEQ ID NO: 28           moltype = DNA  length = 380
FEATURE                 Location/Qualifiers
misc_feature            1..380
                        note = IL-2 enhancer and promoter variant
source                  1..380
                        mol_type = other DNA
                        organism = synthetic construct
SEQUENCE: 28
tgatatcttt tctgagttac ttttgtatcc ccaccccctt aaagaaagga ggaaaaactg    60
tttcatacag aaggcgttaa ttgcatgaat tagagctatc acctaagtgt gggctaatgt   120
aacaaagagg gatttcacct acatccattc agtcagtctt tggggggttta aagaaattcc  180
aaagagtcat cagaagagga aaaatgaagg taatgttttt tcagactggt aaagtctttg   240
aaaatatgtg taatatgtaa aacatttga cacccccata atattttcc agaattaaca    300
gtataaattg catctcttgt tcaagagttc cctatcactc tctttaatca ctactcacag   360
taacctcaac tcctgccaca                                              380

SEQ ID NO: 29           moltype = DNA  length = 373
FEATURE                 Location/Qualifiers
misc_feature            1..373
                        note = L-2 enhancer and promoter variant
source                  1..373
                        mol_type = other DNA
                        organism = synthetic construct
SEQUENCE: 29
ttttctgagt tactttttgta tccccacccc cttaaagaaa ggaggaaaaa ctgtttcata    60
cagaaggcgt taattgcatg aattagagct atcacctaag tgtgggctaa tgtaacaaag   120
agggatttca cctacatcca ttcagtcagt ctttgggggt ttaaagaaat tccaaagagt   180
catcagaaga ggaaaaatga aggtaatgtt ttttcagact ggtaaagtct ttgaaaatat   240
gtgtaatatg taaaacattt tgacaccccc ataatatttt tccagaatta acagtataaa   300
ttgcatctct tgttcaagag ttccctatca ctctctttaa tcactactca cagtaacctc   360
aactcctgcc aca                                                     373

SEQ ID NO: 30           moltype = DNA  length = 161
FEATURE                 Location/Qualifiers
misc_feature            1..161
                        note = (NF-KB)1-IL2 promoter variant
source                  1..161
```

```
                          mol_type = other DNA
                          organism = synthetic construct
SEQUENCE: 30
aattggtccc atcgaagagg gatttcacct acataattgg tcccgggaca ttttgacacc    60
cccataatat ttttccagaa ttaacagtat aaattgcatc tcttgttcaa gagttcccta   120
tcactctctt taatcactac tcacagtaac ctcaactcct g                       161

SEQ ID NO: 31             moltype = DNA   length = 201
FEATURE                   Location/Qualifiers
misc_feature              1..201
                          note = (NF-KB)3-IL2 promoter variant
source                    1..201
                          mol_type = other DNA
                          organism = synthetic construct
SEQUENCE: 31
aattggtccc atcgaagagg gatttcacct acataagagg gatttcacct acataagagg    60
gatttcacct acataattgg tcccgggaca ttttgacacc cccataatat ttttccagaa   120
ttaacagtat aaattgcatc tcttgttcaa gagttcccta tcactctctt taatcactac   180
tcacagtaac ctcaactcct g                                             201

SEQ ID NO: 32             moltype = DNA   length = 268
FEATURE                   Location/Qualifiers
misc_feature              1..268
                          note = (NF-kB)6-IL2 promoter variant
source                    1..268
                          mol_type = other DNA
                          organism = synthetic construct
SEQUENCE: 32
aattggtccc atcgaagagg gatttcacct acataagagg gatttcacct acataagagg    60
gatttcacct acataattgg taagagggat ttcacctaca taagagggat ttcacctaca   120
taagagggat ttcacctaca taattggtcc cgggacattt tgacaccccc ataatatttt   180
tccagaatta acagtataaa ttgcatctct tgttcaagag ttccctatca ctctctttaa   240
tcactactca cagtaacctc aactcctg                                      268

SEQ ID NO: 33             moltype = DNA   length = 177
FEATURE                   Location/Qualifiers
misc_feature              1..177
                          note = 1X NFAT response elements-IL2 promoter variant
source                    1..177
                          mol_type = other DNA
                          organism = synthetic construct
SEQUENCE: 33
aattggtccc atcgaattag gaggaaaaac tgtttcatac agaaggcgtc aattggtccc    60
gggacatttt gacaccccca taatattttt ccagaattaa cagtataaat tgcatctctt   120
gttcaagagt tccctatcac tctctttaat cactactcac agtaacctca actcctg      177

SEQ ID NO: 34             moltype = DNA   length = 256
FEATURE                   Location/Qualifiers
misc_feature              1..256
                          note = 3X NFAT response elements-IL2 promoter variant
source                    1..256
                          mol_type = other DNA
                          organism = synthetic construct
SEQUENCE: 34
tgatatcaat tggtcccatc gaattaggag gaaaaactgt ttcatacaga aggcgtcaat    60
taggaggaaa aactgtttca tacagaaggc gtcaattagg aggaaaaact gtttcataca   120
gaaggcgtca attggtcccg ggacattttg acaccccccat aatattttc cagaattaac   180
agtataaatt gcatctcttg ttcaagagtt ccctatcact ctctttaatc actactcaca   240
gtaacctcaa ctcctg                                                   256

SEQ ID NO: 35             moltype = DNA   length = 249
FEATURE                   Location/Qualifiers
misc_feature              1..249
                          note = 3X NFAT response elements-IL2 promoter variant
source                    1..249
                          mol_type = other DNA
                          organism = synthetic construct
SEQUENCE: 35
aattggtccc atcgaattag gaggaaaaac tgtttcatac agaaggcgtc aattaggagg    60
aaaaactgtt tcatacagaa ggcgtcaatt aggaggaaaa actgtttcat acagaaggcg   120
tcaattggtc ccgggacatt ttgacacccc cataatattt ttccagaatt aacagtataa   180
attgcatctc ttgttcaaga gttccctatc actctcttta atcactactc acagtaacct   240
caactcctg                                                           249

SEQ ID NO: 36             moltype = DNA   length = 358
FEATURE                   Location/Qualifiers
misc_feature              1..358
                          note = 6X NFAT response elements-IL2 promoter variant
source                    1..358
```

```
                              mol_type = other DNA
                              organism = synthetic construct
SEQUENCE: 36
gaattaggag gaaaaactgt ttcatacaga aggcgtcaat taggaggaaa aactgtttca    60
tacagaaggc gtcaattagg aggaaaaact gtttcataca gaaggcgtca attggtccca   120
tcgaattagg aggaaaaact gtttcataca gaaggcgtca attaggagga aaaactgttt   180
catacagaag gcgtcaatta ggaggaaaaa ctgtttcata cagaaggcgt caattggtcc   240
cgggacattt tgacaccccc ataatatttt tccagaatta acagtataaa ttgcatctct   300
tgttcaagag ttccctatca ctctccttaa tcactactca cagtaacctc aactcctg     358

SEQ ID NO: 37           moltype = DNA   length = 374
FEATURE                 Location/Qualifiers
misc_feature            1..374
                        note = 6X NFAT response elements-IL2 promoter variant
source                  1..374
                        mol_type = other DNA
                        organism = synthetic construct
SEQUENCE: 37
tgatatcgaa ttaggaggaa aaactgtttc atacagaagg cgtcaattag gagaaaaaac    60
tgtttcatac agaaggcgtc aattaggagg aaaaactgtt tcatacagaa ggcgtcaatt   120
ggtcccatcg aattaggagg aaaaactgtt tcatacagaa ggcgtcaatt aggaggaaaa   180
actgtttcat acagaaggcg tcaattagga ggaaaaactg tttcatacag aaggcgtcaa   240
ttggtcccgg gacattttga cacccccata atatttttcc agaattaaca gtataaattg   300
catctcttgt tcaagagttc cctatcactc tctttaatca ctactcacag taacctcaac   360
tcctgaattc catg                                                     374

SEQ ID NO: 38           moltype = DNA   length = 358
FEATURE                 Location/Qualifiers
misc_feature            1..358
                        note = 6X NFAT response elements-IL2 promoter variant
source                  1..358
                        mol_type = other DNA
                        organism = synthetic construct
SEQUENCE: 38
gaattaggag gaaaaactgt ttcatacaga aggcgtcaat taggaggaaa aactgtttca    60
tacagaaggc gtcaattagg aggaaaaact gtttcataca gaaggcgtca attggtccca   120
tcgaattagg aggaaaaact gtttcataca gaaggcgtca attaggagga aaaactgttt   180
catacagaag gcgtcaatta ggaggaaaaa ctgtttcata cagaaggcgt caattggtcc   240
cgggacattt tgacaccccc ataatatttt tccagaatta acagtataaa ttgcatctct   300
tgttcaagag ttccctatca ctctctttaa tcactactca cagtaacctc aactcctg     358

SEQ ID NO: 39           moltype = DNA   length = 365
FEATURE                 Location/Qualifiers
misc_feature            1..365
                        note = 6X NFAT response elements-IL2 promoter variant
source                  1..365
                        mol_type = other DNA
                        organism = synthetic construct
SEQUENCE: 39
tgatatcgaa ttaggaggaa aaactgtttc atacagaagg cgtcaattag gagaaaaaac    60
tgtttcatac agaaggcgtc aattaggagg aaaaactgtt tcatacagaa ggcgtcaatt   120
ggtcccatcg aattaggagg aaaaactgtt tcatacagaa ggcgtcaatt aggaggaaaa   180
actgtttcat acagaaggcg tcaattagga ggaaaaactg tttcatacag aaggcgtcaa   240
ttggtcccgg gacattttga cacccccata atatttttcc agaattaaca gtataaattg   300
catctcttgt tcaagagttc cctatcactc tctttaatca ctactcacag taacctcaac   360
tcctg                                                               365

SEQ ID NO: 40           moltype = DNA   length = 244
FEATURE                 Location/Qualifiers
misc_feature            1..244
                        note = human EEF1A1 promoter variant
source                  1..244
                        mol_type = other DNA
                        organism = synthetic construct
SEQUENCE: 40
gagcgtgcgt gaggctccgg tgcccgtcag tgggcagagc gcacatcgcc cacagtcccc    60
gagaagttgg ggggagggggg tcggcgattg aaccggtgcc tagagaaggt ggcgcggggt   120
aaaactggga agtgatgtcg tgtactggct ccgcctttt  cccagggtg ggggagaacc   180
gtatataagt gcagtagtcg ccgtgaacgt tctttttcgc aacgggtttg ccgccagaac   240
acag                                                                244

SEQ ID NO: 41           moltype = DNA   length = 236
FEATURE                 Location/Qualifiers
misc_feature            1..236
                        note = human EEF1A1 promoter variant
source                  1..236
                        mol_type = other DNA
                        organism = synthetic construct
SEQUENCE: 41
```

```
gcgtgaggct ccggtgcccg tcagtgggca gagcgcacat cgcccacagt ccccgagaag   60
ttgggggggag gggtcggcaa ttgaaccggt gcctagagaa ggtggcgcgg ggtaaactgg  120
gaaagtgatg tcgtgtactg gctccgcctt tttcccgagg gtgggggaga accgtatata  180
agtgcagtag tcgccgtgaa cgttcttttt cgcaacgggt ttgccgccag aacaca      236
```

```
SEQ ID NO: 42           moltype = DNA  length = 1266
FEATURE                 Location/Qualifiers
misc_feature            1..1266
                        note = human EEF1A1 promoter and enhancer
source                  1..1266
                        mol_type = other DNA
                        organism = synthetic construct
SEQUENCE: 42
gagctttgca aagatggata aagttttaaa cagagaggaa tctttgcagc taatggacct   60
tctaggtctt gaaaggagtg ggaattggct ccggtgcccg tcagtgggca gagcgcacat  120
cgcccacagt ccccgagaag ttgggggggag gggtcggcaa ttgaaccggt gcctagagaa  180
ggtggcgcgg ggtaaactgg gaaagtgatg tcgtgtactg gctccgcctt tttcccgagg  240
gtgggggaga accgtatata agtgcagtag tcgccgtgaa cgttcttttt cgcaacgggt  300
ttgccgccag aacacaggta agtgccgtgt gtggttcccg cgggcctggc ctctttacgg  360
gttatgccc ttgcgtgcct tgaattactt ccacctggct gcagtacgtg attcttgatc  420
ccgagcttcg ggttggaagt gggtgggaga gttcgaggcc ttgcgcttaa ggagcccctt  480
cgcctcgtgc ttgagttgag gcctggcctg ggcgctgggg ccgccgcgtg cgaatctgac  540
ggcaccttcg cgcctgtctc gctgctttcg ataagtctct agccatttaa aattttttgat  600
gacctgctgc gacgcttttt ttctggcaag atagtcttgt aaatgcgggc caagatctgc  660
acactggtat ttcggttttt ggggccgcgg gcggcgacgg ggcccgtgcg tcccagcgca  720
catgttcggc gaggcgggggc ctgcgagcgc ggccaccgag aatcgacggg gggtagtctc  780
aagctggccg gcctgctctg gtgcctggcc tcgcgccgcc gtgtatcgcc ccgcctggg   840
cggcaaggct ggcccggtcg gcaccagttg cgtgagcgga aagatggccg cttcccggcc  900
ctgctgcagg gagctcaaaa tggaggacgc ggcgctcggg agagcgggcg ggtgagtcac  960
ccacacaaag gaaaagggcc tttccgtcct cagccgtgcc ttcatgtgac tccacggagt 1020
accgggcgcc gtccaggcac ctcgattagt tctcgagctt ttggagtacg tcgtctttag 1080
gttgggggga ggggttttat gcgatggagt ttccccacac tgagtgggtg gagactgaag 1140
ttaggccagc ttggcacttg atgtaattct ccttggaatt tgccctttt gagttttgat 1200
cttggttcat tctcaagcct cagacagtgg ttcaaagttt ttttcttcca tttcaggtgt 1260
cgtgag                                                            1266
```

```
SEQ ID NO: 43           moltype = DNA  length = 571
FEATURE                 Location/Qualifiers
misc_feature            1..571
                        note = human UBC promoter
source                  1..571
                        mol_type = other DNA
                        organism = synthetic construct
SEQUENCE: 43
ggcctccgcg ccgggttttg gcgcctcccg cgggcgcccc cctcctcacg gcgagcgctg   60
ccacgtcaga cgaagggcgc agcgagcgtc ctgatccttc cgcccggacg ctcaggacag  120
cggcccgctg ctcataagac tcggccttag aaccccagta tcagcagaag gacattttag  180
gacgggactt gggtgactct agggcactgg tttctcttcc agagagcgga acaggcgagg  240
aaaagtagtc ccttctcggc gattctgcgg agggatctcc gtgggcggt gaacgccgat   300
gattatataa ggacgcgccg ggtgtggcac agctagttcc gtcgcagccg ggatttgggt  360
cgcggttctt gtttgtggat cgctgtgatc gtcacttgtt gagtagcggg ctgctgggtc  420
gggtacgtgc gctcggggtt ggcgagtgtg ttttgtgaag ttttttaggc accttttgaa  480
atgtaatcat ttgggtcaat atgtaatttt cagtgttaga ctagtaaatt gtccgctaaa  540
ttctggccgt ttttggcttt tttgttagac g                                571
```

```
SEQ ID NO: 44           moltype = DNA  length = 81
FEATURE                 Location/Qualifiers
misc_feature            1..81
                        note = synthetic minimal promoter 1
source                  1..81
                        mol_type = other DNA
                        organism = synthetic construct
SEQUENCE: 44
aggtctatat aagcagagct cgtttagtga accctcattc tggagacgga tcccgagccg   60
agtgttttga cctccataga a                                            81
```

```
SEQ ID NO: 45           moltype = AA  length = 10
FEATURE                 Location/Qualifiers
REGION                  1..10
                        note = HBV Peptides from Core 1
source                  1..10
                        mol_type = protein
                        organism = synthetic construct
SEQUENCE: 45
FLPSDFFPSV                                                         10
```

```
SEQ ID NO: 46           moltype = AA  length = 8
FEATURE                 Location/Qualifiers
REGION                  1..8
```

```
                         note = HBV Peptides from Core 2
source                   1..8
                         mol_type = protein
                         organism = synthetic construct
SEQUENCE: 46
CWGELMTL                                                               8

SEQ ID NO: 47            moltype = AA  length = 9
FEATURE                  Location/Qualifiers
REGION                   1..9
                         note = HBV Peptides from Core 3
source                   1..9
                         mol_type = protein
                         organism = synthetic construct
SEQUENCE: 47
GVWIRTPPA                                                              9

SEQ ID NO: 48            moltype = AA  length = 11
FEATURE                  Location/Qualifiers
REGION                   1..11
                         note = HBV Peptides from Core 4
source                   1..11
                         mol_type = protein
                         organism = synthetic construct
SEQUENCE: 48
STLPETTVVR R                                                          11

SEQ ID NO: 49            moltype = AA  length = 11
FEATURE                  Location/Qualifiers
REGION                   1..11
                         note = HBV Peptides from Core 5
source                   1..11
                         mol_type = protein
                         organism = synthetic construct
SEQUENCE: 49
LTFGRETVLE Y                                                          11

SEQ ID NO: 50            moltype = AA  length = 10
FEATURE                  Location/Qualifiers
REGION                   1..10
                         note = HBV Peptides from Core 6
source                   1..10
                         mol_type = protein
                         organism = synthetic construct
SEQUENCE: 50
DLLDTASALY                                                            10

SEQ ID NO: 51            moltype = AA  length = 10
FEATURE                  Location/Qualifiers
REGION                   1..10
                         note = HBV Peptides from Core 7
source                   1..10
                         mol_type = protein
                         organism = synthetic construct
SEQUENCE: 51
LWFHISCLTF                                                            10

SEQ ID NO: 52            moltype = AA  length = 9
FEATURE                  Location/Qualifiers
REGION                   1..9
                         note = HBV Peptides from Core 8
source                   1..9
                         mol_type = protein
                         organism = synthetic construct
SEQUENCE: 52
EYLVSFGVW                                                              9

SEQ ID NO: 53            moltype = AA  length = 9
FEATURE                  Location/Qualifiers
REGION                   1..9
                         note = HBV Peptides from Polymerase 1
source                   1..9
                         mol_type = protein
                         organism = synthetic construct
SEQUENCE: 53
FLKQQYMNL                                                              9

SEQ ID NO: 54            moltype = AA  length = 9
FEATURE                  Location/Qualifiers
```

```
REGION                  1..9
                        note = HBV Peptides from Polymerase 2
source                  1..9
                        mol_type = protein
                        organism = synthetic construct
SEQUENCE: 54
FLSKQYMDL                                                                    9

SEQ ID NO: 55           moltype = AA  length = 9
FEATURE                 Location/Qualifiers
REGION                  1..9
                        note = HBV Peptides from Polymerase 3
source                  1..9
                        mol_type = protein
                        organism = synthetic construct
SEQUENCE: 55
TVSTKLCKI                                                                    9

SEQ ID NO: 56           moltype = AA  length = 9
FEATURE                 Location/Qualifiers
REGION                  1..9
                        note = HBV Peptides from Polymerase 4
source                  1..9
                        mol_type = protein
                        organism = synthetic construct
SEQUENCE: 56
GLSRYVARL                                                                    9

SEQ ID NO: 57           moltype = AA  length = 9
FEATURE                 Location/Qualifiers
REGION                  1..9
                        note = HBV Peptides from Polymerase 5
source                  1..9
                        mol_type = protein
                        organism = synthetic construct
SEQUENCE: 57
KLHLYSHPI                                                                    9

SEQ ID NO: 58           moltype = AA  length = 9
FEATURE                 Location/Qualifiers
REGION                  1..9
                        note = HBV Peptides from Polymerase 6
source                  1..9
                        mol_type = protein
                        organism = synthetic construct
SEQUENCE: 58
FLLSLGIHL                                                                    9

SEQ ID NO: 59           moltype = AA  length = 9
FEATURE                 Location/Qualifiers
REGION                  1..9
                        note = HBV Peptides from Polymerase 7
source                  1..9
                        mol_type = protein
                        organism = synthetic construct
SEQUENCE: 59
SLYADSPSV                                                                    9

SEQ ID NO: 60           moltype = AA  length = 9
FEATURE                 Location/Qualifiers
REGION                  1..9
                        note = HBV Peptides from Polymerase 8
source                  1..9
                        mol_type = protein
                        organism = synthetic construct
SEQUENCE: 60
ALMPLYACI                                                                    9

SEQ ID NO: 61           moltype = DNA  length = 10410
FEATURE                 Location/Qualifiers
misc_feature            1..10410
                        note = GCAd-RTS-IL12 design 1
source                  1..10410
                        mol_type = other DNA
                        organism = synthetic construct
SEQUENCE: 61
ttcaaatatg tatccgctca tgagacaata accctgataa atgcttcaat aatattgaaa           60
aaggaagagt atgagtattc aacatttccg tgtcgcccctt attcccttttt ttgcggcatt        120
ttgccttcct gttttttgctc acccagaaac gctggtgaaa gtaaaagatg ctgaagatca        180
```

```
gttgggtgca cgagtgggtt acatcgaact ggatctcaac agcggtaaga tccttgagag    240
ttttcgcccc gaagaacgtt ttccaatgat gagcacttt aaagttctgc tatgtggcgc    300
ggtattatcc cgtattgacg ccgggcaaga gcaactcggt cgccgcatac actattctca    360
gaatgacttg gttgagtact caccagtcac agaaaagcat cttacggatg gcatgacagt    420
aagagaatta tgcagtgctg ccataaccat gagtgataac actgcggcca acttacttct    480
gacaacgatc ggaggaccga aggagctaac cgcttttttg cacaacatgg gggatcatgt    540
aactcgcctt gatcgttggg aaccggagct gaatgaagcc ataccaaacg acgagcgtga    600
caccacgatg cctgtagcaa tggcaacaac gttgcgcaaa ctattaactg gcgaactact    660
tactctagct tcccggcaac aattaataga ctggatggag gcggataaag ttgcaggacc    720
acttctgcgc tcggcccttc cggctggctg gtttattgct gataaatctg gagccggtga    780
gcgtgggtct cgcggtatca ttgcagcact ggggccagat ggtaagccct cccgtatcgt    840
agttatctac acgacgggga gtcaggcaac tatggatgaa cgaaatagac agatcgctga    900
gataggtgcc tcactgatta agcattggta actgtcagac caagtttact catatatact    960
ttagattgat ttaaaacttc attttaatt taaaaggatc taggtgaaga tccttttga   1020
taatctcatg accaaaatcc cttaacgtga gttttcgttc cactgagcgt cagacccgt   1080
agaaaagatc aaaggatctt cttgagatcc tttttttctg cgcgtaatct gctgcttgca   1140
aacaaaaaaa ccaccgctac cagcggtggt ttgtttgccg gatcaagagc taccaactct   1200
ttttccgaag gtaactggct tcagcagagc gcagatacca aatactgttc ttctagtgta   1260
gccgtagtta ggccaccact tcaagaactc tgtagcaccg cctacatacc tcgctctgct   1320
aatcctgtta ccagtggctg ctgccagtgg cgataagtcg tgtcttaccg ggttggactc   1380
aagacgatag ttaccggata aggcgcagcg gtcgggctga acggggggtt cgtgcacaca   1440
gcccagcttg gagcgaacga cctacaccga actgagatac ctacagcgtg agctatgaga   1500
aagcgccacg cttcccgaag ggagaaaggc ggacaggtat ccggtaagcg cagggtcgg   1560
aacaggagag cgcacgaggg agcttccagg gggaaacgcc tggtatcttt atagtcctgt   1620
cgggtttcgc cacctctgac ttgagcgtcg atttttgtga tgctcgtcag gggggcggag   1680
cctatggaaa aacgccagca acgcggcctt tttacggttc ctggcctttt gctggccttt   1740
tgctcacatg ttctttcctg cgttatcccc tgattctgtg ataaccgta ttaccgcctt    1800
tgagtgagct gataccgctc gccgcagccg aacgaccgag cgcagcgagt cagtgagcga   1860
ggaagcggaa gagcgcccaa tacgcaaacc gcctctcccc gcgcgttggc cgattcatta   1920
atgcagctgg cacgacaggt ttcccgactg gaaagcgggc agtgagcgca acgcaattaa   1980
tgtgagttag ctcactcatt aggcacccca ggctttacac tttatgcttc cggctcgtat   2040
gttgtgtgga attgtgagcg gataacaatt tcacacagga aacagctatg accatgatta   2100
cgccaagctg ggtcaagtct tccagtttaa gcagcagagc ggtcagtttc tcatcccgag   2160
cagacgcgcg agaggccgcg ccgctcgcca ccaaagagct gtaaaggtcc gtagccatgc   2220
tgcgcgcggt cgcggcggcg gcggaggcgg cggcgagtcc agcggcgtcc agcggagttc   2280
ctcccacggt cgcgtaggcc attgtagacg aatttgaagg cagaacgggg cgtccatcca   2340
cgttggaacc catcacattc tgacgcactc cagcccagtg aggcatgcgc actgtcagat   2400
agggggctaaa gatgcttcca tcaaagctgt tgccggtgtc gctcatgcg gcggctgttg   2460
caagacaaaa cagagagacc cttagacccc caatttatac acgccccacc cttctagcca   2520
cgcccacctt acccacctca atcggtatcc tcatcgctag acccaaactc ggccctggtg   2580
caggccagca ccagatggtc aggcctgcag gccgcaataa aatatcttta ttttcattac   2640
atctgtgtgt tggtttttg tgtgaatcga tagtactaac atacgctctc atcaaaaca   2700
aaacgaaaca aaacaaacta gcaaaataqq ctgtccccaq tgcaaqtgca qgtgccagaa   2760
catttctcta tcgataatgc aggtcggagt actgtcctcc gagcggagta ctgtcctccg   2820
agcggagtac tgtcctccga gcggagtact gtcctccgag cggagtactg tcctccgagc   2880
ggagtactgt cctccgagcg gagactcttc gaaggaagag gggcggggtc gatcgacccc   2940
gccccctcttc cttcgaagga agagggggcgg ggtcgaagga ctagaggta tataatgggt   3000
gccttagctg gtgtgtgagc tcatcttcct gtagatcacg cgtgccacca tgggtcacca   3060
gcagttggtc atctcttggt tttccctggt ttttctggca tctcccctcg tggccatatg   3120
ggaactgaag aaagatgttt atgtcgtaga attggattgg tatccggatg cccctggaga   3180
aatggtgatc ctcacctgtg acaccctga agaagatggt atcacctgga ccttggacca   3240
gagcagtgag gtcttaggct ctggcaaaac cctgaccatc caagtcaaag agtttggaga   3300
tgctggccag tacacctgtc acaaaggagg cgaggttcta agccattgc tcctgctgct   3360
tcacaaaaag gaagatggaa tttggtccac tgatattta aaggaccaga aagaacccaa   3420
aaataagacc tttctaagat gcgaggccaa gaattattct ggacgtttca cctgctggtg   3480
gctgacgaca atcagtactg atttgacatt cagtgtcaaa acagcagag gctcttctga   3540
cccccaaggg gtgacgtgcg gagctgctac actctctgca gagagagtca gaggggacaa   3600
caaggagtat gagtactcag tggagtgcca ggaggacagt gcctgccag ctgctgagga   3660
gagtcgtgcc attgaggtca tggtggatgc cgttcacaag ctcaagtatg aaaactacac   3720
cagcagcttc ttcatcaggg acatcatcaa acctgaccca cccaagaact tgcagctgaa   3780
gccattaaag aattctcggc aggtggaggt cagctgggag tacctgaca cctggagtac   3840
tccacattcc tacttctccc tgacattctg cgttcaggtc cagggcaaga gcaagagaga   3900
aaagaaagat agagtcttca cggacaagac ctcagccacg gtcatctgcc gcaaaaatgc   3960
cagcattagc gtgcgggccc aggaccgcta ctatagctca tcttgagcg aatgggcatc   4020
tgtgccctgc agttaggttg ggcgagctcg aattcattga tccccgggc tgcaggaatt   4080
cgatatcaag ctcgggatcc gaattccgcc cccccccccc ccccccccct aacgttactg   4140
gccgaagccg cttggaataa ggccggtgtg cgtttgtcta tatgttattt tccaccatat   4200
tgccgtcttt tggcaatgtg agggcccgga acctggcc tgtcttcttg acgagcattc   4260
ctaggggtct ttcccctctc gccaaaggaa tgcaaggtct gttgaatgtc gtgaaggaag   4320
cagttcctct ggaagcttct tgaagacaaa caacgtctgt agcgacctt tgcaggcagc   4380
ggaaccccc acctgcgac aggtgcctct gcggccaaaa gccacgtgta taagatacac   4440
ctgcaaaggc ggcacaaccc cagtgccacg ttgtgagttg atagttgtg aaagagtca   4500
aatggctctc ctcaagcgta ttcaacaagg gctgaagga tgcccagaag taccccatt   4560
gtatggatc tgatctgggg cctcggtgca catgctttac atgtgtttag tcgaggttaa   4620
aaaaacgtct aggccccccg aaccacgggg acgtggtttt cctttgaaaa acacgatgat   4680
aatatgggcca caaccatggg tccagcgcgc agcctcctcc ttgtggctac cctggtcctc   4740
ctggaccacc tcagtttggc cagaaacctc ccgtggcca ctccagaccc aggaatgttc   4800
ccatgccttc accactccca aaacctgctg agggccgtca gcaacatgct ccagaaggcc   4860
agacaaactc tagaatttta cccttgcact tctgaagaga ttgatcatga agatatcaca   4920
```

```
aaagataaaa ccagcacagt ggaggcctgt ttaccattgg aattaaccaa gaatgagagt    4980
tgcctaaatt ccagagagac ctctttcata actaatggga gttgcctggc ctccagaaag    5040
acctctttta tgatggccct gtgccttagt agtatttatg aagacttgaa gatgtaccag    5100
gtggagttca agaccatgaa tgcaaagctt ctgatggatc ctaagaggca gatctttcta    5160
gatcaaaaca tgctggcagt tattgatgag ctgatgcagg ccctgaattt caacagtgag    5220
actgtgccac aaaaatcctc ccttgaagaa ccggattttt ataaaactaa aatcaagctc    5280
tgcatacttc ttcatgcttt cagaattcgg gcagtgacta ttgatagagt gatgagctat    5340
ctgaatgctt cctaacgtac gtcgacatcg agaacttgtt tattgcagct tataatggtt    5400
acaaataaag caatagcatc acaaatttca caaataaagc attttttca ctgcattcta    5460
gttgtggttt gtccaaactc atcaatgtat cttatcatgt ctgggcgcgc cggcctccgc    5520
gccgggtttt ggcgcctccc gcgggcgccc ccctcctcac ggcgagcgct gccacgtcag    5580
acgaagggcg cagcgagcgt cctgatcctt ccgcccggac gctcaggaca gcggcccgct    5640
gctcataaga ctcggcctta gaaccccagt atcagcagaa ggacatttta ggacgggact    5700
tgggtgactc tagggcactg gttttctttc cagagagcgg aacaggcgag gaaaagtagt    5760
cccttctcgg cgattctgcg gagggatctc cgtgggcgg tgaacgccga tgattatata    5820
aggacgcgcc gggtgtggca cagctagttc cgtcgcagcc gggatttggg tcgcggttct    5880
tgtttgtgga tcgctgtgat cgtcacttgg tgagtagcgg gctgctggc tgggtacgtg    5940
cgctcggggt tggcgagtgt gttttgtgaa gttttttagg caccttttga aatgtaatca    6000
tttgggtcaa tatgtaattt tcagtgttag actagtaaat tgtccgctaa attctggccg    6060
tttttggctt ttttgttaga cgagctagcg ccgccaccat gggccctaaa agaagcgta    6120
aagtcgcccc cccgaccgat gtcagcctgg gggacgagct ccacttagac ggcgaggacg    6180
tggcgatggc gcatgccgac gcgctagacg atttcgatct agacatgttg ggggacgggg    6240
attcccccggg tccggattt accccccacg actccgcccc ctacggcgct ctggatatgg    6300
ccgacttcga gtttgagcag atgtttaccg atgcccttgg aattgacgag tacggtgggg    6360
aattcgagat gcctgtggac aggatcctgg aggcagagct tgctgtggaa cagaagagtg    6420
accagggcgt tgagggtcct gggggaaccg ggggtagccg cagcagccca aatgaccctg    6480
tgactaacat ctgtcaggca gctgacaaac agctattcac gcttgttgag tgggcgaaga    6540
ggatcccaca cttttcctcc ttgcctctgg atgatcaggt catattgctg cgggcaggct    6600
ggaatgaact cctcattgcc tccttttcac accgatccat tgatgttcga gatggcatcc    6660
tccttgccac aggtcttcac gtgcaccgca actcagccca ttcagcagga gtaggagcca    6720
tctttgatcg ggtgctgaca gagctagtgt ccaaaatgcg tgacatgagg atggacaaga    6780
cagagcttgg ctgcctgagg gcaatcattc tgtttaatcc agaggtgagg ggtttgaaat    6840
ccgcccagga agttgaactt ctacgtgaaa aagtatatgc cgctttggaa gaatatacta    6900
gaacaacaca tcccgatgaa ccaggaagat ttgcaaaact tttgcttctt    6960
tacgttccat aggccttaag tgtttggagc atttgttttt ctttcgcctt attggagatg    7020
ttccaattga tacgttcctg atggagatgc ttgaatcacc ttctgattca taatctagcc    7080
tagcccccct ctccctcccc cccccctaac gttactggcc gaagccgctt ggaataaggc    7140
cggtgtgcgt ttgtctatat gttattttcc accatattgc cgtcttttgg caatgtgagg    7200
gcccgaaac ctggccctgt cttcttgacg agcattccta gggtctttc ccctctcgcc    7260
aaaggaatgc aaggtctgtt gaatgtcgtg aaggaagcag ttcctctgga agcttcttga    7320
agacaaacaa cgtctgtagc gacccttgc aggcagcgga acccccacc tggcgacagg    7380
tgcctctgcg gccaaaagcc acgtgtataa gatacacctg caaaggcggc acaacccag    7440
tgccacgttg tgagttggat agttgtgaa agagtcaaat ggctctcctc aagcgtattc    7500
aacaaggggc tgaaggatgc ccagaaggta ccccattgta tgggatctga tctgggcct    7560
cggtgcacat gctttacatg tgtttagtcg aggttaaaaa acgtctaggc cccccgaacc    7620
acggggacgt ggttttcctt tgaaaaacac gatctctagg cgccaccatg aagctactgt    7680
cttctatcga acaagcatgc gatatttgcc gacttaaaaa gctcaagtgc tccaaagaaa    7740
aaccgaagtg cgccaagtgt ctgaagaaca actgggagtg tcgctactct cccaaaacca    7800
aaaggtctcc gctgactagg gcacatctga cagaagtgga atcaaggcta gaagactgg    7860
aacagctatt tctactgatt tttcctcgag aagaccttga catgattttg aaaatggatt    7920
ctttacagga tataaaagca ttgttaacag gattatttgt acaagataat gtgaataaag    7980
atgccgtcac agatagattg gcttcagtgg agactgatat gcctctaaca ttgagacagc    8040
atagaataag tgcgacatca tcatcggaag agagtagtaa caaggtcaa agacagttga    8100
ctgtatcgcc ggaattcccg gggatccggc ctgagtgcgt agtacccgag actcagtgcg    8160
ccatgaagcg gaaagagaag aaagcacaga aggagaagga caactgcct gtcagcacga    8220
cgacggtgga cgaccacatg ccgcccatta tgcagtgtga acctccacct cctgaagcag    8280
caaggattca cgaagtggtc ccaaggtttc tctccgacaa gctgttggtg acaaaccggc    8340
agaaaaacat ccccccagttg acagccaacc agcagttcct tatcgccagg ctcatctggt    8400
accaggacgg gtacgagcag cctttctgatg aagatttgaa ggagattcag cagacgtgc    8460
agcaagcgga cgatgaaaac gaagagtcgg cacactccctt ccgccagatc acagagatga    8520
ctatcctcac ggtccaactt atcgtggagt tcgcgaaggg attgccaggg ttcgccaaga    8580
tctcgcagcc tgatcaaatt acgctgctta aggcttgctc aagtgaggta atgatgctcc    8640
gagtcgcgcg acgatacgat gcggcctcag acagtattct gttcgcgaac aaccaagcgt    8700
acactccgca caactaccgc aaggctcgca tggccgaggt catcgaggat ctactgccat    8760
tctgccggtg catgtactct atggcgttgg acaacatcca ttacgcgctg ctcacgctg    8820
tcgtcatctt ttctgaccgg ccaggggttgg agcagccgca actggtggaa gagatccagc    8880
ggtactacct gaatacgctc cgcatctata tcctgaacca gctgagcggg tcggcgcgtt    8940
cgtccgtcat atacggcaag atcctctcaa tcctctctga gctacgcacg ctcggcatgc    9000
aaaactccaa catgtgcatc tccctcaagc tcaagaacag aaagctgccg ccttttcctcg    9060
aggagatctg ggatgtggcg gacatgtcgc acacccaacc gccgcctatc ctcgagtccc    9120
ccacgaatct ctaggcggcc tctagagcgg ccgccaccgc gggagatcc agacatgata    9180
agatacattg atgagtttgg acaaaccaca actagaatgc agtgaaaaaa atgctttatt    9240
tgtgaaattt gtgatgctat tgctttattt gtaaccatta taagctgcaa taaacaagtt    9300
aacaacaaca attgcattca ttttatgttt caggttcagg gggaggtgtg ggaggttttt    9360
taaagcaagt aaaacctcta caaatgtggt atggctgatt atgatcaccg gtcaaatgac    9420
ggtgacaata aaacggagac tttgacccgg aacgcggaaa ttcacgtaaa aaacacctgg    9480
gcgagtcctc cacgtaatcg gtcaaagtcc ctcggccctc ggtaaatatt acgcactatg    9540
actaacgccc tattattcag ttttcacttc cccgtttcac ttttcgcgcg aaaatggcca    9600
aatcttacat ggtcccgccc aaaattacta cgatatccgg tgaaaagcgc gcgaaaattg    9660
```

```
gcacttccgg aggtaggcgg cgctcatcaa aaacgtcaca ttttccgcga cggaagcttg    9720
catgtgagct cctcccactt gcaaatgcca cacttccgcc acacctccca accctactcg    9780
cgcgtcctac gtcacccgcc ccgcctctcc ccgcccacct cattatcata ttggccacaa    9840
tccaaaataa ggtatattat tgatgatggt ttaaacgccc aattcactgg ccgtcgtttt    9900
acaacgtcgt gactgggaaa accctggcgt tacccaactt aatcgccttg cagcacatcc    9960
cccttcgcc agctggcgta atagcgaaga ggcccgcacc gatcgccctt cccaacagtt   10020
gcgcagcctg aatggcgaat ggcgcctgat gcggtatttt ctccttacgc atctgtgcgg   10080
tatttcacac cgcatatggt gcactctcag tacaatctgc tctgatgccg catagttaag   10140
ccagccccga cacccgccaa cacccgctga cgcgccctga cgggcttgtc tgctcccggc   10200
atccgcttac agacaagctg tgaccgtctc cgggagctgc atgtgtcaga ggttttcacc   10260
gtcatcaccg aaacgcgcga gacgaaaggg cctcgtgata cgcctatttt tataggttaa   10320
tgtcatgata ataatggttt cttagacgtc aggtggcact tttcggggaa atgtgcgcgg   10380
aacccctatt tgtttatttt tctaaataca                                    10410
```

```
SEQ ID NO: 62           moltype = DNA   length = 10040
FEATURE                 Location/Qualifiers
misc_feature            1..10040
                        note = GCAd-RTS-IL12 design 2
source                  1..10040
                        mol_type = other DNA
                        organism = synthetic construct
SEQUENCE: 62
ttcaaatatg tatccgctca tgagacaata accctgataa atgcttcaat aatattgaaa      60
aaggaagagt atgagtattc aacatttccg tgtcgccctt attccctttt ttgcggcatt     120
ttgccttcct gttttgctc acccagaaac gctggtgaaa gtaaaagatg ctgaagatca     180
gttgggtgca cgagtgggtt acatcgaact ggatctcaac agcggtaaga tccttgagag     240
ttttcgcccc gaagaacgtt ttccaatgat gagcactttt aaagttctgc tatgtggcgc     300
ggtattatcc cgtattgacg ccgggcaaga gcaactcggt cgccgcatac actattctca     360
gaatgacttg gttgagtact caccagtcac agaaaagcat cttacggatg gcatgacagt     420
aagagaatta tgcagtgctg ccataaccat gagtgataac actgcggcca acttacttct     480
gacaacgatc ggaggaccga aggagctaac cgcttttttg cacaacatgg gggatcatgt     540
aactcgcctt gatcgttggg aaccggagct gaatgaagcc ataccaaacg acgagcgtga     600
caccacgatg cctgtagcaa tggcaacaac gttgcgcaaa ctattaactg gcgaactact     660
tactctagct tcccggcaac aattaataga ctggatggag gcggataaag ttgcaggacc     720
acttctgcgc tcggcccttc cggctggctg gtttattgct gataaatctg gagccggtga     780
gcgtgggtct cgcggtatca ttgcagcact ggggccagat ggtaagccct cccgtatcgt     840
agttatctac acgacgggga gtcaggcaac tatggatgaa cgaaatagac agatcgctga     900
gataggtgcc tcactgatta agcattggta actgtcagac caagtttact catatatact     960
ttagattgat ttaaaacttc atttttaatt taaaaggatc taggtgaaga tcctttttga    1020
taatctcatg accaaaatcc cttaacgtga gttttcgttc cactgagcgt cagacccgcg    1080
agaaaagatc aaaggatctt cttgagatcc tttttttctg cgcgtaatct gctgcttgca    1140
aacaaaaaaa ccaccgctac cagcggtggt ttgtttgccg gatcaagagc taccaactct    1200
ttttccgaag gtaactggct tcagcagagc gcagatacca aatactgttc ttctagtgta    1260
gccgtagtta ggccaccact tcaagaactc tgtagcaccg cctacatacc tcgctctgct    1320
aatcctgtta ccagtggctg ctgccagtgg cgataagtcg tgtcttaccg ggttggactc    1380
aagacgatag ttaccggata aggcgcagcg gtcgggctga acggggggtt cgtgcacaca    1440
gcccagcttg gagcgaacga cctacaccga actgagatac ctacagcgtg agctatgaga    1500
aagcgccacg cttcccgaag ggagaaaggc ggacaggtat ccggtaagcg gcagggtcgg    1560
aacaggagag cgcacgaggg agcttccagg gggaaacgcc tggtatcttt atagtcctgt    1620
cgggtttcgc cacctctgac ttgagcgtcg atttttgtga tgctcgtcag ggggggcgag    1680
cctatggaaa aacgccagca acgcggcctt tttacggttc ctggccttt gctggccttt    1740
tgctcacatg ttctttcctg cgttatcccc tgattctgtg gataaccgta ttaccgcctt    1800
tgagtgagct gataccgctc gccgcagccg aacgaccgag cgcagcgagt cagtgagcga    1860
ggaagcggaa gagcgcccaa tacgcaaacc gcctctcccc gcgcgttggc cgattcatta    1920
atgcagctgg cacgacaggt ttcccgactg gaaagcgggc agtgagcgca acgcaattaa    1980
tgtgagttag ctcactcatt aggcacccca ggctttacac tttatgcttc cggctcgtat    2040
gttgtgtgga attgtgagcg gataacaatt tcacacagga aacagctatg accatgatta    2100
cgccaagctg ggtcaagtct tccagtttaa gcagcagagc ggtcagtttc tcatcccgag    2160
cagacgcgcg agaggccgcg ccgctcgcca ccaaagagct gtaaaggtcc gtagccatgc    2220
tgcgcgcggt cgcggcggcg gcggaggcgg cggcggcgtcc gcggcgtcc agcggagttc    2280
ctccacggt cgcgtaggcc attgtagacg aatttgaagg cagaacgggg cgtccatcca    2340
cgttggaacc catcacattc tgacgcactc cagcccagtg aggcatgcgc actgtcagat    2400
aggggctaaa gatgcttcca tcaaagctgt tgccggtgtc gctcatggcg gcggctgttg    2460
caagacaaaa cagagagacc cttagacccc caatttatac acgccccacc cttctagcca    2520
cgccacctt acccacctca atcggtatcc tcatcgctag acccaaactc ggccctggtg    2580
caggccagca ccagatggtc aggcctcag gtacgtagcc gcaataaaat atctttattt    2640
tcattacatc tgtgtgttgg ttttttgtgt gaatccatag tactaacata cgctctccat    2700
caaaacaaaa cgaaacaaaa caaactagca aaataggctg tcccagtgca agtccaggt    2760
gccagaacat ttctctatcc ataatgcagg ggtaccggaa ggaagagggg cgggtcgat    2820
cgaccccgcc cctcttcctt cgaaggaaga gggggggggt ccaattgcgg agtactgtcc    2880
tccgagcgga gtactgtcct ccgagcgag tactgtcctc cgagcggagt actgtcctcc    2940
gagcggagta ctgtcctccg agcggagtac tgtcctccga gcggagagtc ccgggggacc    3000
tagagggtat ataatgggtg ccttagctgg tgtgtgacct catcttcctg tacgcccctg    3060
caggagatca cgcgtgccac catgggtcac agcagtttgc tcatctcttg gttttcctg    3120
gtttttctgg catctccct cgtgccata tgggaactga agaaagatgt ttatgtcgta    3180
gaattggatt ggtatccgga tgcccctgga gaaatggtgg tcctcacctg tgacaccct    3240
gaagaagatg gtatcacctg gaccttggac cagagcagtg aggtcttagg ctctggcaaa    3300
accctgacca tccaagtcaa agagtttgga gatgctggag tacacctgtc acaaaggga    3360
ggcgaggttc taagccattc gctcctgctg cttcacaaaa aggaagatgg aatttggtcc    3420
```

```
actgatattt taaaggacca gaaagaaccc aaaaataaga cctttctaag atgcgaggcc   3480
aagaattatt ctggacgttt cacctgctgg tggctgacga caatcagtac tgatttgaca   3540
ttcagtgtca aaagcagcag aggctcttct gaccccaag gggtgacgtg cggagctgct    3600
acactctctg cagagagagt cagaggggac aacaaggagt atgagtactc agtggagtgc   3660
caggaggaca gtgcctgccc agctgctgag gagagtctgc ccattgaggt catggtggat   3720
gccgttcaca agctcaagta tgaaaactac accagcagct tcttcatcag ggacatcatc   3780
aaacctgacc cacccaagaa cttgcagctg aagccattaa agaattctcg gcaggtggag   3840
gtcagctggg agtaccctga cacctggagt actccacatt cctacttctc cctgacattc   3900
tgcgtttcagg tccagggcaa gagcaagaga gaaaagaaag atagagtctt cacggacaag   3960
acctcagcca cggtcatctg ccgcaaaaat gccagcatta gcgtgcgggc ccaggaccgc   4020
tactatagct catcttggag cgaatgggca tctgtgccct gcagtctcga gggcggcgga   4080
gagggcagag gaagtcttct aacatgcgg gacgtggagg agaatcccgg ccctaggatg     4140
ggtccagcgc gcagcctcct ccttgtggct accctggtcc tcctggacca cctcagtttg   4200
gccagaaacc tccccgtggc cactccagac ccaggaatgt tcccatgcct tcaccactcc   4260
caaaacctgc tgagggccgt cagcaacatg ctccagaagg ccagacaaac tctagaattt   4320
taccccttgca cttctgaaga gattgatcat gaagatatca caaagataa aaccagcaca    4380
gtggaggcct gtttaccatt ggaattaacc aagaatgaga gttgcctaaa ttccagagag   4440
acctcttttca taactaatgg gagttgcctg gcctccagaa agacctcttt tatgatggcc   4500
ctgtgcctta gtagtattta tgaagacttg aagatgtacc aggtggagtt caagaccatg   4560
aatgcaaagc ttctgatgga tcctaagagg cagatctttc tagatcaaaa catgctggca   4620
gttattgatg agctgatgca ggccctgaat ttcaacagtg agactgtgcc acaaaaatcc   4680
tcccttgaag aaccggattt ttataaaact aaaatcaagc tctgcatact tcttcatgct   4740
ttcagaattc gggcagtgac tattgataga gtgatgagct atctgaatgc ttcctaaatc   4800
gatttattta tcggcataaa taatttttttt gaagaagtaa tactatttttt cttttttttt   4860
gtaaataaat gggttaaggg atgtaacatt gtttgttgtt tggtggggggt tgggcctcc    4920
gcgccgggtt ttggcgcctc ccgcgggcgc cccctcctcc acggcgagcg ctgccacgtc   4980
agacgaaggg cgcagcgagc gtcctgatcc ttccgcccgg acgctcagga cagcggcccg   5040
ctgctcataa gactcggcct tagaaccca gtatcagcag aaggacattt taggacggga    5100
cttgggtgac tctagggcac tggttttctt tccagagagc ggaacaggcg aggaaaagta   5160
gtcccttctc ggcgattctg cggagggatc tccgtgggcg ggtgaacgcc gatgattata   5220
taaggacgcg ccgggtgtgg cacagctagt tccgtcgcag ccgggatttg ggtcgcggtt   5280
cttgttttgtg gatcgctgtg atcgtcactt ggtgagtagc gggctgctgg gctgggtacg   5340
tgcgctcggg gttggcgagt gtgtttttgtg aagtttttta ggcacttttt gaaatgtaat   5400
catttgggtc aatatgtaat tttcagtgtt agactagtaa attgtccgct aaattctggc   5460
cgttttttggc ttttttgtta gacgagctag cgccgccacc atgggccta aaaagaagcg   5520
taaagtcgcc ccccgaccg atgtcagcct gggggacgag ctccacttag acggcgagga   5580
cgtgccgatg gcgcatgccg acgcgctaga cgatttcgat ctggacatgt ggggggacgg   5640
ggattccccg ggtccgggat ttaccccca cgactccgcc cctacgcg ctctggatat      5700
ggccgacttc gagtttgagc agatgtttac cgatgccgtt ggaattgacg agtacggtgg   5760
ggaattcgag atgcctgtgg acaggatcct ggaggcagag cttgctgtgg aacagaagag   5820
tgaccagggc gttgagggtc ctgggggaac cgggggtagc ggcagcagcc caaatgaccc   5880
tgtgactaac atctgtcagg cagctgacaa acagctattc acgcttgttg agtgggcgaa   5940
gaggatccca cacttttcct ccttgcctct ggatgatcag gtcatattgc tgcgatgcagg   6000
ctggaatgaa ctcctcattg cctcctttttc acaccgatcg attgatgttc gagatggcat   6060
cctccttgcc acaggtcttc acgtgcaccg caactcagcc cattcagcag gagtaggagc   6120
catctttgat cgggtgctga cagagctagt gtccaaatg cgtgacatga ggatggacaa    6180
gacagagctt ggctgcctga gggcaatcat tctgtttaat ccagagggtg gggtttgaa    6240
atccgcccag gaagttgaac ttctacgtga aaaagtatat gccgctttgg aagaatatac   6300
tagaacaaca catcccgatg aaccaggaag atttgcaaaa cttttgcttc gtctgccttc   6360
tttacgttcc ataggcctta agtgtttgga gcatttgttt ttctttcgcc ttattggaga   6420
tgttccaatt gatacgttcc tgatggagat gcttgaatca ccttctgatt cataatctag   6480
cctagcccc ctctccctcc cccccccta acgttactgg ccgaagccgc ttggaataag     6540
gccggtgtgc gtttgtctat atgttatttt ccaccatatt gccgtctttt ggcaatgtga   6600
gggcccggaa acctggccct gtcttcttga cgagcattcc taggggtctt tccctctcg    6660
ccaaaggaat gcaaggtctg ttgaatgtcg tgaaggaagc agttcctctg gaagcttctt   6720
gaagacaaac aacgtctgta gcgaccctttt gcaggcagcg gaacccccca cctggcgaca   6780
ggtgcctctg cggccaaaag ccacgtgtat aagatacacc tgcaaaggcg gcacaacccc   6840
agtgccacgt tgtgagttgg atagttgtgg aaagagtcaa atggctctcc tcaagcgtat   6900
tcaacagggg gctgaaggat gcccagaagg taccccattg tatgggatct gatctggggc   6960
ctcggtgcac atgctttaca tgtgtttagt cgaggttaaa aaacgtctag gcccccgag    7020
ccacggggac gtggttttcc tttgaaaaac acgatctcta ggcgccacca tgaagctact   7080
gtcttctatc gaacaagcat gcgatatttg ccgacttaaa aagctcaagt gctccaaaga   7140
aaaaccgaag tgcgccaagt gtctgaagaa caactgggag tgtcgctact ctcccaaaac   7200
caaaaggtct ccgctgacta gggcacatct gacagaagtg gaattcaaggc tagaaagact   7260
ggaacagcta tttctactga tttttcctcg agaagacctt gacatgattt tgaaaatgaa   7320
ttctttacag gatataaaag cattgttaac aggattattt gtacaagata atgtgaataa   7380
agatgccgtc acagatagat tggcttcagt ggagactgat atgcctctaa cattgagaca   7440
gcatagaata agtcgacat catcatcgga agagagtagt aacaaaggtc aaagacagtt    7500
gactgtatcg ccggaattcc cggggatccg gcctgagtgc gtagtaccccg agactcagtt   7560
cgccatgaag cggaaagaga agaaagcaca gaaggagaag gacaaactgc ctgtcagcac   7620
gacgacggtg gacgaccaca tgccgcccat tatgcagtgt gaacctccac ctcctgaagc   7680
agcaaggatt cacgaagtgg tcccaaggtt tctctccgac aagctgttgg tgacaaaccg   7740
gcagaaaaac atccccagt tgacagccaa ccagcagttc cttatcgcca ggctcatctg    7800
gtaccaggag gggtacgagc agccttctga tgaagatttg aagaggatta cgacgacgtg   7860
gcagcaagcg gacgatgaaa acgaagagtc ggacactccc ttccgccaga tcacagagat   7920
gactatcctc acggtccaac ttatcgtgga gttcgcgaag ggattgcaag gttcgccaa    7980
gatctcgcag cctgatcaaa ttacgctgct aagcgttgc tcaagtgagg taatgatgct    8040
ccgagtcgcg cgacgatacg atgcggcctc agacagtatt ctgttcgcga caaccaagc    8100
gtacactcgc gacaactacc gcaaggctgg catggccgag gtcatcgagg atctactgca   8160
```

```
cttctgccgg tgcatgtact ctatggcgtt ggacaacatc cattacgcgc tgctcacggc 8220
tgtcgtcatc ttttctgacc ggccagggtt ggagcagccg caactggtgg aagagatcca 8280
gcggtactac ctgaatacgc tccgcatcta tatcctgaac cagctgagcg ggtcggcgcg 8340
ttcgtccgtc atatacggca agatcctctc aatcctctct gagctacgca cgctcggcat 8400
gcaaaactcc aacatgtgca tctccctcaa gctcaagaac agaaagctgc cgcctttcct 8460
cgaggagatc tgggatgtgg cggacatgtc gcacacccaa ccgccgccta tcctcgagtc 8520
ccccacgaat ctctaaatcg attacgctcc tctactcttt gagacatcac tggcctataa 8580
taaatgggtt aatttatgta acaaaattgc cttggcttgt aactttatt agacattctg 8640
atgtttgcat tgtgtaaata ctgttgtatt ggaaaagcgt gccaagatgg attattgtaa 8700
ttcagtgtct tttttagtag cgtcacgtgc caaacactgt tagtcacaga gggcatgaga 8760
cagcctgtgc tggaacagct cagttcatag ggctatggag atggggagaa aggggcgctt 8820
ctgtcagaga caagctgtgg tctgggaagg ccttagcact aaaagcacca caatgagaag 8880
caaccgccag aagcagggcc cgcaggcctt tgttccagct gcaaagagaa aggaaaaagt 8940
ggggaataag agttggggct gcggaggggg tggggagcag tgtgcaggtt ccgtacttga 9000
acagaaagca gggaccaaca caaggaaggg cgcgccaccg gtcaaatgac ggtgacaata 9060
aaacggagac tttgacccgg aacgcggaaa ttcacgtaaa aaacacctgg gcgagtcctc 9120
cacgtaatcg gtcaaagtcc ctcggccctc ggtaaatatt acgcactatg actaacgccc 9180
tattattcag ttttcacttc cccgtttcac ttttcgcgcg aaaatggcca aatcttacat 9240
ggtcccgccc aaaattacta cgatatccgg tgaaaagcgc gcgaaaattg gcacttccgg 9300
aggtaggcgg cgctcatcaa aaacgtcaca ttttccgcga cggaagcttg catgtgagct 9360
cctcccactt gcaaatgcca cacttccgcc acacctccca ccctactcg cgcgtcctac 9420
gtcaccggcc ccgcctctcc ccgccacct cattatcata ttggccacaa tccaaaataa 9480
ggtatattat tgatgatggt ttaaacgccc aattcactgg ccgtcgtttt acaacgtcgt 9540
gactgggaaa accctggcgt tacccaactt aatcgccttg cagcacatcc cccttttcgcc 9600
agctggcgta atagcgaaga ggcccgcacc gatcgccctt ccaacagtt gcgcagcctg 9660
aatggcgaat ggcgcctgat gcggtatttt ctccttacgc atctgtgcgg tatttcacac 9720
cgcatatggt gcactctcag tacaatctgc tctgatgccg catagttaag ccagccccga 9780
cacccgccaa cacccgctga cgcgccctga cgggcttgtc tgctcccggc atccgcttac 9840
agacaagctg tgaccgtctc cgggagctgc atgtgtcaga ggttttcacc gtcatccacg 9900
aaacgcgcga gacgaaaggg cctcgtgata cgcctatttt tataggttaa tgtcatgata 9960
ataatggttt cttagacgtc aggtggcact tttcggggaa atgtgcgcgg aacccctatt 10020
tgtttatttt tctaaataca                                              10040
```

SEQ ID NO: 63        moltype = DNA  length = 9949
FEATURE               Location/Qualifiers
misc_feature       1..9949
                      note = GCAd-RTS-IL12 design 3
source                1..9949
                      mol_type = other DNA
                      organism = synthetic construct

SEQUENCE: 63

```
ttcaaatatg tatccgctca tgagacaata accctgataa atgcttcaat aatattgaaa 60
aaggaagagt atgagtattc aacatttccg tgtcgccctt attccctttt tgcgcattc 120
ttgccttcct gttttgctc acccagaaac gctggtgaaa gtaaaagatg ctgaagatca 180
gttgggtgca cgagtgggtt acatcgaact ggatctcaac agcggtaaga tccttgagag 240
ttttcgcccc gaagaacgtt ttccaatgat gagcactttt aaagttctgc tatgtggcgc 300
ggtattatcc cgtattgacg ccgggcaaga gcaactcggt cgccgcatac actattctca 360
gaatgacttg gttgagtact caccagtcac agaaaagcat cttacggatg gcatgacagt 420
aagagaatta tgcagtgctg ccataaccat gagtgataac actgcggcca acttacttct 480
gacaacgatc ggaggaccga aggagctaac cgcttttttg cacaacatgg gggatcatgt 540
aactcgcctt gatcgttggg aaccggagct gaatgaagcc ataccaaacg acgagcgtgt 600
caccacgatg cctgtagcaa tggcaacaac gttgcgcaaa ctattaactg gcgaactact 660
tactctagct tccggcaac aattaataga ctggatggag gcggataaag ttgcaggacc 720
acttctgcgc tcggcccttc cggctggctg gtttattgct gataaatctg gagccggtga 780
gcgtgggtct cgcggtatca ttgcagcact ggggccagat ggtaagccct cccgtatcgt 840
agttatctac acgacgggga gtcaggcaac tatggatgaa cgaaatagac agatcgctga 900
gataggtgcc tcactgatta gcattggta actgtcagac caagtttact catatatact 960
ttagattgat ttaaaacttc attttttaatt taaaaggatc taggtgaaga tccttttttga 1020
taatctcatg accaaaatcc cttaacgtga gttttcgttc cactgagcgt cagaccccgt 1080
agaaaagatc aaaggatctt cttgagatcc ttttttctg cgcgtaatct gctgcttgca 1140
aacaaaaaaa ccaccgctac cagcggtggt ttgtttgccg gatcaagagc taccaactct 1200
ttttccgaag gtaactggct tcagcagagc gcagatacca aatactgttc ttctagtgta 1260
gccgtagtta ggccaccact tcaagaactc tgtagcaccg cctacatacc tcgctctgct 1320
aatcctgtta ccagtggctg ctgccagtgg cgataagtcg tgtcttaccg ggttggactc 1380
aagacgatag ttaccggata aggcgcagcg gtcgggctga acggggggtt cgtgcacaca 1440
gcccagcttg gagcgaacga cctacaccga actgagatac ctacagcgtg agctatgaga 1500
aagcgccacg cttcccgaag ggagaaaggc ggacaggtat ccggtaagcg gcagggtcgg 1560
aacaggagag cgcacgaggg agcttccagg gggaaacgcc tggtatcttt atagtcctgt 1620
cgggtttcgc cacctctgac ttgagcgtcg atttttgtga tgctcgtcag ggggggcgag 1680
cctatggaaa aacgccagca acgcggcctt tttacggttc ctggcctttt gctggccttt 1740
tgctcacatg ttctttcctg cgttatcccc tgattctgtg ataaccgta ttaccgcctt 1800
tgagtgagct gataccgctc gccgcagccg aacgaccgag cgcagcgagt cagtgagcga 1860
ggaagcggaa gagcgcccaa tacgcaaacc gcctctcccc gcgcgttggc cgattcatta 1920
atgccgacag gttcccgactg gaaagcgggc agtgagcgca acgcaattaa 1980
tgtgagttag ctcactcatt aggcacccca ggctttacac tttatgcttc cggctcgtat 2040
gttgtgtgga attgtgagcg gataacaatt tcacacagga aacagctatg accatgatta 2100
cgccaagctg ggtcaagtct tccagtttaa gcagcagagc ggtcagtttc tcatcccgag 2160
cagacgcgcg agaggccgcg ccgctcgcca ccaaagagct gtaaaggtcc gtagccatgc 2220
tgcgcgcggt cgcggcggcg gcggaggcgg cggcggaggt cgcggcgtcc agcggagttc 2280
```

```
ctcccacggt cgcgtaggcc attgtagacg aatttgaagg cagaacgggg cgtccatcca    2340
cgttggaacc catcacattc tgacgcactc cagcccagtg aggcatgcgc actgtcagat    2400
aggggctaaa gatgcttcca tcaaagctgt tgccggtgtc gctcatggcg gcggctgttg    2460
caagacaaaa cagagagacc cttagacccc caatttatac acgccccacc cttctagcca    2520
cgcccacctt acccacctca atcggtatcc tcatcgctag acccaaactc ggccctggtg    2580
caggccagca ccagatggtc aggcctgcag gtacgtagcc gcaataaaat atctttattt    2640
tcattacatc tgtgtgttgg ttttttgtgt gaatccatag tactaacata cgctctccat    2700
caaaacaaaa cgaaacaaaa caaactagca aaataggctg tccccagtgc aagtccaggt    2760
gccagaacat ttctctatcc ataatgcagg ggtaccggaa ggaagagggg cggggtcgat    2820
cgacccgcc cctcttcctt cgaaggaaga ggggcggggt ccaattgcgg agtactgtcc    2880
tccgagcgga gtactgtcct ccgagcggag tactgtcctc cgagcggagt actgtcctcc    2940
gagcggagta ctgtcctccg agcggagtac tgtcctccga gcggagagtc cccggggacc    3000
tagagggtat ataatgggtg cctagctgg tgtgtgacct catcttcctg tacgcccctg    3060
caggcagccg ctaaatccaa ggtaaggtca gaagagctag cgccaccatg tgtcaccagc    3120
agttggtcat ctcttggttc agcctggttt tctggcatc tcccctcgtg gccatctggg    3180
aactgaagaa agatgtttat gtcgtagaat tggattggta tcccgacgcc cctggagaaa    3240
tggtggtcct gacatgtgac acccctgaag aagatggtat cacctggacc ttggaccaga    3300
gcagtgaggt cttaggctct ggcaagaccc tgaccatcca agtcaaagag tttggagatg    3360
ctggccagta cacctgtcac aaaggaggcg aggttctaag ccattcgctc ctgctgcttc    3420
acaaaaagga agatggaatt tggtccactg acattctgaa ggaccagaaa gaacccaaga    3480
ataagacctt tctaagatgc gaggccaaga attattctgg acgtttcacc tgctggtggc    3540
tgacgacaat cagtactgat ttgacattca gtgtcaaaag cagcagaggc tcttctgacc    3600
cccaagggt gacgtgcgga gctgctacac tcagcgccga gagagtcaga ggggacaaca    3660
aggagtatga gtactcagtg gagtgccagg aggacagtgc ctgccagct gctgaggaga    3720
gtctgcccat tgaggtcatg gtggatgccg ttcacaagct caagtatgaa aactacacca    3780
gcagcttctt catcagggac atcatcaaac ctgacccacc caagaacttg cagctgaagc    3840
ccctgaagaa cagcagacag gtggaggtca gctgggagta ccctgacacc tggagtactc    3900
cacattccta cttctccctg acattctgcg ttcaggtcca gggcaagagc aagagagaaa    3960
agaaagatag agtcttcacg gacaagacct cagccacggt catctgccgc aaaaatgcca    4020
gcattagcgt gcgggcccag gaccgctact atagctcatc ttggagcgaa tgggcatctg    4080
tgccctgctc cggtggcggt ggcggcggat ctagaaacct ccccgtggcc actccagaca    4140
caggaatgtt cccatgcctt caccacagcc agaacctgct gagggccgtc agcaacatgc    4200
tccagaaggc cagacaaact ctagaatttt accttgcac ttctgaagag attgatcatg    4260
aagatatcac aaaagataaa accagacacag tggaggcctg tttaccattg gaattaacca    4320
agaatgagag ttgcctaaat tccagagaga cctcttcat aactaatgag agttgcctga    4380
cctccagaaa gacctctttt atgatggccc tgtgccttag tagtatttat gaagacttga    4440
agatgtacca ggtggagttc aagaccatga atgcaaagct gctgatggac cccaagaggc    4500
agatcttct agatcaaaac atgctggcag ttattgatga gctgatgcag gccctgaatt    4560
tcaacagtga gactgtgcca caaaaatcct cccttgaaga accggatttt tataaaacta    4620
aaatcaagct ctgcatactt cttcatgctt tcagaatcag agcagtgact attgatagag    4680
tgatgagcta tctgaatgct tcctaaatcg atttatttat cggcataaat aattttttg    4740
aagaagtaat actatttttc tttttttttg taaataaatg ggttaaggga tgtaacattg    4800
tttgttgttt ggtgggggtt ggggcctccg cgcgggttt tggcgcctcc cgcgggcgcc    4860
cccctcctca cggcgagcgc tgccacgtca gacgaagggc gcagcgagcg tcctgatcct    4920
tccgcccgga cgctcaggac agcggcccgc tgctcataag actcggcctt agaacccag    4980
tatcagcaga aggacatttt aggacgggac ttgggtgact ctaggggcact ggttttctttt    5040
ccagagagcg gaacaggcga ggaaaagtag tcccttctcg gcgattctgc ggagggatct    5100
ccgtggggcg gtgaacgccg atgattatat aaggacgcgc cgggtgtggc acagctagtt    5160
ccgtcgcagc cgggatttgg gtcgcggttc ttgtttgtgg atcgctgtga tcgtcacttg    5220
gtgagtagcg ggctgctggg ctgggtacgt gcgctcgggg ttggcgagtg tgttttgtga    5280
agttttttag gcaccttttg aaatgtaatc atttgggtca atatgtaatt ttcagtgtta    5340
gactagtaaa ttgtccgcta aattctggcc gttttttggct tttttgttag acgagctagc    5400
gccgccacca tgggccctaa aaagaagcgt aaagtcgccc ccccgaccga tgtcagcctg    5460
ggggacgagc tccacttaga cggcgaggac gtggcgatgg cgcatgccga cgcgctagac    5520
gatttcgatc tggacatgtt ggggacgggg gattccccg gtccgggatt tacccccag    5580
gactccgccc cctacggcgc tctgatatg gccgacttcg agtttgagca gatgtttacc    5640
gatgcccttg gaattgacga gtacggtggg gaattcgaga tgcctgtgga caggatcctg    5700
gaggcagagc ttgctgtgga acagaagagt gaccagggcg ttgagggtcc tgggggaacc    5760
gggggtagcg gcagcagccc aaatgaccct gtgaccaaca tctgtcaggc agctgacaaa    5820
cagctattca cgcttgttga gtgggcgaag aggatcccac actttctc cttgcctctg    5880
gatgatcagg tcatattgct gcgggcaggc tggaatgaac tcctcattgc ctccttttca    5940
caccgatcca ttgatgttcg agatggcatc ctccttgcca caggtcttca cgtgcaccgc    6000
aactcagccc attcagcagg agtaggagcc atctttgatc gggtgctgac agagctagtg    6060
tccaaaatgc gtgacatgga gatggacaag acagagcttg gctgctgag ggcaatcatt    6120
ctgtttaatc cagaggtgag gggtttgaaa tccgccagg aagttgaact tctacgtgaa    6180
aaagtatatg ccgctttgga agaatatact agaacaacac atcccgatga accaggaaga    6240
tttgcaaaac ttttgcttcg tctgcctctt tacgttcca taggccttaa gtgtttggag    6300
catttgtttt tctttcgcct tattggagat gttccaattg atacgttcct gatggagatg    6360
cttgaatcac cttctgattc ataatctagc ctagccccc tctccatccc ccccccctaa    6420
cgttactggc cgaagccgct tggaataagg ccggtgtgcg tttgtctata tgttatttc    6480
caccatattg ccgtcttttg gcaatgtgag ggcccggaaa cctggccctg tcttcttgac    6540
gagcattcct aggggtcttt cccctctcgc caaggaatg caaggtctgt tgaatgtcgt    6600
gaaggaagca gttcctctgg aagcttcttg aagacaaaca acgtctgtag cgacccttg    6660
caggcagcgg aacccccac ctggcgacag gtgcctctgc ggccaaacc cacgtgtata    6720
agatacacct gcaaaggcgg cacaaccccca gtgccacgtt gtgagttgga tagttgtgga    6780
aagagtcaaa tggctctcct caagcgtatt caacaagggg ctgaaggatg cccagaaggt    6840
accccattgt atgggatctg atctgggcc tcggtgcaca tgctttacat gtgtttagtc    6900
gaggttaaaa aacgtctagg cccccgaac cacgggacg tggttttcct ttgaaaaaca    6960
cgatctctag gcgccaccat gaagctactg tcttctatcg aacaagcatg cgatatttgc    7020
```

```
cgacttaaaa agctcaagtg ctccaaagaa aaaccgaagt gcgccaagtg tctgaagaac   7080
aactgggagt gtcgctactc tcccaaaacc aaaaggtctc cgctgactag ggcacatctg   7140
acagaagtgg aatcaaggct agaaagactg gaacagctat ttctactgat ttttcctcga   7200
gaagaccttg acatgatttt gaaaatggat tctttacagg atataaaagc attgttaaca   7260
ggattatttg tacaagataa tgtgaataaa gatgccgtca cagatagatt ggcttcagtg   7320
gagactgata tgcctctaac attgagacag catagaataa gtgcgacatc atcatcggaa   7380
gagagtagta acaaaggtca aagacagttg actgtatcgc cggaattccc ggggatccgg   7440
cctgagtgcg tagtacccga gactcagtgc gccatgaagc ggaaagagaa gaaagcacag   7500
aaggagaagg acaaactgcc tgtcagcacg acgacggtgg acgaccacat gccgcccatt   7560
atgcagtgtg aacctccacc tcctgaagca gcaaggattc acgaagtggt cccaaggttt   7620
ctctccgaca agctgttggt gacaaaccgg cagaaaaaca tcccccagtt gacagccaac   7680
cagcagttcc ttatcgccag gctcatctgg taccaggacg ggtacgagca gccttctgat   7740
gaagatttga gaggattac gcagacgtgg cagcaagcgg acgatgaaaa cgaagagtcg   7800
gacactccct tccgccagat cacagagatg tctatcctca ggctccaact tatcgtggag   7860
ttcgcgaagg gattgccagg gttcgccaag atctcgcagc ctgatcaaat tacgctgctt   7920
aaggcttgct caagtgaggt aatgatgctc cgagtcgcgc gacgatacga tgcggcctca   7980
gacagtattc tgttcgcgaa caaccaagcg tacactcgcg acaactaccg caaggctggc   8040
atggccgagg tcatcgagga tctactgcac ttctgccggt gcatgtactc tatgcgcgttg   8100
gacaacatcc attacgcgct gctcacggct gtcgtcatct tttctgaccg gccagggttg   8160
gagcagccgc aactggtgga agagatccag cggtactacc tgaatacgct ccgcatctat   8220
atcctgaacc agctgagcgg gtcggcgcgt tcgtccgtca tatacggcaa gatcctctca   8280
atcctctctg agctacgcac gctcggcatg caaaactcca acatgtgcat ctccctcaag   8340
ctcaagaaca gaaagctgcc gccttttcctc gaggagatct gggatgtggc ggacatgtcg   8400
cacacccaac cgccgcctat cctcgagtcc cccacgaatc tctaaatcga ttacgctcct   8460
ctactctttg agacatcact ggcctataat aaatgggtta atttatgtaa caaaattgcc   8520
ttggcttgtt aactttatta gacattctga tgtttgcatt gtaaatac tgttgtattg   8580
gaaaagcgtg ccaagatgga ttattgtaat tcagtgtctt ttttagtagc gtcacgtgcc   8640
aaacactgtt agtcacagag ggcatgagac agcctgtgct ggaacagctc agttcatagg   8700
gctatggaga tggggagaaa ggggcgcttc tgtcagagac aagctgtggt ctgggaaggc   8760
cttagcacta aaagcaccac aatgagaagc aaccgccaga agcaggggcc gcaggccttt   8820
gttccagctg caaagagaaa ggaaaaagtg gggaataaga gttggggctg cggaggggt   8880
ggggagcatt gtgcaggttc cgtacttgaa cagaaagcag ggaccaacac aaggaagggc   8940
gcgccaccgg tcaaatgacg gtgacaataa acgggagact ttgacccgga acgcggaaat   9000
tcacgtaaaa aacacctggg cgagtcctcc acgtaatcgg tcaaagtccc tcggccctcg   9060
gtaaatatta cgcactatga ctaacgcct attattcagt tttcacttcc ccgtttcact   9120
tttcgcgcga aaatgccaa atcttacatg gtcccgccca aaattactac gatatccggt   9180
gaaaagcgcg cgaaaattgg cacttccgga ggtaggcggc gctcatcaaa aacgtcacat   9240
tttccgcgac ggaagcttgc atgtgagctc ctcccacttg caaatgccac acttccgcca   9300
cacctcccaa ccctactcgc gcgtcctacg tcaccgccc ctcctctccc cgccaccctc   9360
attatcatat tggccacaat ccaaaataag gtatattatt gatgatggtt taaacgccca   9420
attcactggc cgtcgtttta caacgtcgtg actgggaaaa ccctggcgtt acccaactta   9480
atcgccttgc agcacatccc cctttcgcca gctggcgtaa tagcgaagag gcccgcaccg   9540
atcgccctc ccaacagttg cgcagcctga atggcgaatg gcgcctgatg cggtattttc   9600
tccttacgca tctgtgcggt atttcacacc gcatatggtg cactctcagt acaatctgct   9660
ctgatgccgc atagttaagc cagccccgac acccgccaac acccgctgac gcgccctgac   9720
gggcttgtct gctcccggca tccgcttaca gacaagctgt gaccgtctcc gggagctgca   9780
tgtgtcagag gttttcaccg tcatcaccga aacgcgcgag gcagaagggc ctcgtgatac   9840
gcctatttt ataggttaat gtcatgataa taatgtttc ttagacgtca ggtggcactt   9900
ttcggggaaa tgtgcgcgga acccctattt gtttattttt ctaaataca              9949

SEQ ID NO: 64          moltype = DNA   length = 54
FEATURE                Location/Qualifiers
misc_feature           1..54
                       note = Whitlow Linker
source                 1..54
                       mol_type = other DNA
                       organism = synthetic construct
SEQUENCE: 64
ggcagcacct ccggcagcgg caagcctggc agcggcgagg gcagcaccaa gggc              54

SEQ ID NO: 65          moltype = DNA   length = 78
FEATURE                Location/Qualifiers
misc_feature           1..78
                       note = Linker
source                 1..78
                       mol_type = other DNA
                       organism = synthetic construct
SEQUENCE: 65
tctggcggag gatctggagg aggcggatct ggaggaggag gcagtggagg cggaggatct              60
ggcggaggat ctctgcag                                                            78

SEQ ID NO: 66          moltype =   length =
SEQUENCE: 66
000

SEQ ID NO: 67          moltype = DNA   length = 12
FEATURE                Location/Qualifiers
misc_feature           1..12
                       note = SGSG linker
```

```
source                  1..12
                        mol_type = other DNA
                        organism = synthetic construct
SEQUENCE: 67
agtggcagcg gc                                                        12

SEQ ID NO: 68           moltype = DNA  length = 45
FEATURE                 Location/Qualifiers
misc_feature            1..45
                        note = (G4S)3 linker
source                  1..45
                        mol_type = other DNA
                        organism = synthetic construct
SEQUENCE: 68
ggtggcggtg gctcgggcgg tggtgggtcg ggtggcggcg gatct                    45

SEQ ID NO: 69           moltype = DNA  length = 12
FEATURE                 Location/Qualifiers
misc_feature            1..12
                        note = Furin cleavage site
source                  1..12
                        mol_type = other DNA
                        organism = synthetic construct
SEQUENCE: 69
cgtgcaaagc gt                                                        12

SEQ ID NO: 70           moltype = DNA  length = 84
FEATURE                 Location/Qualifiers
misc_feature            1..84
                        note = Fmdv
source                  1..84
                        mol_type = other DNA
                        organism = synthetic construct
SEQUENCE: 70
agagccaaga gggcaccggt gaaacagact ttgaattttg accttctgaa gttggcagga  60
gacgttgagt ccaaccctgg gccc                                           84

SEQ ID NO: 71           moltype = DNA  length = 54
FEATURE                 Location/Qualifiers
misc_feature            1..54
                        note = Thosea asigna virus 2A region (T2A)
source                  1..54
                        mol_type = other DNA
                        organism = synthetic construct
SEQUENCE: 71
gagggcagag gaagtctgct aacatgcggt gacgtcgagg agaatcctgg acct          54

SEQ ID NO: 72           moltype = DNA  length = 75
FEATURE                 Location/Qualifiers
misc_feature            1..75
                        note = Furin-GSG-T2A
source                  1..75
                        mol_type = other DNA
                        organism = synthetic construct
SEQUENCE: 72
agagctaaga ggggaagcgg agagggcaga ggaagtctgc taacatgcgg tgacgtcgag  60
gagaatcctg gacct                                                     75

SEQ ID NO: 73           moltype = DNA  length = 78
FEATURE                 Location/Qualifiers
misc_feature            1..78
                        note = Furin-SGSG-T2A
source                  1..78
                        mol_type = other DNA
                        organism = synthetic construct
SEQUENCE: 73
agggccaaga ggagtggcag cggcgagggc agaggaagtc ttctaacatg cggtgacgtg  60
gaggagaatc ccggccct                                                  78

SEQ ID NO: 74           moltype = DNA  length = 57
FEATURE                 Location/Qualifiers
misc_feature            1..57
                        note = Porcine teschovirus-1 2A region (P2A)
source                  1..57
                        mol_type = other DNA
                        organism = synthetic construct
SEQUENCE: 74
gcaacgaact tctctctcct aaaacaggct ggtgatgtgg aggagaatcc tggtcca       57
```

```
SEQ ID NO: 75              moltype = DNA  length = 66
FEATURE                    Location/Qualifiers
misc_feature               1..66
                           note = GSG-P2A
source                     1..66
                           mol_type = other DNA
                           organism = synthetic construct
SEQUENCE: 75
ggaagcggag ctactaactt cagcctgctg aagcaggctg agacgtgga ggagaaccct    60
ggacct                                                              66

SEQ ID NO: 76              moltype = DNA  length = 60
FEATURE                    Location/Qualifiers
misc_feature               1..60
                           note = Equine rhinitis A virus 2A region (E2A)
source                     1..60
                           mol_type = other DNA
                           organism = synthetic construct
SEQUENCE: 76
cagtgtacta attatgctct cttgaaattg gctggagatg ttgagagcaa ccctggacct    60

SEQ ID NO: 77              moltype = DNA  length = 66
FEATURE                    Location/Qualifiers
misc_feature               1..66
                           note = Foot-and-mouth disease virus 2A region (F2A)
source                     1..66
                           mol_type = other DNA
                           organism = synthetic construct
SEQUENCE: 77
gtcaaacaga ccctaaactt tgatctgcta aaactggccg gggatgtgga aagtaatccc    60
ggcccc                                                              66

SEQ ID NO: 78              moltype = DNA  length = 93
FEATURE                    Location/Qualifiers
misc_feature               1..93
                           note = FP2A
source                     1..93
                           mol_type = other DNA
                           organism = synthetic construct
SEQUENCE: 78
cgtgcaaagc gtgcaccggt gaaacaggga agcggagcta ctaacttcag cctgctgaag    60
caggctggag acgtggagga gaaccctgga cct                                93

SEQ ID NO: 79              moltype = DNA  length = 24
FEATURE                    Location/Qualifiers
misc_feature               1..24
                           note = Linker-GSG
source                     1..24
                           mol_type = other DNA
                           organism = synthetic construct
SEQUENCE: 79
gcaccggtga aacagggaag cgga                                          24

SEQ ID NO: 80              moltype = DNA  length = 15
FEATURE                    Location/Qualifiers
misc_feature               1..15
                           note = Linker
source                     1..15
                           mol_type = other DNA
                           organism = synthetic construct
SEQUENCE: 80
gcaccggtga aacag                                                    15

SEQ ID NO: 81              moltype = AA  length = 18
FEATURE                    Location/Qualifiers
REGION                     1..18
                           note = Whitlow Linker Amino Acid Sequence
source                     1..18
                           mol_type = protein
                           organism = synthetic construct
SEQUENCE: 81
GSTSGSGKPG SGEGSTKG                                                 18

SEQ ID NO: 82              moltype = AA  length = 26
FEATURE                    Location/Qualifiers
REGION                     1..26
                           note = Linker Amino Acid Sequence
source                     1..26
                           mol_type = protein
```

```
                        organism = synthetic construct
SEQUENCE: 82
SGGGSGGGGS GGGGSGGGGS GGGSLQ                                          26

SEQ ID NO: 83           moltype =   length =
SEQUENCE: 83
000

SEQ ID NO: 84           moltype = AA  length = 4
FEATURE                 Location/Qualifiers
REGION                  1..4
                        note = SGSG Linker Amino Acid Sequence
source                  1..4
                        mol_type = protein
                        organism = synthetic construct
SEQUENCE: 84
SGSG                                                                  4

SEQ ID NO: 85           moltype = AA  length = 15
FEATURE                 Location/Qualifiers
REGION                  1..15
                        note = G4S LINKER Amino Acid Sequence
source                  1..15
                        mol_type = protein
                        organism = synthetic construct
SEQUENCE: 85
GGGGSGGGGS GGGGS                                                      15

SEQ ID NO: 86           moltype = AA  length = 4
FEATURE                 Location/Qualifiers
REGION                  1..4
                        note = Furin Cleavage site Amino Acid Sequence
source                  1..4
                        mol_type = protein
                        organism = synthetic construct
SEQUENCE: 86
RAKR                                                                  4

SEQ ID NO: 87           moltype = AA  length = 28
FEATURE                 Location/Qualifiers
REGION                  1..28
                        note = FMDV Amino Acid Sequence
source                  1..28
                        mol_type = protein
                        organism = synthetic construct
SEQUENCE: 87
RAKRAPVKQT LNFDLLKLAG DVESNPGP                                        28

SEQ ID NO: 88           moltype = AA  length = 18
FEATURE                 Location/Qualifiers
REGION                  1..18
                        note = Thosea asigna virus 2a Region (T2A) Amino Acid
                         Sequence
source                  1..18
                        mol_type = protein
                        organism = synthetic construct
SEQUENCE: 88
EGRGSLLTCG DVEENPGP                                                   18

SEQ ID NO: 89           moltype = AA  length = 25
FEATURE                 Location/Qualifiers
REGION                  1..25
                        note = FURIN-SGSG-T2A Amino Acid Sequence
source                  1..25
                        mol_type = protein
                        organism = synthetic construct
SEQUENCE: 89
RAKRGSGEGR GSLLTCGDVE ENPGP                                           25

SEQ ID NO: 90           moltype = AA  length = 26
FEATURE                 Location/Qualifiers
REGION                  1..26
                        note = FURIN-SGSG-T2A Amino Acid Sequence
source                  1..26
                        mol_type = protein
                        organism = synthetic construct
SEQUENCE: 90
RAKRSGSGEG RGSLLTCGDV EENPGP                                          26
```

```
SEQ ID NO: 91              moltype = AA  length = 19
FEATURE                    Location/Qualifiers
REGION                     1..19
                           note = Porcine teschovirus-1 2A region (P2A) Amino Acid
                            Sequence
source                     1..19
                           mol_type = protein
                           organism = synthetic construct
SEQUENCE: 91
ATNFSLLKQA GDVEENPGP                                                    19

SEQ ID NO: 92              moltype = AA  length = 22
FEATURE                    Location/Qualifiers
REGION                     1..22
                           note = GSG-P2A Amino Acid Sequence
source                     1..22
                           mol_type = protein
                           organism = synthetic construct
SEQUENCE: 92
GSGATNFSLL KQAGDVEENP GP                                                22

SEQ ID NO: 93              moltype = AA  length = 20
FEATURE                    Location/Qualifiers
REGION                     1..20
                           note = GSG-P2A Amino Acid Sequence
source                     1..20
                           mol_type = protein
                           organism = synthetic construct
SEQUENCE: 93
QCTNYALLKL AGDVESNPGP                                                   20

SEQ ID NO: 94              moltype = AA  length = 22
FEATURE                    Location/Qualifiers
REGION                     1..22
                           note = Foot-and-motuh disease virus 2A region (F2A) Amino
                            Acid Sequence
source                     1..22
                           mol_type = protein
                           organism = synthetic construct
SEQUENCE: 94
VKQTLNFDLL KLAGDVESNP GP                                                22

SEQ ID NO: 95              moltype = AA  length = 31
FEATURE                    Location/Qualifiers
REGION                     1..31
                           note = FP2A Amino Acid Sequence
source                     1..31
                           mol_type = protein
                           organism = synthetic construct
SEQUENCE: 95
RAKRAPVKQG SGATNFSLLK QAGDVEENPG P                                      31

SEQ ID NO: 96              moltype = AA  length = 8
FEATURE                    Location/Qualifiers
REGION                     1..8
                           note = LINKER-GSG Amino Acid Sequence
source                     1..8
                           mol_type = protein
                           organism = synthetic construct
SEQUENCE: 96
APVKQGSG                                                                8

SEQ ID NO: 97              moltype = AA  length = 5
FEATURE                    Location/Qualifiers
REGION                     1..5
                           note = LINKER Amino Acid Sequence
source                     1..5
                           mol_type = protein
                           organism = synthetic construct
SEQUENCE: 97
APVKQ                                                                   5

SEQ ID NO: 98              moltype = AA  length = 154
FEATURE                    Location/Qualifiers
REGION                     1..154
                           note = HBV HBx domain of HBV design 1
source                     1..154
                           mol_type = protein
                           organism = synthetic construct
```

```
SEQUENCE: 98
MAARLCCQLD PARDVLCLRP VGAESRGRPF SGPLGALSSS SPPAVPTDHG AHLSLRGLPV  60
CAFSSAGPCA LRFTSARRME TTVNAHQFLP KVLHKRTLGL SAMSTTDLEA YFKDCLFKDW  120
EELGEELRLK VFVLGGCRHK LVCAPAPCNF FTSA                              154

SEQ ID NO: 99          moltype = AA  length = 454
FEATURE                Location/Qualifiers
REGION                 1..454
                       note = HBV Pol domain of HBV design 1
source                 1..454
                       mol_type = protein
                       organism = synthetic construct
SEQUENCE: 99
GPCAEHGEHH IRIPRTPARV TGGVFLVDKN PHNTAESRLV VDFSQFSRGN YRVSWPKFAV  60
PNLQSLTNLL SSNLCWLSLD VSAAFYHLPL HPAAMPHLLV GSSGLSRYVA RLSSNSRIIN  120
HQHGTLQNLH DSCSRNLYVS LLLLYKTFGW KLHLYSHPII LGFRKIPMGV GLSPFLLAQF  180
TSAICSVVRR AFPHCLAFSG AKSVQHLESL FTAVTNFLLS LGIHLNPNKT KRWGYSLNFM  240
GYVIGSWGSL PQDHIRHKIK ECFRKLPVHR PIDWKVCQRI VGLLGFAAPF TQCGYPALMP  300
LYACIQSKQA FTFSPTYKAF LCKQYLNLYP VARQRPGLCQ VFADATPTGW GLVMGHQRMR  360
GTFSSRKYTS FPWLLGCAAN WILRGTSFVY VPSALNPADD PSRGRLGPCR PLLHLPFRPT  420
TGRTSLYADS PSVPSHLPDR VHFASPLHVA WRPP                              454

SEQ ID NO: 100         moltype = AA  length = 226
FEATURE                Location/Qualifiers
REGION                 1..226
                       note = HBV Surface (Env1) domain of HBV domain 1
source                 1..226
                       mol_type = protein
                       organism = synthetic construct
SEQUENCE: 100
MENITSGFLG PLLVLQAGFF LLTRILTIPQ SLDSWWTSLS FLGGTTVCLG QNSQSPTSNH  60
SPTSCPPTCV GYRWMCLRRF IIFLFILLLC LIFLLVLLDY QGMLPVCPLI PGSSTTSTGP  120
CRTCTTPAQG TSMYPSCCCT KPSDGNCTCI PIPSSWAFGK FLWEWASARF SWLSLLVPFV  180
QWFVGLSPTV WLSVIWMMWY WGPSLYNTLS PFLPLLPIFF YLWVYI                 226

SEQ ID NO: 101         moltype = AA  length = 180
FEATURE                Location/Qualifiers
REGION                 1..180
                       note = HBV Core domain of HBV design 1
source                 1..180
                       mol_type = protein
                       organism = synthetic construct
SEQUENCE: 101
MQLFHLCLII SCSCPTVQAS KLCLGWLWDM DIDPYKEFGA SVELLSFLPS DFFPSVRDLL  60
DTATALYRDA LESPEHCTPH HTALRHVCLC WGDLMNLATW VGTNLEDQAS RDLVVSYVNT  120
NMGLKFRQLL WFHISCLTFG RDLVLEYLVS FGVWIRTPPA YRPSNAPILS TLPETTVVRQ  180

SEQ ID NO: 102         moltype = AA  length = 226
FEATURE                Location/Qualifiers
REGION                 1..226
                       note = SHB(Env) domain
source                 1..226
                       mol_type = protein
                       organism = synthetic construct
SEQUENCE: 102
MENITSGFLG PLLVLQAGFF LLTRILTIPQ SLDSWWTSLS FLGGTTVCLG QNSQSPTSNH  60
SPTSCPPTCV GYRWMCLRRF IIFLFILLLC LIFLLVLLDY QGMLPVCPLI PGSSTTSTGP  120
CRTCTTPAQG TSMYPSCCCT KPSDGNCTCI PIPSSWAFGK FLWEWASARF SWLSLLVPFV  180
QWFVGLSPTV WLSVIWMMWY WGPSLYNTLS PFLPLLPIFF YLWVYI                 226

SEQ ID NO: 103         moltype = AA  length = 180
FEATURE                Location/Qualifiers
REGION                 1..180
                       note = HBeAg domain
source                 1..180
                       mol_type = protein
                       organism = synthetic construct
SEQUENCE: 103
MQLFHLCLII SCSCPTVQAS KLCLGWLWDM DIDPYKEFGA SVELLSFLPS DFFPSVRDLL  60
DTATALYRDA LESPEHCTPH HTALRHVCLC WGDLMNLATW VGTNLEDQAS RDLVVSYVNT  120
NMGLKFRQLL WFHISCLTFG RDLVLEYLVS FGVWIRTPPA YRPSNAPILS TLPETTVVRQ  180

SEQ ID NO: 104         moltype = AA  length = 154
FEATURE                Location/Qualifiers
REGION                 1..154
                       note = HBx domain
source                 1..154
                       mol_type = protein
                       organism = synthetic construct
```

```
SEQUENCE: 104
MAARLCCQLD PARDVLCLRP VGAESRGRPF SGPLGALSSS SPPAVPTDHG AHLSLRGLPV    60
CAFSSAGPCA LRFTSARRME TTVNAHQFLP KVLHKRTLGL SAMSTTDLEA YFKDCLFKDW   120
EELGEELRLK VFVLGGCRHK LVCAPAPCNF FTSA                                154

SEQ ID NO: 105           moltype = AA  length = 454
FEATURE                  Location/Qualifiers
REGION                   1..454
                         note = Pol domain
source                   1..454
                         mol_type = protein
                         organism = synthetic construct
SEQUENCE: 105
GPCAEHGEHH IRIPRTPARV TGGVFLVDKN PHNTAESRLV VDFSQFSRGN YRVSWPKFAV    60
PNLQSLTNLL SSNLCWLSLD VSAAFYHLPL HPAAMPHLLV GSSGLSRYVA RLSSNSRIIN   120
HQHGTLQNLH DSCSRNLYVS LLLLYKTFGW KLHLYSHPII LGFRKIPMGV GLSPFLLAQF   180
TSAICSVVRR AFPHCLAFSG AKSVQHLESL FTAVTNFLLS LGIHLNPNKT KRWGYSLNFM   240
GYVIGSWGSL PQDHIRHKIK ECFRKLPVHR PIDWKVCQRI VGLLGFAAPF TQCGYPALMP   300
LYACIQSKQA FTFSPTYKAF LCKQYLNLYP VARQRPGLCQ VFADATPTGW GLVMGHQRMR   360
GTFSSRKYTS FPWLLGCAAN WILRGTSFVY VPSALNPADD PSRGRLGPCR PLLHLPFRPT   420
TGRTSLYADS PSVPSHLPDR VHFASPLHVA WRPP                                454

SEQ ID NO: 106           moltype = AA  length = 1014
FEATURE                  Location/Qualifiers
REGION                   1..1014
                         note = HBV design 1
source                   1..1014
                         mol_type = protein
                         organism = synthetic construct
SEQUENCE: 106
MENITSGFLG PLLVLQAGFF LLTRILTIPQ SLDSWWTSLS FLGGTTVCLG QNSQSPTSNH    60
SPTSCPPTCV GYRWMCLRRF IIFLPILLLC LIFLLVLLDY QGMLPVCPLI PGSSTTSTGP   120
CRTCTTPAQG TSMYPSCCCT KPSDGNCTCI PIPSSWAFGK FLWEWASARF SWLSLLVPFV   180
QWFVGLSPTV WLSVIWMMWY WGPSLYNTLS PFLPLLPIFF YLWVYIMQLF HLCLIISCSC   240
PTVQASKLCL GWLWDMDIDP YKEFGASVEL LSFLPSDFFP SVRDLLDTAT ALYRDALESP   300
EHCTPHHTAL RHVCLCWGDL MNLATWVGTN LEDQASRDLV VSYVNTNMGL KFRQLLWFHI   360
SCLTFGRDLV LEYLVSFGVW IRTPPAYRPS NAPILSTLPE TTVVRQMAAR LCCQLDPARD   420
VLCLRPVGAE SRGRPFSGPL GALSSSSPPA VPTDHGAHLS LRGLPVCAFS SAGPCALRFT   480
SARRMETTVN AHQFLPKVLH KRTLGLSAMS TTDLEAYFKD CLFKDWEELG EELRLKVFVL   540
GGCRHKLVCA PAPCNFFTSA GPCAEHGEHH IRIPRTPARV TGGVFLVDKN PHNTAESRLV   600
VDFSQFSRGN YRVSWPKFAV PNLQSLTNLL SSNLCWLSLD VSAAFYHLPL HPAAMPHLLV   660
GSSGLSRYVA RLSSNSRIIN HQHGTLQNLH DSCSRNLYVS LLLLYKTFGW KLHLYSHPII   720
LGFRKIPMGV GLSPFLLAQF TSAICSVVRR AFPHCLAFSG AKSVQHLESL FTAVTNFLLS   780
LGIHLNPNKT KRWGYSLNFM GYVIGSWGSL PQDHIRHKIK ECFRKLPVHR PIDWKVCQRI   840
VGLLGFAAPF TQCGYPALMP LYACIQSKQA FTFSPTYKAF LCKQYLNLYP VARQRPGLCQ   900
VFADATPTGW GLVMGHQRMR GTFSSRKYTS FPWLLGCAAN WILRGTSFVY VPSALNPADD   960
PSRGRLGPCR PLLHLPFRPT TGRTSLYADS PSVPSHLPDR VHFASPLHVA WRPP        1014

SEQ ID NO: 107           moltype = AA  length = 1021
FEATURE                  Location/Qualifiers
REGION                   1..1021
                         note = HBV design 2
source                   1..1021
                         mol_type = protein
                         organism = synthetic construct
SEQUENCE: 107
SVELLSFLPS DFFPSVRDLL DTATALYRDA LESPEHCTPH HTALRHVCLC WGDLMNLATW    60
VGTNLEDQAS RDLVVSYVNT NMGLKFRQLL WFHISCLTFG RDLVLEYLVS FGVWIRTPPA   120
YRPSNAPILS TLPETTVVRQ RGRTIVLHKR TLGLMGQNLS TSNPLGFFPD HQLDPAFRAN   180
TNNPDWDFNP NKDTWPDANK VGAGAFGLGF TPPHGGLLGW SPQAQGIMQT LPANPPPAST   240
NRQSGRQPTP LLPKVLHKRT LMPLSYQHFR KLLLLDNEAG PLEEELPRLA DEDLNRRVAE   300
DLNLGNLNVS IPWTHKVGNF TGLYSSSVPV FNPHWKTPSF PNIHLHQDII KKCEQFVGPL   360
TVNEKRRLKL IMPARFYPNF TKYLPLDKGI KPYYPEHLVN HYPHTRHYLH TLWKAGILYK   420
RVSTHSASFC GSPYSWEQEL QHGAESFHQQ SSGILSRPSV GSSLQSKHQQ SRLGLQSQGG   480
HLARRQQGRS WSIRTRVHPT ARRPSGVEPS GSGHNANLAS KSASCLYQST VRTAAYPAVS   540
TSENHSSSGH AVELHNLPPN SARSQSERPV SPCWWLQFRN SKPCSDYCLS HIVNLLEDWG   600
PCHKRTLGLS AMSPPLRTTH PQAMQWNSTT FHQTLQDPRV RGLYLPAGGS SSGTVNPVPT   660
TASPTLSTSS RIGDPALNQF LPKVLHKRSR GNYRVSWPKF AVPNLQSLTN LLSSNLCWLS   720
LDVSAAFYHL PLHPAAMPHL LVGSSGLSRY VARLSSNSRI INHQHGTLQN LHDSCSRNLY   780
VSLLLLYKTF GWKLHLYSHP IILGFRKIPM GVGLSPFLLA QFTSAITVNA HQFLPKQNSQ   840
SPTSNHSPTS CPPTCVGYRW MCLRRFIIFL FILLLCLIFL LVLLDYQGML PVCPLIPGSS   900
TTSTGPCRTC TTPAQGTSMY PSCCCTKPSD GNCTCIPIPS SWAFGKFLWE WASARFSWLS   960
LLVPFVQWFV GLSPTVWLSV IWMMWYWGPS LYNTLSPFLP LLPIFFYLWV YILSAMSTTD  1020
L                                                                 1021

SEQ ID NO: 108           moltype = AA  length = 532
FEATURE                  Location/Qualifiers
REGION                   1..532
                         note = HBV design 3
```

```
source                        1..532
                              mol_type = protein
                              organism = synthetic construct
SEQUENCE: 108
MQTDRTGETA LHLAARYSRS DFLPSDFFPS VADAGVWIRT PPADNMEYLV SFGVWPLHAA    60
VSADCWGELM TLRNRATDLG GPNLDNILMH DILRSFIPLL PLILAARLAV STLPETTVVR   120
RSHADVFLGG PPVCLDDLFL LTRILTIALH WAAAVNNVLT FGRETVLEYG ANKWLSLLVP   180
FVNNRFLKQQ YMNLPLFLAA REGSYEDLLD TASALYANRF LSKQYMDLDH MTVSTKLCKI   240
PRDLWFHISC LTFIVRLLDL EVSQTSKLTR QTDRTGETAL HLAARYSRSD LTTVPAASLL   300
AADAGLSRYV ARLDNMKLHL YSHPIPLHAA VSADGLSPTV WLSVRNRATD LFLLSLGIHL   360
MHDSLYADSP SVPLILAARL AVHKRTLGLS AMSHADVTLC IPHVAVDDLL LLKATLCIAL   420
HWAAAVNNVQ FLPKVLHKRG ANKALMPLYA CINNRTVNAH QFLPKPLFLA AREGSYELPK   480
VLHKRTLANR VLHKRTLGLD HMLSAMSTTD LPRDLLVPFV QWFVIVRLLD LE           532

SEQ ID NO: 109                moltype = AA   length = 368
FEATURE                       Location/Qualifiers
REGION                        1..368
                              note = HBV design 4
source                        1..368
                              mol_type = protein
                              organism = synthetic construct
SEQUENCE: 109
KKFLPSDFFP SVKKCWGELM TLKKGVWIRT PPAKKSTLPE TTVVRRKKLT FGRETVLEYK    60
KDLLDTASAL YKKLWFHISC LTFKKEYLVS FGVWKKGGPN LDNILKKLTT VPAASLLAKK   120
ILRSFIPLLK KFLGGPPVCL KKFLLTRILT IKKWLSLLVP FVKKGLSPTV WLSVKKLLVP   180
FVQWFVKKFL KQQYMNLKKF LSKQYMDLKK TVSTKLCKKL KGLSRYVARL KKKLHLYSHP   240
IKKFLLSLGI HLKKSLYADS PSVKKALMPL YACIKKLLLK ATLCIKKTLC IPHVAVKKVL   300
HKRTLGLKKL PKVLHKRTLK KHKRTLGLSA MKKQFLPKVL HKRKKTVNAH QFLPKKKLSA   360
MSTTDLKK                                                            368

SEQ ID NO: 110                moltype = AA   length = 20
FEATURE                       Location/Qualifiers
REGION                        1..20
                              note = splice primer
source                        1..20
                              mol_type = protein
                              organism = synthetic construct
SEQUENCE: 110
TGCCAAGAGT GACGTGTCCA                                                20

SEQ ID NO: 111                moltype = AA   length = 9
FEATURE                       Location/Qualifiers
REGION                        1..9
                              note = Cleavable linker
source                        1..9
                              mol_type = protein
                              organism = synthetic construct
SEQUENCE: 111
VSQTSKLTR                                                             9

SEQ ID NO: 112                moltype = AA   length = 9
FEATURE                       Location/Qualifiers
REGION                        1..9
                              note = HBV Peptides from Surface 1
source                        1..9
                              mol_type = protein
                              organism = synthetic construct
SEQUENCE: 112
GGPNLDNIL                                                             9

SEQ ID NO: 113                moltype = AA   length = 11
FEATURE                       Location/Qualifiers
REGION                        1..11
                              note = HBV Peptides from Surface 2
source                        1..11
                              mol_type = protein
                              organism = synthetic construct
SEQUENCE: 113
LTTVPAASLL A                                                         11

SEQ ID NO: 114                moltype = AA   length = 9
FEATURE                       Location/Qualifiers
REGION                        1..9
                              note = HBV Peptides from Surface 3
source                        1..9
                              mol_type = protein
                              organism = synthetic construct
SEQUENCE: 114
ILRSFIPLL                                                             9
```

```
SEQ ID NO: 115          moltype = AA   length = 9
FEATURE                 Location/Qualifiers
REGION                  1..9
                        note = HBV Peptides from Surface 4
source                  1..9
                        mol_type = protein
                        organism = synthetic construct
SEQUENCE: 115
FLGGPPVCL                                                                    9

SEQ ID NO: 116          moltype = AA   length = 9
FEATURE                 Location/Qualifiers
REGION                  1..9
                        note = HBV Peptides from Surface 5
source                  1..9
                        mol_type = protein
                        organism = synthetic construct
SEQUENCE: 116
FLLTRILTI                                                                    9

SEQ ID NO: 117          moltype = AA   length = 9
FEATURE                 Location/Qualifiers
REGION                  1..9
                        note = HBV Peptides from Surface 6
source                  1..9
                        mol_type = protein
                        organism = synthetic construct
SEQUENCE: 117
WLSLLVPFV                                                                    9

SEQ ID NO: 118          moltype = AA   length = 10
FEATURE                 Location/Qualifiers
REGION                  1..10
                        note = HBV Peptides from Surface 7
source                  1..10
                        mol_type = protein
                        organism = synthetic construct
SEQUENCE: 118
GLSPTVWLSV                                                                  10

SEQ ID NO: 119          moltype = AA   length = 10
FEATURE                 Location/Qualifiers
REGION                  1..10
                        note = HBV Peptides from Surface 8
source                  1..10
                        mol_type = protein
                        organism = synthetic construct
SEQUENCE: 119
LLVPFVQWFV                                                                  10

SEQ ID NO: 120          moltype = AA   length = 9
FEATURE                 Location/Qualifiers
REGION                  1..9
                        note = Hepatitis B Spliced Protein 1
source                  1..9
                        mol_type = protein
                        organism = synthetic construct
SEQUENCE: 120
LLLKATLCI                                                                    9

SEQ ID NO: 121          moltype = AA   length = 9
FEATURE                 Location/Qualifiers
REGION                  1..9
                        note = Hepatitis B Spliced Protein 2
source                  1..9
                        mol_type = protein
                        organism = synthetic construct
SEQUENCE: 121
TLCIPHVAV                                                                    9

SEQ ID NO: 122          moltype = AA   length = 9
FEATURE                 Location/Qualifiers
REGION                  1..9
                        note = HBx protein
source                  1..9
                        mol_type = protein
                        organism = synthetic construct
SEQUENCE: 122
```

```
VLHKRTLGL                                                                      9

SEQ ID NO: 123          moltype = AA  length = 10
FEATURE                 Location/Qualifiers
REGION                  1..10
                        note = HBx protein
source                  1..10
                        mol_type = protein
                        organism = synthetic construct
SEQUENCE: 123
LPKVLHKRTL                                                                    10

SEQ ID NO: 124          moltype = AA  length = 10
FEATURE                 Location/Qualifiers
REGION                  1..10
                        note = HBx protein
source                  1..10
                        mol_type = protein
                        organism = synthetic construct
SEQUENCE: 124
HKRTLGLSAM                                                                    10

SEQ ID NO: 125          moltype = AA  length = 10
FEATURE                 Location/Qualifiers
REGION                  1..10
                        note = HBx protein
source                  1..10
                        mol_type = protein
                        organism = synthetic construct
SEQUENCE: 125
QFLPKVLHKR                                                                    10

SEQ ID NO: 126          moltype = AA  length = 10
FEATURE                 Location/Qualifiers
REGION                  1..10
                        note = HBx protein
source                  1..10
                        mol_type = protein
                        organism = synthetic construct
SEQUENCE: 126
TVNAHQFLPK                                                                    10

SEQ ID NO: 127          moltype = AA  length = 9
FEATURE                 Location/Qualifiers
REGION                  1..9
                        note = HBx protein
source                  1..9
                        mol_type = protein
                        organism = synthetic construct
SEQUENCE: 127
LSAMSTTDL                                                                      9

SEQ ID NO: 128          moltype = AA  length = 21
FEATURE                 Location/Qualifiers
REGION                  1..21
                        note = splice probe
source                  1..21
                        mol_type = protein
                        organism = synthetic construct
SEQUENCE: 128
CCCAGGTCCA ACTGCAGCCG G                                                       21

SEQ ID NO: 129          moltype = AA  length = 10
FEATURE                 Location/Qualifiers
REGION                  1..10
                        note = Rigid Linker
source                  1..10
                        mol_type = protein
                        organism = synthetic construct
SEQUENCE: 129
EAAAKEAAAK                                                                    10

SEQ ID NO: 130          moltype = DNA  length = 12
FEATURE                 Location/Qualifiers
misc_feature            1..12
                        note = Furin Linker
source                  1..12
                        mol_type = other DNA
                        organism = synthetic construct
```

```
SEQUENCE: 130
agagctaaga gg                                                          12

SEQ ID NO: 132          moltype = AA   length = 5
FEATURE                 Location/Qualifiers
source                  1..5
                        mol_type = protein
                        organism = synthetic construct
SEQUENCE: 131
EAAAK                                                                   5

SEQ ID NO: 132          moltype = AA   length = 212
FEATURE                 Location/Qualifiers
source                  1..212
                        mol_type = protein
                        organism = Synthetic construct
SEQUENCE: 132
MQLFHLCLII SCSCPTVQAS KLCLGWLWGM DIDPYKEFGA SVELLSFLPS DFFPSIRDLL       60
DTASALYREA LESPEHCSPH HTALRQAILC WGELMNLATW VGSNLEDPAS RELVVSYVNV      120
NMGLKIRQLL WFHISCLTFG RETVLEYLVS FGVWIRTPPA YRPPNAPILS TLPETTVVRR      180
RGRSPRRRTP SPRRRRSQSP RRRRSQSRES QC                                    212

SEQ ID NO: 133          moltype = AA   length = 214
FEATURE                 Location/Qualifiers
source                  1..214
                        mol_type = protein
                        organism = Synthetic construct
SEQUENCE: 133
LQLFHLCLII FCTCSTFQAS KLCLGWLWDM DIDTYKEFGA TAELLSFLPA DFFPSVRDLL       60
DTAAALYRDA LESPEHCTPN HTAIRQAVVC WVDLMTLASW VGNNLQDQIA RDLIVNYVNT      120
NVGLKFRQIL WFHISCLTFG RDTVIEYLVS FGVWIRTPTP YRPQNAPILS TLPENCVIRQ      180
RDRCRTPRRR TPSPRRRRSQ SPRRRRSKSP APQC                                  214

SEQ ID NO: 134          moltype = AA   length = 212
FEATURE                 Location/Qualifiers
source                  1..212
                        mol_type = protein
                        organism = Synthetic construct
SEQUENCE: 134
MQLFHLCLII SCSCPTVQAS KLCLGWLWGM DIDPYKEFGA SVELLSFLPT DFFPSIRDLL       60
DTATALYREA LESPEHCSPH HTALRQAILC WGELMNLATW VGVNLDDPTS RELVVGYVNV      120
NMGLKLRQLL WFHISCLTFG RETVLEYLVS FGVWIRTPQA YRPPNAPILS TLPETTVVRC      180
RGRSPRRRTP SPRRRRSQSP RRRRSQSRGS QC                                    212

SEQ ID NO: 135          moltype = AA   length = 212
FEATURE                 Location/Qualifiers
source                  1..212
                        mol_type = protein
                        organism = Synthetic construct
SEQUENCE: 135
MQLFHLCLII SCSCPTVQAS KLCLGWLWGM DIDPYKEFGA SVELLSFLPS DFFPSIRDLL       60
DTASALYREA LESPEHCSPH HTALRQAILC WGELMNLATW VGGNLEDPAS RELVVSYVNV      120
NMGLKIRQLL WFHISCLTFG RETVLEYLVS FGVWIRTPLA YRPPNAPILS TLPETTVVRR      180
RGRSPRRRTP SPRRRRSQSP RRRRSQSRES QC                                    212

SEQ ID NO: 136          moltype = AA   length = 212
FEATURE                 Location/Qualifiers
source                  1..212
                        mol_type = protein
                        organism = Synthetic construct
SEQUENCE: 136
MQLFHLCLII SCSCPTVQAS KLCLGWLWGM DIDPYKEFGA SVELLSFLPS DFFPSIRDLL       60
DTASALYREA LESPEHCSPH HTALRQAILC WGELMNLATW VGTNLEDPAS RELVVSYVNV      120
NMGLKIRQLL WFHISCLTFG RETVLEYLVS FGVWIRTPPA YRPPNAPILS TLPETTVVRR      180
RGRSPRRRTP SPRRRRSQSP RRRSQSRES QC                                     212

SEQ ID NO: 137          moltype = AA   length = 15
FEATURE                 Location/Qualifiers
source                  1..15
                        mol_type = protein
                        organism = Synthetic construct
SEQUENCE: 137
HQLDPAFGAN STNPD                                                       15

SEQ ID NO: 138          moltype = AA   length = 23
FEATURE                 Location/Qualifiers
source                  1..23
                        mol_type = protein
                        organism = Synthetic construct
```

```
SEQUENCE: 138
NSTTFHQALL DPRVRGLYFP AGG                                                23

SEQ ID NO: 139           moltype = AA  length = 14
FEATURE                  Location/Qualifiers
source                   1..14
                         mol_type = protein
                         organism = Synthetic construct
SEQUENCE: 139
ILPKVLHKRT LGLS                                                          14

SEQ ID NO: 140           moltype = AA  length = 26
FEATURE                  Location/Qualifiers
source                   1..26
                         mol_type = protein
                         organism = Synthetic construct
SEQUENCE: 140
EYIKDCVFKD WEELGEEIRL KVFVLG                                             26

SEQ ID NO: 141           moltype = AA  length = 9
FEATURE                  Location/Qualifiers
source                   1..9
                         mol_type = protein
                         organism = Synthetic construct
SEQUENCE: 141
VCWGELMNL                                                                9

SEQ ID NO: 142           moltype = AA  length = 9
FEATURE                  Location/Qualifiers
source                   1..9
                         mol_type = protein
                         organism = Synthetic construct
SEQUENCE: 142
STLPETTVV                                                                9

SEQ ID NO: 143           moltype = AA  length = 360
FEATURE                  Location/Qualifiers
source                   1..360
                         mol_type = protein
                         organism = Synthetic construct
SEQUENCE: 143
MDIDPYKEFG ASVELLSFLP SDFFPSVRDL LDTATALYRD ALESPEHCTP HHTALRHVCL         60
CWGDLMNLAT WVGTNLEDQA SRDLVVSYVN TNMGLKFRQL LWFHISCLTF GRDLVLEYLV        120
SFGVWIRTPP AYRPSNAPIL STLPETTVMP LSYQHFRRLL LLDDEAGPLE EELPRLADEG        180
LNRRVAEDLN LGNLNVSIPW THKVGNFTGL YSSTVPVFNP HWKTPSFPNI HLHQDIIKKC        240
EQFVGPLTVN EKRRLQLIMP ARFYPNVTKY LPLDKGIKPY YPEHLVNHYF QTRHYLHTLW        300
KAGILYKRET THSASFCGSP YSWEQKLQHG AESFHQQSSG ILSRPPVGSS LQSKHRKSRL        360

SEQ ID NO: 144           moltype = AA  length = 148
FEATURE                  Location/Qualifiers
source                   1..148
                         mol_type = protein
                         organism = Synthetic construct
SEQUENCE: 144
MDIDPYKEFG ATVELLSFLP SDFFPSVRDL LDTASALYRE ALESPEHCSP HHTALRQAIL         60
CWGELMTLAT WVGGNLEDPI SRDLVVSYVN TNMGLKFRQL LWFHISCLTF GRETVIEYLV        120
SFGVWIRTPP AYRPPNAPIL STLPETTV                                          148

SEQ ID NO: 145           moltype = AA  length = 1051
FEATURE                  Location/Qualifiers
source                   1..1051
                         mol_type = protein
                         organism = Synthetic construct
SEQUENCE: 145
MDIDPYKEFG ASVELLSFLP SDFFPSVRDL LDTATALYRD ALESPEHCTP HHTALRHVCL         60
CWGDLMNLAT WVGTNLEDQA SRDLVVSYVN TNMGLKFRQL LWFHISCLTF GRDLVLEYLV        120
SFGVWIRTPP AYRPSNAPIL STLPETTVMP LSYQHFRRLL LLDDEAGPLE EELPRLADEG        180
LNRRVAEDLN LGNLNVSIPW THKVGNFTGL YSSTVPVFNP HWKTPSFPNI HLHQDIIKKC        240
EQFVGPLTVN EKRRLQLIMP ARFYPNVTKY LPLDKGIKPY YPEHLVNHYF QTRHYLHTLW        300
KAGILYKRET THSASFCGSP YSWEQKLQHG AESFHQQSSG ILSRPPVGSS LQSKHRKSRL        360
GLQSQQGHLA RRQQGRSWSI RAGIHPTARR SFGVEPSGSG HSTNLASKSA SCLYQSPVRK        420
AAYPAVSTFE KHSSSGHAVE LHNLPPNSAR SQSERPVFPC WWLQFRNSKP CSDYCLSHIV        480
NLLEDWGPCA EHGEHHIRIP RTPARVTGGV FLVDKNPHNT AESRLVVDFS QFSRGNYRVS        540
WPKFAVPNLQ SLTNLLSSNL SWLSLDVSAA FYHLPLHPAA MPHLLVGSSG LSRYVARLSS        600
NSRIFNYQHG TMQNLHDSCS RNLYVSLLLL YQTFGRKLHV LQAGFFLLTR ILTIPQSLDS        660
WWTSLSFLGG TTVCLGQWGL SPFLAQFTS AICSVVRRAF PHCLAFSFPD HQLDPAFRAN         720
TANPDWDFNP NKDTWPDANK VGAGAGAKSV QHLESLFTAV TNFLLSLGIH LNPNKTKRWG        780
YSLHFMGYVI GCYGSLPQDH IIQKIKECFR KLPVNRPIDW KVCQRIVGLL GFAAPFTQCG        840
YPALMPLYAC IQSWASARFS WLSLLVPFVQ WFVGLSPTVW LSVYKAFLCK QYLNLYPVAR        900
```

```
QRPGLCQVFA HATPTGWGLV MGHQRMRGTF LENITSGFLG PLLVLQAGFF LLTRILTIPQ   960
SSRKYTSFPW LLGCAANWIL RGTSFVYYPS ALNPYHDPSR GRLGLSRPLL RLPFRPTTGR  1020
TSLYADSPSV PSHLPDRVHF ASPLHVAWRP P                                1051

SEQ ID NO: 146           moltype = AA   length = 903
FEATURE                  Location/Qualifiers
source                   1..903
                         mol_type = protein
                         organism = synthetic construct
SEQUENCE: 146
MPLSYQHFRR LLLLDDEAGP LEEELPRLAD EGLNRRVAED LNLGNLNVSI PWTHKVGNFT    60
GLYSSTVPVF NPHWKTPSFP NIHLHQDIIK KCEQFVGPLT VNEKRRLQLI MPARFYPNVT   120
KYLPLDKGIK PYYPEHLVNH YFQTRHYLHT LWKAGILYKR ETTHSASFCG SPYSWEQKLQ   180
HGAESFHQQS SGILSRPPVG SSLQSKHRKS RLGLQSQQGH LARRQQGRSW SIRAGIHPTA   240
RRSFGVEPSG SGHSTNLASK SASCLYQSPV RKAAYPAVST FEKHSSSGHA VELHNLPPNS   300
ARSQSERPVF PCWWLQFRNS KPCSDYCLSH IVNLLEDWGP CAEHGEHHIR IPRTPARVTG   360
GVFLVDKNPH NTAESRLVVD FSQFSRGNYR VSWPKFAVPN LQSLTNLLSS NLSWLSLDVS   420
AAFYHLPLHP AAMPHLLVGS SGLSRYVARL SSNSRIFNYQ HGTMQNLHDS CSRNLYVSLL   480
LLYQTFGRKL HVLQAGFFLL TRILTIPQSL DSWWTSLSFL GGTTVCLGQW GLSPFLLAQF   540
TSAICSVVRR AFPHCLAFSF PDHQLDPAFR ANTANPDWDF NPNKDTWPDA NKVGAGAGAK   600
SVQHLESLFT AVTNFLLSLG IHLNPNKTKR WGYSLHFMGY VIGCYGSLPQ DHIIQKIKEC   660
FRKLPVNRPI DWKVCQRIVG LLGFAAPFTQ CGYPALMPLY ACIQSWASAR FSWLSLLVPF   720
VQWFVGLSPT VWLSVYKAFL CKQYLNLYPV ARQRPGLCQV FADATPTGWG LVMGHQRMRG   780
TFLENITSGF LGPLLVLQAG FFLLTRILTI PQSSRKYTSF PWLLGCAANW ILRGTSFVYV   840
PSALNPTDDP SRGRLGLSRP LLRLPFRPTT GRTSLYADSP SVPSHLPDRV HFASPLHVAW   900
RPP                                                                903

SEQ ID NO: 147           moltype = AA   length = 1014
FEATURE                  Location/Qualifiers
source                   1..1014
                         mol_type = protein
                         organism = synthetic construct
SEQUENCE: 147
MENITSGFLG PLLVLQAGFF LLTRILTIPQ SLDSWWTSLS FLGGTTVCLG QNSQSPTSNH    60
SPTSCPPTCV GYRWMCLRRF IIFLFILLLC LIFLLVLLDY QGMLPVCPLI PGSSTTSTGP   120
CRTCTTPAQG TSMYPSCCCT KPSDGNCTCI PIPSSWAFGK FLWEWASARF SWLSLLVPFV   180
QWFVGLSPTV WLSVIWMMWY WGPSLYNTLS PFLPLLPIFF YLWVYIMQLF HLCLIISCSC   240
PTVQASKLCL GWLWDMDIDP YKEFGASVEL LSFLPSDFFP SVRDLLDTAT ALYRDALESP   300
EHCTPHHTAL RHVCLCWGDL MNLATWVGTN LEDQASRDLV VSYVNTNMGL KFRQLLWFHI   360
SCLTFGRDLV LEYLVSFGVW IRTPPAYRPS NAPILSTLPE TTVVRQMAAR LCCQLDPARD   420
VLCLRPVGAE SRGRPFSGPL GALSSSSPPA VPTDHGAHLS LRGLPVCAFS SAGPCALRFT   480
SARRMETTVN AHQFLPKVLH KRTLGLSAMS TTDLEAYFKD CLFKDWEELG EELRLKVFVL   540
GGCRHKLVCA PAPCNFFTSA GPCAEHGEHH IRIPRTPARV TGGVFLVDKN PHNTAESRLV   600
VDFSQFSRGN YRVSWPKFAV PNLQSLTNLL SSNLCWLSLD VSAAFYHLPL HPAAMPHLLV   660
GSSGLSRYVA RLSSNSRIIN HQHGTLQNLH DSCSRNLYVS LLLLYKTFGW KLHLYSHPII   720
LGFRKIPMGV GLSPFLLAQF TSAICSVVRR AFPHCLAFSG AKSVQHLESL FTAVTNFLLS   780
LGIHLNPNKT KRWGYSLNFM GYVIGSWGSL PQDHIRHKIK ECFRKLPVHR PIDWKVCQRI   840
VGLLGFAAPF TQCGYPALMP LYACIQSKQA FTFSPTYKAF LCKQYLNLYP VARQRPGLCQ   900
VFADATPTGW GLVMGHQRMR GTFSSRKYTS FPWLLGCAAN WILRGTSFVY VPSALNPADD   960
PSRGRLGPCR PLLHLPFRPT TGRTSLYADS PSVPSHLPDR VHFASPLHVA WRPP        1014

SEQ ID NO: 148           moltype = AA   length = 1054
FEATURE                  Location/Qualifiers
source                   1..1054
                         mol_type = protein
                         organism = Synthetic construct
SEQUENCE: 148
MENITSGFLG PLLVLQAGFF LLTRILTIPQ SLDSWWTSLS FLGGTTVCLG QNSQSPTSNH    60
SPTSCPPTCV GYRWMCLRRF IIFLFILLLC LIFLLVLLDY QGMLPVCPLI PGSSTTSTGP   120
CRTCTTPAQG TSMYPSCCCT KPSDGNCTCI PIPSSWAFGK FLWEWASARF SWLSLLVPFV   180
QWFVGLSPTV WLSVIWMMWY WGPSLYNTLS PFLPLLPIFF YLWVYIMQLF HLCLIISCSC   240
PTVQASKLCL GWLWDMDIDP YKEFGASVEL LSFLPSDFFP SVRDLLDTAT ALYRDALESP   300
EHCTPHHTAL RHVCLCWGDL MNLATWVGTN LEDQASRDLV VSYVNTNMGL KFRQLLWFHI   360
SCLTFGRDLV LEYLVSFGVW IRTPPAYRPS NAPILSTLPE TTVVRQMAAR LCCQLDPARD   420
VLCLRPVGAE SRGRPFSGPL GALSSSSPPA VPTDHGAHLS LRGLPVCAFS SAGPCALRFT   480
SARRMETTVN AHQFLPKVLH KRTLGLSAMS TTDLEAYFKD CLFKDWEELG EELRLKVFVL   540
GGCRHKLVCA PAPCNFFTSA GPCAEHGEHH IRIPRTPARV TGGVFLVDKN PHNTAESRLV   600
VDFSQFSRGN YRVSWPKFAV PNLQSLTNLL SSNLCWLSLD VSAAFYHLPL HPAAMPHLLV   660
GSSGLSRYVA RLSSNSRIIN HQHGTLQNLH DSCSRNLYVS LLLLYKTFGW KLHLYSHPII   720
LGFRKIPMGV GLSPFLLAQF TSAICSVVRR AFPHCLAFSY MDDVVLGAKS VQHLESLFTA   780
VTNFLLSLGI HLNPNKTKRW GYSLNFMGYV IGSWGSLPQD HIRHKIKECF RKLPVHRPID   840
WKVCQRIVGL LGFAAPFTQC GYPALMPLYA CIQSKQAFTF SPTYKAFLCK QYLNLYPVAR   900
QRPGLCQVFA DATPTGWGLV MGHQRMRGTF SAPLPIHTAE LLAACFARSR SGANILGTDN   960
SVVLSRKYTS FPWLLGCAAN WILRGTSFVY VPSALNPADD PSRGRLGPCR PLLHLPFRPT  1020
TGRTSLYADS PSVPSHLPDR VHFASPLHVA WRPP                             1054
```

What is claimed is:

1. A polypeptide construct comprising:
   (a) (i) an HBV Pol domain consisting of SEQ ID NO: 99, and (ii) at least one additional domain selected from: an HBV Envelope domain consisting of SEQ ID NO: 100; an HBV Core domain consisting of SEQ ID NO: 101; and an HBx domain consisting of SEQ ID NO: 98; or
   (b) (i) an ankyrin-like repeat domain, and (ii) an HBV polypeptide.

2. The polypeptide construct of claim 1, wherein the polypeptide construct comprises: (a) an ankyrin-like repeat domain; and (b) an HBV polypeptide; wherein:
   the ankyrin-like repeat domain is a human ankyrin-like repeat domain; and/or
   the HBV polypeptide comprises a sequence of any one of SEQ ID NOs: 45-60 and 112-127.

3. The polypeptide construct of claim 1, comprising the sequence of any one of SEQ ID NOs: 106, 108, and 109.

4. A polynucleotide encoding the polypeptide construct of claim 1.

5. A polynucleotide construct comprising: (a) the polynucleotide of claim 4; and (b) one or more additional polynucleotides encoding components of a gene switch system, wherein the gene switch system is operably linked to regulate the expression of the polypeptide construct encoded by the polynucleotide of (a).

6. The polynucleotide construct of claim 5, wherein the gene switch is an ecdysone receptor-based (EcR-based) gene switch system.

7. A method of regulating the expression of a polypeptide construct in a cell, the method comprising:
   (a) introducing into the cell the polynucleotide construct of claim 4 that encodes the polypeptide construct, and
   (b) exposing the cell to a compound in an amount sufficient to modulate expression of the polypeptide construct.

8. The method of claim 7, wherein the gene switch system comprises a ligand binding domain derived from a receptor selected from: an ecdysone receptor (EcR), a ubiquitous receptor, an orphan receptor 1, an NER-1, a steroid hormone nuclear receptor 1, a retinoid X receptor interacting protein-15, a liver X receptor b, a steroid hormone receptor like protein, a liver X receptor, a liver X receptor a, a farnesoid X receptor, a receptor interacting protein 14, and a farnesol receptor.

9. A vector comprising the polynucleotide of claim 4.

10. The vector of claim 9, wherein the vector is a gorilla adenoviral vector.

11. The vector of claim 10, wherein the vector is a GC46 vector.

12. The polypeptide construct of claim 1, comprising the following HBV polypeptides:
   (a) an HBV Envelope domain consisting of SEQ ID NO: 100;
   (b) an HBV Core domain consisting of SEQ ID NO: 101;
   (c) an HBx domain consisting of SEQ ID NO: 98; and
   (d) an HBV Pol domain consisting of SEQ ID NO: 99;
   wherein at least two of the HBV polypeptides are connected by a linker.

13. The polypeptide construct of claim 1, comprising, from N-terminus to C-terminus, the following domains: (a) the HBV Envelope domain; (b) the HBV Core domain; (c) the HBx domain; and (d) the HBV Pol domain.

14. The polypeptide construct of claim 13, wherein: the HBV Envelope domain and the HBV Core domain are connected by a first linker; the HBV Core domain and the HBx domain are connected by a second linker; the HBx domain and the HBV domain are connected by a third linker; and each linker comprises the amino acid sequence SEQ ID NO: 129.

15. A polynucleotide encoding the polypeptide construct of claim 14.

16. The polypeptide construct of claim 1, comprising the sequence of SEQ ID NO: 106.

* * * * *